United States Patent [19]

Oppermann et al.

[11] Patent Number: 5,266,683
[45] Date of Patent: *Nov. 30, 1993

[54] OSTEOGENIC PROTEINS

[75] Inventors: Hermann Oppermann, Medway; Engin Ozkaynak, Milford; Thangavel Kuberasampath, Medway; David C. Rueger, Hopkinton; Roy H. L. Pang, Medway, all of Mass.

[73] Assignee: Stryker Corporation, Kalamazoo, Mich.

[*] Notice: The portion of the term of this patent subsequent to Nov. 2, 2010 has been disclaimed.

[21] Appl. No.: 841,646

[22] Filed: Feb. 21, 1992

Related U.S. Application Data

[60] Continuation-in-part of Ser. No. 827,052, Jan. 28, 1992, Pat. No. 5,250,302, Ser. No. 579,865, Oct. 7, 1990, Pat. No. 5,108,753, Ser. No. 621,849, Dec. 4, 1990, abandoned, Ser. No. 621,988, Dec. 4, 1990, abandoned, Ser. No. 810,560, Dec. 20, 1991, abandoned, Ser. No. 569,920, Aug. 20, 1990, abandoned, Ser. No. 600,024, Oct. 18, 1990, abandoned, Ser. No. 599,543, Oct. 18, 1990, abandoned, Ser. No. 616,374, Nov. 21, 1990, Pat. No. 5,162,114, and Ser. No. 483,913, Feb. 22, 1990, Pat. No. 5,171,574, said Ser. No. 827,052, is a division of Ser. No. 179,406, Apr. 8, 1988, Pat. No. 4,968,590, said Ser. No. 579,865, is a division of Ser. No. 179,406, Apr. 8, 1988, said Ser. No. 621,849, is a division of Ser. No. 232,630, Aug. 15, 1988, abandoned, which is a continuation-in-part of Ser. No. 179,406, Aug. 15, 1988, said Ser. No. 621,988, is a division of Ser. No. 315,342, Feb. 23, 1989, Pat. No. 5,011,691, which is a continuation-in-part of Ser. No. 232,630, Feb. 23, 1989, said Ser. No. 810,560, is a continuation of Ser. No. 660,162, Feb. 22, 1991, abandoned, which is a continuation of Ser. No. 422,699, Oct. 17, 1989, abandoned, which is a continuation-in-part of Ser. No. 315,342, Oct. 17, 1989, said Ser. No. 569,920, is a continuation-in-part of Ser. No. 422,699, Oct. 17, 1989, and Ser. No. 483,913, Oct. 17, 1989, which is a continuation-in-part of Ser. No. 422,613, Oct. 17, 1989, Pat. No. 4,975,526, which is a continuation-in-part of Ser. No. 315,342, Oct. 17, 1989, said Ser. No. 600,024, is a continuation-in-part of Ser. No. 569,920, Oct. 17, 1989, said Ser. No. 599,543, is a continuation-in-part of Ser. No. 569,920, Oct. 17, 1989.

[51] Int. Cl.[5] .............. A61K 37/02; C07K 5/00; C07K 7/00; C07K 15/00
[52] U.S. Cl. .................... 530/326; 530/327; 530/328; 530/350; 530/395; 530/840
[58] Field of Search .............. 530/326, 327, 328, 395, 530/840, 300, 350

[56] References Cited

U.S. PATENT DOCUMENTS

| | | | |
|---|---|---|---|
| 4,172,128 | 10/1979 | Thiele et al. | 424/95 |
| 4,294,753 | 10/1981 | Urist | 530/356 |
| 4,394,370 | 7/1983 | Jefferies | 424/15 |
| 4,434,094 | 2/1984 | Seyedin et al. | 530/356 |
| 4,455,256 | 6/1984 | Urist | 530/356 |
| 4,563,350 | 1/1986 | Nathan et al. | 424/95 |
| 4,563,489 | 1/1986 | Urist | 524/21 |

(List continued on next page.)

FOREIGN PATENT DOCUMENTS 069260  6/1982  European Pat. Off. .

(List continued on next page.)

OTHER PUBLICATIONS

Canalis et al., Science 210:1021–1023 (1980).
Glowacki et al., Lancet 1:959–963 (1981).
Reddi, Collagen Rel. Res. 1:209–226 (1981).
Sampath et al. Proc. Natl. Acad. Sci. USA 78:7599–7603 (1981).

(List continued on next page.)

*Primary Examiner*—Nathan M. Nutter
*Attorney, Agent, or Firm*—Testa, Hurwitz & Thibeault

[57] ABSTRACT

Disclosed are (1) osteogenic devices comprising a matrix containing substantially pure natural-sourced mammalian osteogenic protein; (2) DNA and amino acid sequences for novel polypeptide chains useful as subunits of dimeric osteogenic proteins; (3) vectors carrying sequences encoding these novel polypeptide chains and host cells transfected with these vectors; (4) methods of producing these polypeptide chains using recombinant DNA technology; (5) antibodies specific for these novel polypeptide chains; (6) osteogenic devices comprising these recombinantly produced proteins in association with an appropriate carrier matrix; and (7) methods of using the osteogenic devices to mimic the natural course of endochondral bone formation in mammals.

58 Claims, 47 Drawing Sheets

U.S. PATENT DOCUMENTS

| | | | |
|---|---|---|---|
| 4,657,548 | 4/1987 | Nichols | 623/10 |
| 4,703,108 | 10/1987 | Silver et al. | 530/356 |
| 4,725,671 | 2/1988 | Chu et al. | 530/356 |
| 4,774,322 | 9/1988 | Seyedin et al. | 530/353 |
| 4,789,663 | 12/1988 | Wallace et al. | 514/21 |
| 4,795,467 | 1/1989 | Piez et al. | 623/16 |
| 4,804,744 | 2/1989 | Sen | 530/350 |
| 4,810,691 | 3/1989 | Seyedin et al. | 514/2 |
| 4,812,120 | 3/1989 | Flanagan et al. | 433/173 |
| 4,824,939 | 4/1989 | Simpson | 530/356 |
| 4,837,285 | 6/1989 | Bero et al. | 530/356 |
| 4,843,063 | 6/1989 | Seyedin et al. | 514/2 |
| 4,877,864 | 10/1989 | Wang et al. | 530/324 |
| 4,894,441 | 1/1990 | Menicagli | 530/356 |
| 5,013,649 | 5/1991 | Wang et al. | 435/69.2 |
| 5,106,626 | 4/1992 | Parsons et al. | 424/423 |
| 5,106,748 | 4/1992 | Wozney et al. | 435/252.3 |
| 5,108,922 | 4/1992 | Wang et al. | 435/252.3 |
| 5,116,738 | 5/1992 | Wang et al. | 435/69.1 |
| 5,141,905 | 8/1992 | Rosen et al. | 435/69.1 |
| 5,166,058 | 11/1992 | Wang et al. | 435/69.1 |
| 5,187,076 | 2/1993 | Wozney et al. | 435/69.1 |

FOREIGN PATENT DOCUMENTS

| | | |
|---|---|---|
| 128041 | 12/1984 | European Pat. Off. |
| 148155 | 1/1985 | European Pat. Off. |
| 169001 | 7/1985 | European Pat. Off. |
| 182483 | 10/1985 | European Pat. Off. |
| 169016 | 1/1986 | European Pat. Off. |
| 170979 | 2/1986 | European Pat. Off. |
| 212474 | 8/1986 | European Pat. Off. |
| 230647 | 5/1987 | European Pat. Off. |
| 309241 | 9/1988 | European Pat. Off. |
| 8505274 | 12/1985 | PCT Int'l Appl. |
| 8600526 | 1/1986 | PCT Int'l Appl. |
| 8800205 | 1/1988 | PCT Int'l Appl. |
| 9118098 | 11/1988 | PCT Int'l Appl. |
| 8909605 | 10/1989 | PCT Int'l Appl. |
| 8910409 | 11/1989 | PCT Int'l Appl. |
| 9003733 | 4/1990 | PCT Int'l Appl. |
| WO90/11366 | 10/1990 | PCT Int'l Appl. |
| WO91/19510 | 12/1991 | PCT Int'l Appl. |
| WO92/05199 | 4/1992 | PCT Int'l Appl. |
| WO92/17584 | 10/1992 | PCT Int'l Appl. |
| WO93/00049 | 1/1993 | PCT Int'l Appl. |
| 2178447 | 2/1987 | United Kingdom . |

OTHER PUBLICATIONS

Farley et al., Biochem. 21:3508-3513 (1982).
Maugh et al., Science 217:819 (1982).
Sampath et al., Proc. Natl. Acad. Sci. USA 80:6591-6595 (1983).
Seyedin et al., J. Cell Biol. 17:1950-1953 (1983).
Urist et al., Proc. Soc. Exp. Bio. Med. 173:194-199 (1983).
Simpson et al., Trends Biochem. Sci. 9:527-530 (1984).
Strand et al., Biotech. Boeing. 26:503-507 (1984).
Urist et al., Clin. Orth. Rel. Res. 187:277-280 (1984).
Urist et al. II, Proc. Natl. Acad. Sci. USA 81:371-375 (1984).
Centrella et al., Proc. Natl. Acad. Sci. USA 82:7335-7339 (1985).
Klausner, Biotechnology 3:567-568 (1985).
Olson et al., Analyt. Biochem. 146:232-237 (1985).
Reddi, J., Biomed. Mat. Res. 19:233-239 (1985).
Sampath et al., Extraceluler Matrix: Structure and Function (A. H. Reddi, Ed.) Allen R. Liss, Pub., N.Y., pp. 412-428 (1985).
Seyedin et al., Proc. Natl. Acd. Sci. USA 82:2267-2271 (1985).
Colowick et al., Methods in Enzymology 146:294-312 (1987).
Deatherage et al., Collagen Rel. Res. 7:225-231 (1987).
Padgett et al., Nature 325:81-84 (1987).
Sampath et al., Proc. Natl. Acad. Sci. USA 84:7109-7113 (1987).
Spector, J. Anthroplasty 2:163-177 (1987).
Weeks et al., Cell 51:861-867 (1987).
Aspenberg et al., J. Bone Joint Surg. 70:625-627 (1988).
Bendig, Genetic Engineering 7:91-121 (1988).
Cook et al., Clin. Orthopaed. Rel. Res. 232:225-243 (1988).
Deatherage et al., Int. J. Oral Macillofac. Surg. 17:395-399 (1988).
LeGendre et al., Biotechniques 6:154-159 (1988).
Sedivy, Bio/Technology 6:1192-1196 (1988).
Wang et al., Calcified Tissue Int. (Supplement) Abs. No. 146, p. A37 (1988).
Wang et al., II, Proc. Natl. Acad. Sci. USA 85:9484-9488 (1988).
Wozney et al., Calcified Tissue Int. (Supplement) Abs. No. 147, p. A37 (1988).
Wozney et al., II, Science 242:1528-1534.
Lyons et al., Proc. Natl. Acad. Sci. USA 86:4554-4558 (1989).
Wang et al., PNAS 87:2220-2224 (1990).

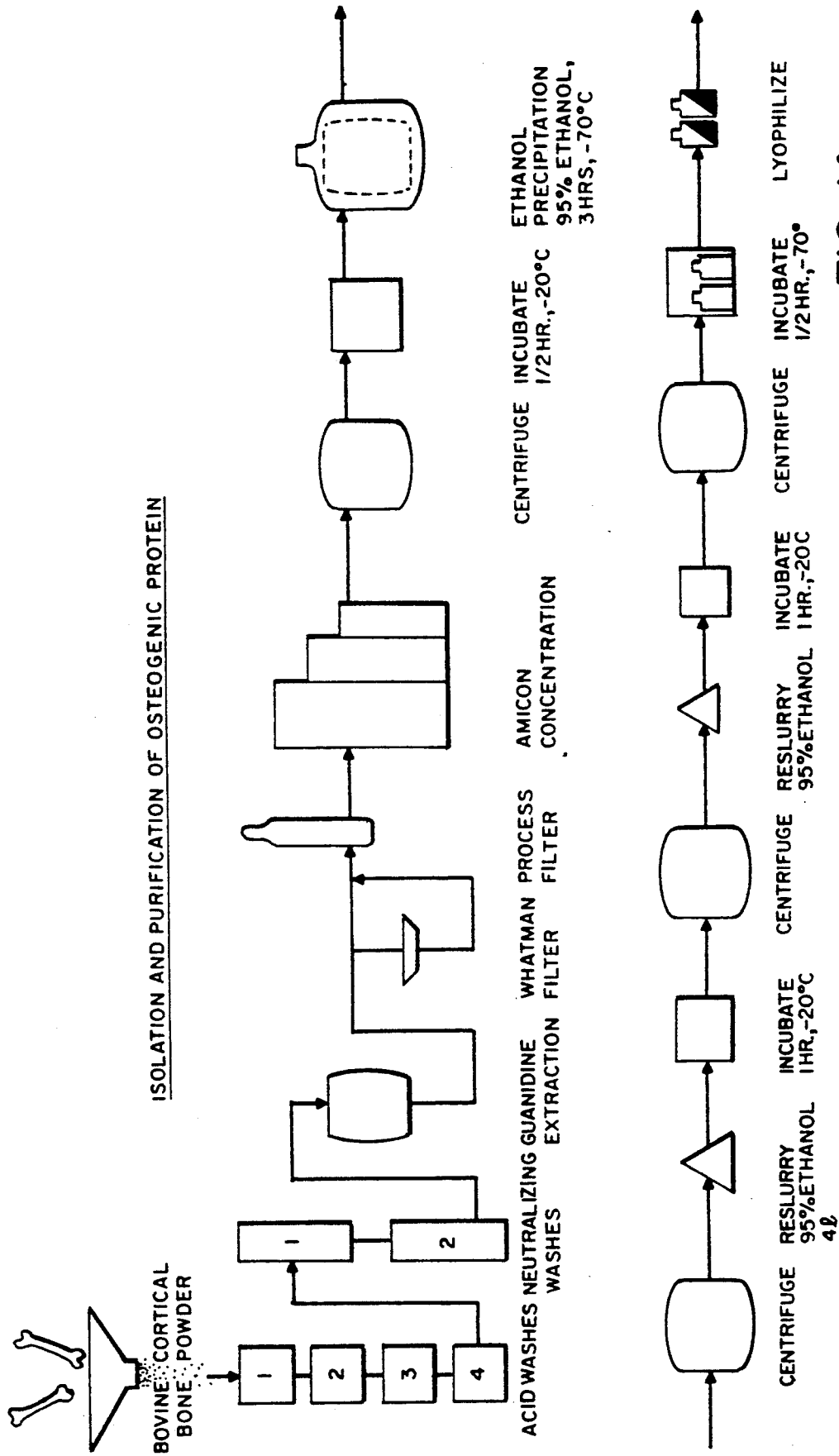
FIG. IA

 
*Fig. 3A*     *Fig. 3B*
 
*Fig. 4A*     *Fig. 4B*

Consensus gene/probe:

```
            10        20        30        40
    GATCCTAATGGGCTGTACGTGGACTTCCAGCGCGACGTGGGCTGGGAC
     D  P  N  G  L  Y  V  D  F  Q  R  D  V  G  W  D
    Sau3A          RsaI            AccII
                                   HhaI 50        60        70        80        90
    GACTGGATCATCGCCCCCGTCGACTTCGACGCCTACTACTGCTCCGGA
     D  W  I  I  A  P  V  D  F  D  A  Y  Y  C  S  G
        Sau3A          Accl   TaqI           BspMII
                       HincII AhaII          HpaII
                       SalI   HgaI+
                              TaqI 100       110       120       130       140
    GCCTGCCAGTTCCCCTCTGCGGATCACTTCAACAGCACCAACCACGCCG
     A  C  Q  F  P  S  A  D  H  F  N  S  T  N  H  A
              MnlI+    Sau3A                  DraIII
                                              PflMI 150       160       170       180       190
    TGGTGCAGACCCTGGTGAACAACATGAACCCCGGCAAGGTACCCAAGC
     V  V  Q  T  L  V  N  N  M  N  P  G  K  V  P  K
             EcoRII              HpaII   BanI
              HphI+               NciI   KpnI
             ScrFI                ScrFI  RsaI
```

Fig. 13

```
          200         210         220         230         240
CCTGCTGCGTGCCCACCGAGCTGTCCGCCATCAGCATGCTGTACCTGGA
  P   C   C   V   P   T   E   L   S   A   I   S   M   L   Y   L   D
  Fnu4HI            AluI                    NspHI       EcoRII
                                            SphI    RsaI
                                                        ScrFI 250         260         270         280         290
CGAGAATTCCACCGTGGTGCTGAAGAACTACCAGGAGATGACCGTGGT
   E   N   S   T   V   V   L   K   N   Y   Q   E   M   T   V   V
   EcoRI                       MboII+   EcoRII
                                        ScrFI 300         310
GGGCTGCGGCTGCCGCTAACTGCAG
cccgacgccgacggcgattgacgt
    G   C   G   C   R   *
   Fnu4HIFnu4HI
      Fnu4H
           IFnu4HI
```

Fig. 13 Cont.

```
CONSENSUS PROBE    20        30        40        50        60        70
GATCCTAATGGGCTGTACGTGGACTTCCAGGCGCGACGTGGGCTGGGACGACTGGATCATCGCCCCGTCG
                                         ** ********** *********** **** ***********
TGTAAGAAGCACGAGCTGTATGTCAGCTTCCGAGACCTGGCAGGACTGGATCATCGCCGCCTGAAG
OP4   28        38        48        58        68        78        88

80        90       100       110       120       130       140
ACTTCGACGCCTACTACTGCTCCGGAGCCTGCCAGTTCCCCTCTGCGGATCACTTCAACAGCACCAACCA
** ***   ********** ******   **   ***** *****   ** *** ********* *********
GCTACGCGCGCTACTACTGTGAGGGGAGTGTGCCTTCCCTCTGAACTCCTACATGAACGCCACCAACCA
     98       108       118       128       138       148       158

150       160       170       180       190       200       210
CGCCGTGGTGCAGACCCTGGTGAACAACATGAACCCCGGCAAGGTACCCAAGCCCTGCTGCCCACC
****  *********   ******   ** *** *****     *** ************** ******
CGCCATCGTGCAGACGCTGGTCCACTTCATCAACCCGGAAACGGTGCCCAAGCCCTGTGCGCCCACG
    168       178       188       198       208       218       228

220       230       240       250       260       270       280
GAGCTGTCCGCCATCAGCATGCTGTACCTGGACGAGAATTCCACCGTGGTGCTGAAGAACTACCAGGAGA
****   *   ** ***   ** ***     ** *** *     ***** *** ********* *
CAGCTCAATGCCATCTCCGTCCTCTACTTCGATGACAGCTCCAAGCGTCATCCTGAAGAAATACAGAAACA
    238       248       258       268       278       288       298

290       300       310
TGACCGTGGTGGGCTGCGGCTGCCGCTAACTGCA
**  ** ***   ********** *** ***   **
TGGTGGTCCGGGCCTGCGGCTGCCACTAGCTCCT
    308       318       328
```

Fig. 18

| | | | | | | | | |
|---|---|---|---|---|---|---|---|---|
| hOP1-18Ser | Ser | Thr | Gly | Ser | Lys | Gln | Arg | Ser | Gln |
| mOP1-Ser | ... | ... | ... | Gly | ... | ... | ... | ... | ... |
| | 1 | | | | 5 | | | | |

| | | | | | | | | |
|---|---|---|---|---|---|---|---|---|
| hOP1-18Ser | Asn | Arg | Ser | Lys | Thr | Pro | Lys | Asn | Gln |
| mOP1-Ser | ... | ... | ... | ... | ... | ... | ... | ... | ... |
| | | 10 | | | | 15 | | | |

| | | | | | | | | |
|---|---|---|---|---|---|---|---|---|
| hOP1-18Ser | Glu | Ala | Leu | Arg | Met | Ala | Asn | Val | Ala |
| mOP1-Ser | ... | ... | ... | ... | ... | ... | Ser | ... | ... |
| | | | 20 | | | | 25 | | |

| | | | | | | | | |
|---|---|---|---|---|---|---|---|---|
| hOP1-18Ser | Glu | Asn | Ser | Ser | Ser | Asp | Gln | Arg | Gln |
| mOP1-Ser | ... | ... | ... | ... | ... | ... | ... | ... | ... |
| | | | | 30 | | | | 35 | |

| | | | | | | | | |
|---|---|---|---|---|---|---|---|---|
| hOP1-18Ser | Ala | Cys | Lys | Lys | His | Glu | Leu | Tyr | Val |
| mOP1-Ser | ... | ... | ... | ... | ... | ... | ... | ... | ... |
| | | | | | 40 | | | | 45 |

| | | | | | | | | |
|---|---|---|---|---|---|---|---|---|
| hOP1-18Ser | Ser | Phe | Arg | Asp | Leu | Gly | Trp | Gln | Asp |
| mOP1-Ser | ... | ... | ... | ... | ... | ... | ... | ... | ... |
| | | | | | 50 | | | | |

| | | | | | | | | |
|---|---|---|---|---|---|---|---|---|
| hOP1-18Ser | Trp | Ile | Ile | Ala | Pro | Glu | Gly | Tyr | Ala |
| mOP1-Ser | ... | ... | ... | ... | ... | ... | ... | ... | ... |
| | 55 | | | | | 60 | | | |

| | | | | | | | | |
|---|---|---|---|---|---|---|---|---|
| hOP1-18Ser | Ala | Tyr | Tyr | Cys | Glu | Gly | Glu | Cys | Ala |
| mOP1-Ser | ... | ... | ... | ... | ... | ... | ... | ... | ... |
| | | 65 | | | | 70 | | | |

FIG. 23A-1

| hOP1-18Ser | Phe | Pro | Leu | Asn | Ser | Tyr | Met | Asn | Ala |
|---|---|---|---|---|---|---|---|---|---|
| mOP1-Ser | ... | ... | ... | ... | ... | ... | ... | ... | ... |
| | | | 75 | | | | 80 | | |

| hOP1-18Ser | Thr | Asn | His | Ala | Ile | Val | Gln | Thr | Leu |
|---|---|---|---|---|---|---|---|---|---|
| mOP1-Ser | ... | ... | ... | ... | ... | ... | ... | ... | ... |
| | | | 85 | | | | | 90 | |

| hOP1-18Ser | Val | His | Phe | Ile | Asn | Pro | Glu | Thr | Val |
|---|---|---|---|---|---|---|---|---|---|
| mOP1-Ser | ... | ... | ... | ... | ... | ... | Asp | ... | ... |
| | | | | 95 | | | | | |

| hOP1-18Ser | Pro | Lys | Pro | Cys | Cys | Ala | Pro | Thr | Gln |
|---|---|---|---|---|---|---|---|---|---|
| mOP1-Ser | ... | ... | ... | ... | ... | ... | ... | ... | ... |
| | 100 | | | | 105 | | | | |

| hOP1-18Ser | Leu | Asn | Ala | Ile | Ser | Val | Leu | Tyr | Phe |
|---|---|---|---|---|---|---|---|---|---|
| mOP1-Ser | ... | ... | ... | ... | ... | ... | ... | ... | ... |
| | | 110 | | | | | 115 | | |

| hOP1-18Ser | Asp | Asp | Ser | Ser | Asn | Val | Ile | Leu | Lys |
|---|---|---|---|---|---|---|---|---|---|
| mOP1-Ser | ... | ... | ... | ... | ... | ... | ... | ... | ... |
| | | | 120 | | | | | 125 | |

| hOP1-18Ser | Lys | Tyr | Arg | Asn | Met | Val | Val | Arg | |
|---|---|---|---|---|---|---|---|---|---|
| mOP1-Ser | ... | ... | ... | ... | ... | ... | ... | ... | |
| | | | | 130 | | | | | |

| hOP1-18Ser | Ala | Cys | Gly | Cys | His | | | | |
|---|---|---|---|---|---|---|---|---|---|
| mOP1-Ser | ... | ... | ... | ... | ... | | | | |
| | 135 | | | | | | | | |

Fig. 23A-2

| | | | | | | | | |
|---|---|---|---|---|---|---|---|---|
| hOP2-Ala | Ala | Val | Arg | Pro | Leu | Arg | Arg | Arg | Gln |
| mOP2-Ala | ... | Ala | ... | ... | ... | Lys | ... | ... | ... |
| | 1 | | | | 5 | | | | |

| | | | | | | | | |
|---|---|---|---|---|---|---|---|---|
| hOP2-Ala | Pro | Lys | Lys | Ser | Asn | Glu | Leu | Pro | Gln |
| mOP2-Ala | ... | ... | ... | Thr | ... | ... | ... | ... | His |
| | 10 | | | | | 15 | | | |

| | | | | | | | | |
|---|---|---|---|---|---|---|---|---|
| hOP2-Ala | Ala | Asn | Arg | Leu | Pro | Gly | Ile | Phe | Asp |
| mOP2-Ala | Pro | ... | Lys | ... | ... | ... | ... | ... | ... |
| | | 20 | | | | | 25 | | |

| | | | | | | | | |
|---|---|---|---|---|---|---|---|---|
| hOP2-Ala | Asp | Val | His | Gly | Ser | His | Gly | Arg | Gln |
| mOP2-Ala | ... | Gly | ... | ... | ... | Arg | ... | ... | Glu |
| | | | 30 | | | | | 35 | |

| | | | | | | | | |
|---|---|---|---|---|---|---|---|---|
| hOP2-Ala | Val | Cys | Arg | Arg | His | Glu | Leu | Tyr | Val |
| mOP2-Ala | ... | ... | ... | ... | ... | ... | ... | ... | ... |
| | | | | 40 | | | | | 45 |

| | | | | | | | | |
|---|---|---|---|---|---|---|---|---|
| hOP2-Ala | Ser | Phe | Gln | Asp | Leu | Gly | Trp | Leu | Asp |
| mOP2-Ala | ... | ... | Arg | ... | ... | ... | ... | ... | ... |
| | | | | | 50 | | | | |

| | | | | | | | | |
|---|---|---|---|---|---|---|---|---|
| hOP2-Ala | Trp | Val | Ile | Ala | Pro | Gln | Gly | Tyr | Ser |
| mOP2-Ala | ... | ... | ... | ... | ... | ... | ... | ... | ... |
| | 55 | | | | | 60 | | | |

Fig. 23B-1

| | | | | | | | | |
|---|---|---|---|---|---|---|---|---|
| hOP2-Ala | Ala | Tyr | Tyr | Cys | Glu | Gly | Glu | Cys | Ser |
| mOP2-Ala | ... | ... | ... | ... | ... | ... | ... | ... | Ala |
| | | | 65 | | | | 70 | | |

| | | | | | | | | |
|---|---|---|---|---|---|---|---|---|
| hOP2-Ala | Phe | Pro | Leu | Asp | Ser | Cys | Met | Asn | Ala |
| mOP2-Ala | ... | ... | ... | ... | ... | ... | ... | ... | ... |
| | | | | 75 | | | | 80 | |

| | | | | | | | | |
|---|---|---|---|---|---|---|---|---|
| hOP2-Ala | Thr | Asn | His | Ala | Ile | Leu | Gln | Ser | Leu |
| mOP2-Ala | ... | ... | ... | ... | ... | ... | ... | ... | ... |
| | | | | | 85 | | | | 90 |

| | | | | | | | | |
|---|---|---|---|---|---|---|---|---|
| hOP2-Ala | Val | His | Leu | Met | Lys | Pro | Asn | Ala | Val |
| mOP2-Ala | ... | ... | ... | ... | ... | ... | Asp | Val | ... |
| | | | | | 95 | | | | |

| | | | | | | | | |
|---|---|---|---|---|---|---|---|---|
| hOP2-Ala | Pro | Lys | Ala | Cys | Cys | Ala | Pro | Thr | Lys |
| mOP2-Ala | ... | ... | ... | ... | ... | ... | ... | ... | ... |
| | 100 | | | | | 105 | | | |

| | | | | | | | | |
|---|---|---|---|---|---|---|---|---|
| hOP2-Ala | Leu | Ser | Ala | Thr | Ser | Val | Leu | Tyr | Tyr |
| mOP2-Ala | ... | ... | ... | ... | ... | ... | ... | ... | ... |
| | | 110 | | | | | 115 | | |

| | | | | | | | | |
|---|---|---|---|---|---|---|---|---|
| hOP2-Ala | Asp | Ser | Ser | Asn | Asn | Val | Ile | Leu | Arg |
| mOP2-Ala | ... | ... | ... | ... | ... | ... | ... | ... | ... |
| | | | 120 | | | | | 125 | |

Fig. 23B-2

| hOP2-Ala | Lys | His | Arg | Asn | Met | Val | Val | Lys |
| mOP2-Ala | ... | ... | ... | ... | ... | ... | ... | ... |
| | | | | 130 | | | | |

| hOP2-Ala | Ala | Cys | Gly | Cys | His |
| mOP2-Ala | ... | ... | ... | ... | ... |
| | | | 135 | | |

Fig. 23B-3

| | | | | | | | | |
|---|---|---|---|---|---|---|---|---|
| hOP1-18Ser | Ser | Thr | Gly | Ser | Lys | Gln | Arg | Ser | Gln |
| mOP1-Ser  | ... | ... | ... | Gly | ... | ... | ... | ... | ... |
| hOP2-Ala  | Ala | Val | Arg | Pro | Leu | Arg | ... | Arg | ... |
| mOP2-Ala  | Ala | Ala | Arg | Pro | Leu | Lys | ... | Arg | ... |
| | 1 | | | | 5 | | | | |

| | | | | | | | | |
|---|---|---|---|---|---|---|---|---|
| hOP1-18Ser | Asn | Arg | Ser | Lys | Thr | Pro | Lys | Asn | Gln |
| mOP1-Ser  | ... | ... | ... | ... | ... | ... | ... | ... | ... |
| hOP2-Ala  | Pro | Lys | Lys | Ser | Asn | Glu | Leu | Pro | ... |
| mOP2-Ala  | Pro | Lys | Lys | Thr | Asn | Glu | Leu | Pro | His |
| | | 10 | | | | 15 | | | |

| | | | | | | | | |
|---|---|---|---|---|---|---|---|---|
| hOP1-18Ser | Glu | Ala | Leu | Arg | Met | Ala | Asn | Val | Ala |
| mOP1-Ser  | ... | ... | ... | ... | ... | ... | Ser | ... | ... |
| hOP2-Ala  | Ala | Asn | Arg | Leu | Pro | Gly | Ile | Phe | Asp |
| mOP2-Ala  | Pro | Asn | Lys | Leu | Pro | Gly | Ile | Phe | Asp |
| | | | 20 | | | | 25 | | |

| | | | | | | | | |
|---|---|---|---|---|---|---|---|---|
| hOP1-18Ser | Glu | Asn | Ser | Ser | Ser | Asp | Gln | Arg | Gln |
| mOP1-Ser  | ... | ... | ... | ... | ... | ... | ... | ... | ... |
| hOP2-Ala  | Asp | Val | His | Gly | ... | His | Gly | ... | ... |
| mOP2-Ala  | Asp | Gly | His | Gly | ... | Arg | Gly | ... | Glu |
| | | | | 30 | | | | 35 | |

| | | | | | | | | |
|---|---|---|---|---|---|---|---|---|
| hOP1-18Ser | Ala | Cys | Lys | Lys | His | Glu | Leu | Tyr | Val |
| mOP1-Ser  | ... | ... | ... | ... | ... | ... | ... | ... | ... |
| hOP2 Ala  | Val | ... | Arg | Arg | ... | ... | ... | ... | ... |
| mOP2-Ala  | Val | ... | Arg | Arg | ... | ... | ... | ... | ... |
| | | | | 40 | | | | | 45 |

Fig. 24-1

| | | | | | | | | |
|---|---|---|---|---|---|---|---|---|
| hOP1-18Ser | Ser | Phe | Arg | Asp | Leu | Gly | Trp | Gln | Asp |
| mOP1-Ser | ... | ... | ... | ... | ... | ... | ... | ... | ... |
| hOP2-Ala | ... | ... | Gln | ... | ... | ... | ... | Leu | ... |
| mOP2-Ala | ... | ... | ... | ... | ... | ... | ... | Leu | ... |

50

| | | | | | | | | |
|---|---|---|---|---|---|---|---|---|
| hOP1-18Ser | Trp | Ile | Ile | Ala | Pro | Glu | Gly | Tyr | Ala |
| mOP1-Ser | ... | ... | ... | ... | ... | ... | ... | ... | ... |
| hOP2-Ala | ... | Val | ... | ... | ... | Gln | ... | ... | Ser |
| mOP2-Ala | ... | Val | ... | ... | ... | Gln | ... | ... | Ser |

55       60

| | | | | | | | | |
|---|---|---|---|---|---|---|---|---|
| hOP1-18Ser | Ala | Tyr | Tyr | Cys | Glu | Gly | Glu | Cys | Ala |
| mOP1-Ser | ... | ... | ... | ... | ... | ... | ... | ... | ... |
| hOP2-Ala | ... | ... | ... | ... | ... | ... | ... | ... | Ser |
| mOP2-Ala | ... | ... | ... | ... | ... | ... | ... | ... | ... |

65       70

| | | | | | | | | |
|---|---|---|---|---|---|---|---|---|
| hOP1-18Ser | Phe | Pro | Leu | Asn | Ser | Tyr | Met | Asn | Ala |
| mOP1-Ser | ... | ... | ... | ... | ... | ... | ... | ... | ... |
| hOP2-Ala | ... | ... | ... | Asp | ... | Cys | ... | ... | ... |
| mOP2-Ala | ... | ... | ... | Asp | ... | Cys | ... | ... | ... |

75       80

| | | | | | | | | |
|---|---|---|---|---|---|---|---|---|
| hOP1-18Ser | Thr | Asn | His | Ala | Ile | Val | Gln | Thr | Leu |
| mOP1-Ser | ... | ... | ... | ... | ... | ... | ... | ... | ... |
| hOP2-Ala | ... | ... | ... | ... | ... | Leu | ... | Ser | ... |
| mOP2-Ala | ... | ... | ... | ... | ... | Leu | ... | Ser | ... |

| | | | | | | | | |
|---|---|---|---|---|---|---|---|---|
| hOP1-18Ser | Val | His | Phe | Ile | Asn | Pro | Glu | Thr | Val |
| mOP1-Ser | ... | ... | ... | ... | ... | ... | Asp | ... | ... |
| hOP2-Ala | ... | ... | Leu | Met | Lys | ... | Asn | Ala | ... |
| mOP2-Ala | ... | ... | Leu | Met | Lys | ... | Asp | Val | ... |
| | | | | | 95 | | | | |

| | | | | | | | | |
|---|---|---|---|---|---|---|---|---|
| hOP1-18Ser | Pro | Lys | Pro | Cys | Cys | Ala | Pro | Thr | Gln |
| mOP1-Ser | ... | ... | ... | ... | ... | ... | ... | ... | ... |
| hOP2-Ala | ... | ... | Ala | ... | ... | ... | ... | ... | Lys |
| mOP2-Ala | ... | ... | Ala | ... | ... | ... | ... | ... | Lys |
| | 100 | | | | | 105 | | | |

| | | | | | | | | |
|---|---|---|---|---|---|---|---|---|
| hOP1-18Ser | Leu | Asn | Ala | Ile | Ser | Val | Leu | Tyr | Phe |
| mOP1-Ser | ... | ... | ... | ... | ... | ... | ... | ... | ... |
| hOP2-Ala | ... | Ser | ... | Thr | ... | ... | ... | ... | Tyr |
| mOP2-Ala | ... | Ser | ... | Thr | ... | ... | ... | ... | Tyr |
| | | 110 | | | | | 115 | | |

| | | | | | | | | |
|---|---|---|---|---|---|---|---|---|
| hOP1-18Ser | Asp | Asp | Ser | Ser | Asn | Val | Ile | Leu | Lys |
| mOP1-Ser | ... | ... | ... | ... | ... | ... | ... | ... | ... |
| hOP2-Ala | ... | Ser | ... | Asn | ... | ... | ... | ... | Arg |
| mOP2-Ala | ... | Ser | ... | Asn | ... | ... | ... | ... | Arg |
| | | | 120 | | | | | 125 | |

| | | | | | | | | |
|---|---|---|---|---|---|---|---|---|
| hOP1-18Ser | Lys | Tyr | Arg | Asn | Met | Val | Val | Arg | |
| mOP1-Ser | ... | ... | ... | ... | ... | ... | ... | ... | |
| hOP2-Ala | ... | His | ... | ... | ... | ... | ... | Lys | |
| mOP2-Ala | ... | His | ... | ... | ... | ... | ... | Lys | |
| | | | | 130 | | | | | |

Fig. 24-3

| | | | | | |
|---|---|---|---|---|---|
| hOP1-18Ser | Ala | Cys | Gly | Cys | His |
| mOP1-Ser | ... | ... | ... | ... | ... |
| hOP2-Ala | ... | ... | ... | ... | ... |
| mOP2-Ala | ... | ... | ... | ... | ... |
| | 135 | | | | |

Fig. 24-4

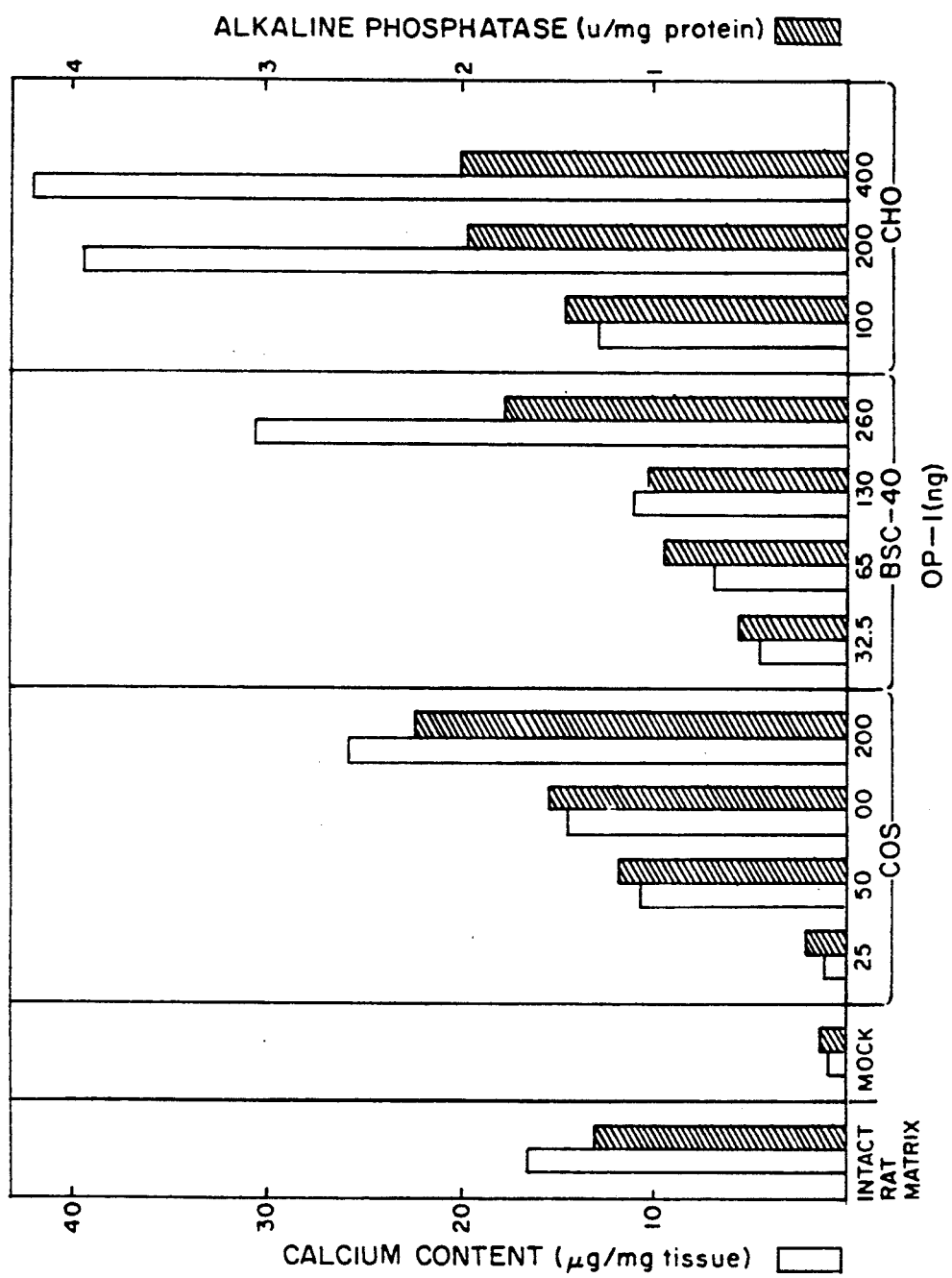

N-Termini of Active OP1 Sequences

|  | 1 |  |  |  | 5 |  |  |  |  | 10 |  |  |  |  | 15 |  |  |  |  | 20 |
|---|---|---|---|---|---|---|---|---|---|---|---|---|---|---|---|---|---|---|---|---|
| OP1-18Ser | Ser | Thr | Gly | Ser | Lys | Gln | Arg | Ser | Gln | Asn | Arg | Ser | Lys | Thr | Pro | Lys | Asn | Gln | Glu | Ala |
| OP1-16Ser |  |  |  | Ser | Lys | Gln | Arg | Ser | Gln | Asn | Arg | Ser | Lys | Thr | Pro | Lys | Asn | Gln | Glu | Ala |
| OP1-16Leu |  |  |  |  |  |  |  |  |  |  |  |  |  |  |  |  |  |  |  |  |
| OP1-16Met |  |  |  |  |  |  |  |  |  |  |  |  |  |  |  |  |  |  |  |  |
| OP1-16Ala |  |  |  |  |  |  |  |  |  |  |  |  |  |  |  |  |  |  |  |  |
| OP1-16Val |  |  |  |  |  |  |  |  |  |  |  |  |  |  |  |  |  |  |  |  |
| OP7 |  |  |  |  |  |  |  |  |  |  |  |  |  |  |  |  |  |  |  |  |
| OPS |  |  |  |  |  |  |  |  |  |  |  |  |  |  |  |  |  |  |  |  |

|  |  |  |  |  | 25 |  |  |  |  | 30 |  |  |  |  | 35 |  |  |  |  | 40 |
|---|---|---|---|---|---|---|---|---|---|---|---|---|---|---|---|---|---|---|---|---|
| OP1-18Ser | Leu | Arg | Met | Ala | Asn | Val | Ala | Glu | Asn | Ser | Ser | Ser | Asp | Gln | Arg | Gln | Ala | Cys | Lys | Lys |
| OP1-16Ser | Leu | Arg | Met | Ala | Asn | Val | Ala | Glu | Asn | Ser | Ser | Ser | Asp | Gln | Arg | Gln | Ala | Cys | Lys | Lys |
| OP1-16Leu | Leu | Arg | Met | Ala | Asn | Val | Ala | Glu | Asn | Ser | Ser | Ser | Asp | Gln | Arg | Gln | Ala | Cys | Lys | Lys |
| OP1-16Met |  |  | Met | Ala | Asn | Val | Ala | Glu | Asn | Ser | Ser | Ser | Asp | Gln | Arg | Gln | Ala | Cys | Lys | Lys |
| OP1-16Ala |  |  |  | Ala | Asn | Val | Ala | Glu | Asn | Ser | Ser | Ser | Asp | Gln | Arg | Gln | Ala | Cys | Lys | Lys |
| OP1-16Val |  |  |  |  |  | Val | Ala | Glu | Asn | Ser | Ser | Ser | Asp | Gln | Arg | Gln | Ala | Cys | Lys | Lys |
| OP7 |  |  |  |  |  |  |  |  |  |  |  |  |  |  |  |  |  |  |  |  |
| OPS |  |  |  |  |  |  |  |  |  |  |  |  |  |  |  |  |  |  | Cys | Lys | Lys |

|  |  |  |  |  | 45 |  |
|---|---|---|---|---|---|---|
| OP1-18Ser | His | Glu | Leu | Tyr | Val | : |
| OP1-16Ser | His | Glu | Leu | Tyr | Val | : |
| OP1-16Leu | His | Glu | Leu | Tyr | Val | : |
| OP1-16Met | His | Glu | Leu | Tyr | Val | : |
| OP1-16Ala | His | Glu | Leu | Tyr | Val | : |
| OP1-16Val | His | Glu | Leu | Tyr | Val | : |
| OP7 | His | Glu | Leu | Tyr | Val | : |
| OPS |  |  | Leu | Tyr | Val | : |

Fig. 33

OSTEOGENIC PROTEINS

REFERENCE TO RELATED APPLICATIONS

This application is a continuation-in-part of copending U.S. application Ser. Nos.: 1) 07/827,052, filed Jan. 28, 1992, and now U.S. Pat. No. 5,250,302 which is a divisional of U.S. Ser. No. 07/179,406, filed Apr. 8, 1988, now U.S. Pat. No. 4,968,590; 2) 07/579,865, filed Sep. 7, 1990, and now U.S. Pat. No. 5,108,753 which is a divisional of U.S. Ser. No. 07/179,406 and now U.S. Pat. No. 4,968,590; 3) 07/621,849, filed Dec. 4, 1990, and now abandoned which is a divisional of U.S. Ser. No. 07/232,630, filed Aug. 15, 1988, now abandoned, that was a continuation-in-part of Ser. No. 07/179,406 and now U.S. Pat. No. 4,968,590; 4) 07/621,988, filed Dec. 4, 1990 and now abandoned, which is a divisional of Ser. No. 07/315,342 filed Feb. 23, 1989, now U.S. Pat. No. 5,011,691 and which is a continuation-in-part of Ser. No. 07/232,630 and now abandoned; 5) 07/810,560, filed Dec. 20, 1991 and now abandoned, was a continuation of Ser. No. 07/660,162, filed Feb. 22, 1991, now abandoned, that was a continuation of Ser. No. 07/422,699, filed Oct. 17, 1989, now abandoned, that was a continuation-in-part of Ser. No. 07/315,342 and now U.S. Pat. No. 5,011,691; 6) 07/569,920, filed Aug. 20, 1990 and now abandoned, which is a continuation-in-part of Ser. No. 07/422,699 and now abandoned and Ser. No. 07/483,913 and now U.S. Pat. No. 5,171,574, which is continuation-in-part of Ser. No. 07/422,613, filed Oct. 17, 1989, now U.S. Pat. No. 4,975,526 and which is a continuation-in-part of Ser. No. 07/315,342 and now U.S. Pat. No. 5,011,691; 7) 07/600,024, filed Oct. 18, 1990 and now abandoned, which is a continuation-in-part of Ser. No. 07/569,920 and now abandoned; 8) 07/599,543, filed Oct. 18, 1990 and now abandoned, and which is a continuation-in-part of Ser. No. 07/569,920 and now abandoned; 9) 07/616,374, filed Nov. 21, 1990 and now U.S. Pat. No. 5,162,114, which is a divisional of Ser. No. 07/422,613 and now U.S. Pat. No. 4,975,526; and 10) 07/483,913, filed Feb. 22, 1990 and now U.S. Pat. No. 5,171,574.

TECHNICAL FIELD OF THE INVENTION

This invention relates to osteogenic devices, to DNA sequences encoding proteins which can induce new bone formation in mammals, and to methods for the production of these proteins in mammalian cells using recombinant DNA techniques, including host cells capable of expressing these sequences. The invention also relates to the proteins expressed from these DNA sequences, to antibodies capable of binding specifically to these proteins, and to bone and cartilage repair procedures using the osteogenic devices. The invention further relates to matrix materials useful for allogenic or xenogenic implants and which act as a carrier of the osteogenic protein to induce new bone formation in mammals.

BACKGROUND OF THE INVENTION

Mammalian bone tissue is known to contain one or more proteinaceous materials, presumably active during growth and natural bone healing, which can induce a developmental cascade of cellular events resulting in endochondral bone formation. This active factor (or factors) has variously been referred to in the literature as bone morphogenetic or morphogenic protein, bone inductive protein, osteogenic protein, osteogenin, or osteoinductive protein.

The developmental cascade of bone differentiation consists of recruitment and proliferation of mesenchymal cells, differentiation of progenitor cells, calcification of cartilage, vascular invasion, bone formation, remodeling, and finally marrow differentiation (Reddi (1981) *Collagen Rel. Res.* 1:209-226).

Though the precise mechanisms underlying these phenotypic transformations are unclear, it has been shown that the natural endochondral bone differentiation activity of bone matrix can be dissociatively extracted and reconstituted with inactive residual collagenous matrix to restore full bone induction activity (Sampath and Reddi (1981) *Proc. Natl. Acad. Sci. USA* 78:7599-7603). This provides an experimental method for assaying protein extracts for their ability to induce endochondral bone in vivo. Several species of mammals produce closely related protein as demonstrated by the ability of cross species implants to induce bone formation (Sampath and Reddi (1983) *Proc. Natl. Acad. Sci. USA* 80:6591-6595).

The potential utility of these proteins has been recognized widely. It is contemplated that the availability of the protein would revolutionize orthopedic medicine, certain types of plastic surgery, dental and various periodontal and craniofacial reconstructive procedures.

The observed properties of these protein fractions have induced an intense research effort in several laboratories directed to isolating and identifying the pure factor or factors responsible for osteogenic activity. The current state of the art of purification of osteogenic protein from mammalian bone is disclosed by Sampath et al. (1987) *Proc. Natl. Acad. Sci. USA* 84:7109-7113. Urist et al. (1983) *Proc. Soc. Exp. Biol. Med.* 173:194-199 disclose a human osteogenic protein fraction which was extracted from demineralized cortical bone by means of a calcium chloride-urea inorganic-organic solvent mixture, and retrieved by differential precipitation in guanidine-hydrochloride and preparative gel electrophoresis. The authors report that the protein fraction has an amino acid composition of an acidic polypeptide and a molecular weight in a range of 17-18 kDa. This material was said to be distinct from a protein called "bone derived growth factor" disclosed by Canalis et al. (1980 *Science* 210:1021-1023, and by Farley et al. (1982) *Biochem* 21:3508-3513.

Urist et al. (1984) *Proc. Natl. Acad. Sci. USA* 81:371-375 disclose a bovine bone morphogenetic protein extract having the properties of an acidic polypeptide and a molecular weight of approximately 18 kDa. The authors reported that the protein was present in a fraction separated by hydroxyapatite chromatography, and that it induced bone formation in mouse hindquarter muscle and bone regeneration in trephine defects in rat and dog skulls. Their method of obtaining the extract from bone results in ill-defined and impure preparations.

European Patent Application Serial No. 148,155, published Oct. 7, 1985, purports to disclose osteogenic proteins derived from bovine, porcine, and human origin. One of the proteins, designated by the inventors as a P3 protein having a molecular weight of 22-24 kDa, is said to have been purified to an essentially homogeneous state. This material is reported to induce bone formation when implanted into animals.

International Application No. PCT/087/01537, published Jan. 14, 1988 (Int. Pub. No. WO88/00205), discloses an impure fraction from bovine bone which has bone induction qualities. The named applicants also disclose putative "bone inductive factors" produced by recombinant DNA techniques. Four DNA sequences were retrieved from human or bovine genomic or cDNA libraries and expressed in recombinant host cells. While the applicants stated that the expressed proteins may be bone morphogenic proteins, bone induction was not demonstrated. This same group reported subsequently ((1988) *Science* 242:1528-1534) that three of the four factors induce cartilage formation, and postulate that bone formation activity "is due to a mixture of regulatory molecules" and that "bone formation is most likely controlled . . . by the interaction of these molecules." Again, no bone induction was attributed to the products of expression of the cDNAs. See also Urist et al., EPO 0,212,474 entitled "Bone Morphogenic Agents".

Wang et al. (1988) *Proc. Nat. Acad. Sci. USA* 85: 9484-9488, disclose the partial purification of a bovine bone morphogenetic protein from guanidine extracts of demineralized bone having cartilage and bone formation activity as a basic protein corresponding to a molecular weight of 30 kDa determined from gel elution. Separation of the 30 kDa fraction yielded proteins of 30, 18 and 16 kDa which, upon separation, were inactive. In view of this result, the authors acknowledged that the exact identity of the active material had not been determined.

Wang et al. (1990) *Proc. Nat. Acad. Sci. USA* 87: 2220-2224 describe the expression and partial purification of one of the cDNA sequences described in PCT 87/01537. Consistent cartilage and/or bone formation with their protein requires a minimum of 600 ng of 50% pure material.

International Application No. PCT/89/04458 published Apr. 19, 1990 (Int. Pub. No. WO90/003733), describes the purification and analysis of a family of osteogenic factors called "P3 OF 31-34". The protein family contains at least four proteins, which are characterized by peptide fragment sequences. The impure mixture P3 OF 31-34 is assayed for osteogenic activity. The activity of the individual proteins is neither assessed nor discussed.

It also has been found that successful implantation of the osteogenic factors for endochondral bone formation requires association of the proteins with a suitable carrier material capable of maintaining the proteins at an in vivo site of application. The carrier should be biocompatible, in vivo biodegradable and porous enough to allow cell infiltration. The insoluble collagen particles remaining after guanidine extraction and delipidation of pulverized bone generally have been found effective in allogenic implants in some species. However, studies have shown that while osteoinductive proteins are useful cross species, the collagenous bone matrix generally used for inducing endochondral bone formation is species-specific (Sampath and Reddi (1983) *Proc. Nat. Acad. Sci. USA* 80: 6591-6594). Demineralized, delipidated, extracted xenogenic bone matrix carriers implanted in vivo invariably fail to induce osteogenesis, presumably due to inhibitory or immunogenic components in the bone matrix. Even the use of allogenic bone matrix in osteogenic devices may not be sufficient for osteoinductive bone formation in many species. For example, allogenic, subcutaneous implants of demineralized, delipidated monkey bone matrix is reported not to induce bone formation in the monkey. (Asperberg et al. (1988) *J. Bone Joint Surg.* (Br) 70-B: 625-627).

U.S. Pat. No. 4,563,350, issued Jan. 7, 1986, discloses the use of trypsinized bovine bone matrix as a xenogenic matrix to effect osteogenic activity when implanted with extracted, partially purified bone-inducing protein preparations. Bone formation is said to require the presence of at least 5%, and preferably at least 10%, non-fibrillar collagen. The named inventors claim that removal of telopeptides which are responsible in part for the immunogenicity of collagen preparations is more suitable for xenogenic implants.

European Patent Application Serial No. 309,241, published Mar. 29, 1989, discloses a device for inducing endochondral bone formation comprising an osteogenic protein preparation, and a matrix carrier comprising 60-98% of either mineral component or bone collagen powder and 2-40% atelopeptide hypoimmunogenic collagen.

Deatherage et al. (1987) *Collagen Rel. Res.* 7: 2225-2231, purport to disclose an apparently xenogenic implantable device comprising a bovine bone matrix extract that has been minimally purified by a one-step ion exchange column and reconstituted, highly purified human Type-I placental collagen.

U.S. Pat. No. 3,394,370, issued Jul. 19, 1983, describes a matrix of reconstituted collagen purportedly useful in xenogenic implants. The collagen fibers are treated enzymatically to remove potentially immunogenic telopeptides (also the primary source of interfibril cross-links) and are dissolved to remove associated non-collagen components. The matrix is formulated by dispersing the reconstituted collagen in acetic acid to form a disordered matrix of elementary collagen molecules that is then mixed with osteogenic factor and lyophilized to form a "semi-rigid foam or sponge" that is preferably crosslinked. The formulated matrix is not tested in vivo.

U.S. Pat. No. 4,172,128, issued Oct. 23, 1979, describes a method for degrading and regenerating bone-like material of reduced immunogenicity, said to be useful cross-species. Demineralized bone particles are treated with a swelling agent to dissolve any associated mucopolysaccharides (glycosaminoglycans) and the collagen fibers subsequently dissolved to form a homogenous colloidal solution. A gel of reconstituted fibers then can be formed using physiologically inert mucopolysaccharides and an electrolyte to aid in fibril formation.

It is an object of this invention to provide osteogenic devices comprising matrices containing dispersed osteogenic protein, purified from naturally-sourced material or produced from recombinant DNA, and capable of bone induction in allogenic and xenogenic implants. Another object is to provide novel polypeptide chains useful as subunits of dimeric osteogenic proteins, as well as DNA sequences encoding these polypeptide chains and methods for their production using recombinant DNA techniques. Still another object is to provide recombinant osteogenic proteins expressed from procaryotic or eucaryotic cells, preferably mammalian cells, and capable of inducing endochondral bone formation in mammals, including humans, and to provide methods for their production, including host cells capable of producing these proteins. Still another object is to provide antibodies capable of binding specifically to the proteins of this invention. Yet another object is to provide a biocompatible, in vivo biodegradable matrix capable, in combination with an osteoinductive protein, of producing endochondral bone formation in mammals, including humans.

These and other objects and features of the invention will be apparent from the description, drawings, and claims which follow.

SUMMARY OF THE INVENTION

This invention provides osteogenic proteins and devices which, when implanted in a mammalian body, can induce at the locus of the implant the full developmental cascade of endochondral bone formation including vascularization, mineralization, and bone marrow differentiation. The devices comprise a carrier material, referred to herein as a matrix, having the characteristics disclosed below, and containing dispersed substantially pure osteogenic protein either purified from naturally sourced material or produced using recombinant DNA techniques. Recombinantly produced osteogenic protein may be expressed from procaryotic or eucaryotic cells, most preferably mammalian cells. As used herein "substantially pure" means substantially free of other contaminating proteins having no endochondral bone formation activity.

The substantially pure osteogenic protein may include forms having varying glycosylation patterns, a family of related proteins having regions of amino acid sequence homology, and active truncated or mutated forms of native proteins, no matter how derived.

Preferred embodiments of the recombinant protein dispersed in the matrix disclosed herein closely mimic the physiological activity of native form protein extracted from natural sources and reconstituted in allogenic demineralized, guanidine-extracted bone powder matrix material. The preferred proteins have a specific activity far higher than any biosynthetic material heretofore reported, an activity which, within the limits of precision of the activity assay, appears essentially identical to the substantially pure material produced as set forth in U.S. Pat. No. 4,968,590. Thus, this application discloses how to make and use osteogenic devices which induce the full developmental cascade of endochondral bone formation essentially as it occurs in natural bone healing.

A key to these developments was the elucidation of amino acid sequence and structure data of native osteogenic protein "OP". A protocol was developed which results in retrieval of active, substantially pure osteogenic protein from mammalian bone (e.g., bovine or human) having a half-maximum bone forming activity of about 0.8 to 1.0 ng per mg of implant matrix, as compared to implanted rat demineralized bone matrix (see U.S. Pat. No. 4,968,590). The availability of the material enabled the inventors to elucidate all structural details of the protein necessary to achieve bone formation. Knowledge of the protein's amino acid sequence and other structural features enabled the identification and cloning of genes encoding native osteogenic proteins.

The osteogenic protein in its mature native form is a glycosylated dimer and has an apparent molecular weight of about 30 kDa as determined by SDS-PAGE. When reduced, the 30 kDa protein gives rise to two glycosylated polypeptide chains (subunits) having apparent molecular weights of about 16 kDa and 18 kDa. In the reduced state, the 30 kDa protein has no detectable osteogenic activity. The unglycosylated protein, which has osteogenic activity, has an apparent molecular weight of about 27 kDa. When reduced, the 27 kDa protein gives rise to two unglycosylated polypeptides having molecular weights of about 14 kDa to 16 kDa.

Naturally-sourced osteogenic protein derived from bovine bone, herein referred to as "bOP" and in related applications as "BOP", is further characterized by the approximate amino acid composition set forth below:

| Amino acid residue | Rel. no. res./molec. |
| --- | --- |
| Asp/Asn | 22 |
| Glu/Gln | 24 |
| Ser | 24 |
| Gly | 29 |
| His | 5 |
| Arg | 13 |
| Thr | 11 |
| Ala | 18 |
| Lys | 12 |
| Tyr | 11 |
| Val | 14 |
| Met | 3 |
| Cys | 16 |
| Ile | 15 |
| Leu | 15 |
| Pro | 14 |
| Phe | 7 |
| Trp | ND |

Analysis of digestion fragments from naturally-sourced material purified from bone indicates that the substantially pure material isolated from bone contains the following amino acid sequences:

(1) Ser-Phe-Asp-Ala-Tyr-Tyr-Cys-Ser-Gly-Ala-Cys-Gln-Phe-Pro-Met-Pro-Lys;

(2) Ser-Leu-Lys-Pro-Ser-Asn-Tyr-Ala-Thr-Ile-Gln-Ser-Ile-Val;

(3) Ala-Cys-Cys-Val-Pro-Thr-Glu-Leu-Ser-Ala-Ile-Ser-Met-Leu-Tyr-Leu-Asp-Glu-Asn-Glu-Lys;

(4) Met-Ser-Ser-Leu-Ser-Ile-Leu-Phe-Phe-Asp-Glu-Asn-Lys;

(5) Val-Gly-Val-Val-Pro-Gly-Ile-Pro-Glu-Pro-Cys-Cys-Val-Pro-Glu;

(6) Val-Asp-Phe-Ala-Asp-Ile-Gly;

(7) Val-Pro-Lys-Pro; and (8) Ala-Pro-Thr.

A consensus DNA gene sequence based in part on these partial amino acid sequence data and on observed homologies with structurally related genes reported in the literature (or the sequences they encode), having a presumed or demonstrated unrelated developmental function, was used as a probe for identifying and isolating genes encoding osteogenic proteins from genomic and cDNA libraries. The consensus sequence probe enabled isolation of a previously unidentified DNA sequence from human genomic and cDNA libraries, portions of which, when appropriately cleaved and ligated, encode a protein comprising a region capable of inducing endochondral bone formation when properly modified, incorporated in a suitable matrix, and implanted as disclosed herein. The predicted amino acid sequence of the encoded protein includes sequences identified in peptide fragments obtained from the substantially pure osteogenic protein (see infra and Kuber Sampath et al. (1990) J. Biol. Chem. 265:13198-13205.) The protein has been expressed from the full length cDNA sequence (referred to herein as "hOP1"), as well as from various truncated DNAs and fusion constructs in both procaryotes (e.g., E. coli) and eucaryotes (various mammalian cells and cell lines) and shown to exhibit osteogenic activity. The OP1 protein in combination with BMP2B also is active (see infra).

Table I lists the various species of the hOP1 protein identified to date, including their expression sources and nomenclature and Sequence Listing references. In its native form, hOP1 expression yields an immature translation product ("hOP1-PP", where "PP" refers to "prepro form") of about 400 amino acids that subsequently is processed to yield a mature sequence of 139 amino acids ("OP1-18Ser".) The active region (functional domain) of the protein includes the C-terminal 97 amino acids of the OP1 sequence ("OPS"). A longer active sequence is OP7 (comprising the C-terminal 102 amino acids).

The consensus sequence probe also retrieved human DNA sequences identified in PCT/087/01537, referenced above, designated therein as BMP2 (Class I and II), and BMP3. The inventors herein discovered that certain subparts of the sequences designated in PCT/087/01537 as BMP-2 Class I and BMP-2 Class II, also referred to in the literature as BMP2 and BMP4, respectively, when properly assembled, encode proteins (referred to herein as "CBMP2A" and "CBMP2B," respectively) which have true osteogenic activity, i.e., induce the full cascade of events leading to endochondral bone formation when properly folded, dimerized, and implanted in a mammal. Seq. Listing ID Nos. 4 and 6 disclose the cDNA sequences and encoded "prepro" forms of CBMP2A and CBMP2B, respectively. (Nomenclature note: as used herein, "CBMP2(a)" and "CBMP2(b)" refer to the DNA sequence; "CBMP2A" and "CBMP2B" refer to the encoded proteins.) The functional domain (active region) of the CBMP2 proteins comprises essentially amino acid residues 301-396 of Seq. ID No. 4 (designated "CBMP2AS") and residues 313-408 of ID No. 6 (designated "CBMP2BS"). Longer active regions are defined by residues 296-396 of Seq. ID No. 4 ("CBMP2AL") and residues 308-408 of Seq. ID No. 6 ("CBMP2BL"). The CBMP2 proteins share approximately 58-60% amino acid sequence homology with OP1 in the active region (e.g., with OPS or OP7).

As indicated above, the natural-sourced osteogenic protein is a glycosylated dimer comprising an 18 kDa subunit and a 16 kDa subunit. Protein sequencing data indicate that the larger of the two subunits is mature OP1 protein, the other is mature CBMP2A or CBMP2B. CBMP2B differs from CBMP2A at only five residues in the active region. Recombinant versions of both CBMP2A and CBMP2B are active cross species, either as homodimers or in combination with OP1 proteins. The recombinant data also indicates that the osteoinductive effect is not dependent on the presence of the entire mature form amino acid sequences of either subunit. Properly folded dimers comprising minimal structure, as short as 96 amino acids, are active. Furthermore, analogs of the active region, e.g., non-native forms never before known in nature, designed based on the observed homologies and known structure and properties of the native protein are capable of inducing bone formation. See, for example, COP5 and COP7 in U.S. Pat. No. 5,011,691. As far as applicants are aware, the biosynthetic constructs disclosed therein constitute the first instance of the design of a functional, active protein without preexisting knowledge of the active region of a native form nucleotide or amino acid sequence.

Further probing of mammalian cDNA libraries with sequences specific to hOP1 also have identified a sequence in mouse sharing almost complete identity with the mature hOP1 amino acid sequence (approximately 98% homology with OP1-18). Additional probing in both human and mouse cDNA and genomic libraries also has identified OP1-like sequences herein referred to as "OP2" ("hOP2" or "mOP2"). The OP2 proteins share significant amino acid sequence homology, approximately 74%, with the active region of the OP1 proteins (e.g., OP7), and less homology with the intact mature form (e.g., OP1-18Ser - 58% amino acid homology). Table I lists the OP1 and OP2 species identified to date.

The amino acid sequence of the osteogenic proteins disclosed herein share significant homology with various regulatory proteins on which the consensus probe was modeled. In particular, the proteins share significant homology in their C-terminal sequences, which comprise the active region of the osteogenic proteins. (Compare, for example, OP7 with DPP from Drosophila and Vgl from Xenopus. See, for example, U.S. Pat. No. 5,011,691). In addition, these proteins share a conserved six or seven cysteine skeleton in this region (e.g., the linear arrangement of these C-terminal cysteine residues is conserved in the different proteins.) See, for example, OP7, whose sequence defines the seven cysteine skeleton, or OPS, whose sequence defines the six cysteine skeleton. In addition, the OP2 proteins contain an additional cysteine residue within this region.

TABLE I

| | OP1, OP2 NOMENCLATURE |
|---|---|
| hOP1 | DNA sequence encoding human OP1 protein (Seq. ID No. 1 or 3). Also referred to in related applications as "OP1," "hOP-1" and "OP-1". |
| OP1 | Refers generically to the family of osteogenically active proteins produced by expression of part or all of the hOP1 gene. Also referred to in related applications as "OPI" and "OP-1". |
| hOP1-PP | Amino acid sequence of human OP1 protein (prepro form), Seq. ID No. 1, residues 1-431. Also referred to in related applications as "OP1-PP" and "OPP". |
| OP1-18Ser | Amino acid sequence of mature human OP1 protein, Seq. ID No. 1, residues 293-431. N-terminal amino acid is serine. Originally identified as migrating at 18 kDa on SDS-PAGE in COS cells. Depending on protein glycosylation pattern in different host cells, also migrates at 23kDa, 19kDa and 17kDa on SDS-PAGE. Also referred to in related applications as "OP1-18." |
| OPS | Human OP1 protein species defining the conserved 6 cysteine skeleton in the active region (97 amino acids, Seq. ID No. 1, residues 335-431.) "S" stands for "short". |
| OP7 | Human OP1 protein species defining the conserved 7 cysteine skeleton in the active region (102 amino acids, Seq. ID No. 1, residues 330-431). |
| OP1-16Ser | N-terminally truncated mature human OP1 protein species. (Seq. ID No. 1, residues 300-431). N-terminal amino acid is serine; protein migrates at 16kDa or 15kDa on SDS-PAGE, depending on glycosylation pattern. Also referred to in related applications as "OP-16S." |
| OP1-16Leu | N-terminally truncated mature human OP1 protein species, Seq. ID No. 1, residues 313-431. N-terminal amino acid is leucine; protein migrates at 16 or 15kDa on SDS-PAGE, depending on glycosylation pattern. Also referred to in related applications as "OP-16L." |
| OP1-16Met | N-terminally truncated mature human OP1 |

TABLE I-continued
OP1, OP2 NOMENCLATURE

| | |
|---|---|
| | protein species, Seq. ID No. 1, residues 315–431. N-terminal amino acid is methionine; protein migrates at 16 or 15kDa on SDS-PAGE, depending on glycosylation pattern. Also referred to in related applications as "OP-16M." |
| OP1-16Ala | N-terminally truncated mature human OP1 protein species, Seq. ID No. 1, residues 316–431. N-terminal amino acid is alanine, protein migrates at 16 or 15 kDa on SDS-PAGE, depending on glycosylation pattern. Also referred to in related applications as "OP-16A." |
| OP1-16Val | N-terminally truncated mature human OP1 protein species, Seq. ID No. 1, residues 318–431. N-terminal amino acid is valine; protein migrates at 16 or 15 kDa on SDS-PAGE, depending on glycosylation pattern. Also referred to in related applications as "OP-16V." |
| mOP1 | DNA encoding mouse OP1 protein, Seq. ID No. 24. Also referred to in related applications as "mOP-1". |
| mOP1-PP | Prepro form of mouse protein, Seq. ID No. 24, residues 1–430. Also referred to in related applications as "mOP-1-PP." |
| mOP1-Ser | Mature mouse OP1 protein species (Seq. ID No. 24, residues 292–430). N-terminal amino acid is serine. Also referred to in related applications as "mOP1" and "mOP-1". |
| mOP2 | DNA encoding mouse OP2 protein, Seq. ID No. 26. Also referred to in related applications as "mOP-2". |
| mOP2-PP | Prepro form of mOP2 protein, Seq. ID No. 26, residues 1–399. Also referred to in related applications as "mOP-2-PP" |
| mOP2-Ala | Mature mouse OP2 protein, Seq. ID No. 26, residues 261–399. N-terminal amino acid is alanine. Also referred to in related applications as "mOP2" and "mOP-2". |
| hOP2 | DNA encoding human OP2 protein, Seq. ID No. 28. Also referred to in related applications as "hOP-2". |
| hOP2-PP | Prepro form of human OP2 protein, Seq. ID No. 28, res. 1–402). Also referred to in related applications as "hOP-2-PP". |
| hOP2-Ala | Possible mature human OP2 protein species: Seq. ID No. 28, residues 264–402. Also referred to in related applications as "hOP-2". |
| hOP2-Pro | Possible mature human OP2 protein species: Seq. ID NO. 28, residues 267–402. N-terminal amino acid is proline. Also referred to in related applications as "hOP-2P." |
| hOP2-Arg | Possible mature human OP2 protein species: Seq. ID No. 28, res. 270–402. N-terminal amino acid is arginine. Also referred to in related applications as "hOP-2R". |
| hOP2-Ser | Possible mature human OP2 protein species: Seq. ID No. 28, res. 243–402. N-terminal amino acid is serine. Also referred to in related applications as "hOP-2S." |

The invention thus provides recombinant dimeric proteins comprising any of the polypeptide chains described above, as well as allelic variants, and naturally-occurring or biosynthetic mutants thereof, and osteogenic devices comprising any of these proteins. In addition, the invention is not limited to these specific constructs. Thus, the osteogenic proteins of this invention comprising any of these polypeptide chains may include forms having varying glycosylation patterns, varying N-termini, a family of related proteins having regions of amino acid sequence homology which may be naturally occurring or biosynthetically derived, and active truncated or mutated forms of the native amino acid sequence, produced by expression of recombinant DNA in procaryotic or eucaryotic host cells. Active sequences useful in an osteogenic device of this invention are envisioned to include osteogenic proteins having greater than 60% identity, preferably greater than 65% identity, with the amino acid sequence of OPS. This family of proteins includes longer forms of a given protein, as well as allelic variants and biosynthetic mutants, including addition and deletion mutants, such as those which may alter the conserved C-terminal cysteine skeleton, provided that the alteration still allows the protein to form a dimeric species having a conformation capable of inducing bone formation in a mammal when implanted in the mammal in association with a matrix. Particularly envisioned within the family of related proteins are those proteins exhibiting osteogenic activity and wherein the amino acid changes from the OPS sequence include conservative changes, e.g., those as defined by Dayoff, et al., *Atlas of Protein Sequence and Structure*; vol.5, Supp.3, pp.345-362, (M. O. Dayoff,ed. Nat'l Biomed. Research Fdn., Washington, D.C., 1979.)

The novel polypeptide chains and the osteogenic proteins they comprise can be expressed from intact or truncated cDNA or from synthetic DNAs in procaryotic or eucaryotic host cells, and then purified, cleaved, refolded, dimerized, and implanted in experimental animals. Useful host cells include *E.coli, Saccharomyces*, the insect/baculovirus cell system, myeloma cells and mammalian cells. Currently preferred procaryotic host cells include *E. coli*. Currently preferred eucaryotic host cells include mammalian cells, such as chinese hamster ovary (CHO) cells, or simian kidney cells (e.g., COS or BSC cells.) Thus, in view of this disclosure, skilled genetic engineers can isolate genes from cDNA or genomic libraries which encode appropriate amino acid sequences, modify existing sequences, or construct DNAs from oligonucleotides and then can express them in various types of procaryotic or eucaryotic host cells to produce large quantities of active proteins capable of inducing bone formation in mammals, including humans.

In one preferred aspect, the invention comprises dimeric osteogenic proteins and osteogenic devices containing these proteins, wherein the proteins comprise a polypeptide chain having an amino acid sequence sufficiently duplicative of the encoded amino acid sequence of Sequence ID No. 1 (hOP1) or 28 (hOP2) such that a dimeric protein comprising this polypeptide chain has a conformation capable of inducing endochondral bone formation when implanted in a mammal in association with a matrix. As used herein, the term "sufficiently duplicative" is understood to encompass all proteins capable of inducing endochondral bone formation when implanted in a mammal in association with a matrix and whose amino acid sequence comprises at least the conserved six cysteine skeleton and shares greater than 60% amino acid sequence identity in its active region with OPS.

In another preferred aspect, the invention comprises osteogenic proteins comprising species of polypeptide chains having the generic amino acid sequence herein referred to as "OPX" which accommodates the homologies between the various identified species of these osteogenic OP1 and OP2 proteins, and which is described by the amino acid sequence of Sequence ID No. 30.

The identification of mOP2 and hOP2 represents the discovery of osteogenic proteins having an additional cysteine residue in their active region in addition to the conserved six cysteine skeleton defined by OPS, or the conserved seven cysteine skeleton defined by OP7. Thus, in another aspect, the invention comprises species of polypeptide chains herein referred to as "OPX-7C", comprising the conserved six cysteine skeleton plus the additional cysteine residue identified in the OP2 proteins, and "OPX-8C", comprising the conserved seven cysteine skeleton plus the additional cysteine residue identified in the OP2 proteins. The OPX-7C and OPX-8C amino acid sequences are described in Seq. ID Nos. 31 and 32, respectively. Each Xaa in Seq. ID Nos. 31 and 32 independently represents one of the 20 naturally occurring L-isomer, α-amino acids or a derivative thereof which, together with the determined cysteine residues, define a polypeptide chain such that dimeric osteogenic proteins comprising this polypeptide chain have a conformation capable of inducing endochondral bone formation when implanted in a mammal in association with a matrix.

In still another preferred aspect, the invention comprises nucleic acids and the osteogenically active polypeptide chains encoded by these nucleic acids which hybridize to DNA or RNA sequences encoding the active region of OP1 or OP2 under stringent hybridization conditions. As used herein, stringent hybridization conditions are defined as hybridization in 40% formamide, 5×SSPE, 5×Denhardt's Solution, and 0.1% SDS at 37° C. overnight, and washing in 0.1×SSPE, 0.1% SDS at 50° C.

The invention further comprises nucleic acids and the osteogenically active polypeptide chains encoded by these nucleic acids which hybridize to the "pro" region of the OP1 or OP2 proteins under stringent hybridization conditions. As used herein, "osteogenically active polypeptide chains" is understood to mean those polypeptide chains which, when dimerized, produce a protein species having a conformation such that the pair of polypeptide chains is capable of inducing endochondral bone formation in a mammal when implanted in a mammal in association with a matrix.

The proteins of this invention, including fragments thereof, also may be used to raise monoclonal or polyclonal antibodies capable of binding specifically to an epitope of the osteogenic protein. These antibodies may be used, for example, in osteogenic protein purification protocols.

The osteogenic proteins are useful in clinical applications in conjunction with a suitable delivery or support system (matrix). As disclosed herein, the matrix may be combined with osteogenic protein to induce endochondral bone formation reliably and reproducibly in a mammalian body. The matrix is made up of particles of porous materials. The pores must be of a dimension to permit progenitor cell migration into the matrix and subsequent differentiation and proliferation. The particle size should be within the range of 70 μm–850 μm, preferably 70 μm–420 μm, most preferably 150 μm–420 μm. It may be fabricated by close packing particulate material into a shape spanning the bone defect, or by otherwise structuring as desired a material that is biocompatible, and preferably biodegradable in vivo to serve as a "temporary scaffold" and substratum for recruitment of migratory progenitor cells, and as a base for their subsequent anchoring and proliferation. Useful matrix materials comprise, for example, collagen; homopolymers or copolymers of glycolic acid, lactic acid, and butyric acid, including derivatives thereof; and ceramics, such as hydroxyapatite, tricalcium phosphate and other calcium phosphates. Combinations of these matrix materials also may be useful.

Currently preferred carriers include particulate, demineralized, guanidine extracted, species-specific (allogenic) bone, and specially treated particulate, protein extracted, demineralized, xenogenic bone. Optionally, such xenogenic bone powder matrices also may be treated with proteases such as trypsin. Preferably, the xenogenic matrices are treated with one or more fibril modifying agents to increase the intraparticle intrusion volume (porosity) and surface area. Useful agents include solvents such as dichloromethane, trichloroacetic acid, acetonitrile and acids such as trifluoroacetic acid and hydrogen fluoride.

The currently preferred fibril-modifying agent useful in formulating the matrices of this invention is a heated aqueous medium, preferably an acidic aqueous medium having a pH less than about pH 4.5, most preferably having a pH within the range of about pH 2–pH 4. A currently preferred heated acidic aqueous medium is 0.1% acetic acid which has a pH of about 3. Heating demineralized, delipidated, guanidine-extracted bone collagen in an aqueous medium at elevated temperatures (e.g., in the range of about 37° C.–65° C., preferably in the range of about 45° C.–60° C.) for approximately one hour generally is sufficient to achieve the desired surface morphology. Although the mechanism is not clear, it is hypothesized that the heat treatment alters the collagen fibrils, resulting in an increase in the particle surface area. Thus, one aspect of this invention includes osteogenic devices comprising matrices which have been treated to increase the surface area and porosity of matrix collagen particles substantially.

Examination of solvent-treated bone collagenous matrix shows that demineralized guanidine-extracted xenogenic bovine bone comprises a mixture of additional materials and that extracting these materials can improve matrix properties. Chromatographic separation of components in the extract, followed by addition back to active matrix of the various extract fractions corresponding to the chromatogram peaks, indicates that there is a fraction which can inhibit the osteoinductive effect. The identity of the substance or substances in this inhibiting fraction has not as yet been determined. Thus, in one aspect of this invention, a matrix is provided comprising treated Type-I bone collagen particles of the type described above, further characterized in that they are depleted in this inhibiting component.

In still another aspect of this invention, a matrix is provided that is substantially depleted in residual heavy metals. Treated as disclosed herein, individual heavy metal concentrations in the matrix can be reduced to less than about 1 ppm.

In view of this disclosure, one skilled in the art can create a biocompatible matrix of choice having a desired porosity or surface microtexture useful in the production of osteogenic devices, and useful in other implantable contexts, e.g., as a packing to promote bone induction, or as a biodegradable sustained release implant. In addition, synthetically formulated matrices, prepared as disclosed herein, may be used.

The osteogenic proteins and implantable osteogenic devices disclosed herein will permit the physician to obtain predictable bone formation to correct, for example, acquired and congenital craniofacial and other skeletal or dental anomalies (e.g., Glowacki et al. (1981) Lancet 1:959-963). The devices may be used to induce local endochondral bone formation in non-union fractures as demonstrated in animal tests, and in other clinical applications including dental and periodontal applications where bone formation is required. Another potential clinical application is in cartilage repair, for example, in the treatment of osteoarthritis.

BRIEF DESCRIPTION OF THE DRAWINGS

The foregoing and other objects of the invention, the various features thereof, as well as the invention itself, may be more fully understood from the following description, when read together with the accompanying drawings, in which:

FIGS. 1A and 1B are flow diagrams of a purification procedure for isolating osteogenic protein;

FIGS. 3A and 3B are photographic reproductions of a Coomassie blue stained SDS polyacrylamide gel of the osteogenic protein under non-reducing (A) and reducing (B) conditions;

FIGS. 4A and 4B are photographic reproductions of a Con A blot of an SDS polyacrylamide gel showing the presence of a carbohydrate component in the oxidized (A) and reduced (B) 30 kDa protein;

FIG. 5 is a photographic reproduction of an autoradiogram of an SDS polyacrylamide gel of $^{125}$I-labelled glycosylated (A) and deglycosylated (B) osteogenic protein under non-reducing (1) and reducing (2) conditions;

FIGS. 13 and FIG. 13 Conti are a schematic representation of the DNA sequence, restriction sites, and corresponding amino acid sequence of the consensus gene/probe for osteogenic protein;

FIG. 18 is a representation of the hybridization of the consensus gene/probe to the OP1 gene;

FIGS. 23A-1 through 23A-2 and 23B-1 through 23B-3 compare the amino acid sequences of the mature hOP1 and mOP1 polypeptide chains: OP1-18Ser and mOP1-Ser (A); and mature mOP2 and hOP2 polypeptide chains: hOP2-Ala and mOP2-Ala (B);

FIGS. 24-1 through 24-4 compares the amino acid sequences of the mature OP1 and OP2 polypeptide chains: OP1-18Ser, mOP1-Ser, hOP2-Ala and mOP2-Ala;

FIG. 31 describes the dose dependence of osteogenic implants for day 12 implants, as determined by alkaline phosphatase activity and calcium content, for allogenic implants containing OP1 expressed from COS, BSC and CHO cells;

FIG. 33 compares the N-termini of the various forms of human OP1 protein identified to date.

DESCRIPTION

Figure 1B:
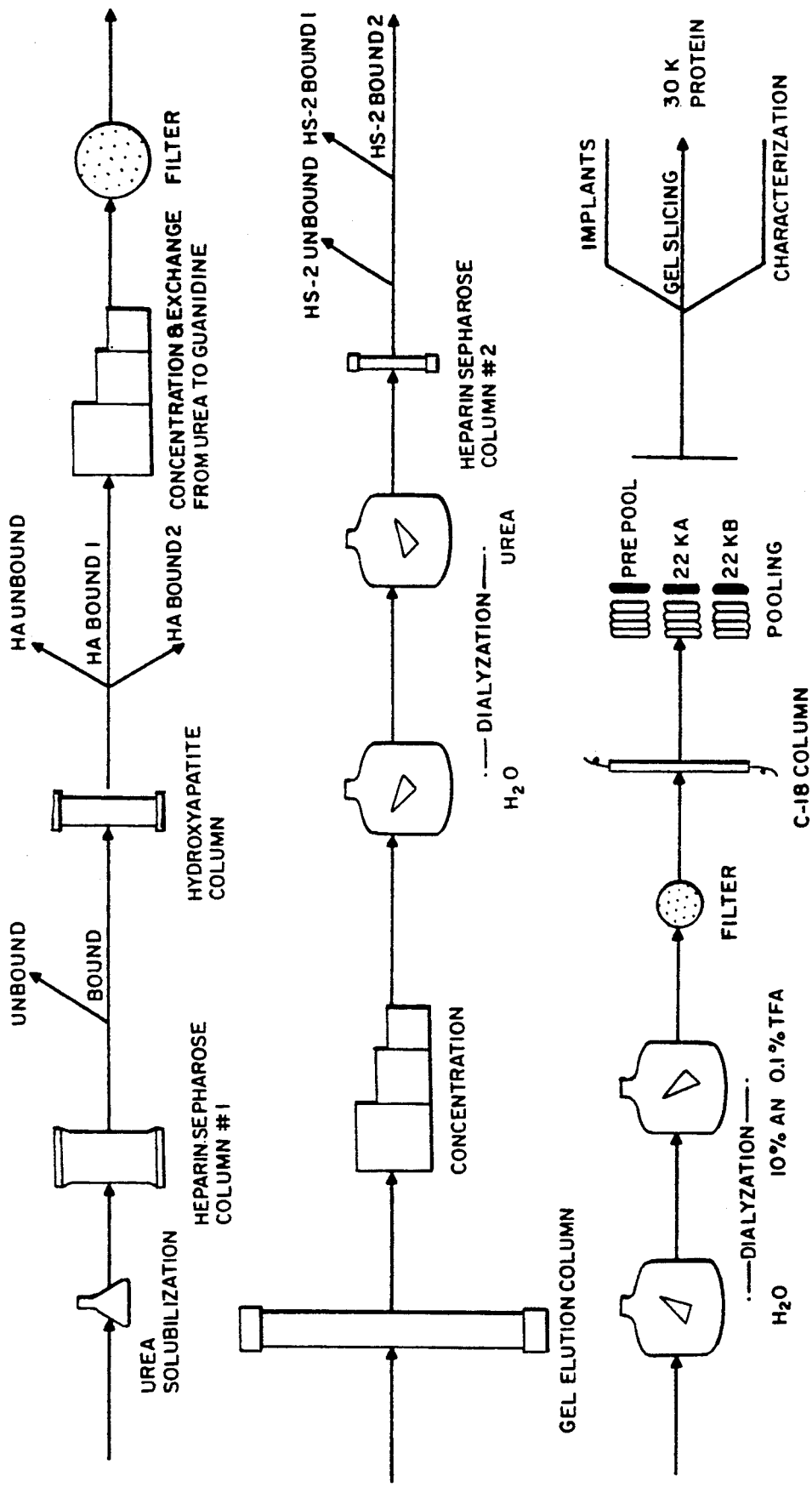

Purification protocols first were developed which enabled isolation of the osteogenic protein present in crude protein extracts from mammalian bone (e.g., from bovine bone, "bOP," and human bone. See U.S. Ser. No. 179,406 filed Apr. 8, 1988, now U.S. Pat. No. 4,968,590). Sequence data obtained from the bovine material suggested a probe design which was used to isolate human genes. The human counterpart osteogenic proteins have now been expressed and extensively characterized.

These discoveries have enabled preparation of DNAs encoding totally novel, non-native (e.g., not known to occur in nature) protein constructs which individually as homodimers and combined with other related species are capable of producing true endochondral bone (see U.S. Ser. No. 315,342, filed Feb. 23, 1989, now U.S. Pat. No. 5,011,691). They also permitted expression of the natural material, truncated forms, muteins, analogs, fusion proteins, and various other variants and constructs, from cDNAs and genomic DNAs retrieved from natural sources or from synthetic DNA produced using the techniques disclosed herein and using automated, commercially available equipment. The DNAs may be expressed using well established molecular biology and recombinant DNA techniques in procaryotic or eucaryotic host cells, and may be oxidized and refolded in vitro if necessary, to produce biologically active protein.

One of the DNA sequences isolated from human genomic and cDNA libraries encoded a previously unidentified gene, referred to herein as hOP1. The protein encoded by the isolated DNA was identified originally by amino acid homology with proteins in the TGF-β superfamily. Consensus splice signals were found where predicted amino acid homologies ended, designating exon-intron boundaries. Three exons were combined to obtain a functional TGF-β-like domain containing seven cysteines. (See, for example, U.S. Ser. No. 315,342 filed Feb. 23, 1989, now U.S. Pat. No. 5,011,691, and Ozkaynak, E. et al., (1990) EMBO. 9: pp. 2085–2093).

The full-length cDNA sequence for hOP1, and its encoded "prepro" form (hOP1-PP), which includes an N-terminal signal peptide sequence, are disclosed in Seq. ID No. 1 (residues 1–431). The mature form of hOP1 protein expressed in mammalian cells ("OP1-18Ser") is described by amino acid residues 293 to 431 of Seq. ID No. 1. The full length form of hOP1, as well as various truncated forms of the gene, and fusion DNA constructs, have been expressed in E. coli, and numerous mammalian cells as disclosed herein, and all have been shown to have osteogenic activity when implanted in a mammal in association with a matrix.

Given the foregoing amino acid and DNA sequence information, various DNAs can be constructed which encode at least the active region of the hOP1 protein (e.g., OPS or OP7), and various analogs thereof (including allelic variants and those containing genetically engineered mutations), as well as fusion proteins, truncated forms of the mature proteins, and similar constructs. Moreover, DNA hybridization probes can be constructed from fragments of the hOP1 DNA or designed de novo based on the hOP1 DNA or amino acid sequence. These probes then can be used to screen different genomic and cDNA libraries to identify additional genes encoding other osteogenic proteins.

The DNAs can be produced by those skilled in the art using well known DNA manipulation techniques involving genomic and cDNA isolation, construction of synthetic DNA from synthesized oligonucleotides, and cassette mutagenesis techniques. 15–100mer oligonucleotides may be synthesized on a Biosearch DNA Model 8600 Synthesizer, and purified by polyacrylamide gel electrophoresis (PAGE) in Tris-Borate-EDTA buffer. The DNA then may be electroeluted from the gel. Overlapping oligomers may be phosphorylated by T4 polynucleotide kinase and ligated into larger blocks which may also be purified by PAGE.

DNAs used as hybridization probes may be labelled (e.g., as with a radioisotope, by nick-translation or by random hexanucleotide priming) and used to identify clones in a given library containing DNA to which the probe hybridizes, following techniques well known in the art. The libraries may be obtained commercially or they may be constructed de novo using conventional molecular biology techniques. Further information on DNA library construction and hybridization techniques can be found in numerous texts known to those skilled in the art. See, for example, F. M. Ausubel, ed., *Current Protocols in Molecular Biology-Vol. I*, John Wiley & Sons, New York, (1989). In particular, see Unit 5, "Construction of Recombinant DNA Libraries" and Unit 6, "Screening of Recombinant Libraries."

The DNA from appropriately identified clones then can be isolated, subcloned (preferably into an expression vector), and sequenced using any of a number of techniques well known in the art. Vectors containing sequences of interest then can be transfected into an appropriate host cell for protein expression and further characterization. The host may be a procaryotic or eucaryotic cell since the former's inability to glycosylate protein will not destroy the protein's osteogenic activity. Useful host cells include *E. coli, Saccharomyces,* the insect/baculovirus cell system, myeloma cells, and various other mammalian cells. The vector additionally may include various sequences to promote correct expression of the recombinant protein, including transcription promoter and termination sequences, enhancer sequences, preferred ribosome binding site sequences, preferred mRNA leader sequences, preferred signal sequences for protein secretion, and the like. The DNA sequence encoding the protein of interest also may be manipulated to remove potentially inhibiting sequences or to minimize unwanted secondary structure formation. The recombinant osteogenic protein also may be expressed as a fusion protein. After being translated, the protein may be purified from the cells themselves or recovered from the culture medium. All biologically active protein forms comprise dimeric species linked by disulfide bonds or otherwise associated, produced by oxidizing and refolding one or more of the various recombinant polypeptide chains within an appropriate eucaryotic cell or in vitro after expression of individual subunits. A detailed description of osteogenic protein purified from natural sources or expressed from recombinant DNA in *E. coli* and numerous different mammalian cells is disclosed below.

In view of this disclosure, and using standard immunology techniques well known in the art, those skilled in the art also may raise polyclonal or monoclonal antibodies against all or part of the polypeptide chains described herein. Useful protocols for antibody production may be found, for example, in *Molecular Cloning-A Laboratory Manual* (Sambrook et al., eds.) Cold Spring Harbor Press, 2nd ed., 1989). See Book 3, Section 18. The polypeptide chains useful as antigens may be purified from natural-sourced material, synthesized by chemical means, or expressed from recombinant nucleic acid as disclosed herein. Antibodies specific for the osteogenic proteins disclosed herein may be particularly useful in osteogenic protein preparation. For example, when purifying a given osteogenic protein from bone or a cell culture supernatant, the osteogenic protein may be selectively extracted from a mixture by exposing the mixture to the antibody under conditions such that the antibody specifically binds the osteogenic protein to form an antibody-osteogenic protein complex. This complex then may be separated from the mixture by conventional methods, and the complex dissociated to yield substantially purified osteogenic protein.

I. PURIFICATION OF OSTEOGENIC PROTEIN FROM BONE

A. BOVINE BONE

1. PURIFICATION

1.1 Preparation of Demineralized Bone

Figures 1, 21A:
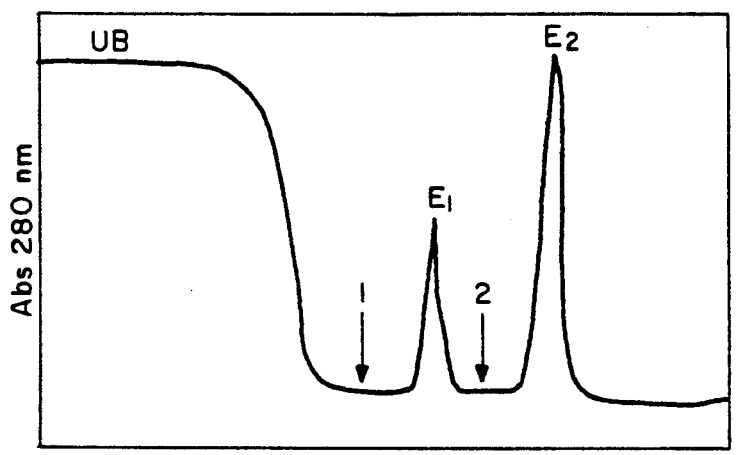
FIGS. 21A-1 through 21C-1 and 21A-2 through 21C-2 are (1) elution profiles and (2) photoreproductions of SDS-PAGE gels expressed from BSC cells and purified (in order) on: (A) S-Sepharose, (B) phenyl-Sepharose, and (c) C-18 columns.
Figures 1, 21B:
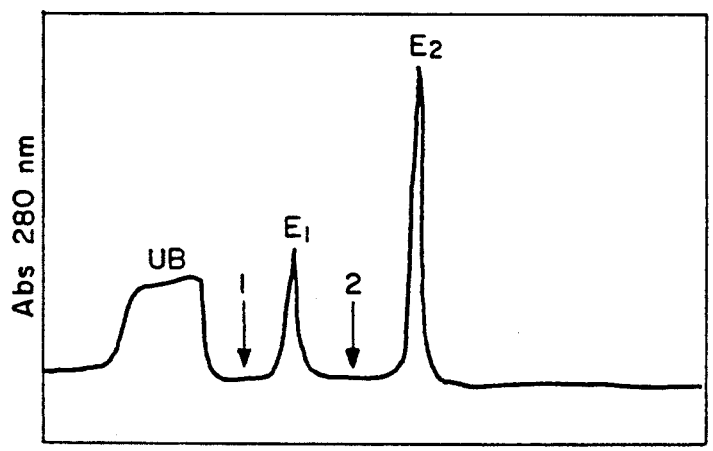
Figures 1, 21C:
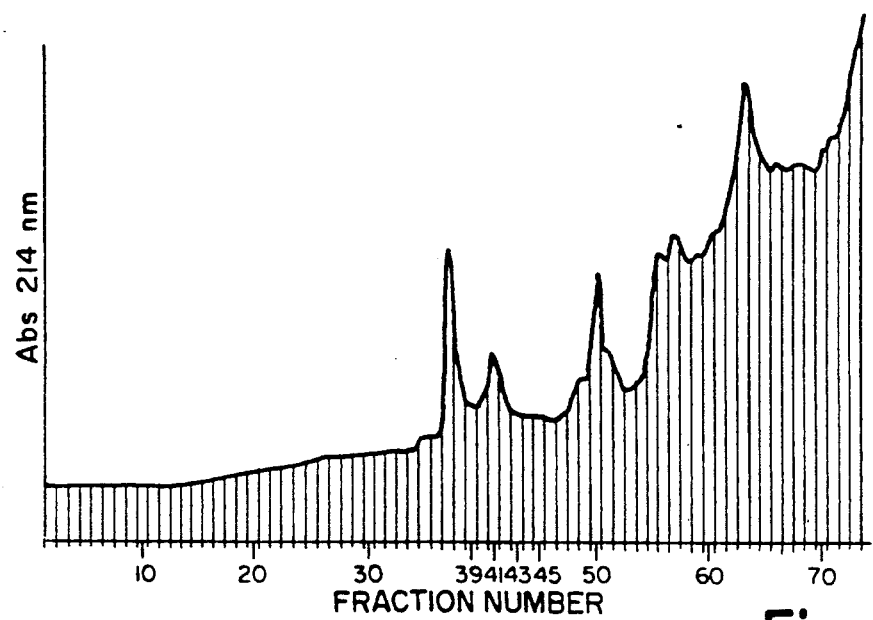

A schematic representation of the general protocol disclosed herein for purifying osteogenic protein from bone is illustrated in FIG. 1. Demineralized bovine bone matrix is prepared by previously published procedures (Sampath and Reddi (1983) *Proc. Natl. Acad. Sci. USA* 80:6591-6595). Bovine diaphyseal bones (age 1-10 days) are obtained from a local slaughterhouse and used fresh. The bones are stripped of muscle and fat, cleaned of periosteum, demarrowed by pressure with cold water, dipped in cold absolute ethanol, and stored at $-20°$ C. They are then dried and fragmented by crushing and pulverized in a large mill. Care is taken to prevent heating by using liquid nitrogen. The pulverized bone is milled to a particle size between 70-420 $\mu$m and is defatted by two washes of approximately two hours duration with three volumes of chloroform and methanol (3:1). The particulate bone is then washed with one volume of absolute ethanol and dried over one volume of anhydrous ether. The defatted bone powder is then demineralized with 20 volumes of 0.5N HCl at $4°$ C. for 24 hours. The acid is removed every eight hours and fresh acid is added. Finally, the demineralized bone powder is washed with a large volume of water until the wash solution has a neutral pH. The water may be removed by freeze-drying.

1.2 Dissociative Extraction and Ethanol Precipitation

Demineralized bone matrix thus prepared is dissociatively extracted with 20 volumes of 4M guanidine-HCl, 50 mM Tris-HCl, pH 7.0, containing protease inhibitors (5 mM benzamidine, 0.1M 6-aminohexanoic acid, 5 mM N-ethylmaleimide, 0.5 mM phenylmethylsulfonylfluoride) for 16 hr. at $4°$ C. The suspension is filtered through cheese cloth and centrifuged at $20,000\times g$ for 15 min. at $4°$ C. The supernatant is collected and concentrated to one volume using an Amicon ultrafiltration YM-10 hollow fiber membrane. The concentrate is centrifuged ($40,000\times g$ for 30 min. at $4°$ C.), and the supernatant is then subjected to ethanol precipitation. To one volume of concentrate is added seven volumes of cold ($-20°$ C.) absolute ethanol (100%), which is then kept at $-20°$ C. for 30 min. The precipitate is pelleted upon centrifugation at $10,000\times g$ for 10 min. at $4°$ C. The resulting pellet is resuspended in 250 ml of 85% cold ethanol and recentrifuged. The pellet then is lyophilized.

1.3 Heparin-Sepharose Chromatography I

The ethanol precipitated, lyophilized, extracted crude protein is dissolved in 20 volumes of 6M urea, 50 mM Tris-HCl, pH 7.0 (Buffer A) containing 0.15M NaCl, and clarified by centrifugation at $20,000\times g$ for 30 min. The supernatant is stirred for 15 min. with 50 volumes of hydrated heparin-Sepharose (Pharmacia) equilibrated with Buffer A containing 0.15M NaCl. The heparin-Sepharose is pre-treated with Buffer A containing 1.0M NaCl prior to equilibration. The unabsorbed protein is collected by packing the resin into a column. After washing with three column volumes of initial buffer (Buffer A containing 0.15M NaCl), protein is eluted with Buffer A containing 0.5M NaCl. The absorption of the eluate is monitored continuously at 280 nm. The pool of protein eluted by 0.5M NaCl (approximately 20 column volumes) is collected and stored at $-20°$ C.

Figure 2A:
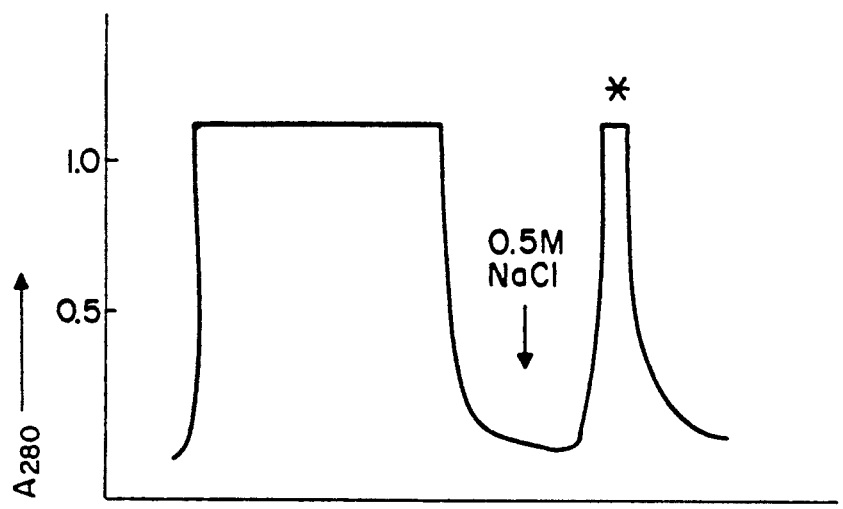
FIGS. 2A through 2D are a collection of plots of protein concentration (as indicated by optical absorption) vs elution volume illustrating the results of bOP fractionation during purification on (A) heparin-Sepharose-I; (B) HAP-Ultragel; (C) TSK 3000; and (D) heparin-Sepharose-II. Asterisk identifies active peak.

As shown in FIG. 2A, most of the protein (about 95%) remains unbound. Approximately 5% of the protein is bound to the column. The unbound fraction has no bone inductive activity when bioassayed as a whole or after a partial purification through Sepharose CL-6B.

1.4 Hydroxyapatite-Ultragel Chromatography

Figure 2B:
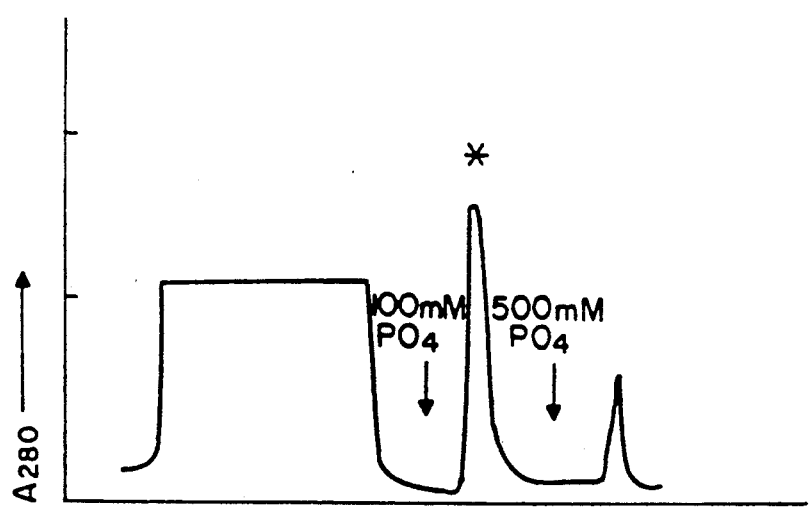

The volume of protein eluted by Buffer A containing 0.5M NaCl from the heparin-Sepharose is applied directly to a column of hydroxyapatite-Ultragel (HAP-Ultragel) (LKB Instruments), and equilibrated with Buffer A containing 0.5M NaCl. The HAP-Ultragel is treated with Buffer A containing 500 mM Na phosphate prior to equilibration. The unadsorbed protein is collected as an unbound fraction, and the column is washed with three column volumes of Buffer A containing 0.5M NaCl. The column subsequently is eluted with Buffer A containing 100 mM Na phosphate (FIG. 2B). The approximately 3 column volume pool of the protein peak eluted by 100 mM Na phosphate is concentrated using an Amicon ultrafiltration YM-10 membrane to one volume, dialysed in a 3.5 kDa molecular weight cut-off bag (Spectrapor) against distilled water, and lyophilized.

The 100 mM Na phosphate eluted component can induce endochondral bone as measured by alkaline phosphatase activity and histology (see section V.5.1, infra). As the biologically active protein is bound to HAP in the presence of 6M urea and 0.5M NaCl, it is likely that the protein has an affinity for bone mineral and may be displaced only by phosphate ions.

1.5 TSK 3000 Gel Exclusion Chromatography

Figure 2C:
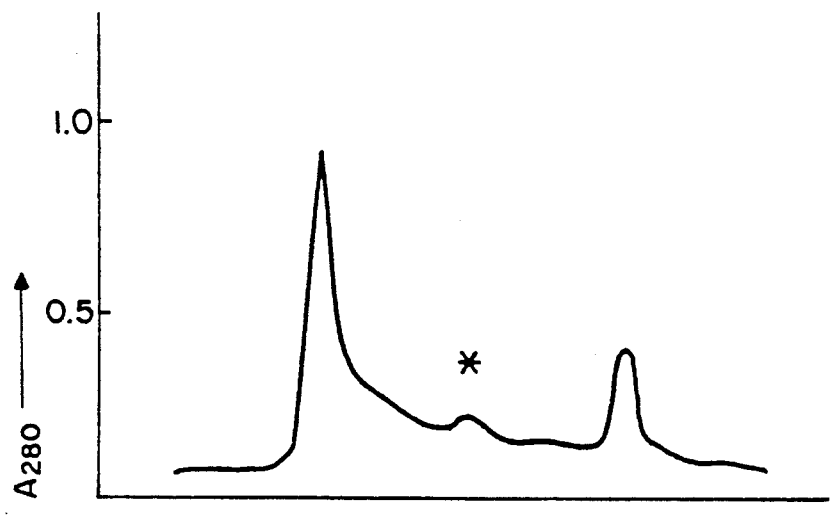

Analytical TSK 3000 gel (silica gel), obtained from Bio Rad, is equilibrated with 4M guanidine-HCl, 50 mm Tris-HCl, pH 7.0. A pre-column (analytical) also is used. A portion of the lyophilized protein from HAP-Ultragel is dissolved in a known volume of 4M guanidine-HCl, 50 mM Tris-HCl, pH 7.0, and the solution is clarified by low speed centrifugation. A 200 µl sample containing approximately 10 mg of protein is loaded onto the column and then chromatographed with 4M guanidine-HCl, 50 mM Tris-HCl, pH 7.0, with a flow rate of 0.3 ml/min. 0.6 ml fractions are collected over 100 min., and the concentration of the protein is measured continuously at $A_{280}$. Fractions are collected and bioassayed as described below; fractions having a molecular weight less than 35 kDa (30-34 kDa) and osteoinductivity are pooled and stored at 4° C. (FIG. 2C).

1.6 Heparin-Sepharose Chromatography-II

Figure 2D:
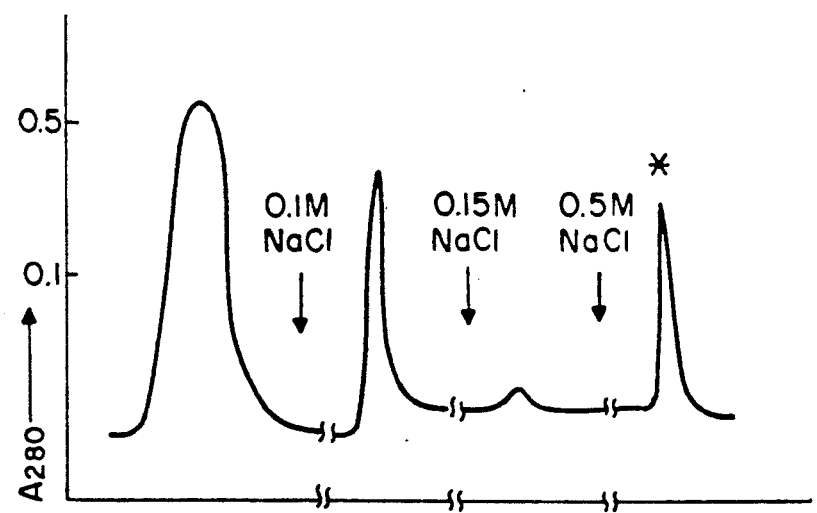
Figure 6A:
FIGS. 6A through 6E are photographic reproductions of an autoradiogram of an SDS polyacrylamide gel of peptides produced upon the digestion of the 30 kDa osteogenic protein with V-8 protease (B), Endo Lys C protease (C), pepsin (D), and trypsin (E). (A) is control.
Figure 6B:
Figure 6C:
Figure 6D:
Figure 6E:

The pooled osteo-inductive fractions obtained from TSK gel exclusion chromatography are dialysed extensively against distilled water and then against one liter of 6M urea, 50 mM Tris-HCl, pH 7.0 (Buffer A, also referred to in related applications as "Buffer B".) The dialysate then is cleared through centrifugation, and the supernatant is stirred for one hr. with 50-100 ml of hydrated heparin-Sepharose (Pharmacia) equilibrated with Buffer A. The heparin-Sepharose is pre-treated with Buffer A containing 1.0M NaCl prior to equilibration. The unadsorbed protein is collected by packing the resin into a column as an unbound fraction. After washing with three column volumes of initial buffer, the column is developed sequentially with Buffer A containing 0.1M NaCl, 0.15M NaCl, and 0.5M NaCl (see FIG. 2D). The protein eluted by 0.5M NaCl is collected and dialyzed extensively against distilled water. It then is dialyzed against one liter of 0.1% trifluoroacetic acid at 4° C.

1.7 Reverse Phase HPLC

Figure 8:
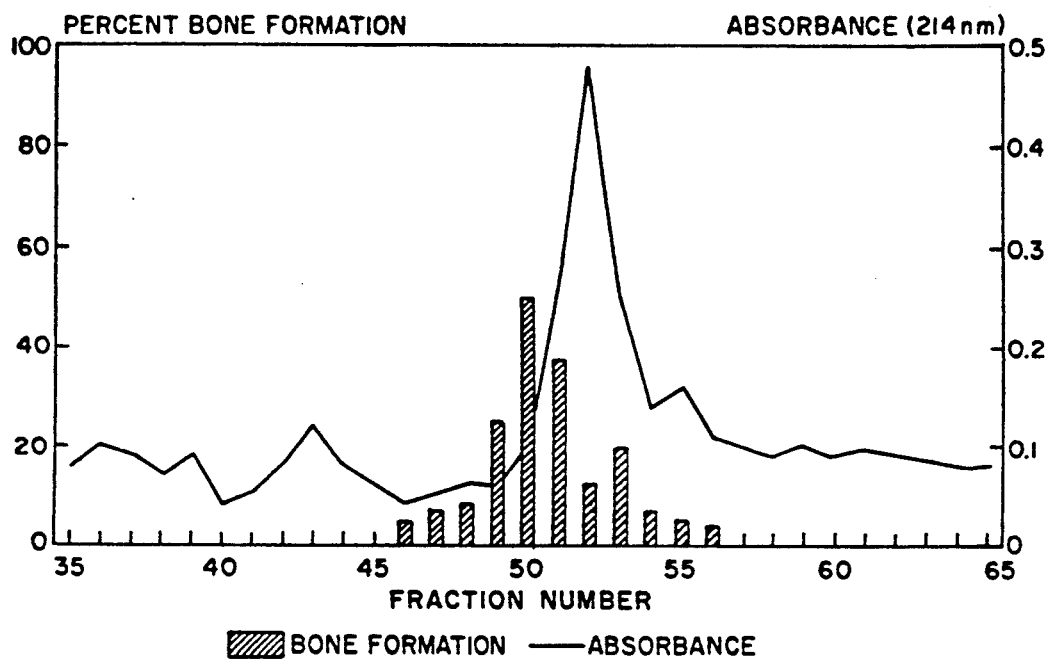
FIG. 8 is an HPLC chromatogram of an elution profile on reverse phase C-18 HPLC of the samples recovered from the second heparin-Sepharose chromatography step (see FIG. 2D). Superimposed is the percent bone formation in each fraction.

The protein further is purified by C-18 Vydac silica-based HPLC column chromatography (particle size 5 µm; pore size 300 Å). The osteoinductive fraction obtained from heparin-Sepharose-II chromatograph is concentrated, loaded onto the column, and washed in 0.1% TFA, 10% acetonitrile for five min. The bound proteins are eluted with a linear gradient of 10-30% acetonitrile over 15 min., 30-50% acetonitrile over 60 min, and 50-70% acetonitrile over 15 min. at 22° C. with a flow rate of 1.0 ml/min, and 1.0 ml samples are collected in polycarbonate tubes. Protein is monitored by absorbance at 214 nm (see FIG. 8). Column fractions are tested for the presence of concanavalin A (Con A)-blottable 30 kDa protein and then pooled. Pools then are characterized biochemically for the presence of 30 kDa protein by autoradiography, concanavalin A blotting, and Coomassie blue dye staining. They are then assayed for in vivo osteogenic activity. Biological activity is not found in the absence of 30 kDa protein.

1.8 Gel Elution

The glycosylated or unglycosylated protein then is eluted from SDS gels for further characterization. $^{125}$I-labelled 30 kDa protein routinely is added to each preparation to monitor yields. TABLE 2 shows the various elution buffers that have been tested and the yields of $^{125}$I-labelled protein.

TABLE 2

| | Elution of 30 kDa Protein from SDS Gel | |
|---|---|---|
| | | % Eluted |
| Buffer | 0.5 mm | 1.5 mm |
| (1) deionized H$_2$O | 22 | |
| (2) Guanidine-HCl, Tris-HCl, pH 7.0 | 2 | |
| (3) Guanidine-HCl, Tris-HCl, pH 7.0, 0.5% Triton | 93 | 52 |
| (4) 0.1% SDS, Tris-HCl, pH 7.0 | 98 | |

TABLE 3 lists the steps used to isolate the 30 kDa or 27 kDa gel-bound protein. The standard protocol uses diffusion elution in Tris-HCl buffer containing 0.1% SDS to achieve greater than 95% elution of the protein from the 27 or 30 kDa region of the gel.

TABLE 3

Preparation of Gel Eluted Protein
(C-18 Pool or deglycoslated protein plus $^{125}$I-labelled 30 kDa protein)

1. Dry using vacuum centrifugation;
2. Wash pellet with H$_2$O;
3. Dissolve pellet in gel sample buffer (no reducing agent);
4. Electrophorese on pre-electrophoresed 0.5 mm mini gel;
5. Cut out 27 or 30 kDa protein;
6. Elute from gel with 0.1% SDS, 50 mM Tris-HCl, pH 7.0;
7. Filter through Centrex membrane;
8. Concentrate in Centricon tube (10 kDa membrane);
9. Chromatograph on TSK-3000 gel filtration column;
10. Concentrate in Centricon tube.

Chromatography in 0.1% SDS on a TSK-3000 gel filtration column is performed to separate gel impurities, such as soluble acrylamide, from the final product. The overall yield of labelled 30 kDa protein from the gel elution protocol is 50-60% of the loaded sample. Most of the loss occurs in the electrophoresis step, due to protein aggregation and/or smearing. In a separate experiment, a sample of gel eluted 30 kDa protein is reduced, electrophoresed on an SDS gel, and transferred to an Immobilon membrane. The membrane is stained with Coomassie blue dye, cut into slices, and the slices are counted. Coomassie blue dye stains the 16 kDa and 18 kDa reduced species almost exclusively. However, the counts showed significant smearing throughout the gel in addition to being concentrated in the 16 kDa and 18 kDa species. This suggests that the $^{125}$I-label can exhibit anomalous behavior on SDS gels and cannot be used as an accurate marker for cold protein under such circumstances.

The yield is 0.5 to 1.0 µg substantially pure osteogenic protein per kg of bone.

1.9 Isolation of the 16 kDa and 18 kDa Species

Figure 15:
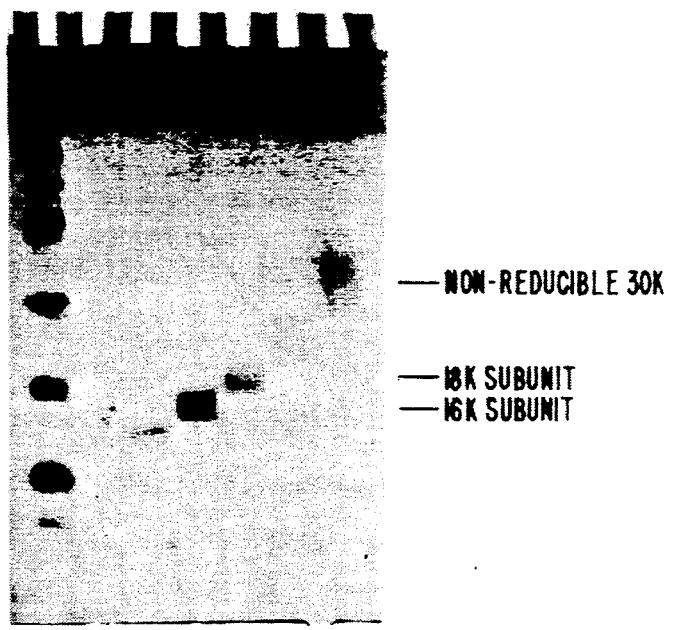
FIG. 15 is a photographic representation of a Coomassie blue stained SDS gel showing gel purified subunits of the 30 kDa protein.

TABLE 4 summarizes the procedures involved in the preparation of the subunits. Gel eluted 30 kDa protein (FIG. 3) is carboxymethylated and electrophoresed on an SDS-gel. The sample contains $^{125}$I-label to trace yields and to use as an indicator for slicing the 16 kDa and 18 kDa regions from the gel. FIG. 15 shows a Coomassie stained gel of aliquots of the protein isolated from the different gel slices. The slices corresponding to the 16 kDa, 18 kDa and non-reducible 30 kDa species contained approximately 10 μg, 3–4 μg, and 6–8 μg, of protein respectively, as estimated by staining intensity. Prior to SDS electrophoresis, all of the 30 kDa species can be reduced to the 16 kDa and 18 kDa species. The non-reducible 30 kDa species observed after electrophoresis appears to be an artifact resulting from the electrophoresis procedure.

TABLE 4

Isolation of the Subunits of the 30kDa protein
(C-18 pool plus $^{125}$I-labeled 30 kDa protein)

1. Electrophorese on SDS gel.
2. Cut out 30 kDa protein.
3. Elute with 0.1% SDS, 50 mM Tris, pH 7.0.
4. Concentrate and wash with H$_2$O in Centricon tube (10 kDa membranes).
5. Reduce and carboxymethylate in 1% SDS, 0.4M Tris, pH 8.5.
6. Concentrate and wash with H$_2$O in Centricon tube.
7. Electrophorese on SDS gel.
8. Cut out the 16 kDa and 18 kDa subunits.
9. Elute with 0.1% SDS, 50 mM Tris, pH 7.0.
10. Concentrate and wash with H$_2$O in Centricon tubes.

2. Characterization of Natural-Sourced bOP 2.1 Molecular Weight and Structure

Electrophoresis of these fractions on non-reducing SDS polyacrylamide gels reveals a single band at about 30 kDa as detected by both Coomassie blue staining (FIG. 3A) and autoradiography.

In order to extend the analysis of bOP, the protein was examined under reducing conditions. FIG. 3B shows an SDS gel of bOP in the presence of dithiothreitol. Upon reduction, 30kDa bOP yields two species which are stained with Coomassie blue dye: a 16 kDa species and an 18 kDa species. Reduction causes loss of biological activity. Methods for the efficient elution of the proteins from SDS gels have been tested, and a protocol has been developed to achieve purification of both proteins. The two reduced bOP species have been analyzed to determine if they are structurally related. Comparison of the amino acid composition of the two species (as disclosed below) shows little differences, indicating that the native protein may comprise two chains having some homology.

2.2 Charge Determination

Isoelectric focusing studies are carried out to further evaluate the 30 kDa protein for possible heterogeneity. The oxidized and reduced species migrate as diffuse bands in the basic region of the isoelectric focusing gel, using the iodinated 30 kDa protein for detection. Using two dimensional gel electrophoresis and Con A for detection, the oxidized 30 kDa protein shows a diffuse species migrating in the same basic region as the iodinated 30 kDa protein. The diffuse character of the band may be traced to the presence of carbohydrate attached to the protein.

2.3 Presence of Carbohydrate

The 30 kDa protein has been tested for the presence of carbohydrate by Con A blotting after SDS-PAGE and transfer to nitrocellulose paper. The results demonstrate that the 30 kDa protein has a high affinity for Con A, indicating that the protein is glycosylated (FIG. 4A). In addition, the Con A blots provide evidence for a substructure in the 30 kDa region of the gel, suggesting heterogeneity due to varying degrees of glycosylation. After reduction (FIG. 4B), Con A blots show evidence for two major components at 16 kDa and 18 kDa. In addition, it has been demonstrated that no glycosylated material remains at the 30 kDa regions after reduction.

Figures 2, 21A:
Figures 2, 21B:
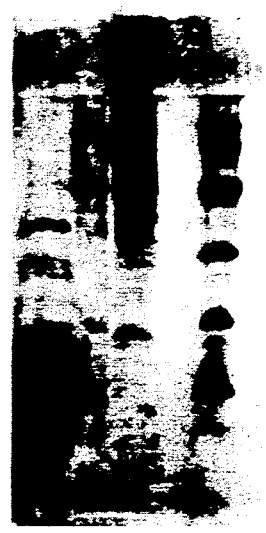
Figures 2, 21C:

In order to confirm the presence of carbohydrate and to estimate the amount of carbohydrate attached, the 30 kDa protein is treated with N-glycanase, a deglycosylating enzyme with a broad specificity. Samples of the $^{125}$I-labelled 30 kDa protein are incubated with the enzyme in the presence of SDS for 24 hours at 37° C. As observed by SDS-PAGE, the treated samples appear as a prominent species at about 27 kDa (FIG. 5B-1). Upon reduction, the 27 kDa species is reduced to species having a molecular weight of about 14 kDa–16 kDa (FIG. 5B-2).

Because the use of N-glycanase for producing deglycosylated protein samples for sequencing or biological activity testing is not advantageous, chemical cleavage of the carbohydrate moieties using hydrogen fluoride (HF) is performed.

Active osteogenic protein fractions pooled from the C-18 chromatography step are derived in vacuo over P$_2$O$_5$ in a polypropylene tube, and 50 μl freshly distilled anhydrous HF at −70° C. is added. After capping the tube tightly, the mixture is kept at 0° C. in an ice-bath with occasional agitation for 1 hr. The HF is then evaporated using a continuous stream of dry nitrogen gas. The tube is removed from the ice bath and the residue dried in vacuo over P$_2$O$_5$ and KOH pellets.

Following drying, the samples are dissolved in 100 μl of 50% acetonitrile/0.1% TFA and aliquoted for SDS gel analysis, Con A binding, and biological assay. Aliquots are dried and dissolved in either SDS gel sample buffer in preparation for SDS gel analysis and Con A blotting, or 4M guanidine-HCl, 50 mM Tris-HCl, pH 7.0 for biological assay. The deglycosylated protein produces a bone formation response in the in vivo rat model described below as determined by histological examination (FIG. 17C).

The results show that samples are completely deglycosylated by the HF treatment: Con A blots after SDS gel electrophoresis and transfer to Immobilon membrane show no binding of Con A to the treated samples, while untreated controls are strongly positive at 30 kDa. Coomassie gels of treated samples show the presence of a 27 kDa band instead of the 30 kDa band present in the untreated controls.

2.4 Chemical and Enzymatic Cleavage

Cleavage reactions with CNBr are analyzed using Con A binding for detection of fragments associated with carbohydrate. Cleavage reactions are conducted using trifluoroacetic acid (TFA) in the presence and absence of CNBr. Reactions are conducted at 37° C. for 18 hours, and the samples are vacuum dried. The samples are washed with water, dissolved in SDS gel sample buffer with reducing agent, boiled and applied to an SDS gel. After electrophoresis, the protein is transferred to Immobilon membrane and visualized by Con A binding. In low concentrations of acid (1%), CNBr cleaves the majority of 16 kDa and 18 kDa species to one product, a species about 14 kDa. In reactions using 10% TFA, a 14 kDa species is observed both with and without CNBr.

Four proteolytic enzymes are used in these experiments to examine the digestion products of the 30 kDa protein: 1) V-8 protease; 2) Endo Lys C protease; 3) pepsin; and 4) tryspin. Except for pepsin, the digestion buffer for the enzymes is 0.1M ammonium bicarbonate, pH 8.3. The pepsin reactions are done in 0.1% TFA. The digestion volume is 100 µl and the ratio of enzyme to substrate is 1:10. $^{125}$I-labelled 30 kDa bOP is added for detection. After incubation at 37° C. for 16 hr., digestion mixtures are dried down and taken up in gel sample buffer containing dithiothreitol for SDS-PAGE. FIG. 6 shows an autoradiograph of an SDS gel of the digestion products. The results show that under these conditions, only trypsin digests the reduced 16 kDa/18 kDa species completely and yields a major species at around 12 kDa. Pepsin digestion yields better defined, lower molecular weight species. However, the 16 kDa/18 kDa fragments were not digested completely. The V-8 digest shows limited digestion with one dominant species at 16 kDa.

2.5 Protein Sequencing

Figure 7A:
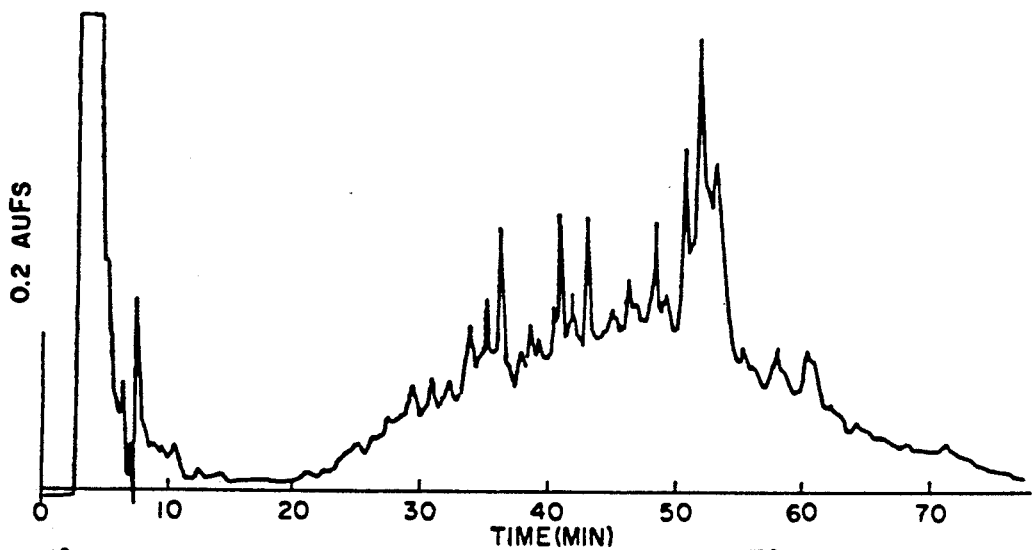
FIGS. 7A through 7C are a collection of HPLC chromatograms of tryptic peptide digestions of 30 kDa bOP (A), the 16 kDa subunit (B), and the 18 kDa subunit (C)

To obtain amino acid sequence data, the protein is cleaved with trypsin. The tryptic digest of reduced and carboxymethylated 30 kDa protein (approximately 10 µg) is fractionated by reverse-phase HPLC using a C-8 narrowbore column (13 cm×2.1 mm ID) with a TFA/acetonitrile gradient and a flow rate of 150 µl/min. The gradient employs (A) 0.06% TFA in water and (B) 0.04% TFA in water and acetonitrile (1:4; v:v). The procedure is 10% B for five min., followed by a linear gradient for 70 min. to 80% B, followed by a linear gradient for 10 min. to 100% B. Fractions containing fragments as determined from the peaks in the HPLC profile (FIG. 7A) are rechromatographed at least once under the same conditions in order to isolate single components satisfactory for sequence analysis.

Figure 7B:
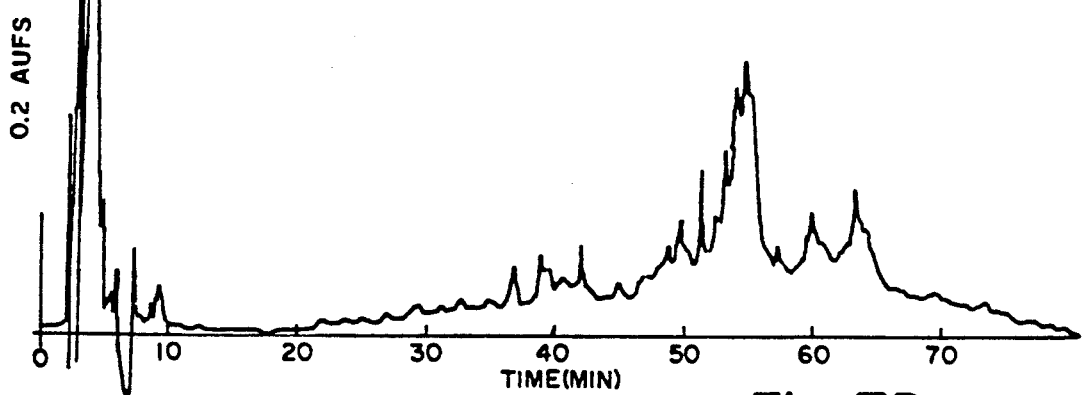
Figure 7C:
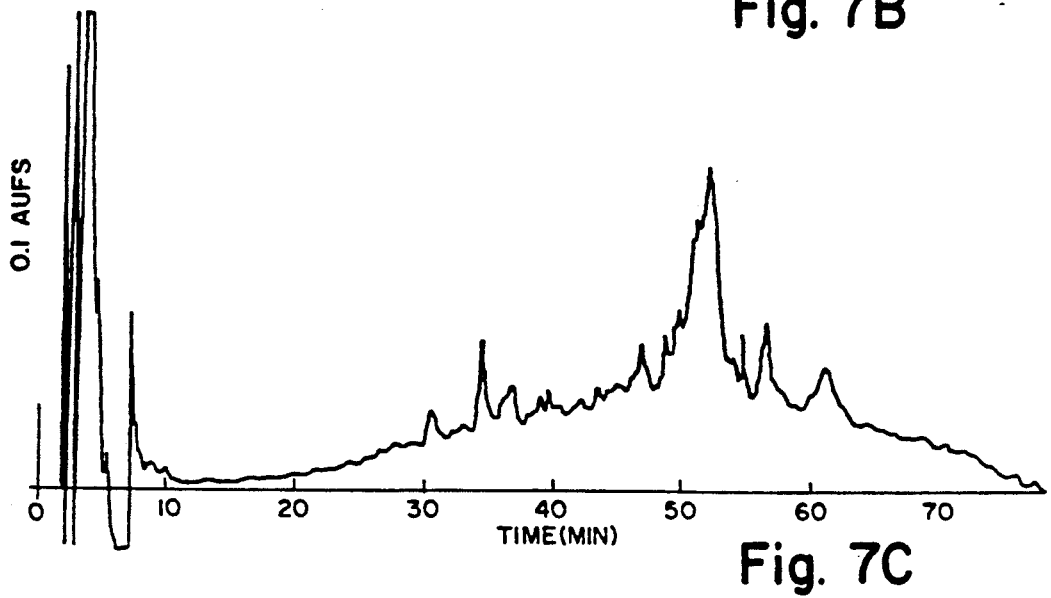

The HPLC profile of the similarly digested 16 kDa and 18 kDa subunits are shown in FIGS. 7B and 7C, respectively. These peptide maps are similar, suggesting that the subunits are identical or are closely related.

Figure 16A:
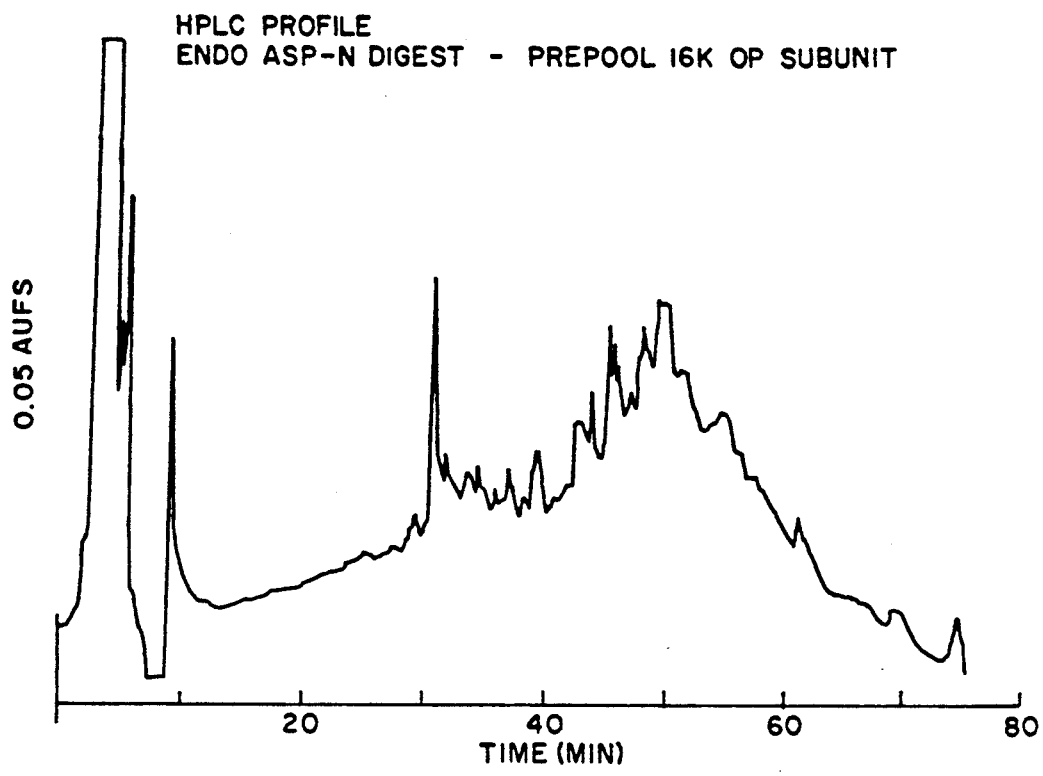
FIGS. 16A and 16B are a pair of HPLC chromatograms of Endo Asp N proteinase digests of the trypsin-resistant cores from the 18 kDa subunit (A) and the 16 kDa subunit (B)
Figure 16B:
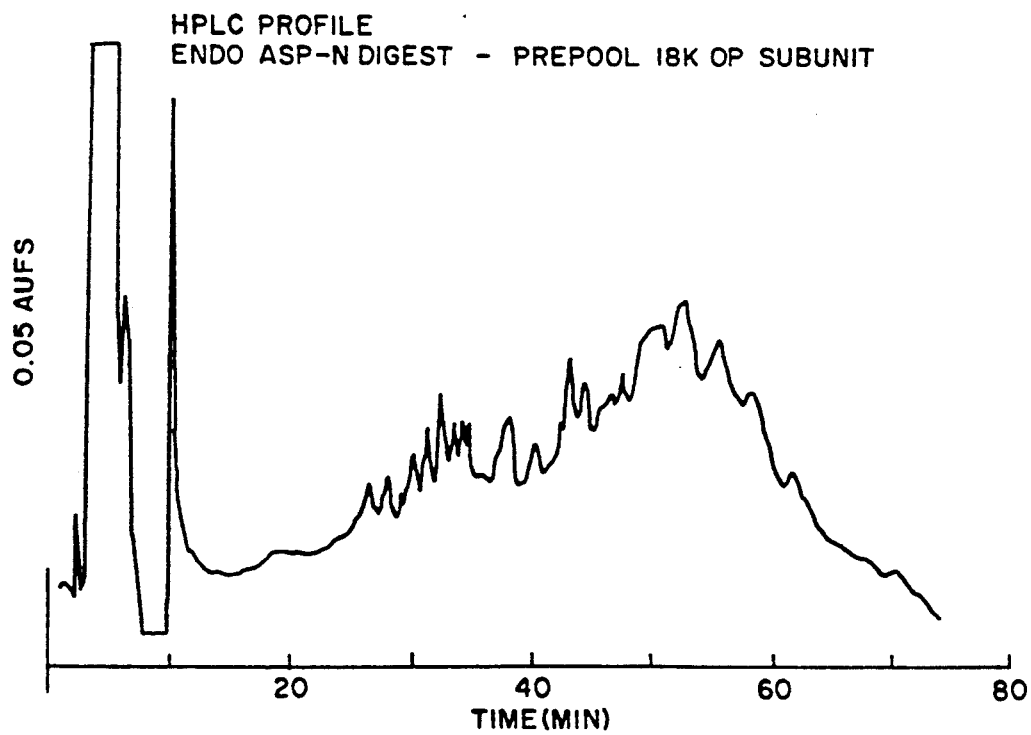

The tryspin resistant core material of the 16 kDa and 18 kDa subunits is digested with Endo Asp N proteinase. The core protein is treated with 0.5 µg Endo Asp N in 50 mM sodium phosphate buffer, pH 7.8 at 36° C. for 20 hr. Subsequently, the samples are centrifuged, and the water soluble peptides injected into the narrow bore HPLC. The water insoluble peptides also are subjected to HPLC fractionation after being dissolved in 50% acetonitrile/0.1% TFA. The conditions for fractionation are the same as those described previously for the 30 kDa, 16 kDa, and 18 kDa digests. The profiles obtained are shown in FIGS. 16A and 16B.

Various of the peptide fragments produced using the foregoing procedures have been analyzed in an automated amino acid sequencer (Applied Biosystems 450A). The following sequence data has been obtained:

(1) Ser-Phe-Asp-Ala-Tyr-Tyr-Cys-Ser-Gly-Ala-Cys-Gln-Phe-Pro-Met-Pro-Lys;
(2) Ser-Leu-Lys-Pro-Ser-Asn-Tyr-Ala-Thr-Ile-Gln-Ser-Ile-Val;
(3) Ala-Cys-Cys-Val-Pro-Thr-Glu-Leu-Ser-Ala-Ile-Ser-Met-Leu-Tyr-Leu-Asp-Glu-Asn-Glu-Lys;
(4) Met-Ser-Ser-Leu-Ser-Ile-Leu-Phe-Phe-Asp-Glu-Asn-Lys;
(5) Val-Gly-Val-Val-Pro-Gly-Ile-Pro-Glu-Pro-Cys-Cys-Val-Pro-Glu;
(6) Val-Asp-Phe-Ala-Asp-Ile-Gly
(7) Val-Pro-Lys-Pro; and
(8) Ala-Pro-Thr.

Several of the residues in these sequences could not be determined with certainty. For example, two amino acids join fragment 8 to the C-terminus of fragment 7. Initial sequencing data suggested these residues were both serines, but subsequent experiments identified the residues as cysteines. Accordingly, these data have been eliminated from the sequencing results presented here. Similarly, a spurious glutamic acid residue at the N-terminus of fragment 7, and a spurious lysine at the C-terminus of fragment 8 also have been eliminated from the data presented here (see U.S. Pat. No. 5,011,691, col. 7, fragment 7 for correct sequence).

Fragments 1,2 and 4-6 are described in the sequences presented in Seq. ID Nos. 20 and 22 (referred to herein as human and murine "CBMP3," respectively.) Specifically, fragment 1 is described essentially by residues 93-109 of Seq. ID No. 20 and fragment 2 is described essentially by residues 121-134 of Seq. ID No. 22 (note that residue 7 in fragment 2 is identified as a tyrosine. In Seq. ID No. 22 this residue is a histidine. By comparison with the CBMP2 and OP1 sequences, the correct residue likely is a histidine.) Fragment 4 is described essentially by residues 153-165 of Seq. ID No. 22 and fragment 5 is described essentially by residues 137-151 of Seq. ID No. 22 (note that residue 5 in fragment 5 is identified as a proline. In Seq. ID No. 22 this residue is a serine. By comparison with the CBMP2 and OP1 sequences, the correct residue likely is a serine.) Fragment 6 is described essentially by residues 77-83 of Seq. ID No. 20. Fragment 3 is described by residues 359-379 in the sequence presented in Seq. ID No. 4 (referred to herein as "CBMP2A"). Fragments 7 and 8 are described by residues 391-394 and 397-399, respectively, of the sequence presented in Seq. ID No.1 (referred to herein as "OP1".)

Subsequent additional peptide digest experiments performed on each of the two subunits purified from the highest activity fractions and digested with either thermolysin or endoproteinase Asp-N followed by endoproteinase Glu-C unequivocally identifies the 18 kDa subunit as comprising OP1, and the 16 kDa subunit as comprising CBMP2 (see U.S. Pat. No. 5,011,691 and Kuber Sampath et al., (1990) *J. Biol. Chem.* 265:13198-13205.)

Specifically, pyridylethylation of C-18 purified, reduced, bOP fractions showing the highest osteogenic activity, followed by separation by SDS-PAGE, gel slicing, elution, and digestion with endoproteinase Asp-N, then Staph V-8 protease, permitted separation of peptide fragments representative of each of the subunits from natural-sourced bovine material. Sequencing of the peptide fragments from the 18 kDa subunit yielded five sequences unequivocally from OP1. Sequencing of peptide fragments from the 16 kDa subunit yielded six sequences unequivocally from CBMP2A, and three that could have been from either CBMP2A or CBMP2B. The five sequences unequivocally from OP1 correspond to residue Nos. 341-345, 342-346, 346-352, 353-360 and 386-399 of Seq. ID No. 1. The six sequences unequivocally from CBMP2A correspond to residue Nos. 312-324, 312-330, 314-322, 323-330, 335-354 and 366-373 of Seq. ID No. 4. Another peptide, analyzed as Asp-Xaa-Pro-Phe-Pro-Leu, was consistent with the presence of CBMP2B. However, the amino terminal aspartic acid could have been a glutamic acid (Glu), in which case the peptide would have indicated the presence of CBMP2A. The Asp-Xaa-Pro-Phe-Pro-Leu sequence determination has not been repeated successfully. From these data, it is apparent that the active natural-sourced osteogenic protein comprises OP1 and CBMP2.

2.6 Amino Acid Analysis

Strategies for obtaining amino acid composition data were developed using gel elution from 15% SDS gels, transfer onto Immobilon, and hydrolysis. Immobilon membrane is a polymer of vinylidene difluoride and, therefore, is not susceptible to acid cleavage. Samples of oxidized (30 kDa) and reduced (16 kDa and 18 kDa) bOP are electrophoresed on a gel and transferred to Immobilon for hydrolysis and analysis as described below. The composition data generated by amino acid analyses of 30 kDa bOP is reproducible, with some variation in the number of residues for a few amino acids, especially cysteine and isoleucine.

Samples are run on 15% SDS gels, transferred to Immobilon, and stained with Coomassie blue. The bands of interest are excised from the Immobilon, with a razor blade and placed in a Corning 6×50 test tube cleaned by pyrolysis at 55° C. When cysteine is to be determined, the samples are treated with performic acid (PFA), which converts cysteine to cysteic acid. Cysteic acid is stable during hyrolysis with HCl, and can be detected during the HPLC analysis by using a modification of the normal Pico Tag eluents (Millipore) and gradient. The PFA is made by mixing 50 μl 30% hydrogen peroxide with 950 μl 99% formic acid, and allowing this solution to stand at room temperature for 2 hr. The samples then are treated with PFA as follows: 20 μl PFA is pipetted onto each sample and placed in an ice bath at 4° C. for 2.5 hours. After 2.5 hours, the PFA is removed by drying in vacuo, and the samples then are hydrolyzed. A standard protein of known composition and concentration containing cysteine is treated with PFA and hydrolyzed concurrently with the bOP samples.

The hydrolysis of the bOP samples is done in vacuo. The samples, with empty tubes and Immobilon blanks, are placed in a hydrolysis vessel which is placed in a dry ice/ethanol bath to keep the HCl from prematurely evaporating. 200 μl 6N HCl containing 2% phenol and 0.1% stannous chloride are added to the hydrolysis vessel outside the tubes containing the samples. The hydrolysis vessel is then sealed, flushed with prepurified nitrogen, evacuated, and then held at 115° C. for 24 hours, after which time the HCl is removed by drying in vacuo.

After hydrolysis, each piece of Immobilon is transferred to a fresh tube, where it is rinsed twice with 100 μl 0.1% TFA, 50% acetonitrile. The washings are returned to the original sample tube, which then is redried as below. A similar treatment of amino acid analysis on Immobilon can be found in the literature (LeGendre and Matsudaira (1988) Biotechniques 6:154–159).

The samples are redried twice using 2:2:1 ethanol:water:triethylamine and allowed to dry at least 30 min. after each addition of redry reagent. These redrying steps bring the sample to the proper pH for derivatization.

The samples are derivatized using standard methodology. The solution is added to each sample tube. The tubes are placed in a desiccator which is partially evacuated, and are allowed to stand for 20 min. The desiccator then is fully evacuated, and the samples are dried for at least 3 hr. After this step the samples may be stored under vacuum at −20° C. or immediately diluted for HPLC. The samples are diluted with Pico Tag Sample Diluent (generally 100 μl) and allowed to stand for 20 min., after which they are analyzed on HPLC using the Pico Tag chromatographic system with some minor changes involving gradients, eluents, initial buffer conditions and oven temperature.

After HPLC analysis, the compositions are calculated. The molecular weights are assumed to be 14.4 kDa, 16.2 kDa, and 27 kDa. The number of residues is approximated by dividing the molecular weight by the average molecular weight per amino acid, which is 115. The total picomoles of amino acid recovered is divided by the number of residues, and then the picomoles recovered for each amino acid is divided by the number of picomoles per residue, determined above. This gives an approximate theoretical number of residues of each amino acid in the protein. Glycine content may be overestimated in this type of analysis.

Composition data obtained are shown in TABLE 5.

TABLE 5

| Amino Acid | bOP Amino Acid Analyses | | |
|---|---|---|---|
| | 30 kDa | 16 kDa | 18 kDa |
| Asp/Asn | 22 | 14 | 15 |
| Glu/Gln | 24 | 14 | 16 |
| Ser | 24 | 16 | 23 |
| Gly | 29 | 18 | 26 |
| His | 5 | * | 4 |
| Arg | 13 | 6 | 6 |
| Thr | 11 | 6 | 7 |
| Ala | 18 | 11 | 12 |
| Pro | 14 | 6 | 6 |
| Tyr | 11 | 3 | 3 |
| Val | 14 | 8 | 7 |
| Met | 3 | 0 | 2 |
| Cys** | 16 | 14 | 12 |
| Ile | 15 | 14 | 10 |
| Leu | 15 | 8 | 9 |
| Phe | 7 | 4 | 4 |
| Trp | ND | ND | ND |
| Lys | 12 | 6 | 6 |

*This result is not integrated because histidine is present in low quantities.
**Cysteine is corrected by percent normally recovered from performic acid hydrolysis of the standard protein.

The results obtained from the 16 kDa and 18 kDa subunits, when combined, closely resemble the numbers obtained from the native 30 kDa protein. The high figures obtained for glycine and serine are most likely the result of gel elution.

3. Demonstration That the 30 kDa Protein is Osteogenic Protein

3.1 Gel Slicing

Gel slicing experiments confirm that the isolated 30 kDa protein is the protein responsible for osteogenic activity.

Figure 14:
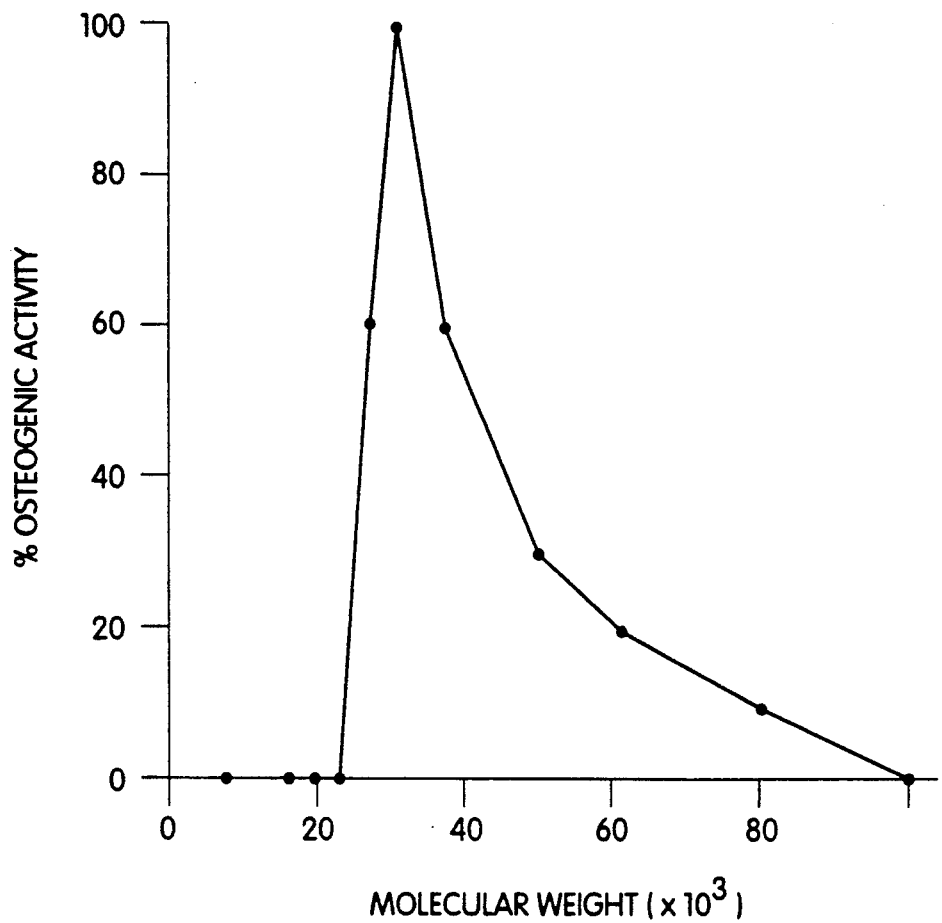
FIG. 14 is a graph of osteogenic activity vs. increasing molecular weight showing peak bone forming activity in the 30 kDa region of an SDS polyacrylamide gel.

Gels from the last step of the purification are sliced. Protein in each fraction is extracted in 15 mM Tris-HCl, pH 7.0 containing 0.1% SDS. The extracted proteins are desalted, concentrated, and assayed for endochondral bone formation activity. The results are set forth in FIG. 14. Activity in higher molecular weight regions apparently is due to protein aggregation. These protein aggregates, when reduced, yield the 16 kDa and 18 kDa species discussed above.

3.2 Con A-Sepharose Chromatography

A sample containing the 30 kDa protein is solubilized using 0.1% SDS, 50 mM Tris-HCl, and is applied to a column of Con A-Sepharose equilibrated with the same buffer. The bound material is eluted in SDS Tris-HCl buffer containing 0.5M alpha-methyl mannoside. After reverse phase chromatography of both the bound and unbound fractions, Con A-bound materials, when implanted, result in extensive bone formation (see Sections III-V, infra, for assay methodologies). Further characterization of the bound materials show a Con A-blottable 30 kDa protein. Accordingly, the 30 kDa glycosylated protein is responsible for the bone forming activity.

3.3 Gel Permeation Chromatography

Figure 9:
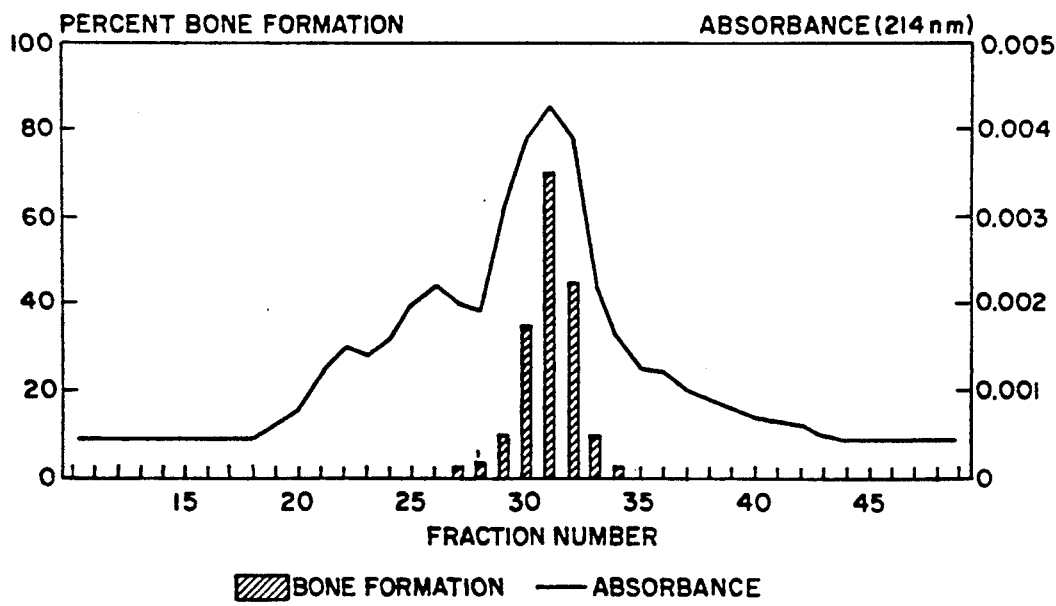
FIG. 9 is a gel permeation chromatogram of an elution profile on TSK 3000/2000 gel of the C-18 purified osteogenic peak fraction. Superimposed is the percent bone formation in each fraction.

TSK-3000/2000 gel permeation chromatography in guanidine-HCl is used to achieve separation of the high specific activity fraction obtained from C-18 chromatography (FIG. 9). The results demonstrate that the peak of bone inducing activity elutes in fractions containing substantially pure 30 kDa protein by Coomassie blue staining. When this fraction is iodinated and subjected to autoradiography, a strong band at 30 kDa accounts for 90% of the iodinated proteins. The fraction induces bone formation in vivo at a dose of 50 to 100 ng per implant.

3.4 Structural Requirements for Biological Activity

Although the role of 30 kDa bOP is clearly established for bone induction, through analysis of proteolytic cleavage products we have begun to search for a minimum structure that is necessary for activity in vivo. The results of cleavage experiments demonstrate that pepsin treatment fails to destroy bone inducing capacity, whereas trypsin or CNBr completely abolishes the activity.

An experiment is performed to isolate and identify pepsin digested product responsible for biological activity. Samples used for pepsin digestion were 20%-30% pure. The buffer used is 0.1% TFA in water. The enzyme to substrate ratio is 1:10. A control sample is made without enzyme. The digestion mixture is incubated at room temperature for 16 hr. The digested product then is separated in 4M guanidine-HCl using gel permeation chromatography, and the fractions are prepared for in vivo assay. The results demonstrate that active fractions from gel permeation chromatography of the pepsin digest correspond to molecular weight of 8 kDa-10 kDa.

In order to understand the importance of the carbohydrates moiety with respect to osteogenic activity, the 30 kDa protein has been chemically degylcosylated using HF. After analyzing an aliquot of the reaction product by Con A blot to confirm the absence of carbohydrate, the material is assayed for its activity in vivo. The bioassay is positive (i.e., the deglycosylated protein produces a bone formation response as determined by histological examination shown in FIG. 17C), demonstrating that exposure to HF did not destroy the biological function of the protein. In addition, the specific activity of the deglycosylated protein is approximately the same as that of the native glycosylated protein.

B. Human Bone

Human bone is obtained from the Bone Bank, (Massachusetts General Hospital, Boston, Mass.), and is milled, defatted, demarrowed and demineralized by the procedure disclosed above. 320 g of mineralized milled bone yields 70-80 g of demineralized milled bone. Dissociative extraction and ethanol precipitation of the demineralized milled bone gives 12.5 g of guanidine-HCl extract.

Figure 10A:
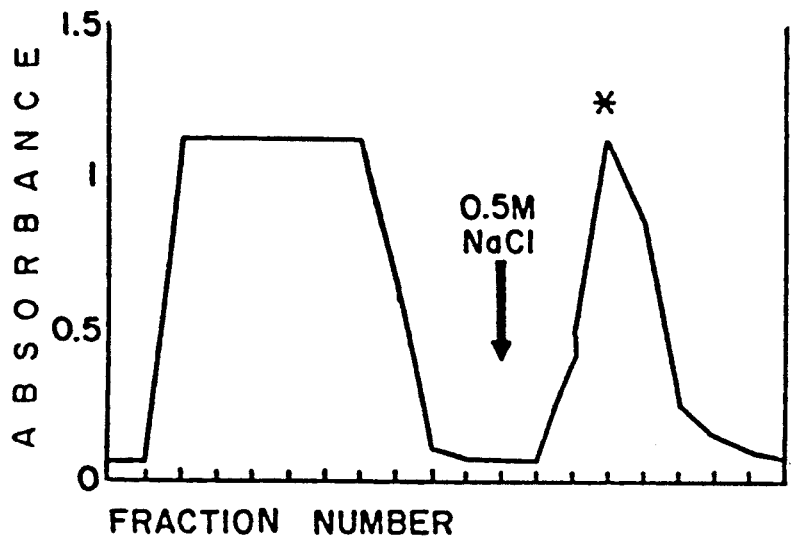
FIGS. 10A through 10D are a collection of graphs of protein concentration (as indicated by optical absorption) vs. elution volume illustrating the results of human osteogenic protein fractionation on heparin-Sepharose I (A), HAP-Ultragel (B), TSK 3000/2000 (C), and heparin-Sepharose II (D). Arrows indicate buffer changes and asterisk identifies active peak.
Figure 10B:
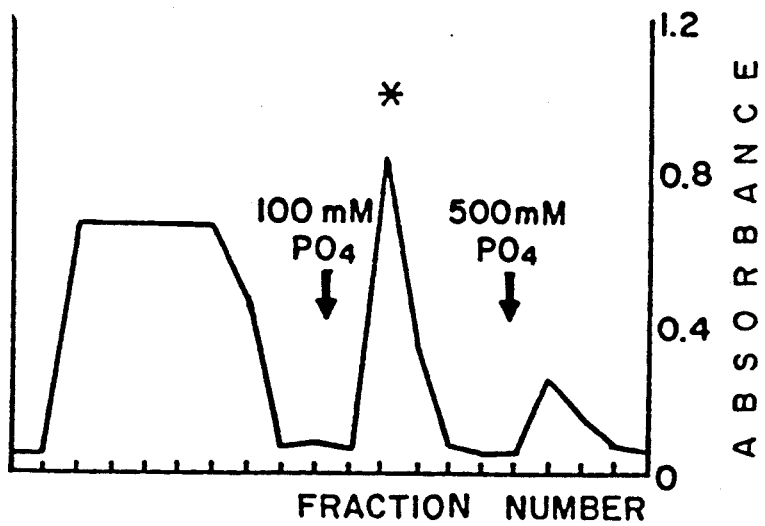
Figure 10C:
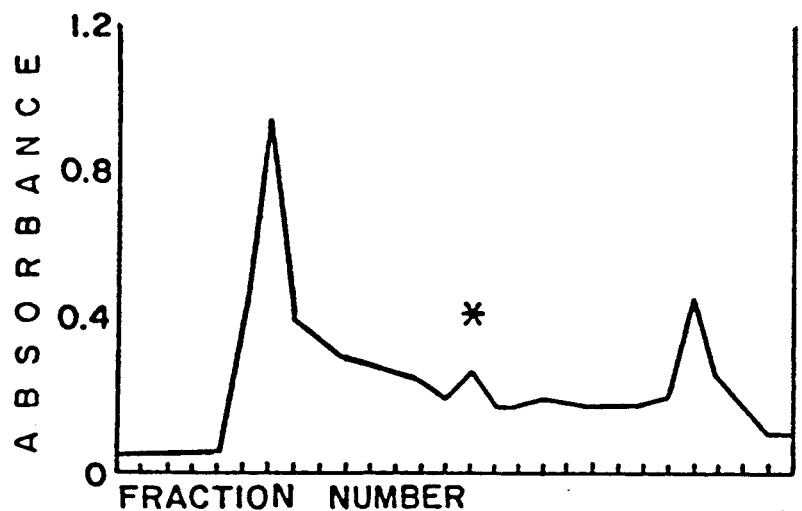
Figure 10D:
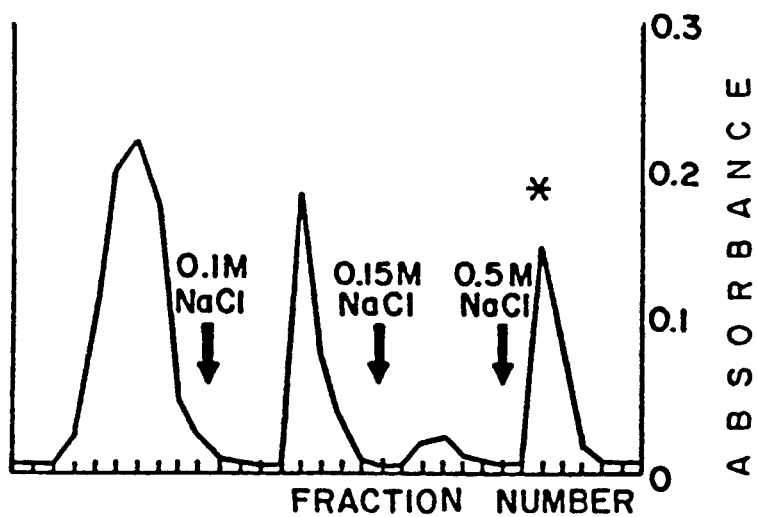

One third of the ethanol precipitate (0.5 g) is used for gel filtration through 4M guanidine-HCl (FIG. 10A). Approximately 70-80 g of ethanol precipitate per run is used. In vivo bone inducing activity is localized in the fractions containing proteins in the 30 kDa range. They are pooled and equilibrated in 6M urea, 0.5M NaCl buffer, and applied directly onto an HAP column; the bound protein is eluted stepwise by using the same buffer containing 100 mM and 500 mM phosphate (FIG. 10B). Bioassay of HAP bound and unbound fractions demonstrates that only the fraction eluted by 100 mM phosphate has bone inducing activity in vivo. The biologically active fraction obtained from HAP chromatography is subjected to heparin-Sepharose affinity chromatography in buffer containing low salt; the bound proteins are eluted by 0.5M NaCl (FIG. 10D. FIG. 10C describes the elution profile for the intervening gel filtration step described above). Assaying the heparin-Sepharose fractions shows that the bound fraction eluted by 0.5M NaCl has bone-inducing activity. The active fraction then is subject to C-18 reverse phase chromatography.

The active fraction subsequently can be subjected to SDS-PAGE as noted above to yield a band at about 30 kDa comprising substantially pure human osteogenic protein.

II. NOVEL OSTEOGENIC SEQUENCES

A. OP1

1. DNA Sequence Identification and Characterization

These discoveries enable preparation of DNAs encoding totally novel, non-native (e.g., not known to occur in nature) protein constructs which individually as homodimers and combined with other related species, possibly as heterodimers, are capable of producing true endochondral bone. They also permit expression of the natural material, truncated forms, muteins, analogs, fusion proteins, and various other variants and constructs, from cDNAs and genomic DNAs retrieved from natural sources or from synthetic DNA produced using the techniques disclosed herein and automated, commercially available equipment. The DNAs may be expressed using well established recombinant DNA technologies in procaryotic or eucaryotic host cells, or in cell-free systems, and may be oxidized and refolded in vitro if necessary for biological activity.

More specifically, a synthetic consensus gene shown in Seq. ID No. 33 and FIG. 18, was designed as a hybridization probe (see U.S. Pat. No. 4,968,590, filed Apr. 8, 1988.) The design was based on amino acid sequence data obtained by sequencing digestion fragments of naturally sourced material and on predictions from observed homologies of these sequences with members of the TGF-$\beta$ gene family. The consensus gene/probe exploited human codon bias as found in human TGF-$\beta$. The designed sequence then was constructed using known assembly techniques for oligonucleotides manufactured in a DNA synthesizer. Table 6, below, shows the identified homologies between tryptic peptides derived from bOP and amino acid sequences from Drosophila DPP protein (as inferred from the gene) and the Xenopus Vgl protein, both of which show strong homology with the bOP peptides, and TGF-beta and inhibin, which share somewhat less homology with the bOP peptides.

TABLE 6

| protein | amino acid sequence | homology |
|---|---|---|
| (bOP) | S F D A Y Y C S G A C Q F P S | |
| (DPP) | G Y D A Y Y C H G K C P F F L | (9/15 matches) |
| (bOP) | S F D A Y Y C S G A C Q F P S | |
| (Vgl) | G Y M A N Y C Y G E C P Y P L | (6/15 matches) |
| (bOP) | S F D A Y Y C S G A C Q F P S | |
| (inhibin) | G Y H A N Y C E G E C P S H I | (5/15 matches) |
| (bOP) | S F D A Y Y C S G A C Q F P S | |
| (TGF-β1) | G Y H A N F C L G P C P Y I W | (4/15 matches) |
| (bOP) | K/ R A C C V P T E L S A I S ML Y L D E N | |
| (Vgl) | L P C C V P T K M S P I S ML F Y D N N | (12/20 matches) |
| (bOP) | K/ R A C C V P T E L S A I S ML Y L D E N | |
| (inhibin) | K S C C V P T K L R P M S ML Y Y D D G | (12/20 matches) |
| (bOP) | K/ R A C C V P T E L S A I S ML Y L D E N | |
| (DPP) | K A C C V P T Q L D S V A ML Y L N D Q | (12/20 matches) |
| (bOP) | K/ R A C C V P T E L S A I S ML Y L D E | |
| (TGF-β1) | A P C C V P Q A L E P L P I V Y Y V G | (6/19/ matches) |
| (bOP) | L Y V D F | |
| (DPP) | L Y V D F | (5/5/ matches) |
| (bOP) | L Y V D F | |
| (Vgl) | L Y V E F | (4/5 matches) |
| (bOP) | L Y V D F | |
| (TGF-β1) | L Y I D F | (4/5 matches) |
| (bOP) | L Y V D F | |
| (inhibin) | F F V S F | (2/4 matches) |

In addition to its function as a probe, the consensus sequence also was designed to act as a synthetic consensus gene for the expression of a consensus osteogenic protein.

In determining the amino acid sequences of a consensus osteogenic protein from which the nucleic acid sequence can be determined, the following points are considered: (1) the amino acid sequence determined by Edman degradation of osteogenic protein tryptic fragments is ranked highest as long as it has a strong signal and shows homology or conservative changes when aligned with the other members of the gene family; (2) where the sequence matches for all four proteins, it is used in the synthetic gene sequence; (3) matching amino acids in DPP and Vgl are used; (4) If Vgl or DPP diverged but either one is matched by TGF-beta or by inhibin, this matched amino acid is chosen; (5) where all sequences diverge, the DPP sequence is initially chosen, with a later plan of creating the Vgl sequence by mutagenesis kept as a possibility. In addition, the consensus sequence is designed to preserve the disulfide crosslinking and the apparent structural homology. Finally, as more amino acid sequences of osteogenic proteins become available, the consensus gene can be improved to match, using known methods of site-directed mutagenesis. In the process, a family of analogs can be developed (see, for example, U.S. Pat. No. 5,011,691, filed Feb. 23, 1989).

A human genomic library (Maniatis-library) carried in lambda phage (Charon 4A) was screened using the probe and the following hybridization conditions: hybridizing in 5× SSPE, 10× Denhardt's Solution, 0.5% SDS at 50° C. and washing in 1× SSPE, 0.5% SDS at 50° C. Twenty-four positive clones were found. Five contained a gene encoding a protein never before reported, designated OP1, osteogenic protein-1, described below. Two others yielded genes corresponding to the BMP-2B protein, and one yielded a gene corresponding to the BMP3 protein (see PCT US 87/01537).

Southern blot analysis of lambda #13 DNA showed that an approximately 3 kb BamHI fragment hybridized to the probe (see nucleotides 1036–1349 of Seq. ID No. 3, and FIG. 18). This fragment was isolated and subcloned. Analysis of this sequence showed that the fragment encoded the carboxyl terminus of a protein, herein named OP1. The protein was identified by amino acid homology with the TGF-β family. Consensus splice signals were found where amino acid homologies ended, designating exon-intron boundaries. Three exons were combined to obtain a functional TGF-β-like domain containing seven cysteines. The DNA sequence of the functional domain then was used as a probe to screen a human cDNA library as described below.

The hOP1 probe was labeled with $^{32}$P and used to screen a human placenta 5' stretch lambda phage cDNA library (Clontech, Palo Alto, Calif.), and a human hippocampus library (Stratagene, Inc., La Jolla, Calif.), using high stringency hybridization conditions. Positive clones obtained from these libraries yielded a full length cDNA (translated region) for hOP1. This cDNA sequence, and the amino acid sequence it encodes, is set forth in Seq. ID No. 1. The partial genomic DNA sequence for the human OP1 gene is listed in Seq. ID No. 3. The protein coding region is encoded in seven exons separated by six introns in the genomic sequence (see Seq. ID No. 3.) It is possible that, as has been found in certain other mammalian genes, one or more of the introns may include sequences having a transcription regulatory function.

The native form protein is expressed originally as an immature translation product referred to herein as a "prepro" form which includes a signal peptide sequence necessary for appropriate secretion of the protein. Removal of the signal peptide yields the "pro" form of the protein, which is processed further to yield the mature secreted protein. Referring to Table I and Seq. ID No. 1, the amino acid sequence of the prepro form of OP1 (herein referred to as hOP1-PP) is described by residues 1–431. The amino acid residues 26 to 30 of Seq. ID No. 1 are believed to constitute a cleavage site for the removal of the N-terminal residues, constituting the signal peptide. Residues 289-292 of Seq ID No. 1 represent the pertinent Arg-Xaa-Xaa-Arg sequence where the pro form is believed to be cut to produce the mature form (e.g., cleavage occurs between residues 292 and 293.) Both the pro form and the prepro form, when properly dimerized, folded, adsorbed on a matrix, and implanted, display osteogenic activity, presumably due to proteolytic degradation resulting in cleavage and generation of mature form protein or active truncated analogs. (See Section II.A.2, infra). Mature OP1 contains 3 potential N glycosylation sites; there is an additional site in the precursor region.

The genomic clone lambda #18 DNA was found to contain the complete sequence encoding the protein referred to herein as CBMP2B. The DNA sequence corresponds to the sequence termed human BMP-2 Class II ("BMP4") in PCT US 87/01537. The CBMP2(b) gene consists of two exons. Exon 1 is approximately 0.37 kb and exon 2 (containing the TGF-β domain) is about 0.86 kb. The two exons are interrupted by an approximately 1 kb intron. Following the methodology used to identify the hOP1 cDNA, the coding sequence of the genomic CBMP2(b) clone was used as a probe to clone the full-length CBMP2(b) cDNA from a human placenta 5'-stretch cDNA library (Clontech, Palo Alto.) This cDNA sequence, and the predicted amino acid sequence it encodes, are set forth in Seq. ID No. 6.

The cDNA encoding the protein referred to herein as CBMP2A was cloned using the CBMP2(b) cDNA as a probe. The murine homolog first was cloned from a murine cDNA library and a portion of this cDNA sequence then used as a probe to clone the human CBMP2(a) cDNA from a human hippocampus cDNA library (Stratagene, Inc., LaJolla) and a human fetal lung library. Each of these human cDNA libraries yielded partial length clones which were then fused to yield the full length CBMP2(a) cDNA clone. The cDNA sequence for CBMP2(a), and its predicted encoded amino acid sequence, are set forth in Seq. ID No. 4. The DNA sequence corresponds to the sequence termed human BMP-2 Class I ("BMP2") in PCT US 87/01537.

The amino acid sequence corresponding to the conserved six cysteine skeleton in the active region of CBMP2B is described by amino acid residues 313 to 408 of Seq. ID No. 6 (herein referred to as "CBMP2BS" where "S" refers to "short form.") Similarly, the corresponding amino acid sequence of CBMP2A ("CBMP2AS") is described by amino acid residues 301 to 396 of Seq. ID No. 4.

Longer sequences defining the seven cysteine skeleton, are "CBMP2AL" (residues 296 to 396 of ID No. 4), and "CBMP2BL" (residues 308 to 408 of ID No. 6), where "L" refers to "long form."

Seq. ID Nos. 4 and 6 describe the human cDNA sequences for CBMP2(a) and CBMP2(b), respectively, as well as the encoded full-length, "prepro" forms of these proteins. Using the prediction methods devised by Von Heijne ((1986) *Nucleic Acids Research* 14:4683-4691), residues 20-24 indicate the region for the presumed signal peptide cleavage site for CBMP2A (Seq. ID No. 4), and residues 23-24 of Seq. ID No. 6 indicate the presumed cleavage site for CBMP2B. The cleavage site yielding the mature sequence of CBMP2A is believed to occur within the region described by residues 271-282 of ID No. 4; and within the region described by residues 280-292 of Seq. ID No. 6 for CBMP2B, although there remains uncertainty regarding where precise cleavage occurs for this protein. Finally, the CBMP2 proteins contain 4 or 5 potential glycosylation sites.

The consensus probe also identified a human genomic clone encoding a protein referred to herein as CBMP3. The DNA sequence corresponds to the sequence termed human BMP3 in PCT US 87/01357. A partial genomic sequence encoding part of the mature region of the CBMP3 protein is set forth in Seq. ID No. 20. Using the same general methodology as described for the cloning of the CBMP2B cDNA sequences, the murine cDNA encoding CBMP3 was cloned ("mCBMP3.") The cDNA encoding the mature region of this protein, and the encoded amino acid sequence, are set forth in Seq. ID No. 22.

Given the foregoing amino acid and DNA sequence information, various DNAs can be constructed which encode at least a minimal sequence encoding the active domain of OP1 and/or CBMP2, and various analogs thereof, as well as fusion proteins, truncated forms of the mature proteins, and similar constructs. Both the pro form and the prepro form are active, presumably because of in situ cleavage events or generation of active products by cleavage during protein processing. These DNAs can be produced by those skilled in the art using well known DNA manipulative techniques involving genomic and cDNA isolation, construction of synthetic DNA from synthesized oligonucleotides, and cassette mutagenesis techniques. 15-100mer oligonucleotides may be synthesized on a Biosearch DNA Model 8600 Synthesizer, and purified by polyacrylamide gel electrophoresis (PAGE) in Tris-Borate-EDTA buffer. The DNA then is electroeluted from the gel. Overlapping oligomers may be phosphorylated by T4 polynucleotide kinase and ligated into larger blocks which may also be purified by PAGE.

The cDNA or synthetic DNA then may be integrated into an expression vector and transfected into an appropriate host cell for protein expression. Because both the glycosylated and unglycosylated protein are active, the host may be a procaryotic or eucaryotic cell. Useful host cells include E. coli, Saccharomyces, the insect/baculovirus cell system, myeloma cells, and various other mammalian cells. The proteins of this invention preferably are expressed in mammalian cells, as disclosed herein. The vector additionally may include various sequences to promote correct expression of the recombinant protein, including transcription promoter and termination sequences, enhancer sequences, preferred ribosome binding site sequences, preferred mRNA leader sequences, preferred protein processing sequences, preferred signal sequences for protein secretion, and the like. The DNA sequence encoding the gene of interest also may be manipulated to remove potentially inhibiting sequences or to minimize unwanted secondary structure formation. The recombinant osteogenic protein also may be expressed as a fusion protein. After being translated, the protein may be purified from the cells themselves or recovered from the culture medium. All biologically active protein forms comprise dimeric species joined by disulfide bonds or otherwise associated, produced by oxidizing and refolding one or more of the various recombinant proteins within an appropriate eucaryotic cell or in vitro after expression of individual subunits.

2. Expression in E. coli

Using such techniques, various fusion genes can be constructed to induce recombinant expression of osteogenic sequences in a procaryotic host such as E. coli. In particular, the following DNAs have been prepared:

| Fusion DNA Sequences | Osteogenic Fusion Proteins | |
|---|---|---|
| OP1(a) | OP1A | (Seq. ID No. 8) |
| OP1(b) | OP1B | (Seq. ID No. 10) |
| OP1(c) | OP1C | (Seq. ID No. 12) |
| OP1(d) | OP1D | (Seq. ID No. 14) |
| CBMP2b1 | CBMP2B1 | (Seq. ID No. 16) |
| CBMP2b2 | CBMP2B2 | (Seq. ID No. 18) |

Construct OP1(a) is a cDNA sequence encoding substantially all of the mature form of OP1 (residues 326–431, Seq. ID No. 1) linked by an Asp-Pro acid cleavage site to a leader sequence ("MLE leader", amino acid residues 1–60 of Seq. ID No. 8) suitable for promoting expression in E. coli. OP1(b) (Seq. ID No. 10) encodes a truncated "pro" form of OP1. The sequence comprises the MLE leader linked to an OP1 sequence which begins within the precursor ("prepro") sequence (beginning at residue 176 of Seq. ID No. 1). OP1(c) comprises an MLE leader peptide (residues 1–53 of Seq. ID No. 12) linked to the full prepro form of OP1 cDNA including the presumed signal peptide (e.g., residues 1–29 of Seq. ID No. 1). OP1(d) comprises a leader sequence ("short TRP," residues 1–13 of Seq. ID No. 14), an Asp-Pro cleavage site, and the presumed entire pro form of the OP1 protein (residues 39–431 of Seq. ID No. 1). CBMP2b1 (Seq. ID No. 16) comprises the MLE leader (residues 1–56, Seq. ID No. 16) linked through an Asp-Pro acid cleavage site to substantially all of the mature form of CBMP2B (residues 296–408 of Seq. ID No. 6). Approximately one half of this construct comprised cDNA; the other half was synthesized from oligonucleotides. CBMP2b2 comprises the MLE leader (residues 1–60 of ID No. 18) linked to substantially all of the full length pro form of CBMP2B (residues 52–408 of Seq. ID No. 6).

The genes were expressed in E. coli under the control of a synthetic trp promoter-operator to produce insoluble inclusion bodies. The inclusion bodies were solubilized in 8M urea following lysis, dialyzed against 1% acetic acid, and partly purified by differential solubilization. Constructs containing the Asp-Pro site were cleaved with acid. The resulting products were passed through a Sephacryl-200HR or SP Trisacyl column to further purify the proteins, and then subjected to HPLC on a semi-prep C-18 column to separate the leader proteins and other minor impurities from the OP1, or CBMP2 constructs. Both the CBMP2 and OP1 proteins may be purified by chromatography on heparin-Sepharose. The output of the HPLC column was lyophilized at pH 2 so that it remains reduced.

Conditions for refolding were at pH 8.0 using Tris buffer and 6M guanidine-HCl at a protein concentration of several mg/ml. Those solutions were diluted with water to produce a 2M or 3M guanidine concentration and left for 18 hours at 4° C. Air dissolved or entrained in the buffer assures oxidation of the protein in these circumstances.

Samples of the various purified constructs and various mixtures of pairs of the constructs refolded together were applied to SDS polyacrylamide gels, separated by electrophoresis, sliced, incorporated in a matrix as disclosed below, and tested for osteogenic activity. These studies demonstrated that each of the constructs disclosed above have true osteogenic activity. Thus, both the pro form and prepro form, when properly dimerized, folded, adsorbed on a matrix, and implanted, display osteogenic activity, presumably due to proteolytic degradation resulting in cleavage and generation of mature form protein or active truncated species. In addition, mixed species also are osteogenically active and may include heterodimers. Specific combinations tested include: OP1A-CBMP2B1, OP1B-CMP2B1, and OP1C-CBMP2B2. Finally, single and mixed species of analogs of the active region, e.g., COP5 and COP7, disclosed in U.S. Pat. No. 5,011,691, also induce osteogenesis, as determined by histological examination.

After N-terminal sequencing of the various constructs to confirm their identity, polyclonal antisera against the recombinant presumed mature form proteins were produced. The human OP1 antisera reacted with both the glycosylated and unglycosylated higher molecular weight subunits of naturally sourced bovine material. Antisera against recombinant mature human CBMP2 reacted with both the glycosylated and unglycosylated lower molecular weight subunit of naturally sourced bovine material. While there was some cross-reactivity, this was expected in view of the significant homology between CBMP2 and OP1 (approx. 60% identity), and the likelihood that degraded OP1 generated during purification contaminates the lower molecular weight subunit. Both antisera react with the naturally sourced 30 kDa dimeric bOP.

3. Mammalian Cell Expression

As stated earlier, it is generally held that recombinant production of mammalian proteins for therapeutic uses are preferably expressed in mammalian cell culture systems in order to produce a protein whose structure is most like that of the natural material. Recombinant protein production in mammalian cells requires the establishment of appropriate cells and cell lines that are easy to transfect, are capable of stably maintaining foreign DNA with an unrearranged sequence, and which have the necessary cellular components for efficient transcription, translation, post-translation modification, and secretion of the protein. In addition, a suitable vector carrying the gene of interest also is necessary. DNA vector design for transfection into mammalian cells should include appropriate sequences to promote expression of the gene of interest as described supra, including appropriate transcription initiation, termination, and enhancer sequences, as well as sequences that enhance translation efficiency, such as the Kozak consensus sequence. Preferred DNA vectors also include a marker gene and means for amplifying the copy number of the gene of interest.

Substantial progress in the development of mammalian cell expression systems has been made in the last decade and many aspects of the system are well characterized. A detailed review of the state of the art of the production of foreign proteins in mammalian cells, including useful cells, protein expression-promoting sequences, marker genes, and gene amplification methods, is disclosed in Bendig, Mary M., (1988) *Genetic Engineering* 7:91–127.

Briefly, among the best characterized transcription promoters useful for expressing a foreign gene in a particular mammalian cell are the SV40 early promoter, the adenovirus promoter (AdMLP), the mouse metallothionein-I promoter (mMT-I), the Rous sarcoma virus (RSV) long terminal repeat (LTR), the mouse mammary tumor virus long terminal repeat (MMTV-LTR), and the human cytomegalovirus major intermediate-early promoter (hCMV). The DNA sequences for all of these promoters are known in the art and are available commercially.

One of the better characterized methods of gene amplification in mammalian cell systems is the use of the selectable DHFR gene in a dhfr-cell line. Generally, the DHFR gene is provided on the vector carrying the gene of interest, and addition of increasing concentrations of the cytotoxic drug methotrexate leads to amplification of the DHFR gene copy number, as well as that of the associated gene of interest. DHFR as a selectable, amplifiable marker gene in transfected chinese hamster ovary cell lines (CHO cells) is particularly well characterized in the art. Other useful amplifiable marker genes include the adenosine deaminase (ADA) and glutamine synthetase (GS) genes.

In the currently preferred expression system, gene amplification is further enhanced by modifying marker gene expression regulatory sequences (e.g., enhancer, promoter, and transcription or translation initiation sequences) to reduce the levels of marker protein produced. As disclosed herein, lowering the level of DHFR transcription has the effect of increasing the DHFR gene copy number (and the associated OP1 gene) in order for a transfected cell to adapt to grow in even low levels of MTX (e.g., 0.1 μM MTX). Preferred expression vectors (pH754 and pH752), have been manipulated using standard recombinant DNA technology, to create a weak DHFR promoter (see infra). As will be appreciated by those skilled in the art, other useful weak promoters, different from those disclosed and preferred herein, can be constructed using standard vector construction methodologies. In addition, other, different regulatory sequences also can be modified to achieve the same effect.

The choice of cells/cell lines is also important and depends on the needs of the experimenter. Monkey kidney cells (COS) provide high levels of transient gene expression, providing a useful means for rapidly testing vector construction and the expression of cloned genes. COS cells are transfected with a simian virus 40 (SV40) vector carrying the gene of interest. The transfected COS cells eventually die, thus preventing the long term production of the desired protein product. However, transient expression does not require the time consuming process required for the development of a stable cell line.

Among established cell lines, CHO cells may be the best characterized to date, and are the currently preferred cell line for mammalian cell expression of recombinant osteogenic protein. CHO cells are capable of expressing proteins from a broad range of cell types. The general applicability of CHO cells and its successful production for a wide variety of human proteins in unrelated cell types emphasizes the underlying similarity of all mammalian cells. Thus, while the glycosylation pattern on a recombinant protein produced in a mammalian cell expression system may not be identical to the natural protein, the differences in oligosaccharide side chains are often not essential for biological activity of the expressed protein.

Methods for expressing and purifying recombinant osteogenic proteins such as OP1 from a variety of mammalian cells, the nature of the xenogenic matrix, and other material aspects concerning the nature, utility, and how to make and how to use the subject matter claimed will be further understood from the following, which constitutes the best method currently known for practicing the invention. The methodology disclosed herein includes the use of COS cells for the rapid evaluation of vector construction and gene expression, and the use of established cell lines for long term protein production. Of the cell lines disclosed, OP1 expression from CHO cell lines currently is most preferred.

3.1 Recombinant Protein Expression In Mammalian Cells

Several different mammalian cell expression systems have been used to express recombinant OP1 proteins of this invention. In particular, COS cells are used for the rapid assessment of vector construction and gene expression, using an SV40 vector to transfect the DNA sequence into COS cells. Stable cell lines are developed using CHO cells (chinese hamster ovary cells) and a temperature-sensitive strain of BSC cells (simian kidney cells, BSC40-tsA58, (1988) *Biotechnology* 6: 1192–1196) for the long term production of OP1. Two different promoters were found most useful to transcribe hOP1: the CMV promoter and the MMTV promoter, boosted by the enhancer sequence from the Rous sarcoma virus LTR. The mMT promoter (mouse metallothionein promoter) and the SV40 late promoter also have been tested. Several selection marker genes also are used, namely, neo (neomycin) and DHFR. The DHFR gene also may be used as part of a gene amplification scheme for CHO cells. Another gene amplification scheme relies on the temperature sensitivity (ts) of BSC40-tsA58 cells transfected with an SV40 vector. Temperature reduction to 33° C. stabilizes the ts SV40 T antigen which leads to the excision and amplification of the integrated transfected vector DNA, thereby also amplifying the associated gene of interest.

Stable cell lines were established for CHO cells as well as BSC40-tsA58 cells (hereinafter referred to as "BSC cells"). The various cells, cell lines and DNA sequences chosen for mammalian cell expression of the OP1 proteins of this invention are well characterized in the art and are readily available. Other promoters, selectable markers, gene amplification methods and cells also may be used to express the OP1 proteins of this invention, as well as other osteogenic proteins. Particular details of the transfection, expression, and purification of recombinant proteins are well documented in the art and are understood by those having ordinary skill in the art. Further details on the various technical aspects of each of the steps used in recombinant production of foreign genes in mammalian cell expression systems can be found in a number of texts and laboratory manuals in the art, such as, for example, F. M. Ausubel et al., ed., *Current Protocols in Molecular Biology*, John Wiley & Sons, New York, (1989.)

3.2 Exemplary Expression Vectors

FIG. 19 (A–F) discloses restriction maps of various exemplary expression vectors designed for OP1 expression in mammalian cells. Each of these vector constructs employs a full-length hOP1 cDNA sequence originally isolated from a human cDNA library (human placenta) and subsequently cloned into a conventional pUC vector (pUC-18) using pUC polylinker sequences at the insertion sites. The hOP1 cDNA fragment cloned into each of these constructs is either the intact SmaI-BamHI hOP1 cDNA fragment (nucleotides 26–1385 of Seq. ID No. 1), or modifications of this fragment where the flanking non-coding 5' and/or 3' sequences have been trimmed back, using standard molecular biology methodology. Each vector also employs an SV40 origin of replication (ori), useful for mediating plasmid replication in primate cells (e.g., COS and BSC cells). In addition, the early SV40 promoter is used to drive transcription of marker genes on the vector (e.g., neo and DHFR). It will be appreciated by those skilled in the art that DNA sequences encoding truncated forms of the osteogenic protein also may be used, provided that the expression vector or host cell then provides the sequences necessary to direct processing and secretion of the expressed protein.

The pH717 expression vector (FIG. 19A) contains the neomycin (neo) gene as a selection marker. This marker gene is well characterized in the art and is available commercially. Alternatively, other selectable markers may be used. The particular vector used to provide the neo gene DNA fragment for pH717 may be obtained from Clontech, Inc., Palo Alto, CA (pMAM-neo-blue). This vector also may be used as the backbone. In pH717, hOP1 DNA transcription is driven by the CMV promoter, boosted by the RSV-LTR and MMTV-LTR (mouse mammary tumor virus) enhancer sequences. These sequences are known in the art, and are available commercially. For example, vectors containing the CMV promoter sequence may be obtained from Invitrogen Inc., San Diego, Calif., (e.g., pCDM8).

Expression vector pH731 (FIG. 19B), utilizes the SV40 late promoter to drive hOP1 transcription. As indicated above, the sequence and characteristics of this promoter also are well known in the art. For example, pH731 may be generated by inserting the SmaI-BamHI fragment of hOP1 into pEUK-Cl (Clontech, Inc., Palo Alto, Calif.).

Figure 19A:
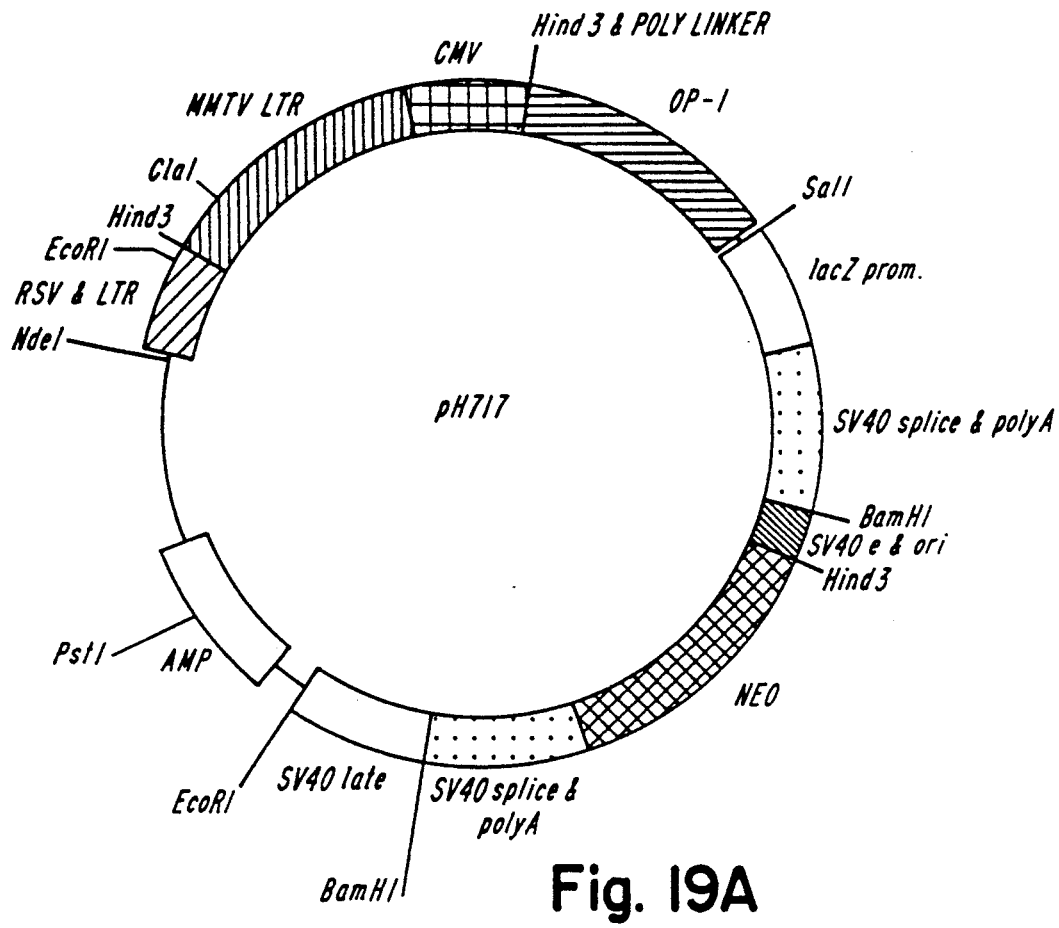
FIGS. 19 A through 19 F are restriction maps of various expression vectors designed for the mammalian cell expression of OP1.
Figure 19B:
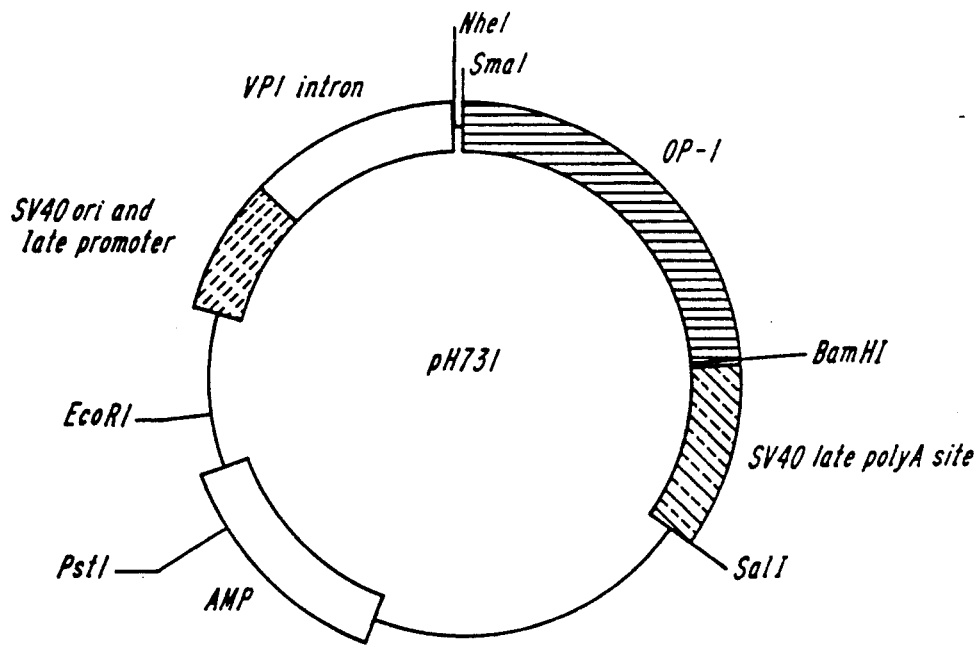
Figure 19C:
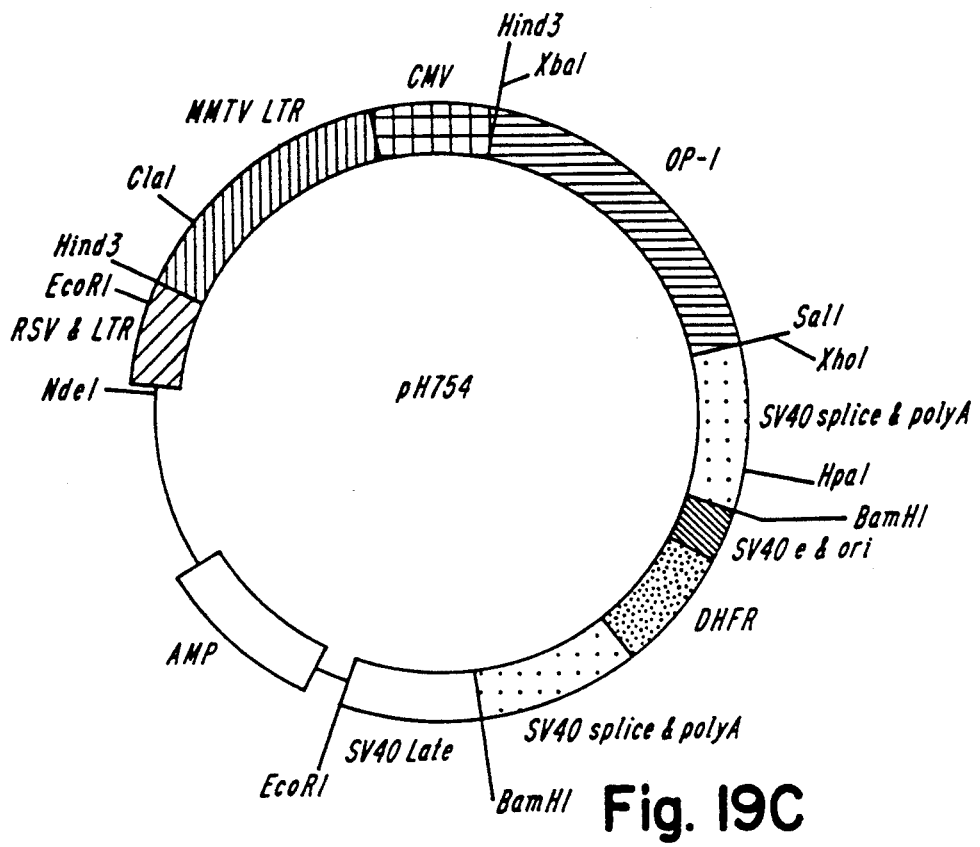
Figure 19D:
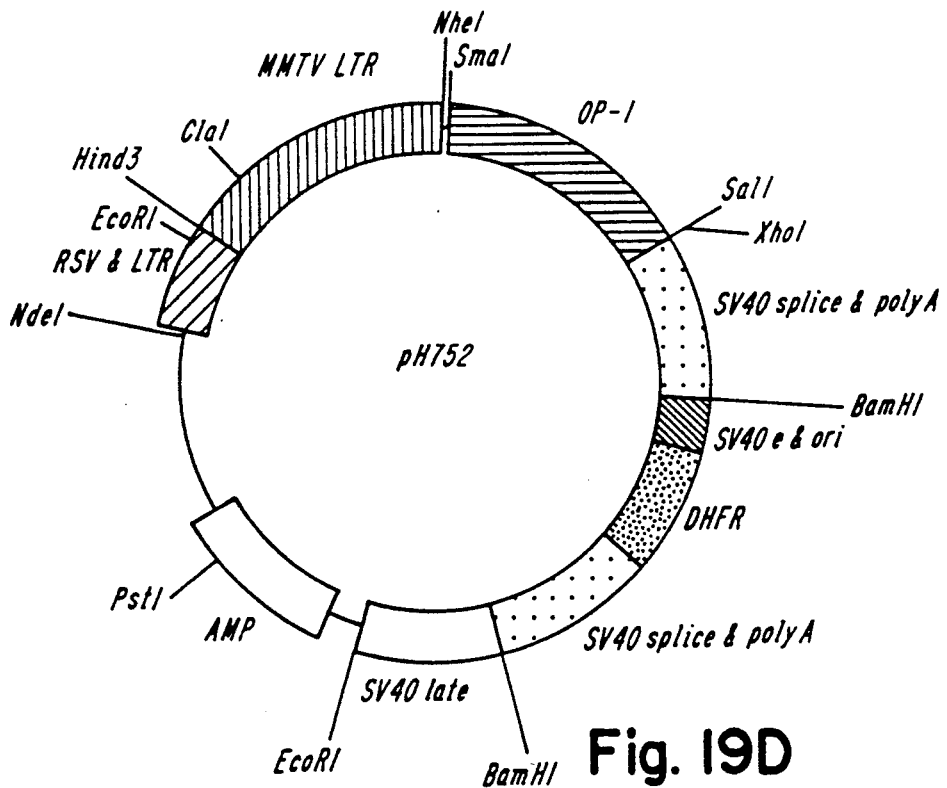
Figure 19E:
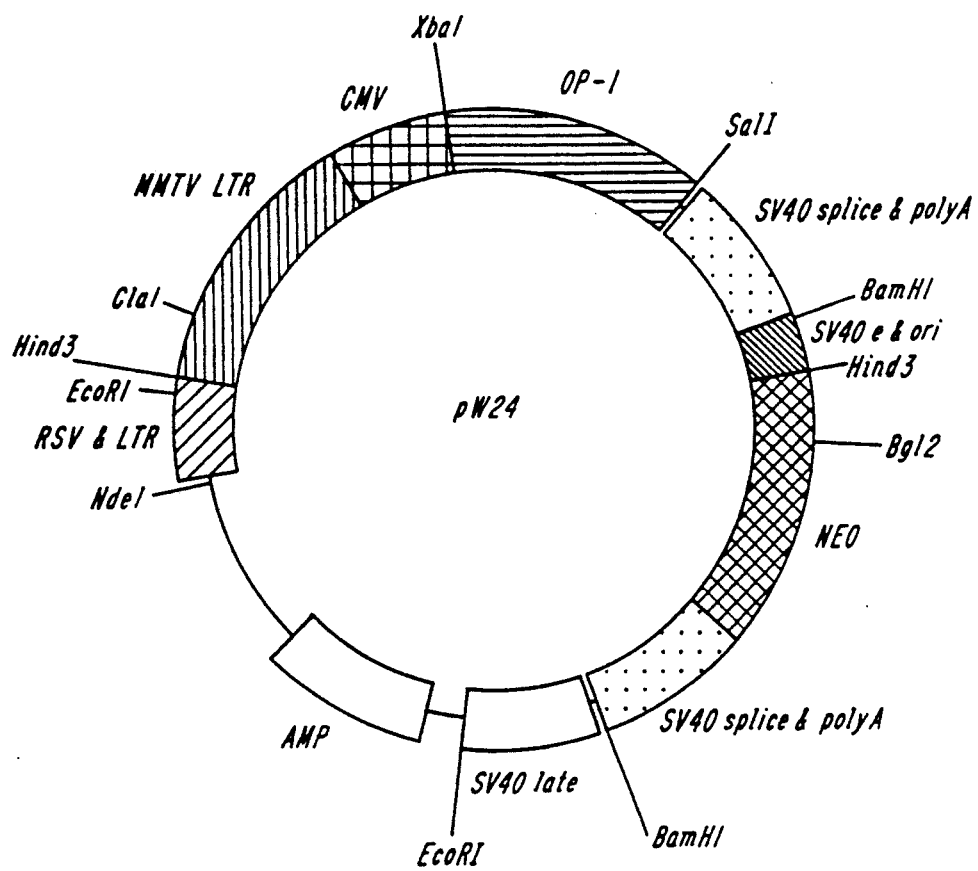
Figure 19F:
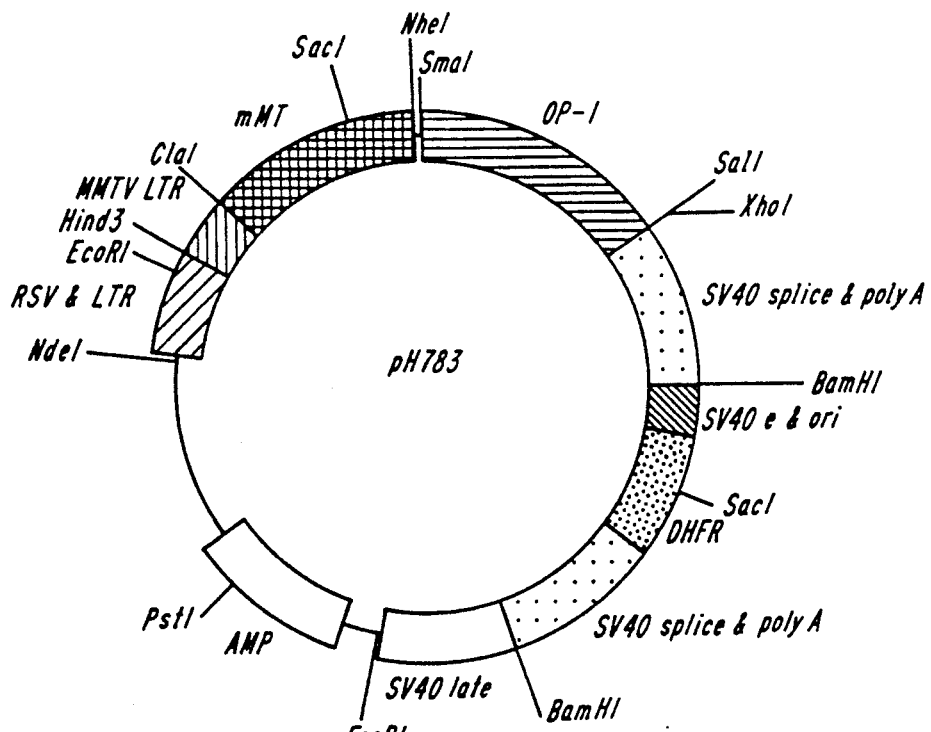

The pH752 and pH754 expression vectors contain the DHFR gene, under SV40 early promoter control, as both a selection marker and as an inducible gene amplifier. The DNA sequence for DHFR is well characterized in the art, and is available commercially. For example, pH754 may be generated from pMAM-neo (Clontech, Inc., Palo Alto, Calif.) by replacing the neo gene (BamHI digest) with an SphI-BamHI, or a PvuII-BamHI fragment from pSV5-DHFR (ATCC #37148), which contains the DHFR gene under SV40 early promoter control. A BamHI site can be engineered at the SphI or PvuII site using standard techniques (e.g., by linker insertion or site-directed mutagenesis) to allow insertion of the fragment into the vector backbone. hOP1 DNA can be inserted into the polylinker site downstream of the MMTV-LTR sequence (mouse mammary tumor virus LTR), yielding pH752 (FIG. 19D). The CMV promoter sequence then may be inserted into pH752 (e.g., from pCDM8, Invitrogen,Inc.), yielding pH754 (FIG. 19C.) The SV40 early promoter, which drives DHFR expression, is modified in these vectors to reduce the level of DHFR mRNA produced. Specifically, the enhancer sequences and part of the promoter sequence have been deleted, leaving only about 200 bases of the promoter sequence upstream of the DHFR gene. Host cells transfected with these vectors are adapted to grow in 0.1 $\mu$M MTX and can increase OP1 production significantly (see Table 8).

The pW24 vector (FIG. 19E), is essentially identical in sequence to p754, except that neo is used as the marker gene (see pH717), in place of DHFR.

Similarly, pH783 (FIG. 19F) contains the amplifiable marker DHFR, but here OP1 is under mMT (mouse metallothionein promoter) control. The mMT promoter is well characterized in the art and is available commercially.

All vectors tested are stable in the various cells used to express OP1, and provide a range of OP1 expression levels.

3.3 Exemplary Mammalian Cells

Recombinant OP1 has been expressed in three different cell expression systems: COS cells for rapidly screening the functionality of the various expression vector constructs, CHO cells for the establishment of stable cell lines, and BSC40-tsA58 cells as an alternative means of producing OP1 protein. The CHO cell expression system disclosed herein is contemplated to be the best mode currently known for long term recombinant OP1 production in mammalian cells.

a) COS CELLS

COS cells (simian kidney cells) are used for rapid screening of vector constructs and for immediate, small scale production of OP1 protein. COS cells are well known in the art and are available commercially. The particular cell line described herein may be obtained through the American Type Culture Collection (ATCC #COS-1, CRL-1650).

OP1 expression levels from different vectors, analyzed by Northern and Western blot assays, are compared in Table 7 below:

TABLE 7

ANALYSIS OF OP1 EXPRESSION IN COS CELLS

| Vector | mRNA | OP1 Production |
|---|---|---|
| pH717 | +++ | ++ |
| pH731 | + | + |
| pH752 | +++ | ++++ |
| pH754 | +++ | ++++ | pH752- and pH754-transfected COS cells appear to produce the highest yield of OP1 to date. However, because transfected COS cells do not divide and die several days post-transfection, large amounts of plasmid DNA are required for each scaled up transformation.

Large scale preparations of OP1 from transfected COS cells may be produced using conventional roller bottle technology. Briefly, $14 \times 10^6$ cells are used to seed each bottle. After 24 hrs of growth, the cells are transfected with 10 μg of vector DNA (e.g., pH717) per $10^6$ cells, using the DEAE-dextran method. Cells are then conditioned in serum-free media for 120 hr before harvesting the media for protein analysis. Following this protocol, OP1 yield is approximately 2-6 ng/ml.

b) BSC CELLS

The BSC40-tsA58 cell line ("BSC cells") is a temperature-sensitive strain of simian kidney cells ((1988), *Biotechnology* 6: 1192-1196) which overcomes some of the problems associated with COS cells. These BSC cells have the advantage of being able to amplify gene sequences rapidly on a large scale with temperature downshift, without requiring the addition of exogenous, potentially toxic drugs. In addition, the cells may be recycled. That is, after induction and stimulation of OP1 expression, the cells may be transferred to new growth medium, grown to confluence at 39.5° C. and induced a second time by downshifting the temperature to 33° C. BSC cells may be used to establish stable cell lines rapidly for protein production.

OP1 expression in transfected BSC cells may be induced by shifting the temperature down to 33° C., in media containing 10% FCS, and harvesting the conditioned media after 96 hrs of incubation. Comparable amounts of OP1 mRNA and protein are obtained, as compared with CHO cells (e.g., 100-150 ng OP1/ml conditioned media from BSC clones transfected with pH717, see infra).

c) CHO Cells

CHO cells (chinese hamster ovary cells) may be used for long term OP1 production and are the currently preferred cell line for mammalian cell expression of OP1. CHO cell lines are well characterized for the small and large scale production of foreign genes and are available commercially. The particular cell line described herein is CHO-DXB11, (Lawrence Chasin, Columbia University, N.Y.). Table 8, below, shows exemplary OP1 yields obtained with a variety of expression vectors.

TABLE 8

| CHO Cells | Plasmid | Selection Marker | OP1 Production ng/ml |
|---|---|---|---|
|  | pH717 | NEO | 2-5 |
| * | pH752/pH754 | DHFR | 100-150 |

*Cells are adapted to grow in 0.1 μM methotrexate

CHO cells may be transfected by conventional calcium phosphate technique. CHO cells preferably are transfected with pH754 or pH752 and are conditioned in media containing serum proteins, as this appears to enhance OP1 yields. Useful media includes media containing 0.1-0.5% dialyzed fetal calf serum (FCS).

The currently preferred best mode for establishing a stable OP1 production cell line with high hOP1 expression levels comprises transfecting a stable CHO cell line, preferably CHO-DXB11, with the pH752 OP1 expression vector, isolating clones with high OP1 expression levels, and subjecting these clones to cycles of subcloning using a limited dilution method described below to obtain a population of high expression clones. Subcloning preferably is performed in the absence of MTX to identify stable high expression clones which do not require addition of MTX to the growth media for OP1 production.

In the subcloning protocol cells are seeded on ten 100 mm petri dishes at a cell density of either 50 or 100 cells per plate, with or preferably without MTX in the culture media. After 14 days of growth, clones are isolated using cloning cylinders and standard procedures, and cultured in 24-well plates. Clones then are screened for OP1 expression by Western immunoblots using standard procedures, and OP1 expression levels compared to parental lines. Cell line stability of high expression subclones then is determined by monitoring OP1 expression levels over multiple cell passages (e.g., four or five passages).

3.4 Evaluation of OP1 transfected cells

Expression levels of transfected OP1 sequences can be measured in the different systems by analyzing mRNA levels (Northern blots), using total cellular RNA and conventional hybridization methodology. Generally, about $1 \times 10^6$ cells are needed for mRNA analysis. Data between individual cell lines can be compared if the total number of cells and the total amount of mRNA is normalized, using rRNA as an internal standard. Ribosomal RNA is visualized in the agarose gel by ethidium bromide stain prior to transfer of the RNA to nitrocellulose sheets for hybridization. Ribosomal RNA also provides an indicator of the integrity of the RNA preparation.

Figure 20:
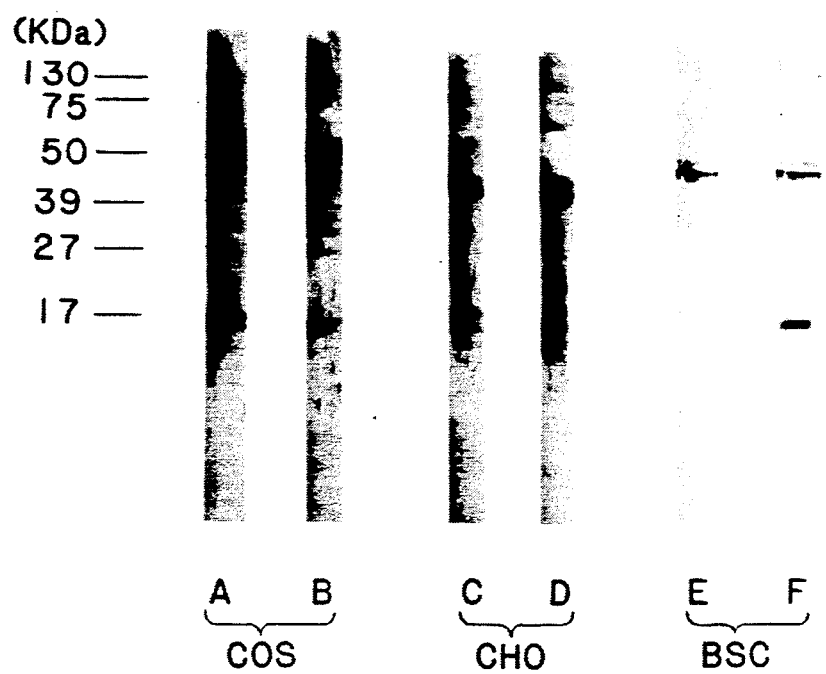
FIG. 20 is a photoreproduction of Western blots (immunoblots) comparing OP1 expressed from: COS cells - (A) pH717, (B) pH731; CHO cells - (C) pH754, (D) pH752; and BSC cells - (E) pH717, (F) pW24.

OP1 protein levels also may be measured by Western blots (immunoblots) using rabbit antisera against human OP1. FIG. 20 is an immunoblot showing OP1 production in: COS cells—(A) pH717, (B) pH731; CHO cells—(C) pH754, (D) pH752; and BSC cells—(E) pH717 and (F) pW24.

Southern blots may be used to assess the state of integrated OP1 sequences and the extent of their copy number amplification. The copy number of excised plasmids in temperature-shifted BSC cells also can be determined using Southern blot analysis.

3.5 Protein Purification

The purification scheme developed to purify the recombinant osteogenic proteins of this invention is rapid and highly effective. The protocol involves three chromatographic steps (S-Sepharose, phenyl-Sepharose and C-18 HPLC), and produces OP1 of about 90% purity.

For a typical 2L preparation of transfected BSC cells conditioned in 0.5% FCS, the total protein is 700 mg. The amount of OP1 in the media, estimated by Western blot, is about 80 μg OP1 media is diluted to 6M urea, 0.05M NaCl, 13 mM HEPES, pH 7.0 and loaded onto an S-Sepharose column, which acts as a strong cation exchanger. OP1 binds to the column in low salt, and serum proteins are removed. The column is subsequently developed with two step salt elutions. The first elution (0.1M NaCl) removes contaminants and approximately 10% of the bound OP1. The remaining 90% of OP1 then is eluted in 6M urea, 0.3M NaCl, 20 mM HEPES, pH 7.0.

Ammonium sulfate is added to the 0.3M NaCl fraction to obtain final solution conditions of 6M urea, 1M $(NH_4)_2SO_4$, 0.3M NaCl, 20 mM HEPES, pH 7.0. The sample then is loaded onto a phenyl-Sepharose column (hydrophobic interaction chromatography). OP1 binds phenyl-Sepharose in the presence of high concentrations of a weak chaotropic salt (e.g., 1M $(NH_4)_2SO_4$). Once OP1 is bound, the column is developed with two step elutions using decreasing concentrations of ammonium sulfate. The first elution (containing 0.6M $(NH_4)_2SO_4$) primarily removes contaminants. The bound OP1 then is eluted with a 6M urea, 0.3M NaCl, 20mM HEPES, pH 7.0 buffer containing no ammonium sulfate.

Figure 22:
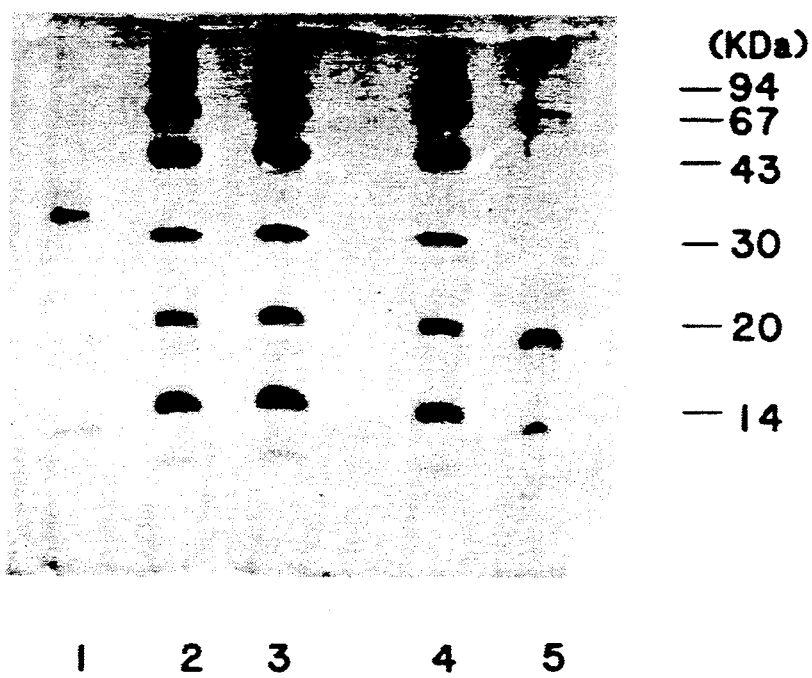
FIG. 22 is a photoreproduction of SDS-PAGE gels of OP1 purified from BSC cells, comparing the intact dimer under oxidized conditions (36 kDa, lane 1) and the corresponding monomer, after reduction with dithiothreitol (18 kDa, lane 5), with molecular weight standards (lanes 2-4)
Figure 25A:
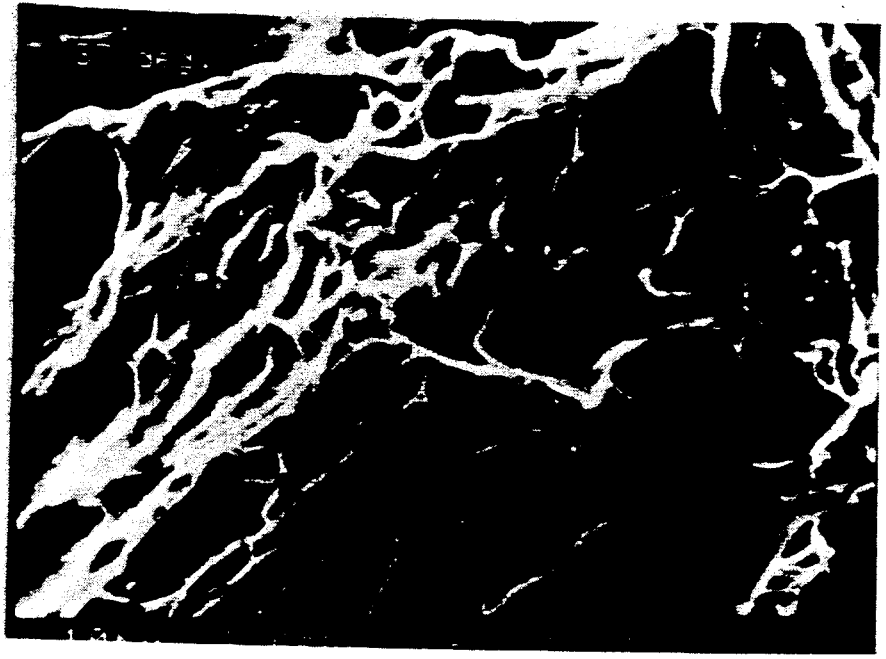
FIGS. 25A through 25D are scanning electron micrographs (approx. 1000×) of demineralized, delipidated bovine bone matrix heat treated in water at (A) 37° C., (B) 45° C., (C) 55° C., and (D) 65° C.
Figure 25B:
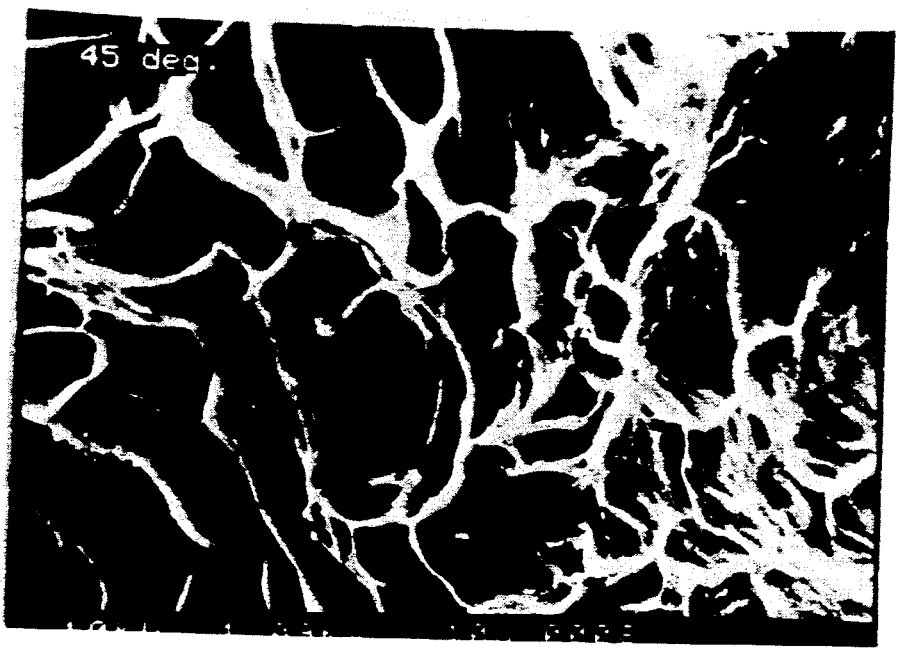
Figure 25C:
Figure 25D:
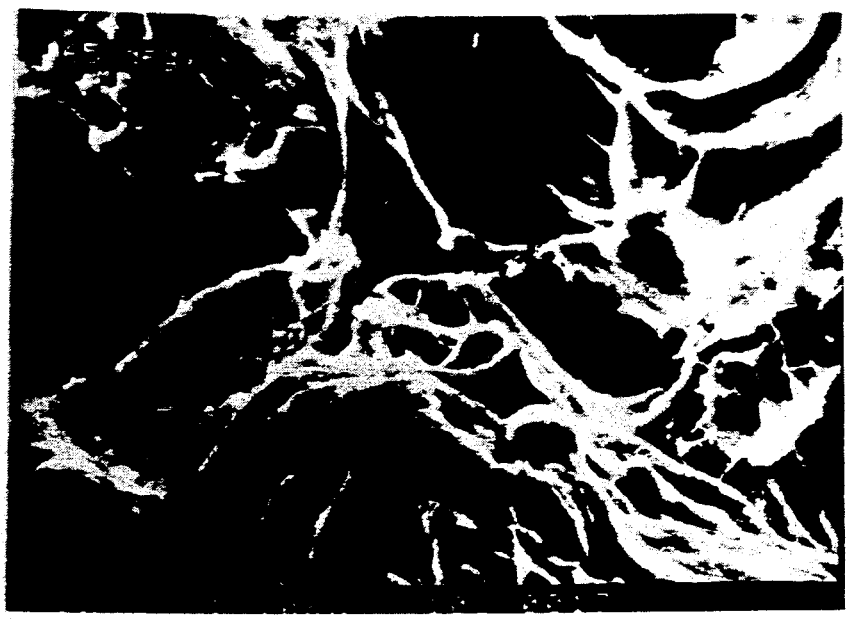

The OP1 eluted from the phenyl-Sepharose column is dialyzed against water, followed by 30% acetonitrile (0.1% TFA), and then applied to a C-18 reverse phase HPLC column. FIGS. 21A, B, and C are (1) chromatograms and (2) Coomassie-stained SDS-PAGE gels of fractions after reduction with dithiothreitol (DTT) eluting from the (A) S-Sepharose, (B) phenyl-Sepharose, and (C) C-18 columns. Gel separation of oxidized and reduced OP1 samples show that the reduced subunit has an apparent molecular weight of about 18 kDa, and the dimer has an apparent molecular weight of about 36 kDa, as illustrated in FIG. 22. The subunit size appears to be identical to that purified from COS cells, as well as that of the naturally-sourced OP purified from bone. This purification protocol yields about 30 μg of OP1 for 2L of conditioned media, a recovery of about 25% of the total OP1 in the conditioned media, as estimated by gel scanning.

An alternative chromatography protocol is to perform the S-Sepharose chromatography in the absence of 6M urea. The bound proteins then are eluted with salt step elutions (e.g., 100-400 mM NaCl). Most of the OP1 is eluted with about 300 mM NaCl. Additional OP1 then can be eluted with 300 mM NaCl in the presence of 6M urea. The 6M urea elution also may be used in place of the non-urea elution to achieve maximum recovery in one step. In addition, OP1 may be eluted from the phenyl-Sepharose column in 38% ethanol-0.01% TFA, thereby eliminating the need to dialyze the eluent before applying it to the C-18 column. Finally, multiple C-18 columns may be used (e.g., three), to further enhance purification and concentration of the protein.

OP1 also will bind hydroxyapatite efficiently, but only in the absence of 6M urea and at low phosphate concentrations (less than 5 mM phosphate). Bound OP1 can be removed from the column with a step elution of 1 mM to 0.5M phosphate (in 0.5M NaCl, 50 mM Tris, pH 7.0). OP1 elutes at about 250 mM phosphate. Additionally, urea (6M) may be added during the elution step.

Other related chromatography methods also may be useful in purifying OP1 from eucaryotic cell culture systems. For example, heparin-Sepharose may be used in combination with the S-Sepharose column. Alternatively, $Cu^{2+}$-immobilized metal-ion affinity chromatography (IMAC) will bind OP1 in a phosphate buffer (pH 7.0) containing 6M urea.

3.6 Protein Characterization

Recombinant osteogenic protein expression in COS cells yields essentially a single species having an apparent molecular weight of 18 kDa, as determined by SDS-PAGE analysis. Subsequent N-terminal sequencing data indicates that this species contains the intact mature OP1 sequence, referred to herein as "OP1-18Ser" ("Ser Thr Gly...", beginning at residue 293 of Seq. ID No.1.) Both the BSC and CHO preparations, by contrast, contain both the intact mature sequence and one or more active degraded species.

BSC cell-derived preparations yield two major species having an apparent molecular weight of about 18 kDa and 16 kDa, and a minor species of about 23 kDa as determined by SDS-PAGE analysis. N-terminal sequencing of the two major species using standard techniques reveals that the 18 kDa species, like the COS-derived OP1 protein, contains the intact mature form of OP1 (OP1-18Ser). The 16 kDa fraction appears to contain five species of the mature sequence, having different N-termini. One form, "OP1-16Ser," has its N-terminus at +8 of the mature sequence ("Ser Gln Asn ...", beginning at residue 300 of Seq. ID No.1.) A second species, referred to herein as "OP1-16Leu", has its N-terminus at +21 of the mature sequence ("Leu Arg Met ...", beginning at residue 313 of Seq. ID No. 1). A third and fourth species, referred to herein as OP1-16Met and OP1-16Ala, have their N-termini at +23 and +24, respectively, of the mature OP1 sequence. (See Seq. ID No.1: OP1-16Met begins at residue 315, "Met Ala Asn ...", and OP1-16Ala begins at residue 316, "Ala Asn Val...".) Finally, a fifth degraded species has its N-terminus at +26 of the mature sequence ("Val Ala Glu ...", beginning at residue 318 of Seq. ID No. 1) and is referred to herein as "OP1-16Val." The various species are listed in Table 1 and their N-termini are presented in FIG. 33. Biochemical analyses and in vivo bioassays indicate all species are active (see infra). Preliminary sequencing data of the minor species migrating at 23 kDa suggests that this species also contains the mature active sequence. Accordingly, the protein's altered mobility on an electrophoresis gel may be due to an altered glycosylation pattern.

Similarly, CHO-derived OP1 preparations generally produce three species having an apparent molecular weight within the range of 15-20 kDa, as determined by SDS-PAGE (specifically, 19 kDa, 17 kDa, and 15 kDa). A minor species also migrates at about 23 kDa. N-terminal and C-terminal sequencing (by CNBr analysis) of proteins in the different fractions reveals that CHO expression produces the same species of OP1 proteins as produced by BSC cell expression, but having different electrophoretic mobility on an SDS polyacrylamide gel. Both the 19 kDa and the 17 kDa protein fractions contain the intact mature form of OP1 (OP1-18Ser) and the OP1-16Ser degraded form. Preliminary sequencing data of the 23 kDa species suggest that this species also contains the intact mature form of OP1. Finally, N-terminal sequencing of the protein species migrating at 15 kDa indicates that proteins in this fraction contain the other four degraded forms of OP1 identified in the BSC cell system: OP1-16Leu, OP1-16Met, OP1-16Ala and OP1-16Val. These data suggest that the apparent molecular weight differences among the various OP1 species detected may be due primarily to variations in their glycosylation patterns. In addition, protein glycosylation pattern variations are a known characteristic of CHO expression systems. In vivo bioassays of all OP1 species detected indicate that all truncated forms are active (see infra).

The glycosylation patterns of the proteins in the various OP1 preparations can be investigated by measuring their reactivity with different lectins, using standard methodologies. Here, reactivity with Concanavalin A (Con A), which binds to the mannose region, and Wheat Germ Agglutinin (WGA), which binds to N-acetyl glucosamine (GlcNAc) and sialic acid (SA) residues, was measured. Results indicate that there may be substantial variation among the glycosylation patterns of the various OP1 species. Con A reacts strongly with both the CHO-derived 17 kDa species and the BSC-derived 16 and 18 kDa species, but only weakly with the other species. Conversely, WGA reacts strongly only with the 19 kDa and 23 kDa CHO-derived species and the 18 and 23 kDa BSC-derived proteins. These results further suggest that variations in the electrophoretic migration patterns of the various OP1 preparations reflect variations in protein glycosylation patterns, which appear to be host cell-specific characteristics.

The various different OP1 preparations also have been analyzed by standard HPLC chromatography. Preparations of OP1 from both CHO and BSC cells have very similar characteristics by HPLC analysis in oxidized, reduced, pyridylethylated or degraded forms. Although distinct by SDS-PAGE analysis, the differences between the different cell type preparations appear insufficient to influence the binding to HPLC C-18 columns.

Accordingly, as will be appreciated by those skilled in the art, it is anticipated that active mature OP1 sequences can be expressed from other different procaryotic and eucaryotic cell expression systems as disclosed herein. The proteins produced may have varying N-termini, and those expressed from eucaryotic cells may have varying glycosylation patterns. Finally, it will also be appreciated that these variations in the recombinant osteogenic protein produced will be characteristic of the host cell expression system used rather than of the protein itself.

B. Identification of Additional, Novel Osteogenic Sequences

In an effort to identify additional DNA sequences encoding osteogenic proteins, a hybridization probe specific to the DNA sequence encoding the C-terminus of the mature OP1 protein was prepared using a StuI-EcoR1 digest fragment of hOP1 (base pairs 1034–1354 in Seq. ID No. 1), and labelled with $^{32}P$ by nick translation, as described in the art. As disclosed supra, applicants have previously shown that the OP1 C-terminus encodes a key functional domain e.g., the "active region" for osteogenic activity (OPS or OP7). The C-terminus also is the region of the protein whose amino acid sequence shares specific amino acid sequence homology with particular proteins in the TGF-$\beta$ superfamily of regulatory proteins and which includes the conserved cysteine skeleton.

Approximately $7 \times 10^5$ phages of an oligo (dT) primed 17.5 days p.c. mouse embryo 5' stretch cDNA (gt10) library (Clontech, Inc., Palo Alto, Calif.) was screened with the labelled probe. The screen was performed using the following hybridization conditions: 40% formamide, 5×SSPE, 5×Denhardt's Solution, 0.1% SDS, at 37° C. overnight, and washing in 0.1×SSPE, 0.1% SDS at 50° C. Where only partial clones were obtained, the complete gene sequence was subsequently determined by screening either a second cDNA library (e.g., mouse PCC4 cDNA (ZAP) library, Stratagene, Inc., La Jolla, Calif.), or a mouse genomic library (e.g., Clontech, Inc., Palo, Alto, Calif.).

Five recombinant phages were purified over three rounds of screening. Phage DNA was prepared from all five phages, subjected to an EcoR1 digest, subcloned into the EcoR1 site of a common pUC-type plasmid modified to allow single strand sequencing, and sequenced using means well known in the art.

Two different mouse DNA sequences, referred to herein as mOP1 and mOP2, were identified by this procedure. The characteristics of the proteins encoded by these sequences are described below.

1. mOP1 mOP1 is the murine homolog of hOP1. The cDNA and encoded amino acid sequence for the full length mOP1 protein is depicted in Sequence ID No. 24. The full-length form of the protein is referred to as the pre-pro form of mOP1 ("mOP1-PP"), and includes a signal peptide sequence at its N-terminus. The amino acid sequence Ser-Ala-Leu-Ala-Asp (amino acid residues 26–30 in Seq. ID No. 24) is believed to constitute the cleavage site for the removal of the signal peptide sequence, leaving an intermediate form of the protein, the "pro" form, to be secreted from the expressing cell. The amino acid sequence Arg-Ser-Ile-Arg-Ser (amino acid residue nos. 288–292 in Sequence ID No. 24) is believed to constitute the cleavage site that produces the mature form of the protein, herein referred to as "mOP1-Ser" and described by amino acid residues 292–430 of Seq. ID No. 24. The amino acid sequence defining the conserved 6 cysteine skeleton of the mOP1 active region is defined by residues 334–430 of Seq. ID No. 24.

FIG. 23A compares the amino acid sequence homology of the mature hOP1 and mOP1 proteins (OP1-18Ser and mOP1-Ser). Amino acid identity is indicated by three dots ( . . . ). As can be seen in this figure, the mature form of mOP1, mOP1-Ser, shares significant amino acid sequence homology with OP1-18Ser (98% identity), differing at only three positions in this region. Like OP1-18Ser, mOP1-Ser has a seven cysteine functional domain. In addition, the prepro form of the mOP1 protein shows substantially the same homology with that of OP1. The high degree of amino acid sequence homology shared by the mature proteins is not surprising as the amino acid sequences of the mature forms of other TGF-$\beta$-like proteins generally also have been found to be highly conserved across different animal species (e.g., compare Vgr and Vgl, two related genes isolated from mouse and Xenopus, respectively). The high degree of amino acid sequence homology exhibited between the mature forms of the two animal species of OP1 proteins suggests that the mOP1 protein will purify essentially as OP1 does, or with only minor modifications of the protocols disclosed for OP1. Similarly, purified mOP1-Ser is predicted to have an apparent molecular weight of about 36 kDa as a glycosylated oxidized homodimer, and about 18 kDa as a reduced single subunit, as determined by comparison with molecular weight standards on an SDS-polyacrylamide electrophoresis gel. There appear to be three potential N glycosylation sites in the mature protein. The unglycosylated homodimer (e.g., one expressed from *E. coli*) is predicted to have a molecular weight of about 27 kDa.

2. OP2

2.1 mOP2

The cDNA encoding the C-terminus of mOP2 protein first was identified following the procedure for retrieving mOP1 DNA. The 5' end of the gene was identified subsequently by screening a second mouse cDNA library (Mouse PCC4 cDNA (ZAP) library, Stratagene, Inc., La Jolla, Calif.).

Mouse OP2 (mOP2) protein shares significant amino acid sequence homology with the amino acid sequence of the OP1 active region, e.g., OPS or OP7, about 74% identity, and less homology with the intact mature form, e.g., OP1-18Ser, about 58% identity. The mOP2 protein differs from the OP1 protein by only one non-conservative amino acid change in the active region. The cDNA sequence, and the encoded amino acid sequence, for the full length mOP2 protein are depicted in Sequence ID No. 26. The full-length form of the protein is referred to as the prepro form of mOP2 ("mOP2-PP"), and includes a signal peptide sequence at its N-terminus. The amino acid sequence Leu-Ala-Leu-Cys-Ala-Leu (amino acid residues 13-18 of Sequence ID No. 26) is believed to constitute the cleavage site for the removal of the signal peptide sequence, leaving an intermediate form of the protein, the "pro" form, to be secreted from the expressing cell. The amino acid sequence Arg-Ala-Pro-Arg-Ala (amino acid residues 257-261 of Seq. ID No. 26) is believed to constitute the cleavage site that produces the mature form of the protein, herein referred to as "mOP2-Ala", and described by residues 261-399 of Seq. ID No. 26. The amino acid sequence defining the conserved 6 cysteine skeleton of the mOP2 active region is defined by residues 303-399 of Seq. ID No. 26.

2.2 hOP2

Using a probe prepared from the pro region of mOP2 (an EcoR1-BamH1 digest fragment, bp 467-771 of Sequence ID No. 26), a human hippocampus library was screened (human hippocampus cDNA lambda ZAP II library, Stratagene, Inc., La Jolla, Calif.) following essentially the same procedure as for the mouse library screens. The procedure identified the N-terminus of a novel DNA encoding an amino acid sequence having substantial homology with the mOP2 protein. The C-terminus of the gene subsequently was identified by probing a human genomic library (in lambda phage EMBL-3, Clontech, Inc., Palo Alto, Calif.) with a labelled fragment from the novel human DNA in hand. The novel polypeptide chain encoded by this DNA is referred to herein as hOP2 protein, and the mature form of which shares almost complete amino acid sequence identity (about 92%) with mOP2-A (see FIG. 23B and infra).

The cDNA sequence, and the encoded amino acid sequence, for the prepro form of hOP2 ("hOP2-PP") is depicted in Seq. ID No. 28. This full-length form of the protein also includes a signal peptide sequence at its N-terminus. The amino acid sequence Leu-Ala-Leu-Cys-Ala-Leu (amino acid residues 13-18 of Seq. ID No. 28) is believed to constitute the cleavage site for the removal of the signal peptide sequence, leaving an intermediate form of the protein, the "pro" form, to be secreted from the expressing cell. The amino acid sequence Arg-Thr-Pro-Arg-Ala (amino acid residues 260-264 of Seq. ID No. 28) is believed to constitute the cleavage site that produces what is believed to be the mature form of the protein, herein referred to as "hOP2-Ala" and described by residues 264 to 402 of Seq. ID No. 28. The amino acid sequence defining the conserved 6 cysteine skeleton of the hOP2 active region is defined by residues 306-402 of Seq. ID No. 28.

Additional mature species of hOP2 thought to be active include truncated short sequences, "hOP2-Pro" (described by residues 267 to 402, Seq. ID No. 28) and "hOP2-Arg" (described by residues 270 to 402, Seq. ID No. 28), and a slightly longer sequence ("hOP2-Ser", described by residues 243 to 402, Seq. ID No. 28).

It should be noted that the nucleic acid sequence encoding the N-terminus of the prepro form of both mOP2 and hOP2 is rich in guanidine and cytosine base pairs. As will be appreciated by those skilled in the art, sequencing such a "G-C rich" region can be problematic, due to stutter and/or band compression. Accordingly, the possibility of sequencing errors in this region can not be ruled out. However, the definitive amino acid sequence for these and other, similarly identified proteins can be determined readily by expressing the protein from recombinant DNA using, for example, any of the means disclosed herein, and sequencing the polypeptide chain by conventional peptide sequencing methods well known in the art.

The genomic sequences of both the murine and human OP2 genes also have been cloned. Like the human OP1gene, the protein coding region of the OP2 gene is contained on seven exons.

FIG. 23B compares the amino acid sequences of the mature mOP2 and hOP2 proteins, mOP2-A and hOP2-Ala. Identity is indicated by three dots ( . . . ) in the mOP2-A sequence. As is evident from the figure, the amino acid sequence homology between the mature forms of these two proteins is substantial (about 92% identity between the mature sequences, about 95% identity within the C-terminal active region).

FIG. 24 compares the amino acid sequences for the mature forms of all four species of OP1 and OP2 proteins. Here again, identity is indicated by three dots ( . . . ). Like the mOP2 protein, the hOP2 protein shares significant homology (about 74% identity) with the amino acid sequence defining the OP1 active region (OPS or OP7, residues 43-139 and 38-139, respectively), and less homology with OP1-18Ser (about 58% identity). Both OP2 proteins share the conserved seven cysteine skeleton seen in the OP1 proteins. In addition, the OP2 proteins comprise an eighth cysteine residue within this region (see position 78 in FIG. 24).

The greatest homology between sequences (about 74% identity, indicated by dots) occurs within the C-terminal active region defined by OPS and OP7. The OP1 and OP2 proteins share less amino acid sequence homology with the active regions of the CBMP2A and CBMP2B proteins. The OP1 proteins share only about 60% sequence identity with the CBMP2 proteins in this region; the OP2 proteins share only about 58% identity with the CBMP2 protein in this region. The CBMP2 proteins are most easily distinguished from the OP1-/OP2 proteins in the active region by at least 9 nonconservative amino acid changes, in addition to munerous conservative amino acid changes which may have smaller effects on activity.

A preferred generic amino acid sequence useful as a subunit of a dimeric osteogenic protein capable of inducing endochondral bone or cartilage formation when implanted in a mammal in association with a matrix, and which incorporates the maximum homology between the identified OP1 and OP2 proteins (see FIG. 24), can be described by the sequence referred to herein as "OPX", described below and in Seq. ID No. 30. OPX is a composite sequence designed from the four sequences presented in FIG. 24 (beginning at residue 38), and includes both the specific amino acid sequence created by the amino acid identity shared by the four OP1, OP2 species, as well as alternative residues for the variable positions within the sequence.

| | | | | | | | | | |
|---|---|---|---|---|---|---|---|---|---|
| Cys<br>1 | Xaa | Xaa | His | Glu<br>5 | Leu | Tyr | Val | Ser | Phe<br>10 |
| Xaa | Asp | Leu | Gly | Trp<br>15 | Xaa | Asp | Trp | Xaa | Ile<br>20 |
| Ala | Pro | Xaa | Gly | Tyr<br>25 | Xaa | Ala | Tyr | Tyr | Cys<br>30 |
| Glu | Gly | Glu | Cys | Xaa<br>35 | Phe | Pro | Leu | Xaa | Ser<br>40 |
| Xaa | Met | Asn | Ala | Thr<br>45 | Asn | His | Ala | Ile | Xaa<br>50 |
| Gln | Xaa | Leu | Val | His<br>55 | Xaa | Xaa | Xaa | Pro | Xaa<br>60 |
| Xaa | Val | Pro | Lys | Xaa<br>65 | Cys | Cys | Ala | Pro | Thr<br>70 |
| Xaa | Leu | Xaa | Ala | Xaa<br>75 | Ser | Val | Leu | Tyr | Xaa<br>80 |
| Asp | Xaa | Ser | Xaa | Asn<br>85 | Val | Ile | Leu | Xaa | Lys<br>90 |
| Xaa | Arg | Asn | Met | Val<br>95 | Val | Xaa | Ala | Cys | Gly<br>100 |
| Cys | His, | | | | | | | | | and wherein Xaa at res. 2=(Lys or Arg); Xaa at res. 3=(Lys or Arg); Xaa at res. 11=(Arg or Gln); Xaa at res. 16=(Gln or Leu); Xaa at res. 19=(Ile or Val); Xaa at res. 23=(Glu or Gln); Xaa at res. 26=(Ala or Ser); Xaa at res. 35=(Ala or Ser); Xaa at res. 39=(Asn or Asp); Xaa at res. 41=(Tyr or Cys); Xaa at res. 50=(Val or Leu); Xaa at res. 52=(Ser or Thr); Xaa at res. 56=(Phe or Leu); Xaa at res. 57=(Ile or Met); Xaa at res. 58=(Asn or Lys); Xaa at res. 60=(Glu, Asp or Asn); Xaa at res. 61=(Thr, Ala or Val); Xaa at res. 65=(Pro or Ala); Xaa at res. 71=(Gln or Lys); Xaa at res. 73=(Asn or Ser); Xaa at res. 75=(Ile or Thr); Xaa at res. 80=(Phe or Tyr); Xaa at res. 82=(Asp or Ser); Xaa at res. 84=(Ser or Asn); Xaa at res. 89=(Lys or Arg); Xaa at res. 91=(Tyr or His); and Xaa at res. 97=(Arg or Lys).

The high degree of homology exhibited between the various OP1 and OP2 proteins suggests that the novel osteogenic proteins identified herein will purify essentially as OP1 does, or with only minor modifications of the protocols disclosed for OP1. Similarly, the purified mOP1, mOP2, and hOP2 proteins are predicted to have an apparent molecular weight of about 18 kDa as reduced single subunits, and an apparent molecular weight of about 36 kDa as oxidized dimers, as determined by comparison with molecular weight standards on an SDS-polyacrylamide electrophoresis gel. Unglycosylated dimers (e.g., proteins produced by recombinant expression in *E. coli*) are predicted to have an apparent molecular weight of about 27 kDa. There appears to be one potential N glycosylation site in the mature forms of the mOP2 and hOP2 proteins.

The identification of osteogenic proteins having an active region comprising eight cysteine residues also allows one to construct osteogenic polypeptide chains patterned after either of the following template amino acid sequences, or to identify additional osteogenic proteins having this sequence. The template sequences contemplated are "OPX-7C", comprising the conserved six cysteine skeleton plus the additional cysteine residue identified in the OP2 proteins, and "OPX-8C", comprising the conserved seven cysteine skeleton plus the additional cysteine residue identified in the OP2 proteins. The OPX-7C and OPX-8C sequences are described below and in Seq. ID Nos. 31 and 32, respectively. Each Xaa in these template sequences independently represents one of the 20 naturally-occurring L-isomer, α-amino acids, or a derivative thereof. Biosynthetic constructs patterned after this template readily are constructed using conventional DNA synthesis or peptide synthesis techniques well known in the art. Once constructed, osteogenic proteins comprising these polypeptide chains can be tested as disclosed herein.

"OPX-7C" (Sequence ID No. 31):

| | | | | | | | | | | |
|---|---|---|---|---|---|---|---|---|---|---|
| Xaa<br>1 | Xaa | Xaa | Xaa | Xaa<br>5 | Xaa | Xaa | Xaa | Xaa | Xaa<br>10 | Xaa |
| Xaa | Xaa | Xaa | Xaa<br>15 | Xaa | Xaa | Xaa | Xaa | Xaa<br>20 | Xaa | Xaa |
| Xaa | Xaa | Cys<br>25 | Xaa | Xaa | Xaa | Cys | Xaa<br>30 | Xaa | Xaa | Xaa |
| Xaa | Xaa<br>35 | Cys | Xaa | Xaa | Xaa | Xaa<br>40 | Xaa | Xaa | Xaa | Xaa |
| Xaa<br>45 | Xaa | Xaa | Xaa | Xaa | Xaa<br>50 | Xaa | Xaa | Xaa | Xaa | Xaa<br>55 |
| Xaa | Xaa | Xaa | Xaa | Xaa<br>60 | Cys | Cys | Xaa | Xaa | Xaa<br>65 | Xaa |
| Xaa | Xaa | Xaa | Xaa<br>70 | Xaa | Xaa | Xaa | Xaa | Xaa<br>75 | Xaa | Xaa |
| Xaa | Xaa | Xaa<br>80 | Xaa | Xaa | Xaa | Xaa | Xaa<br>85 | Xaa | Xaa | Xaa |
| Xaa | Xaa<br>90 | Xaa | Xaa | Xaa | Cys | Xaa<br>95 | Cys | Xaa | | |

"OPX-8C" (Sequence ID No. 32 comprising additional five residues at the N-terminus, including a conserved cysteine residue):

| Cys 1 | Xaa | Xaa | Xaa | Xaa 5 | Xaa | Xaa | Xaa | Xaa | Xaa 10 | Xaa |
|---|---|---|---|---|---|---|---|---|---|---|
| Xaa | Xaa | Xaa | Xaa 15 | Xaa | Xaa | Xaa | Xaa | Xaa 20 | Xaa | Xaa |
| Xaa | Xaa | Xaa 25 | Xaa | Xaa | Xaa | Xaa | Cys 30 | Xaa | Xaa | Xaa |
| Cys | Xaa 35 | Xaa | Xaa | Xaa | Xaa | Xaa 40 | Cys | Xaa | Xaa | Xaa Xaa 45 |
| Xaa | Xaa | Xaa | Xaa | Xaa 50 | Xaa | Xaa | Xaa | Xaa | Xaa 55 | Xaa |
| Xaa | Xaa | Xaa | Xaa 60 | Xaa | Xaa | Xaa | Xaa | Xaa 65 | Cys | |
| Cys | Xaa | Xaa | Xaa 70 | Xaa | Xaa | Xaa | Xaa | Xaa 75 | Xaa | Xaa |
| Xaa | Xaa | Xaa 80 | Xaa | Xaa | Xaa | Xaa | Xaa 85 | Xaa | Xaa | Xaa |
| Xaa | Xaa 90 | Xaa | Xaa | Xaa | Xaa | Xaa 95 | Xaa | Xaa | Xaa | Cys |
| Xaa 100 | Cys | Xaa | | | | | | | | |

III. MATRIX PREPARATION

A. General Consideration of Matrix Properties

The currently preferred carrier material is a xenogenic bone-derived particulate matrix treated as disclosed herein. This carrier may be replaced by either a biodegradable-synthetic or synthetic-inorganic matrix (e.g., HAP, collagen, tricalcium phosphate or polylactic acid, polyglycolic acid, polybutyric acid and various copolymers thereof.)

Studies have shown that surface charge, particle size, the presence of mineral, and the methodology for combining matrix and osteogenic protein all play a role in achieving successful bone induction. Perturbation of the charge by chemical modification abolishes the inductive response. Particle size influences the quantitative response of new bone; particles between 70 μm and 420 μm elicit the maximum response. Contamination of the matrix with bone mineral will inhibit bone formation. Most importantly, the procedures used to formulate osteogenic protein onto the matrix are extremely sensitive to the physical and chemical state of both the osteogenic protein and the matrix.

The sequential cellular reactions in the interface of the bone matrix/osteogenic protein implants are complex. The multistep cascade includes: binding of fibrin and fibronectin to implanted matrix, migration and proliferation of mesenchymal cells, differentiation of the progenitor cells into chondroblasts, cartilage formation, cartilage calcification, vascular invasion, bone formation, remodeling, and bone marrow differentiation.

A successful carrier for osteogenic protein should perform several important functions. It should carry osteogenic protein and act as a slow release delivery system, accommodate each step of the cellular response during bone development, and protect the osteogenic protein from nonspecific proteolysis. In addition, selected materials must be biocompatible in vivo and preferably biodegradable; the carrier must act as a temporary scaffold until replaced completely by new bone. Polylactic acid (PLA), polyglycolic acid (PGA), and various combinations have different dissolution rates in vivo. In bones, the dissolution rates can vary according to whether the implant is placed in cortical or trabecular bone.

Matrix geometry, particle size, the presence of surface charge, and the degree of both intra-and inter-particle porosity are all important to successful matrix performance. It is preferred to shape the matrix to the desired form of the new bone and to have dimensions which span non-union defects. Rat studies show that the new bone is formed essentially having the dimensions of the device implanted.

The matrix may comprise a shape-retaining solid made of loosely adhered particulate material, e.g., with collagen. It may also comprise a molded, porous solid, or simply an aggregation of close-packed particles held in place by surrounding tissue. Masticated muscle or other tissue may also be used. Large allogenic bone implants can act as a carrier for the matrix if their marrow cavities are cleaned and packed with particles and the dispersed osteogenic protein.

The preferred matrix material, prepared from xenogenic bone and treated as disclosed herein, produces an implantable material useful in a variety of clinical settings. In addition to its use as a matrix for bone formation in various orthopedic, periodontal, and reconstructive procedures, the matrix also may be used as a sustained release carrier, or as a collagenous coating for implants. The matrix may be shaped as desired in anticipation of surgery or shaped by the physician or technician during surgery. Thus, the material may be used for topical, subcutaneous, intraperitoneal, or intramuscular implants; it may be shaped to span a nonunion fracture or to fill a bone defect. In bone formation procedures, the material is slowly absorbed by the body and is replaced by bone in the shape of or very nearly the shape of the implant.

Various growth factors, hormones, enzymes, therapeutic compositions, antibiotics, and other bioactive agents also may be adsorbed onto the carrier material and will be released over time when implanted as the matrix material is slowly absorbed. Thus, various known growth factors such as EGF, PDGF, IGF, FGF, TGF-α, and TGF-β may be released in vivo. The material can be used to release chemotherapeutic agents, insulin, enzymes, or enzyme inhibitors.

B. Bone-Derived Matrices

1. Preparation of Demineralized Bone

Demineralized bone matrix, preferably bovine bone matrix, is prepared by previously published procedures (Sampath and Reddi (1983) *Proc. Natl. Acad. Sci. USA* 80:6591-6595). Bovine diaphyseal bones (age 1-10 days) are obtained from a local slaughterhouse and used fresh. The bones are stripped of muscle and fat, cleaned of periosteum, demarrowed by pressure with cold water, dipped in cold absolute ethanol, and stored at −20° C. They are then dried and fragmented by crushing and pulverized in a large mill. Care is taken to prevent heating by using liquid nitrogen. The pulverized bone is milled to a particle size in the range of 70–850 μm, preferably 150–420 μm, and is defatted by two washes of approximately two hours duration with three volumes of chloroform and methanol (3:1). The particulate bone is then washed with one volume of absolute ethanol and dried over one volume of anhydrous ether yielding defatted bone powder. The defatted bone powder is then demineralized by four successive treatments with 10 volumes of 0.5N HCl at 4° C. for 40 min. Finally, neutralizing washes are done on the demineralized bone powder with a large volume of water.

2. Guanidine Extraction

Demineralized bone matrix thus prepared is extracted with 5 volumes of 4M guanidine-HCl, 50 mM Tris-HCl, pH 7.0 for 16 hr. at 4° C. The suspension is filtered. The insoluble material is collected and used to fabricate the matrix. The material is mostly collagenous in nature. It is devoid of osteogenic or chondrogenic activity.

3. Matrix Treatments

The major component of all bone matrices is Type-I collagen. In addition to collagen, demineralized bone extracted as disclosed above includes non-collagenous proteins which may account for 5% of its mass. In a xenogenic matrix, these noncollagenous components may present themselves as potent antigens, and may constitute immunogenic and/or inhibitory components. These components also may inhibit osteogenesis in allogenic implants by interfering with the developmental cascade of bone differentiation. It has been discovered that treatment of the matrix particles with a collagen fibril-modifying agent extracts potentially unwanted components from the matrix, and alters the surface structure of the matrix material. Useful agents include acids, organic solvents or heated aqueous media. Various treatments are described below. A detailed physical analysis of the effect these fibril-modifying agents have on demineralized, quanidine-extracted bone collagen particles is disclosed in copending U.S. patent application Ser. No. 483,913, filed Feb. 22, 1990.

After contact with the fibril-modifying agent, the treated matrix is washed to remove any extracted components, following a form of the procedure set forth below:

1. Suspend in TBS (Tris-buffered saline) 1 g/200 ml and stir at 4° C. for 2 hrs; or in 6M urea, 50 mM Tris-HCl, 500 mM NaCl, pH 7.0 (UTBS) or water and stir at room temperature (RT) for 30 minutes (sufficient time to neutralize the pH);
2. Centrifuge and repeat wash step; and
3. Centrifuge; discard supernatant; water wash residue; and then lyophilize.

3.1 Acid Treatments

1. Trifluoroacetic acid

Trifluoroacetic acid is a strong non-oxidizing acid that is a known swelling agent for proteins, and which modifies collagen fibrils.

Bovine bone residue prepared as described above is sieved, and particles of the appropriate size are collected. These particles are extracted with various percentages (1.0% to 100%) of trifluoroacetic acid and water (v/v) at 0° C. or room temperature for 1–2 hours with constant stirring. The treated matrix is filtered, lyophilized, or washed with water/salt and then lyophilized.

2. Hydrogen Fluoride

Like trifluoroacetic acid, hydrogen fluoride is a strong acid and swelling agent, and also is capable of altering intraparticle surface structure. Hydrogen fluoride is also a known deglycosylating agent. As such, HF may function to increase the osteogenic activity of these matrices by removing the antigenic carbohydrate content of any glycoproteins still associated with the matrix after guanidine extraction.

Bovine bone residue prepared as described above is sieved, and particles of the appropriate size are collected. The sample is dried in vacuo over $P_2O_5$, transferred to the reaction vessel and exposed to anhydrous hydrogen fluoride (10–20 ml/g of matrix) by distillation onto the sample at −70° C. The vessel is allowed to warm to 0° C. and the reaction mixture is stirred at this temperature for 120 minutes. After evaporation of the hydrogen fluoride in vacuo, the residue is dried thoroughly in vacuo over KOH pellets to remove any remaining traces of acid. Extent of deglycosylation can be determined from carbohydrate analysis of matrix samples taken before and after treatment with hydrogen fluoride, after washing the samples appropriately to remove non-covalently bound carbohydrates. SDS-extracted protein from HF-treated material is negative for carbohydrate as determined by Con A blotting.

The deglycosylated bone matrix is next washed twice in TBS (Tris-buffered saline) or UTBS, water-washed, and then lyophilized.

Other acid treatments are envisioned in addition to HF and TFA. TFA is a currently preferred acidifying reagent in these treatments because of its volatility. However, it is understood that other, potentially less caustic acids may be used, such as acetic or formic acid.

3.2 Solvent Treatment

1. Dichloromethane

Dichloromethane (DCM) is an organic solvent capable of denaturing proteins without affecting their primary structure. This swelling agent is a common reagent in automated peptide synthesis, and is used in washing steps to remove components.

Bovine bone residue, prepared as described above, is sieved, and particles of the appropriate size are incubated in 100% DCM or, preferably, 99.9% DCM/0.1% TFA. The matrix is incubated with the swelling agent for one or two hours at 0° C. or at room temperature. Alternatively, the matrix is treated with the agent at least three times with short washes (20 minutes each) with no incubation.

2. Acetonitrile

Acetonitrile (ACN) is an organic solvent, capable of denaturing proteins without affecting their primary structure. It is a common reagent used in high-performance liquid chromatography, and is used to elute proteins from silica-based columns by perturbing hydrophobic interactions.

Bovine bone residue particles of the appropriate size, prepared as described above, are treated with 100% ACN (1.0 g/30 ml) or, preferably, 99.9% ACN/0.1% TFA at room temperature for 1–2 hours with constant stirring. The treated matrix is then water-washed, or washed with urea buffer, or 4M NaCl and lyophilized. Alternatively, the ACN or ACN/TFA treated matrix may be lyophilized without wash.

3. Isopropanol

Isopropanol is also an organic solvent capable of denaturing proteins without affecting their primary structure. It is a common reagent used to elute proteins from silica HPLC columns.

Bovine bone residue particles of the appropriate size prepared as described above are treated with 100% isopropanol (1.0 g/30 ml) or, preferably, in the presence of 0.1% TFA, at room temperature for 1–2 hours with constant stirring. The matrix is then water-washed or washed with urea buffer or 4M NaCl before being lyophilized.

4. Chloroform

Chloroform also may be used to increase surface area of bone matrix like the reagents set forth above, either alone or acidified.

Treatment as set forth above is effective to assure that the material is free of pathogens prior to implantation.

3.3 Heat Treatment

The currently most preferred agent is a heated aqueous fibril-modifying medium such as water, to increase the matrix particle surface area and porosity. The currently most preferred aqueous medium is an acidic aqueous medium having a pH of less than about 4.5, e.g., within the range of about pH 2 - pH 4 which may help to "swell" the collagen before heating. 0.1% acetic acid, which has a pH of about 3, currently is most preferred. 0.1M acetic acid also may be used.

Various amounts of delipidated, demineralized guanidine-extracted bone collagen are heated in the aqueous medium (1 g matrix/30 ml aqueous medium) under constant stirring in a water jacketed glass flask, and maintained at a given temperature for a predetermined period of time. Preferred treatment times are about one hour, although exposure times of between about 0.5 to two hours appear acceptable. The temperature employed is held constant at a temperature within the range of about 37° C. to 65° C. The currently preferred heat treatment temperature is within the range of about 45° C. to 60° C.

After the heat treatment, the matrix is filtered, washed, lyophilized and used for implant. Where an acidic aqueous medium is used, the matrix also is preferably neutralized prior to washing and lyophilization. A currently preferred neutralization buffer is a 200 mM sodium phosphate buffer, pH 7.0. To neutralize the matrix, the matrix preferably first is allowed to cool following thermal treatment, the acidic aqueous medium (e.g., 0.1% acetic acid) then is removed and replaced with the neutralization buffer and the matrix agitated for about 30 minutes. The neutralization buffer then may be removed and the matrix washed and lyophilized (see infra).

Figure 26A:
FIGS. 26A and 26B are scanning electron micrographs (5000×) of demineralized, delipidated (A) rat bone collagen particles, and (B) bovine bone collagen particles.
Figure 26B:
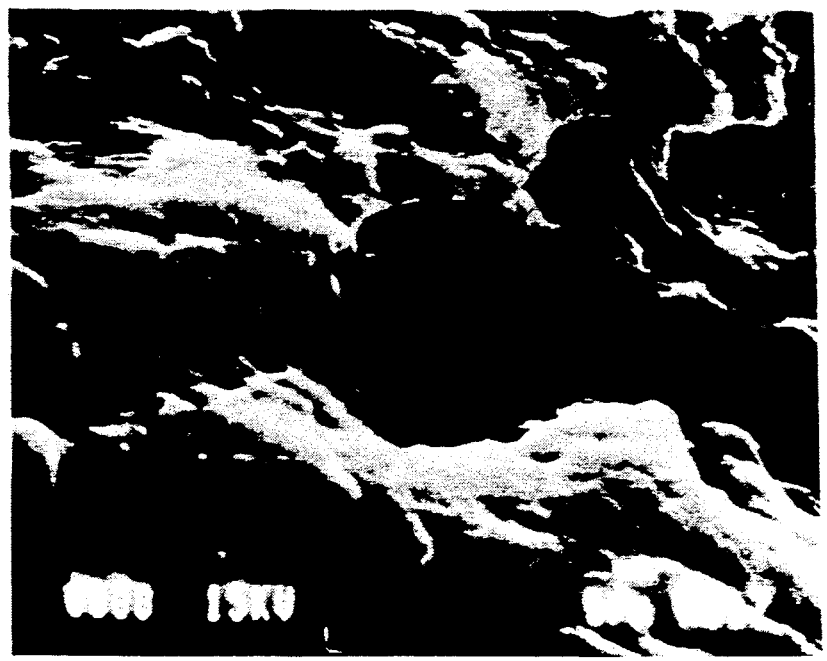

The effects of heat treatment on morphology of the matrix material is apparent from a comparison of the photomicrographs in FIG. 25 with those of FIG. 26. FIG. 25 illustrates the morphology of the successfully altered collagen surface treated with water heated to (a) 37° C., (b) 45° C., (c) 55° C. and (d) 65° C. The photomicrographs of FIG. 26 describe the morphology of untreated rat and bovine bone matrix (A and B, respectively). As is evident from the micrographs, the hot aqueous treatment can increase the degree of micropitting on the particle surface (e.g., about 10-fold,) as well as also substantially increasing the particle's porosity (compare FIG. 26B and 25C, 25D). This alteration of the matrix particle's morphology substantially increases the particle surface area. Careful measurement of the pore and micropit sizes reveals that hot aqueous medium treatment of the matrix particles yields particle pore and micropit diameters within the range of 1 $\mu$m to 100 $\mu$m.

Figure 27:
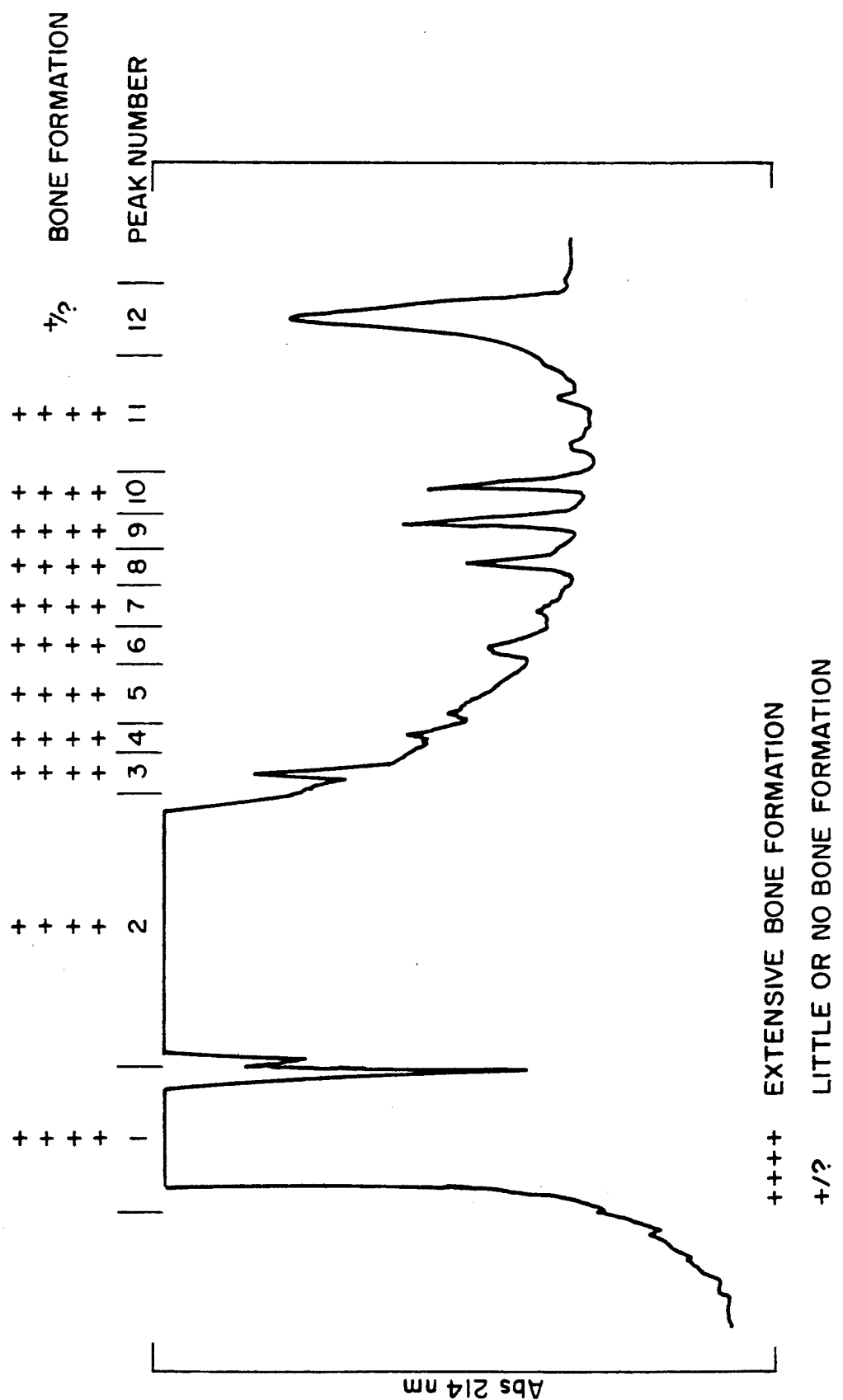
FIG. 27 is a 214 nm absorbance tracing of the extract isolated from hot water-treated bovine matrix, identifying the inhibitory effect of individual fractions on in vivo bone formation.

Characterization of the extract produced by the hot aqueous treatment reveals that the treatment also may be removing component(s) whose association with the matrix may interfere with new bone formation in vivo. FIG. 27 is a 214 nm absorbance tracing of the extract isolated from hot water treated bovine matrix, and indicates the effect of each peak (or fraction) on in vivo bone formation.

The extract from a large scale preparative run (100 g bovine matrix, hot water-treated) was collected, acidified with 0.1% TFA, and run on a C-18 HPLC column, using a Millipore Delta Prep Cartridge. Fractions were collected at 50 mL intervals at a flow rate of 25 ml/min. and pooled appropriately to isolate the individual peaks in the tracing. Each of these fractions then was implanted with recombinant OP1 and an appropriate rat matrix carrier (see infra), and its effect on bone formation activity measured. Fraction 12 alone appears to inhibit bone formation in allogenic implants. The inhibitory activity appears to be dose dependent. It is possible that the removal of the inhibitory component(s) present in this peak may be necessary to support osteogenic activity in xenogenic implants.

Figure 28A:
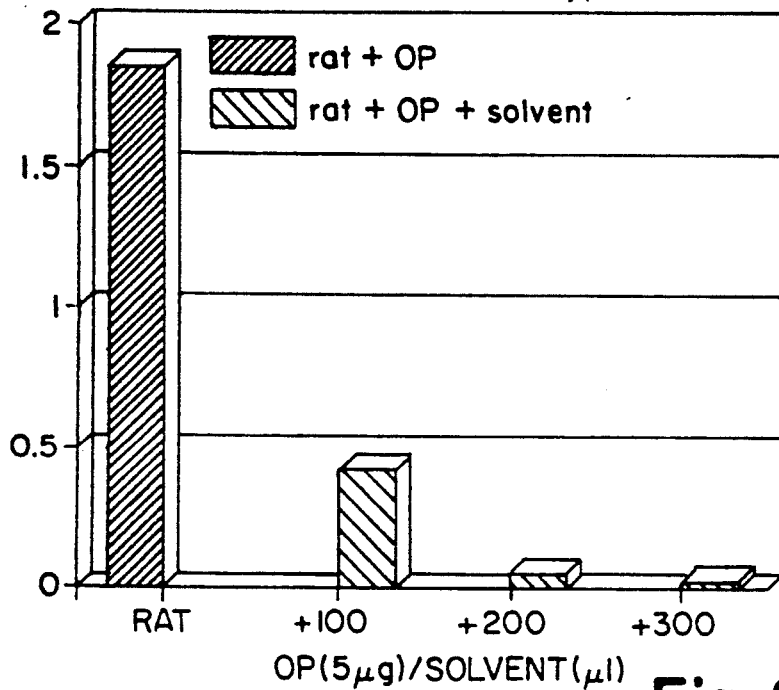
FIGS. 28A and 28B are bar graphs showing the inhibitory effect of hot water-treated matrix extract on OP1 activity, as measured by (A) alkaline phosphatase activity and (B) calcium content in day 12 implants, vs. increasing concentration of extract solvent.
Figure 28B:
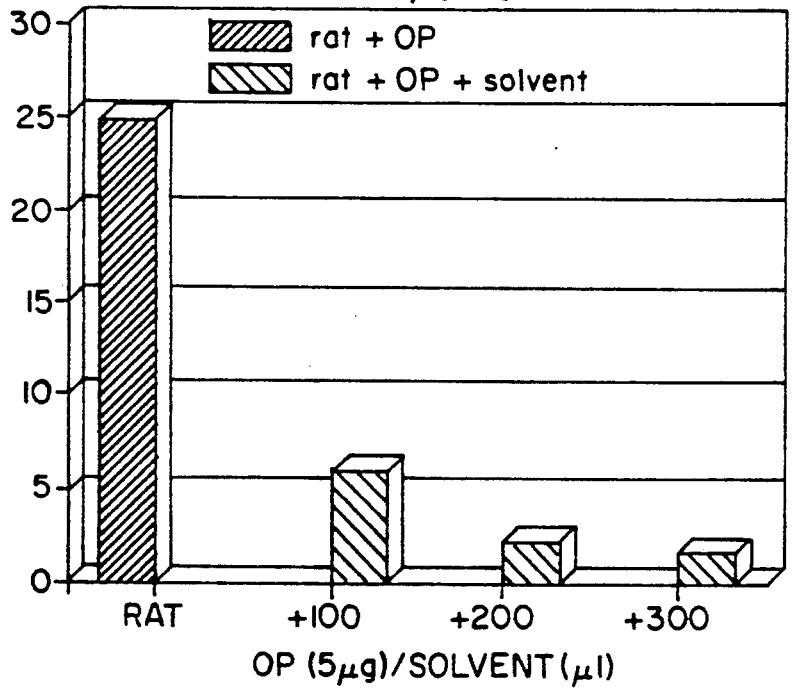
Figure 29A:
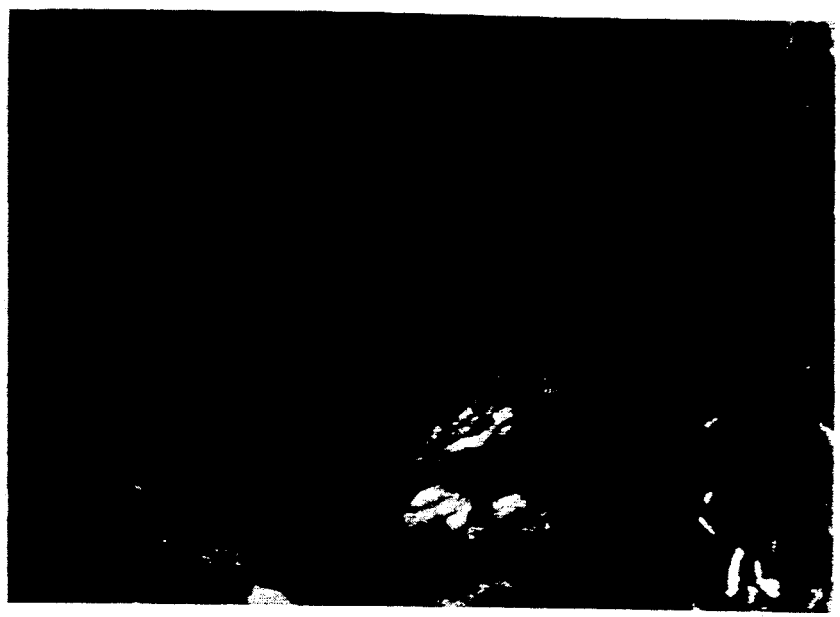
FIGS. 29A through 29F are photomicrographs (220×) of allogenic implants of OP1 expressed from COS, BSC and CHO cells, and which follow the developmental cascade of endochondral bone osteogenesis.
Figure 29B:
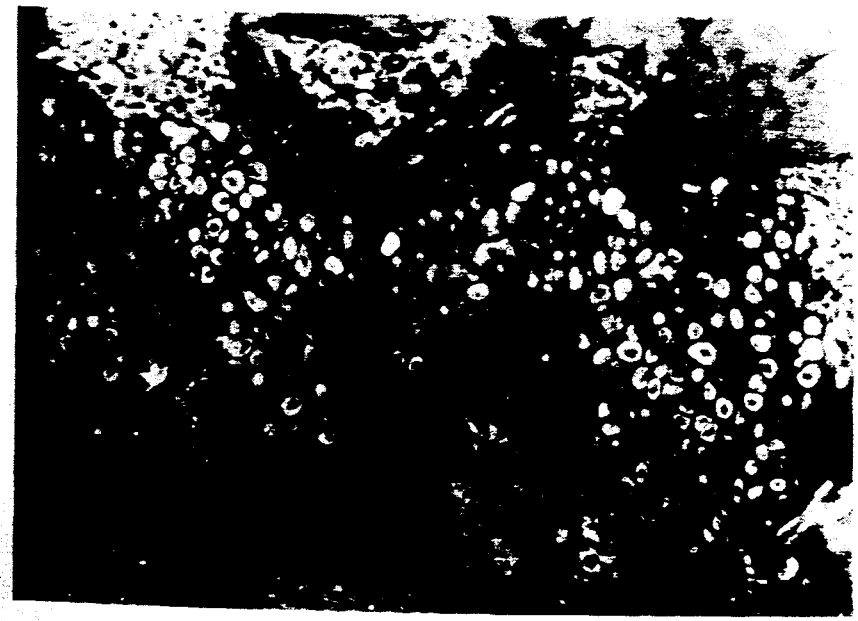
Figure 29C:
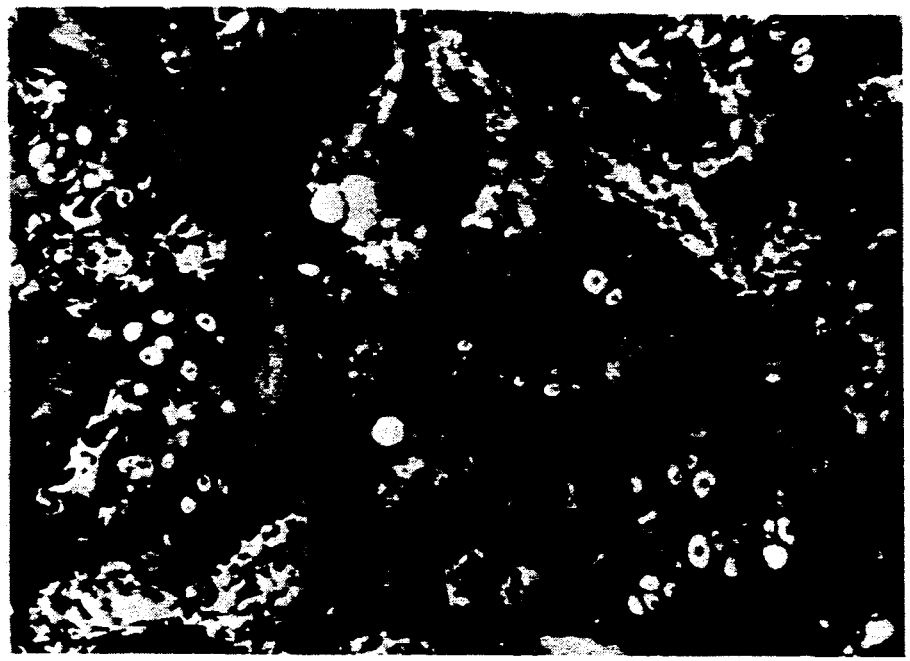
Figure 29D:
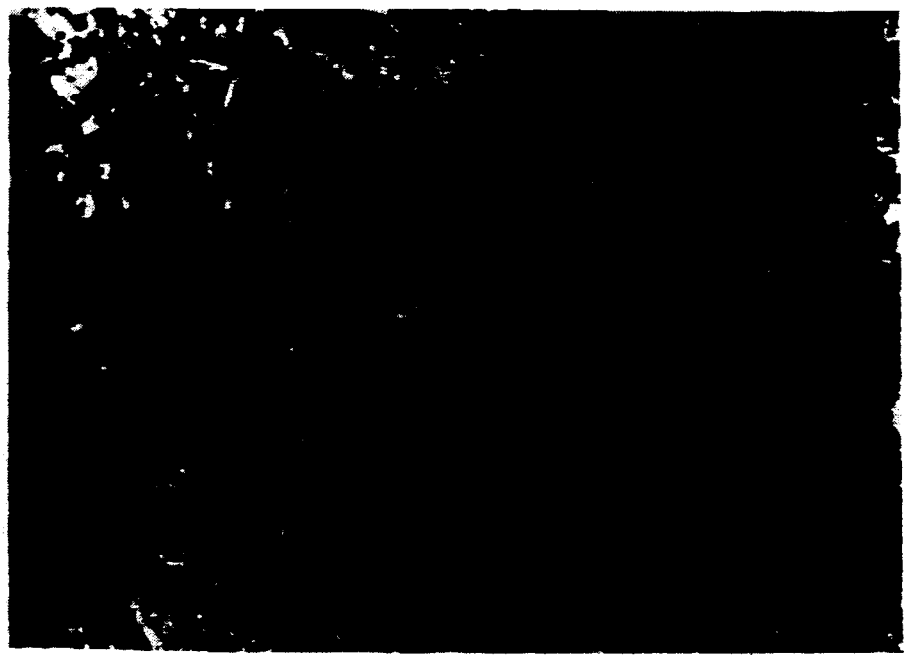
Figure 29E:
Figure 29F:
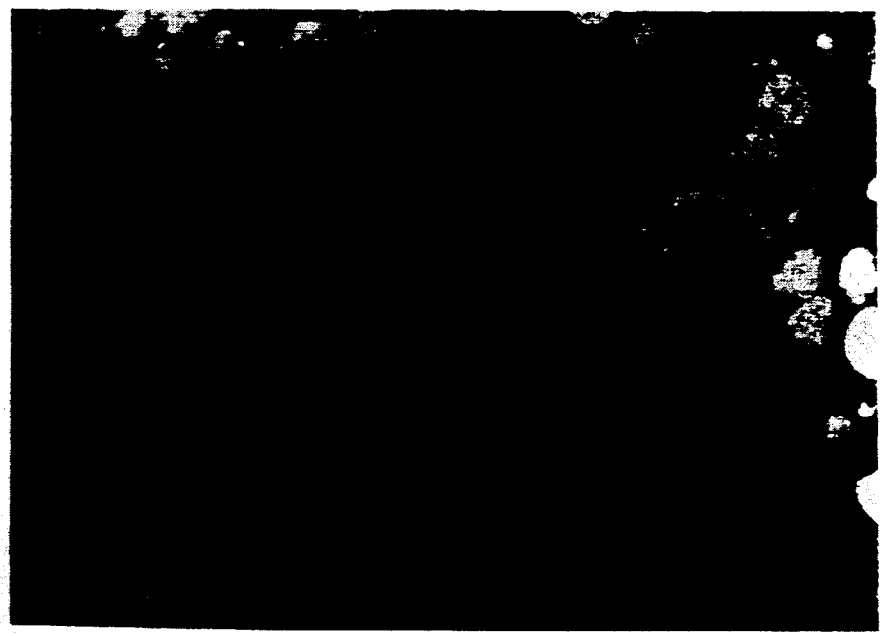

FIG. 28 describes the influence of complete solvent extract from hot water-treated matrix on osteogenic activity as measured in 12-day implants by alkaline phosphatase activity and calcium content. Rat carrier matrix and OP1 implanted without any extract is used as a positive control. The solvent extract obtained from 100 grams of hot water-treated bovine matrix was evaporated and taken up in 6M of 50% acetonitrile/0.1% TFA. 100–300 $\mu$l aliquots then were combined with known amounts of recombinant OP1, and 25 mg of rat matrix carrier, and assayed (see infra). The results clearly show the extract inhibits new bone formation in a dose dependent manner.

The matrix also may be treated to remove contaminating heavy metals, such as by exposing the matrix to a metal ion chelator. For example, following thermal treatment with 0.1% acetic acid, the matrix may be neutralized in a neutralization buffer containing EDTA (sodium ethylenediaminetetraacetic acid), e.g., 200 mM sodium phosphate, 5 mM EDTA, pH 7.0. 5 mM EDTA provides about a 100-fold molar excess of chelator to residual heavy metals present in the most contaminated matrix tested to date. Subsequent washing of the matrix following neutralization appears to remove the bulk of the EDTA. EDTA treatment of matrix particles reduces the residual heavy metal content of all metals tested (Sb, As, Be, Cd, Cr, Cu, Co, Pb, Hg, Ni, Se, Ag, Zn, Tl) to less than about 1 ppm. Bioassays with EDTA-treated matrices indicate that treatment with the metal ion chelator does not inhibit bone inducing activity.

The collagen matrix materials preferably take the form of a fine powder, insoluble in water, comprising nonadherent particles. It may be used simply by packing into the volume where new bone growth or sustained release is desired, held in place by surrounding tissue. Alternatively, the powder may be encapsulated in, e.g., a gelatin or polylactic acid coating, which is absorbed readily by the body. The powder may be shaped to a volume of given dimensions and held in that shape by interadhering the particles using, for example, soluble, species-biocompatible collagen. The material may also be produced in sheet, rod, bead, or other macroscopic shapes.

Demineralized rat bone matrix used as an allogenic matrix in certain of the experiments disclosed herein, is prepared from several of the dehydrated diaphyseal shafts of rat femur and tibia as described herein to produce a bone particle size which passes through a 420 μm sieve. The bone particles are subjected to dissociative extraction with 4M guanidine-HCl. Such treatment results in a complete loss of the inherent ability of the bone matrix to induce endochondral bone differentiation. The remaining insoluble material is used to fabricate the matrix. The material is mostly collagenous in nature, and upon implantation, does not induce cartilage and bone formation. All new preparations are tested for mineral content and osteogenic activity before use. The total loss of biological activity of bone matrix is restored when an active osteoinductive protein fraction or a substantially pure osteoinductive protein preparation is reconstituted with the biologically inactive insoluble collagenous matrix.

C. SYNTHETIC TISSUE-SPECIFIC MATRICES

In addition to the naturally-derived bone matrices described above, useful matrices also may be formulated synthetically if appropriately modified. One example of such a synthetic matrix is the porous, biocompatible, in vivo biodegradable synthetic matrix disclosed in copending U.S. Ser. No. 529,852, filed May 30, 1990, the disclosure of which is hereby incorporated by reference. Briefly, the matrix comprises a porous crosslinked structural polymer of biocompatible, biodegradable collagen, most preferably tissue-specific collagen, and appropriate, tissue-specific glycosaminoglycans as tissue-specific cell attachment factors. Bone tissue-specific collagen (e.g., Type I collagen) derived from a number of sources may be suitable for use in these synthetic matrices, including soluble collagen, acid-soluble collagen, collagen soluble in neutral or basic aqueous solutions, as well as those collagens which are commercially available. In addition, Type II collagen, as found in cartilage, also may be used in combination with Type I collagen.

Glycosaminoglycans (GAGs) or mucopolysaccharides are polysaccharides made up of residues of hexoamines glycosidically bound and alternating in a more-or-less regular manner with either hexouronic acid or hexose moieties. GAGs are of animal origin and have a tissue specific distribution (see, e.g., Dodgson et al. in *Carbohydrate Metabolism and its Disorders* (Dickens et al., eds.) Vol. 1, Academic Press (1968)). Reaction with the GAGs also provides collagen with another valuable property, i.e., inability to provoke an immune reaction (foreign body reaction) from an animal host.

Useful GAGs include those containing sulfate groups, such as hyaluronic acid, heparin, heparin sulfate, chondroitin 6-sulfate, chondroitin 4-sulfate, dermatan sulfate, and keratin sulfate. For osteogenic devices chondroitin 6-sulfate currently is preferred. Other GAGs also may be suitable for forming the matrix described herein, and those skilled in the art will either know or be able to ascertain other suitable GAGs using no more than routine experimentation. For a more detailed description of mucopolysaccharides, see Aspinall, *Polysaccharides*, Pergamon Press, Oxford (1970).

Collagen can be reacted with a GAG in aqueous acidic solutions, preferably in diluted acetic acid solutions. By adding the GAG dropwise into the aqueous collagen dispersion, coprecipitates of tangled collagen fibrils coated with GAG results. This tangled mass of fibers then can be homogenized to form a homogeneous dispersion of fine fibers and then filtered and dried.

Insolubility of the collagen-GAG products can be raised to the desired degree by covalently cross-linking these materials, which also serves to raise the resistance to resorption of these materials. In general, any covalent cross-linking method suitable for cross-linking collagen also is suitable for cross-linking these composite materials, although cross-linking by a dehydrothermal process is preferred.

When dry, the cross-linked particles are essentially spherical with diameters of about 500 μm. Scanning electron microscopy shows pores of about 20 μm on the surface and 40 μm on the interior. The interior is made up of both fibrous and sheet-like structures, providing surfaces for cell attachment. The voids interconnect, providing access to the cells throughout the interior of the particle. The material appears to be roughly 99.5% void volume, making the material very efficient in terms of the potential cell mass that can be grown per gram of microcarrier.

Another useful synthetic matrix is one formulated from biocompatible, in vivo biodegradable synthetic polymers, such as those composed of glycolic acid, lactic acid and/or butyric acid, including copolymers and derivatives thereof. These polymers are well described in the art and are available commercially. For example, polymers composed of polyactic acid (e.g., MW 100 kDa), 80% polylactide/20% glycoside or poly 3-hydroxybutyric acid (e.g., MW 30 kDa) all may be purchased from PolySciences, Inc. The polymer compositions generally are obtained in particulate form and the osteogenic devices preferably fabricated under non-aqueous conditions (e.g., in an ethanol-trifluoroacetic acid solution, EtOH/TFA) to avoid hydrolysis of the polymers. In addition, one can alter the morphology of the particulate polymer compositions, for example to increase porosity, using any of a number of particular solvent treatments known in the art.

Osteogenic devices fabricated with osteogenic protein solubilized in EtOH/TFA and a matrix composed of polylactic acid, poly 3-hydroxybutyric acid, or 80% polylactide/20% glycoside are all osteogenically active when implanted in the rat model and bioassayed as described herein (e.g., as determined by calcium content, alkaline phosphatase levels and histology of 12-day implants, see Section V, infra).

IV. FABRICATION OF OSTEOGENIC DEVICE

The naturally sourced and recombinant proteins as set forth above, as well as other constructs, can be combined and dispersed in a suitable matrix preparation using any of the methods described below. In general, 50–100 ng of active protein is combined with the inactive carrier matrix (e.g., 25 mg matrix for rat bioassays). Greater amounts may be used for large implants.

1. Ethanol Triflouracetic Acid Lyophilization

In this procedure, osteogenic protein is solubilized in an ethanol triflouracetic acid solution (47.5% EtOH/0.01% TFA) and added to the carrier material. Samples are vortexed vigorously and then lyophilized. This method currently is preferred.

2. Acetonitrile Trifluoroacetic Acid Lyophilization

This is a variation of the above procedure, using an acetonitrile trifluroacetic acid (ACN/TFA) solution to solubilize the osteogenic protein that then is added to the carrier material. Samples are vigorously vortexed many times and then lyophilized.

3. Ethanol Precipitation

Matrix is added to osteogenic protein dissolved in guanidine-HCl. Samples are vortexed and incubated at a low temperature (e.g., 4° C.). Samples are then further vortexed. Cold absolute ethanol (5 volumes) is added to the mixture which is then stirred and incubated, preferably for 30 minutes at −20° C. After centrifugation (microfuge, high speed) the supernatant is discarded. The reconstituted matrix is washed twice with cold concentrated ethanol in water (85% EtOH) and then lyophilized.

4. Urea Lyophilization

For those osteogenic proteins that are prepared in urea buffer, the protein is mixed with the matrix material, vortexed many times, and then lyophilized. The lyophilized material may be used "as is" for implants.

5. Buffered Saline Lyophilization

Osteogenic protein preparations in physiological saline may also be vortexed with the matrix and lyophilized to produce osteogenically active material.

These procedures also can be used to adsorb other active therapeutic drugs, hormones, and various bioactive species to the matrix for sustained release purposes.

V. BIOASSAY

The functioning of the various proteins and devices of this invention can be evaluated with an in vivo bioassay. Studies in rats show the osteogenic effect in an appropriate matrix to be dependent on the dose of osteogenic protein dispersed in the matrix. No activity is observed if the matrix is implanted alone. In vivo bioassays performed in the rat model also have shown that demineralized, guanidine-extracted xenogenic bone matrix materials of the type described in the literature generally are ineffective as a carrier, can fail to induce bone, and can produce an inflammatory and immunological response when implanted unless treated as disclosed above. In certain species (e.g., monkey) allogenic matrix materials also apparently are ineffective as carriers (Aspenberg, et al. (1988) *J. Bone Joint Surgery* 70: 625-627.) The following sets forth various procedures for preparing osteogenic devices from the proteins and matrix materials prepared as set forth above, and for evaluating their osteogenic utility.

A. Rat Model

1. Implantation

The bioassay for bone induction as described by Sampath and Reddi ((1983) *Proc. Natl. Acad. Sci. USA* 80 6591-6595), herein incorporated by reference, may be used to monitor endochondral bone differentiation activity. This assay consists of implanting test samples in subcutaneous sites in recipient rats under ether anesthesia. Male Long-Evans rats, aged 28-32 days, were used. A vertical incision (1 cm) is made under sterile conditions in the skin over the thoracic region, and a pocket is prepared by blunt dissection. Approximately 25 mg of the test sample is implanted deep into the pocket and the incision is closed with a metallic skin clip. The day of implantation is designated as day one of the experiment. Implants were removed on day 12. The heterotropic site allows for the study of bone induction without the possible ambiguities resulting from the use of orthotropic sites. As disclosed herein, both allogenic (rat bone matrix) and xenogenic (bovine bone matrix) implants were assayed for bone forming activity. Allogenic implants were used in experiments performed to determine the specific activity of bone purified and recombinant osteogenic protein.

Bone inducing activity is determined biochemically by the specific activity of alkaline phosphatase and calcium content of the day 12 implant. An increase in the specific activity of alkaline phosphatase indicates the onset of bone formation. Calcium content, on the other hand, is proportional to the amount of bone formed in the implant. Bone formation therefore is calculated by determining the calcium content of the implant on day 12 in rats and is expressed as "bone forming units," where one bone forming unit represents the amount of protein that is needed for half maximal bone forming activity of the implant on day 12. Bone induction exhibited by intact demineralized rat bone matrix is considered to be the maximal bone differentiation activity for comparison purposes in this assay.

2. Cellular Events

Successful implants exhibit a controlled progression through the stages of protein-induced endochondral bone development, including: (1) transient infiltration by polymorphonuclear leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoclasts, bone remodeling and dissolution of the implanted matrix on days twelve to eighteen; and (8) hematopoietic bone marrow differentiation in the ossicles on day twenty-one. The results show that the shape of the new bone conforms to the shape of the implanted matrix.

3. Histological Evaluation

Histological sectioning and staining is preferred to determine the extent of osteogenesis in the implants. Implants are fixed in Bouins Solution, embedded in paraffin, and cut into 6–8 μm sections. Staining with toluidine blue or hemotoxylin/eosin demonstrates clearly the ultimate development of endochondral bone. Twelve day implants are usually sufficient to determine whether the implants contain newly induced bone.

4. Biological Markers

Alkaline phosphatase activity may be used as a marker for osteogenesis. The enzyme activity may be determined spectrophotometrically after homogenization of the implant. The activity peaks at 9-10 days in vivo and thereafter slowly declines. Implants showing no bone development by histology have little or no alkaline phosphatase activity under these assay conditions. The assay is useful for quantification and obtaining an estimate of bone formation quickly after the implants are removed from the rat. Alternatively, the amount of bone formation can be determined by measuring the calcium content of the implant.

5. Results

Histological examination of implants indicate that osteogenic devices containing the natural-sourced osteogenic protein or recombinant osteogenic protein have true osteogenic activity. Moreover, the osteogenic specific activity of recombinant OP1 homodimers matches that of the substantially pure natural-sourced material.

5.1 Bone Purified Osteogenic Protein

Implants containing osteogenic protein at several levels of purity have been tested to determine the most effective dose/purity level, in order to seek a formulation which could be produced on an industrial scale. As described supra, the results were measured by alkaline phosphatase activity level, calcium content, and histological examination and represented as bone forming units. Also as described supra, one bone forming unit represents the amount of protein that is needed for half maximal bone forming activity of the implant on day 12. The bone forming activity elicited by intact rat demineralized bone matrix is considered to be the maximal bone differentiation activity for comparison purposes in this assay.

Figure 11:
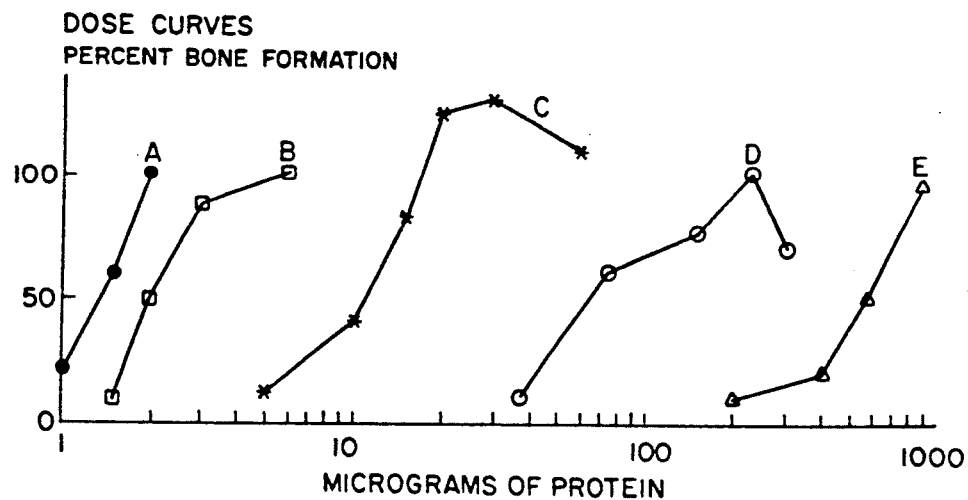
FIG. 11 is a graph showing representative dose response curves for bone-inducing activity in samples from various purification steps including reverse phase HPLC on C-18 (A), heparin-Sepharose II (B), TSK 3000 (C), HAP-ultragel (D), and heparin-Sepharose I (E)

Dose curves were constructed for bone inducing activity in vivo by assaying various concentrations of protein purified from bone at each step of the purification scheme. FIG. 11 shows representative dose curves in rats. Approximately 10–12 μg of the TSK-fraction (FIG. 11C), 3-4 μg of heparin-Sepharose-II fraction (FIG. 11B), 0.5–1 μg of the C-18 column fraction (FIG. 11A), and 25–50 ng of gel eluted highly purified 30 kDa protein is needed for unequivocal bone formation (half maximum activity) when implanted with 25 mg of matrix. Subsequent additional experiments have measured a half maximum activity of about 21–25 ng protein per 25 mg matrix for the highly purified, gel eluted 30 kDa osteogenic protein (see U.S. Pat. No. 5,011,691.) Thus, 0.8–1.0 ng of highly purified osteogenic protein per mg of implant matrix is sufficient to exhibit half maximal bone differentiation in vivo. 50 to 100 ng per 25 mg of implant normally is sufficient to produce maximum endochondral bone. Thus, 2 to 4 ng osteogenic protein per mg of implant matrix is a reasonable dosage, although higher dosages may be used.

Figure 17A:
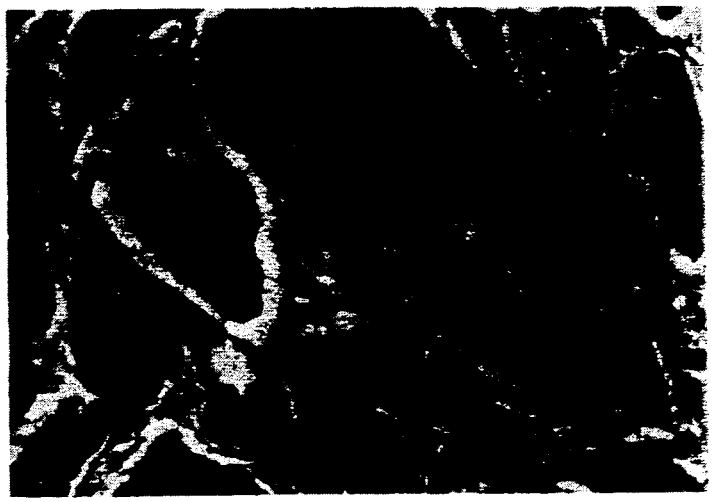
FIGS. 17A through 17C are photographic representations of the histological examination of bone implants in the rat model: carrier alone (A); carrier and glycosylated osteogenic protein (B); and carrier and deglycosylated osteogenic protein (C). Arrows indicate osteoblasts.
Figure 17B:
Figure 17C:
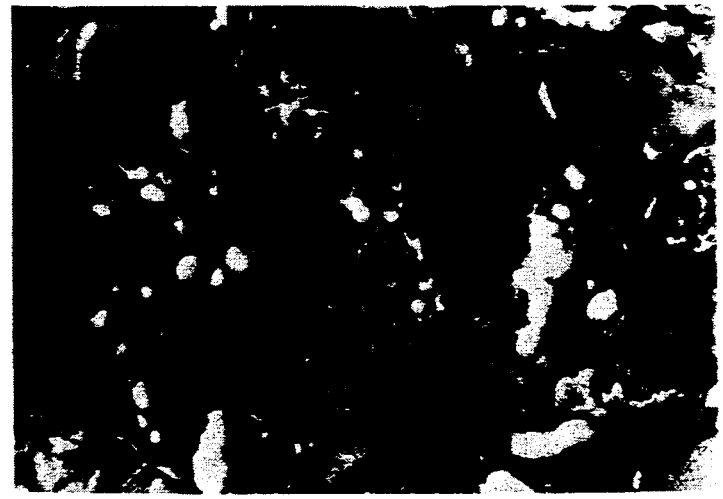

As shown in FIG. 17, osteogenic devices comprising unglycosylated osteogenic protein are osteogenically active. Compare FIGS. 17B (showing carrier and glycosylated protein) and 17C (showing carrier and deglycosylated protein). Arrows indicate osteoblasts. FIG. 17A is a control where carrier alone was implanted. No bone formation is evident in this control implant.

5.2 Recombinant Osteogenic Protein

Homodimers of the various fusion constructs disclosed herein and expressed in *E. coli* all are osteogenically active. In addition, osteogenic activity is present with OP1A-CBMP2B1, OP1B-CBMP2B1, and OP1C-CBMP2B2 protein combinations. In addition, dimeric species of the truncated analog active regions (COP5 and COP7, disclosed in U.S. Pat. No. 5,011,691), alone or in combination, also induce osteogenesis as determined by histological examination.

Recombinant OP1 expressed from different mammalian cell sources and purified to different extents (1–5% pure to 30–90% pure) were tested for osteogenic activity in vivo as set forth above using 25 mg matrix. Table 9 below shows the histology score for OP1 expressed in all three cell types.

TABLE 9

| Mammalian Cells | OP1 Subunit | OP1 Protein Concentration* (ng/implant) | Histology Score (%) |
|---|---|---|---|
| BSC40-tsA58 | 18 kDa (70–90% pure) | 32.5 | 50 |
|  |  | 65.0 | 40 |
|  |  | 130.0 | 80 |
|  |  | 260.0 | 100 |
|  | 16 kDa (30–40% pure) | 12.5 | 20 |
|  |  | 25.0 | 50 |
|  |  | 50.0 | 80 |
|  |  | 100.0 | 100 |
|  |  | 200.0 | 100 |
| CHO | 16–20 kDa (less than 5% pure) | 50.0 | 90 |
|  |  | 100.0 | 90 |
|  |  | 200.0 | 100 |
| COS | 18 kDa (less than 5% pure) | 25.0 | 10 |
|  |  | 50.0 | 30 |
|  |  | 100.0 | 90 |
|  |  | 200.0 | 90 |
| demineralized rat matrix |  |  | 40 |

Figure 32A:
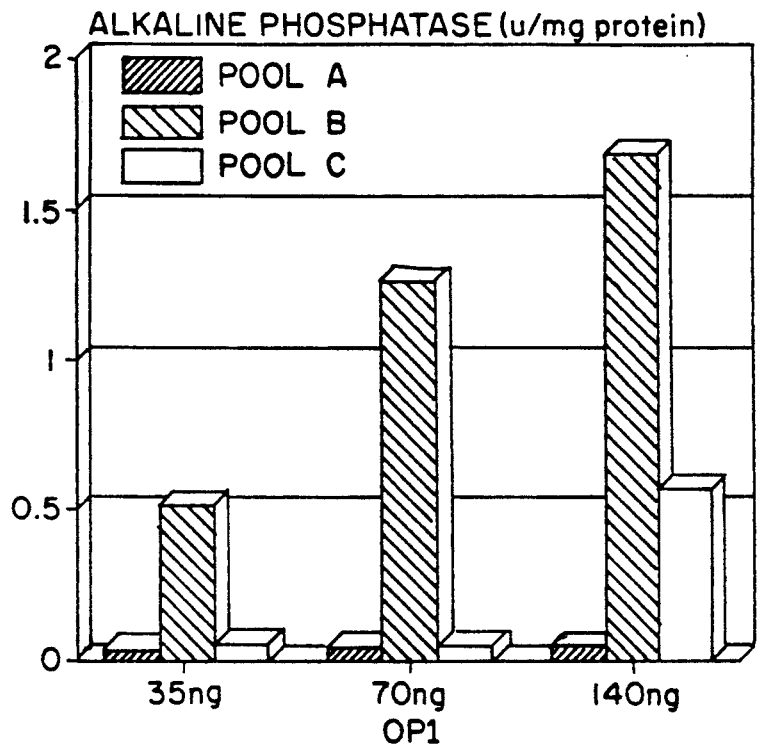
FIGS. 32A and 32B are bar graphs showing the dose dependence of OP1 expressed in COS and BSC cells, as measured by (A) alkaline phosphatase activity and (B) calcium content in xenogenic implants (day 12), vs increasing concentration of protein (dose curve in ng)
Figure 32B:
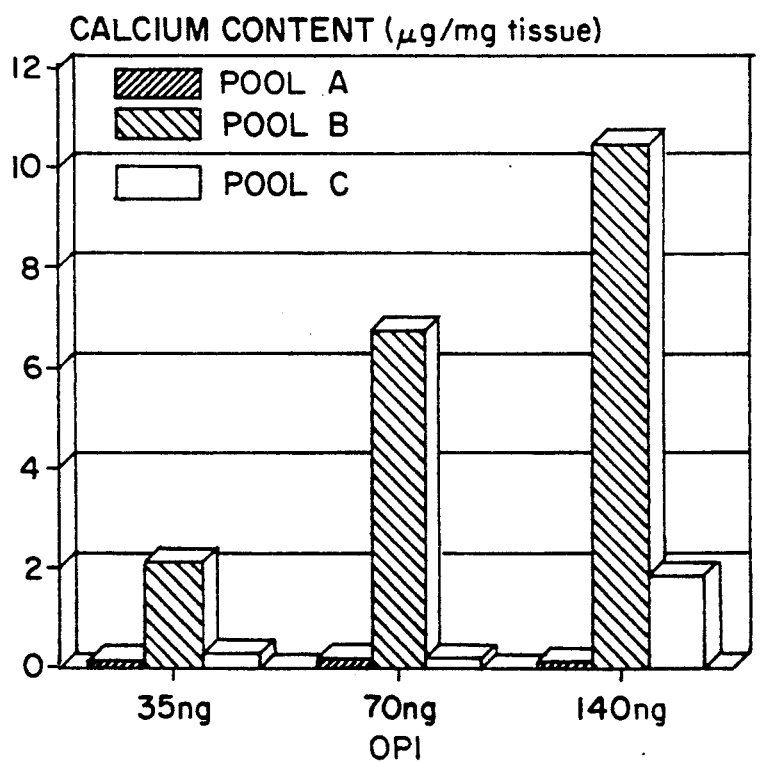

10–30%: moderate bone formation
30–80%: extensive bone formation
above 80%: evidence of hematopoietic bone marrow recruitment.
*estimated by immunoblots or gel scanning The histology scores detailed in Table 9 show that OP1 is active regardless of cell source, and that the activity mimics that of natural-sourced bovine osteogenic protein (see discussion of FIG. 31 and 32, infra.) Moreover, the bone-inducing activity is highly reproducible and dose dependent.

Additional bioassays, performed using highly purified OP1 (90% pure), and formulated with rat matrix by the acetonitrile/TFA method, suggest that CHO-produced OP1 shows slightly more bone-inducing activity when compared to BSC-derived OP1 preparations (at lower protein concentrations). Finally, numerous bioassays have been conducted with the various degraded species identified in the different OP1 preparations (e.g., OP1-16Ala, OP1-16Val, OP1-16Ser, OP1-16Leu and OP1-16Met.) Significant variations in bone inducing activity, as measured by calcium content or histology, could not be detected among these different OP1 species.

Figure 30:
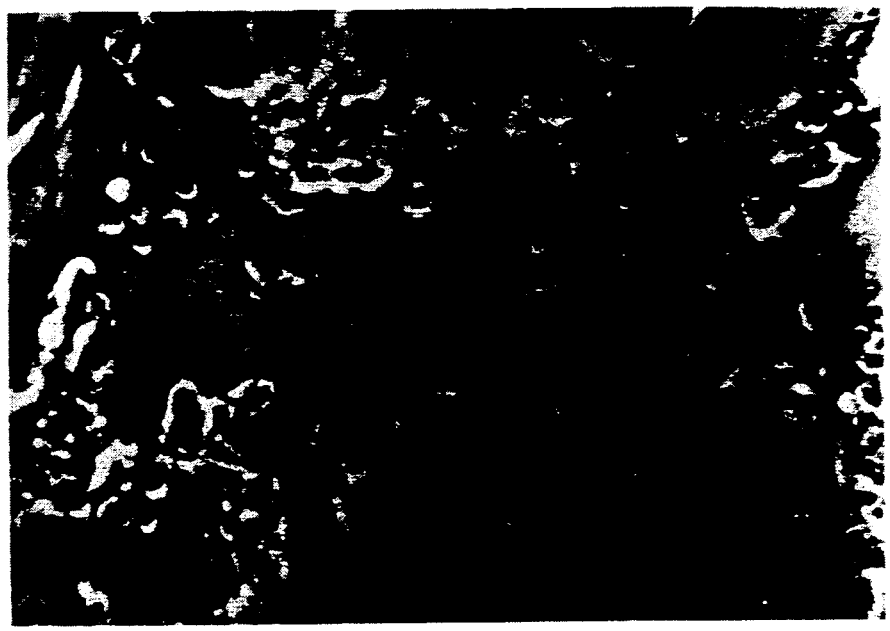
FIG. 30 is a photomicrograph showing the histology (day 12) of a xenogenic implant of this invention using OP1 expressed from BSC cells and hot water-treated xenogenic bovine matrix.

Further evidence of the bone-forming activity of recombinant OP1 is provided in the photomicrographs of FIGS. 29 and 30. FIGS. 29A-F are photomicrographs recording the histology of allogenic implants using recombinant OP1 expressed from COS, BSC, and COS cells. The micrographs (magnified 220×), provide graphic evidence of the full developmental cascade induced by the osteogenic proteins of this invention, confirming that recombinantly produced OP1 alone is sufficient to induce endochondral bone formation, when implanted in association with a matrix. As evidenced in FIG. 29A, allogenic implants that do not contain OP1 show no new bone formation at 12 days post implant. Only the implanted bone matrix (m) and surrounding mesenchyme are seen. Conversely, implants containing OP1 already show evidence of extensive chondrogenesis by 7 days post implant (FIG. 29B, 500 ng BSC-produced protein, 30% pure). Here, newly formed cartilage cells, chondroblasts (Cb) and chondrocytes (Cy) are in close contact with the matrix (m). By 9 days post implant endochondral bone differentiation, cartilage calcification, hypertrophy of chondrocytes, vascular invasion, and the onset of new bone formation are all evident (FIG. 29C, 220 ng COS-produced protein, approx. 5% pure). Invading capillaries (c) and the appearance of basophilic osteoblasts (indicated by arrows) near the vascular endothelium are particularly evident. By 12 days post implant extensive bone formation and remodeling has occurred (FIG. 29D (220×), and 29E (400×), CHO-produced protein, approx. 60% pure). The newly formed bone laid down by osteoblasts is being remodeled by multinucleated osteoclasts (Oc), and the implanted matrix is being reabsorbed and replaced by remodeled bone. Bone marrow recruitment in the newly formed ossicles is also evident. Finally, hematopoietic bone marrow differentiation within the ossicles can be seen by 22 days post implant (FIG. 29F, 500 ng BSC-produced protein, 30% pure). By this time most of the implanted matrix (m) has been resorbed and is occupied by newly-formed bone containing ossicles filled with bone marrow elements including erythrocytic and granulocytic series and megakaryocytes. Similar histological observations have been made for implants incorporating greater than 90% pure OP1 preparations.

FIG. 30 is a photomicrograph showing the histology at 12 days post implant for a xenogenic implant using hot water-treated bovine matrix and OP1 (BSC-produced). The recruitment of hematopoietic bone marrow elements is evident in the photomicrograph, showing that the bone forming activity of xenogenic implants with OP1 parallels that of allogenic implants (compare FIG. 30 with FIGS. 29D and 29E).

The cellular events exhibited by the OP1 matrix implants and evidenced in FIGS. 29 and 30 truly mimic the endochondral bone differentiation that occurs during the foetal development. Although endochondral bone differentiation has been the predominant route, there is also evidence for intra-membraneous bone formation at the outer surface of the implant.

FIGS. 31 and 32 describe the dose dependence of osteogenic activity for 12-day implants comprising recombinant OP1 expressed from different mammalian cell sources, as determined by specific activity of alkaline phosphatase and calcium content of allogenic implants (FIG. 31) and xenogenic implants of this invention (FIG. 32). In all cases, OP1 protein concentration (quantitated by immuno blot staining or by gel scanning), is represented in nanograms. In each case, bone inducing activity is specific to OP1 in a dose dependent manner in all cells. Moreover, osteogenic activity of the mammalian cell-produced protein mimics that of the natural-sourced material. Highly purified gel-eluted osteogenic bovine protein, purified as disclosed herein and in U.S. Pat. Nos. 4,968,590 and 5,011,691, has a half maximal activity of at least about 0.8–1 ng/mg matrix (20–25 ng protein/25 mg matrix). As can be seen in Table 9 and FIGS. 31 and 32, even partially purified recombinantly produced OP1 falls within this range of osteogenic activity (about 20–30 ng/25 mg matrix).

B. Feline Model

The purpose of this study is to establish a large animal efficacy model for the testing of the osteogenic devices of the invention, and to characterize repair of massive bone defects and simulated fracture non-union encountered frequently in the practice of orthopedic surgery. The study is designed to evaluate whether implants of osteogenic protein with a carrier can enhance the regeneration of bone following injury and major reconstructive surgery by use of this large mammal model. The first step in this study design consists of the surgical preparation of a femoral osteotomy defect which, without further intervention, would consistently progress to non-union of the simulated fracture defect. The effects of implants of osteogenic devices into the created bone defects are evaluated by the study protocol described below. While this and the rabbit study, described infra, use allogenic matrices as carrier material, appropriate treatment as described herein of any bone-derived matrix material is anticipated to render the matrix suitable for xenogenic implants. Similarly, while the osteogenic protein used in this and the rabbit study is bOP, it is anticipated that any of the osteogenic proteins disclosed herein may be substituted.

1. Procedure

Sixteen adult cats each weighing less than 10 lbs. undergo unilateral preparation of a 1 cm bone defect in the right femur through a lateral surgical approach. In other experiments, a 2 cm bone defect was created. The femur is immediately internally fixed by lateral placement of an 8-hole plate to preserve the exact dimensions of the defect. There are three different types of materials implanted in the surgically created cat femoral defects: group I (n=3) is a control group which undergoes the same plate fixation with implants of 4M guanidine-HCl-treated (inactivated) cat demineralized bone matrix powder (GuHCl-DBM) (360 mg); group II (n=3) is a positive control group implanted with biologically active demineralized bone matrix powder (DBM) (360 mg); and group III (n=10) undergoes a procedure identical to groups I-II, with the addition of osteogenic protein onto each of the GuHCl-DBM carrier samples. To summarize, the group III osteogenic protein-treated animals are implanted with exactly the same material as the group I animals, but with the singular addition of osteogenic protein.

All animals are allowed to ambulate ad libitum within their cages post-operatively. All cats are injected with tetracycline (25 mg/kg subcutaneously (SQ) each week for four weeks) for bone labelling. All but four group III animals are sacrificed four months after femoral osteotomy.

2. Radiomorphometrics

Figure 12:
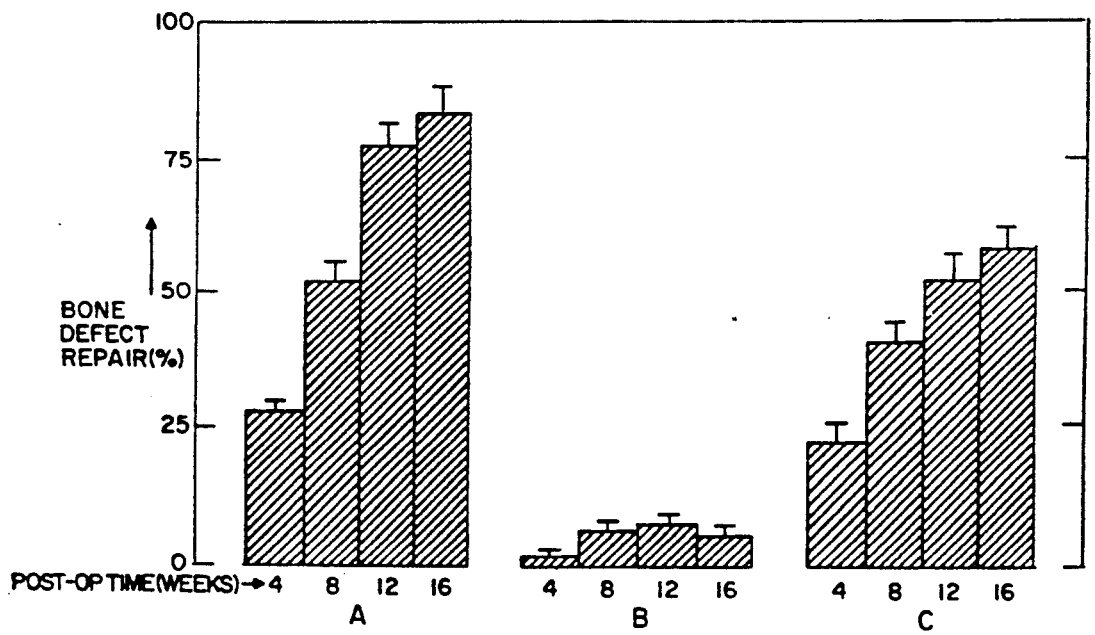
FIG. 12 is a bar graph of radiomorphometric analyses of feline bone defect repair after treatment with an osteogenic device (A), carrier control (B), and demineralized bone (C)

In vivo radiomorphometic studies are carried out immediately post-op at 4, 8, 12 and 16 weeks by taking a standardized X-ray of the lightly anesthesized animal positioned in a cushioned X-ray jig designed to consistently produce a true anterio-posterior view of the femur and the osteotomy site. All X-rays are taken in exactly the same fashion and in exactly the same position on each animal. Bone repair is calculated as a function of mineralization by means of random point analysis. A final specimen radiographic study of the excised bone is taken in two planes after sacrifice. X-ray results are shown in FIG. 12, and displaced as percent of bone defect repair. To summarize, at 16 weeks, 60% of the group III femurs are united with average 86% bone defect regeneration (FIG. 12, sec. A). By contrast, the group I GuHCl-DMB negative-control implants exhibit no bone growth at four weeks, less than 10% at eight and 12 weeks, and 16% (±10%) at 16 weeks with one of the five exhibiting a small amount of bridging bone (FIG. 12, sec. B). The group II DMB positive-control implants exhibited 18% (±3%) repair at four weeks, 35% at eight weeks, 50% (±10%) at 12 weeks and 70%

(±12%) by 16 weeks, a statistical difference of p<0.01 compared to osteogenic protein at every month. One of the three (33%) is united at 16 weeks (FIG. 12, sec. C.)

3. Biomechanics

Excised test and normal femurs are immediately studied by bone densitometry, or wrapped in two layers of saline-soaked towels, placed into sealed plastic bags, and stored at −20° C. until further study. Bone repair strength, load to failure, and work to failure are tested by loading to failure on a specially designed steel 4-point bending jig attached to an Instron testing machine to quantitate bone strength, stiffness, energy absorbed and deformation to failure. The study of test femurs and normal femurs yield the bone strength (load) in pounds and work to failure in joules. Normal femurs exhibit a strength of 96 (±12) pounds. Osteogenic protein-implanted femurs exhibit 35 (±4) pounds, but when corrected for surface area at the site of fracture (due to the "hourglass" shape of the bone defect repair) this correlated closely with normal bone strength. Only one demineralized bone specimen was available for testing with a strength of 25 pounds, but, again, the strength correlated closely with normal bone when corrected for fracture surface area.

4. Histomorphometry/Histology

Following biomechanical testing the bones are immediately sliced into two longitudinal sections at the defect site, weighed, and the volume measured. One-half is fixed for standard calcified bone histomorphometrics with fluorescent stain incorporation evaluation, and one-half is fixed for decalcified hemotoxylin/eosin stain histology preparation.

5. Biochemistry

Selected specimens from the bone repair site (n=6) are homogenized in cold 0.15M NaCl, 3 mM $NaHCO_3$, pH 9.0 by a Spex freezer mill. The alkaline phosphatase activity of the supernatant and total calcium content of the acid soluble fraction of sediment are then determined.

6. Histopathology

The final autopsy reports reveal no unusual or pathologic findings noted at necropsy of any of the animals studied. A portion of all major organs are preserved for further study. A histopathological evaluation is performed on samples of the following organs: heart, lung, liver, both kidneys, spleen, both adrenals, lymph nodes, left and right quadriceps muscles at mid-femur (adjacent to defect site in experimental femur). No unusual or pathological lesions are seen in any of the tissues. Mild lesions seen in the quadriceps muscles are compatible with healing responses to the surgical manipulation at the defect site. Pulmonary edema is attributable to the euthanasia procedure. There is no evidence of any general systemic effects or any effects on the specific organs examined.

7. Feline Study Summary

The 1 cm and 2 cm femoral defect cat studies demonstrate that devices comprising a matrix containing disposed osteogenic protein can: (1) repair a weight-bearing bone defect in a large animal; (2) consistently induces bone formation shortly following (less than two weeks) implantation; and (3) induce bone by endochondral ossification, with a strength equal to normal bone, on a volume for volume basis. Furthermore, all animals remained healthy during the study and showed no evidence of clinical or histological laboratory reaction to the implanted device. In this bone defect model, there was little or no healing at control bone implant sites. The results provide evidence for the successful use of osteogenic devices to repair large, non-union bone defects.

C. Rabbit Model

1. Procedure and Results

Eight mature (less than 10 lbs) New Zealand White rabbits with epiphyseal closure documented by X-ray were studied. The purpose of this study is to establish a model in which there is minimal or no bone growth in the control animals, so that when bone induction is tested, only a strongly inductive substance will yield a positive result. Defects of 1.5 cm are created in the rabbits, with implantation of: osteogenic protein (n=5), DBM (n=8), GuHCl-DBM (n=6), and no implant (n=10). Six osteogenic protein implants are supplied and all control defects have no implant placed.

Of the eight animals (one animal each was sacrificed at one and two weeks), 11 ulnae defects are followed for the full course of the eight week study. In all cases (n=7) following osteo-periosteal bone resection, the no implant animals establish no radiographic union by eight weeks. All no implant animals develop a thin "shell" of bone growing from surrounding bone present at four weeks and, to a slightly greater degree, by eight weeks. In all cases (n=4), radiographic union with marked bone induction is established in the osteogenic protein-implanted animals by eight weeks. As opposed to the no implant repairs, this bone is in the site of the removed bone.

Radiomorphometric analysis reveal 90% osteogenic protein-implant bone repair and 18% no-implant bone repair at sacrifice at eight weeks. At autopsy, the osteogenic protein bone appears normal, while "no implant" bone sites have only a soft fibrous tissue with no evidence of cartilage or bone repair in the defect site.

2. Allograft Device

In another experiment, the marrow cavity of the 1.5 cm ulnar defect is packed with activated osteogenic protein rabbit bone powder and the bones are allografted in an intercalary fashion. The two control ulnae are not healed by eight weeks and reveal the classic "ivory" appearance. In distinct contrast, the osteogenic protein-treated implants "disappear" radiographically by four weeks with the start of remineralization by six to eight weeks. These allografts heal at each end with mild proliferative bone formation by eight weeks.

This type of device serves to accelerate allograph repair.

3. Summary

These studies of 1.5 cm osteo-periosteal defects in the ulnae of mature rabbits show that: (1) it is a suitable model for the study of bone growth; (2) "no implant" or GuHCl negative control implants yield a small amount of periosteal-type bone, but not medullary or cortical bone growth; (3) osteogenic protein-implanted rabbits exhibited proliferative bone growth in a fashion highly different from the control groups; (4) initial studies show that the bones exhibit 50% of normal bone strength (100% of normal correlated vol:vol) at only eight weeks after creation of the surgical defect; and (5) osteogenic protein-allograft studies reveal a marked effect upon both the allograft and bone healing.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

---

What is claimed is:

1. Substantially pure mammalian osteogenic protein comprising a pair of unglycosylated polypeptide chains and capable of inducing endochondral bone formation in association with a matrix when implanted in a mammal said osteogenic protein comprising at least one of the following amino acid sequences:
   a) Ala-Cys-Cys-Val-Pro-Thr-Glu-Leu-Ser-Ala-Ile Ser-Met-Leu-Tyr-Leu-Asp-Glu-Asn-Glu-Lys,
   b) Val-Pro-Lys-Pro, and
   c) Ala-Pro-Thr.

2. The osteogenic protein of claim 1 having an apparent molecular weight of about 27 kDa as determined by comparison to molecular weight standards in SDS-polyacrylamide gel electrophoresis.

3. The osteogenic protein of claim 2 wherein one of said pair of unglycosylated polypeptide chains has an apparent molecular weight of about 14 kDa, and the other has an apparent molecular weight of about 16 kDa, both as determined after reduction by comparison to molecular weight standards in SDS-polyacrylamide gel electrophoresis.

4. The osteogenic protein of claim 1 characterized by the approximate amino acid composition set forth below:

| Amino acid residue | Rel. no. res./molec. |
|---|---|
| Asp/Asn | 22 |
| Glu/Gln | 24 |
| Ser | 24 |
| Gly | 29 |
| His | 5 |
| Arg | 13 |
| Thr | 11 |
| Ala | 18 |
| Lys | 12 |
| Tyr | 11 |
| Val | 14 |
| Met | 3 |
| Cys | 16 |
| Ile | 15 |
| Leu | 15 |
| Pro | 14 |
| Phe | 7 |
| Trp | ND |

5. The osteogenic protein of claim 1 further comprising an amino acid sequence selected from the group consisting of: fragment 1, (residues 93 to 109 of Seq. ID No. 20); fragment 2, (residues 121 to 134 of Seq. ID No. 22); fragment 4, (residues 153 to 165 of Seq. ID No. 22); fragment 5, (residues 137 to 151 of Seq. ID No. 22); and fragment 6, (residues 77 to 83 of Seq. ID No. 20).

6. An isolated protein comprising the amino acid sequence described by residues 335 to 431 of Seq. ID No. 1 (OPS).

7. The protein of claim 6 comprising the amino acid sequence described by residues 330 to 431 of Seq. ID No. 1 (OP7).

8. The protein of claim 7 comprising the amino acid sequence described by residues 318 to 431 of Seq. ID No. 1 (OP1-16Val).

9. The protein of claim 8 comprising the amino acid sequence described by residues 316 to 431 of Seq. ID No. 1 (OP1-16Ala).

10. The protein of claim 9 comprising the amino acid sequence described by residues 315 to 431 of Seq. ID No. 1 (OP1-16Met).

11. The protein of claim 10 comprising the amino acid sequence described by residues 313 to 431 of Seq. ID No. 1 (OP1-16Leu).

12. The protein of claim 11 comprising the amino acid sequence described by residues 300 to 431 of Seq. ID No. 1 (OP1-16Ser).

13. The protein of claim 12 comprising the amino acid sequence described by residues 293 to 431 of Seq. ID No. 1 (OP1-18Ser).

14. The protein of claim 13 comprising the amino acid sequence described by residues 1 to 431 of Seq. ID No. 1 (hOP1-PP).

15. An isolated protein comprising the amino acid sequence described by residues 334 to 430 of Seq. ID No. 24.

16. The protein of claim 15 comprising the amino acid sequence described by residues 292 to 430 of Seq. ID No. 24 (mOP1-Ser).

17. The protein of claim 16 comprising the amino acid sequence described by residues 1 to 430 of Seq. ID No. 24 (mOP1-PP).

18. An isolated protein comprising the amino acid sequence described by residues 303 to 399 of Seq. ID No. 26.

19. The protein of claim 18 comprising the amino acid sequence described by residues 261 to 399 of Seq. ID No. 26 (mOP2-Ala).

20. The protein of claim 19 comprising the amino acid sequence described by residues 1 to 399 of Seq. ID No. 26 (mOP2-PP).

21. An isolated protein comprising the amino acid sequence described by residues 306 to 402 of Seq. ID No. 28.

22. The protein of claim 21 comprising the amino acid sequence described by residues 270–402 of Seq. ID No. 28 (hOP2-Arg).

23. The protein of claim 22 comprising the amino acid sequence described by residues 267 to 402 of Seq. ID No. 28 (hOP2-Pro).

24. The protein of claim 23 comprising the amino acid sequence described by residues 264 to 402 of Seq. ID No. 28 (hOP2-Ala).

25. The protein of claim 24 comprising the amino acid sequence described by residues 243 to 402 of Seq. ID No. 28 (hOP2-Ser).

26. The protein of claim 25 comprising the amino acid sequence described by residues 1 to 402 of Seq. ID No. 28 (hOP2-PP).

27. The protein of claim 6, 15, 18 or 21 capable of inducing cartilage and bone formation when implanted in a mammal in association with a matrix.

28. Osteogenic protein expressed from recombinant DNA in a host cell,
   the protein comprising a pair of oxidized subunits disulfide bonded to produce a dimeric species, one of said subunits having an amino acid sequence sufficiently duplicative of the sequence comprising residues 335 to 431 of Seq. ID No. 1 (OPS), such that the disulfide bonded dimeric species comprising said subunit has a conformation capable of inducing cartilage and endochondral bone formation in a mammal when disposed within a matrix implanted in said mammal.

29. Osteogenic protein expressed from recombinant DNA in a host cell,
the protein comprising a pair of oxidized subunits disulfide bonded to produce a dimeric species, having a conformation capable of inducing cartilage and endochondral bone formation in a mammal when disposed within a matrix implanted in said mammal,
one of said subunits having an amino acid sequence encoded by a nucleic acid capable of hybridizing to a nucleic acid encoding OPS (res. 335–431, Seq. ID No. 1) under stringent hybridization conditions.

30. Osteogenic protein expressed from recombinant DNA in a host cell, the protein comprising a pair of oxidized subunits disulfide bonded to produce a dimeric species having a conformation capable of inducing cartilage and endochondral bone formation in a mammal when disposed within a matrix implanted in said mammal,
one of said subunits having an amino acid sequence comprising OPS (residues 335 to 431 of Seq. ID No. 1), including mutated forms thereof, allelic variants thereof, truncated forms thereof and biosynthetic analogs thereof.

31. The protein of claim 28 or 29 wherein said subunit comprises an amino acid sequence sharing greater than 65% identity with an amino acid sequence comprising OPS.

32. The protein of claim 28 or 29 wherein said subunit comprises OPS.

33. The protein of claim 28, 29 or 30 wherein said subunit comprises OP7 (res. 330 to 431, Seq. ID No. 1).

34. The protein of claim 28, 29 or 30 wherein said subunit is derived from hOP1-PP (res. 1–431, Seq. ID No. 1).

35. The protein of claim 28, 29 or 30 wherein the other said subunit comprises OPS (residues 335 to 431 of Seq. ID No. 1).

36. The protein of claim 28, 29 or 30 wherein the other subunit comprises an amino acid sequence selected from the group consisting of: CBMP2AS (residues 301 to 396 of Seq. ID No. 4); CBMP2BS (residues 313 to 408 of Seq. ID No. 6); CBMP2AL (residues 296 to 396 of Seq. ID No. 4); and CBMP2BL (residues 308 to 408 of Seq. ID No. 6).

37. The protein of claim 28, 29 or 30 wherein the other subunit comprises an amino acid sequence derived from an immature sequence selected from the group consisting of: hOP1-PP (Seq. ID No. 1, res. 1–431); CBMP2A (residues 1 to 396 of Seq. ID No. 4); and CBMP2B (residues 1 to 408 of Seq. ID No. 6).

38. A dimeric protein expressed from a nucleic acid encoding an amino acid sequence sufficiently duplicative of the amino acid sequence encoded by the DNA sequence of Seq. ID No. 1 or Seq. ID No. 3 such that, when said protein is oxidized to produce a disulfide bonded dimeric species, the dimeric species has a conformation that is capable of inducing endochondral bone and cartilage formation when disposed within a matrix and implanted in a mammal.

39. The protein of claim 28 or 29 wherein said subunit comprises at least the osteogenically active region of a protein selected from the group consisting of: mOP1-PP (residues 1–430, Seq. ID No. 24); mOP2-PP (residues 1–399 of Seq. ID No. 26); and hOP2-PP (residues 1–402 of Seq. ID No. 28).

40. The protein of claim 38 expressed from recombinant DNA in a mammalian host cell.

41. An osteogenic protein expressed from recombinant DNA in a mammalian host cell and capable of inducing endochondral bone formation in a mammal when disposed within a matrix implanted in said mammal,
the protein comprising two oxidized subunits, the amino acid sequence of each subunit being sufficiently duplicative of the amino sequence described by residues 335 to 431 of Seq. ID No. 1 (OPS) such that the dimeric species comprising said subunits has a conformation that is capable of inducing endochondral bone formation in a mammal when disposed within said matrix and implanted in said mammal.

42. The protein of claim 41 wherein the amino acid sequence of each said subunit has greater than 65% identity with the amino acid sequence described by residues 335 to 431 of Seq. ID No. 1 (OPS).

43. The protein of claim 41 wherein the amino acid sequence of each said subunit comprises a sequence independently selected from the group consisting of: residues 318 to 431 of Seq. ID No. 1 (OP1-16Val); residues 293 to 431 of Seq. ID No. 1 (OP1-18Ser); residues 300 to 431 of Seq. ID No. 1 (OP1-16Ser); residues 313 to 431 of Seq. ID No. 1 (OP1-16Leu); residues 315 to 431 of Seq. ID No. 1 (OP1-16Met); and residues 316 to 431 of Seq. ID No. 1 (OP1-16Ala).

44. The protein of claim 41 wherein said protein is unglycosylated.

45. An isolated polypeptide chain useful as a subunit of a dimeric osteogenic protein, said polypeptide chain having an amino acid sequence sharing greater than 74% identity with the sequence described by residues 264–402 of Seq. ID No. 28 (hOP2-Ala) such that the disulfide bonded dimeric species comprising said polypeptide chain is capable of inducing endochondral bone formation when implanted in a mammal in association with a matrix.

46. An isolated polypeptide chain useful as a subunit of a dimeric osteogenic protein having a conformation capable of inducing endochondral bone formation in a mammal when implanted in a mammal in association with a matrix,
said polypeptide chain having an amino acid sequence encoded by a nucleic acid capable of hybridizing to a nucleic acid encoding the pro region of mOP2-PP (res. 17–260 of Seq. ID No. 26) or hOP2-PP (res. 17–263 of Seq. ID No. 28) under stringent hybridization conditions.

47. The polypeptide chain of claim 45 or 46 having an amino acid sequence sharing greater than 80% identity with the amino acid sequence of hOP2-Ala.

48. The polypeptide chain of claim 47 having an amino acid sequence sharing greater than 85% identity with the amino acid sequence of hOP2-Ala.

49. The polypeptide chain of claim 45 or 46 wherein said amino acid sequence is selected from the group consisting of: mOP2-Ala (residues 261–399 Seq. ID No. 26); hOP2-Ala (residues 264–402 of Seq. ID No. 28); hOP2-Pro (residues 267–402 of Seq. ID No. 28); hOP2-

Arg (residues 270–402 of Seq. ID No. 28) and hOP2-Ser (residues 243–402 of Seq. ID No. 28).

50. The polypeptide chain of claim 45 or 46 wherein said amino acid sequence is derived from an amino acid sequence selected from the group consisting of: mOP2-PP (residues 1–399 of Seq. ID No. 26) and hOP2-PP (residues 1–402 of Seq. ID No. 28) including allelic variants thereof, and natural and biosynthetic mutants thereof.

51. The polypeptide chain of claim 45 or 46 that is glycosylated.

52. An isolated dimeric protein capable of inducing cartilage or endochondral bone formation in a mammal when implanted in said mammal in association with a matrix,
said protein comprising a pair of disulfide-bonded polypeptide chains constituting a dimeric species, wherein each said polypeptide chain is the polypeptide chain of claim 45 or 46.

53. The dimeric protein of claim 52 wherein each said polypeptide chain is independently selected and comprises at least the osteogenically active region of mOP2-PP (residues 1–399 of Seq. ID No. 26) or hOP2-PP (residues 1–402 of Seq. ID No. 28).

54. The dimeric protein of claim 53, wherein each said polypeptide chain is independently selected from the group consisting of: mOP2-Ala (residues 261–399 Seq. ID No. 26); hOP2-Ala (residues 264–402 of Seq. ID No. 28); hOP2-Pro (residues 267–402 of Seq. ID No. 28); hOP2-Arg (residues 270–402 of Seq. ID No. 28) and hOP2-Ser (residues 243–402 of Seq. ID No. 28).

55. An isolated osteogenic protein comprising a pair of oxidized subunits disulfide bonded to produce a dimeric species, one of said subunits comprising a polypeptide chain having an amino acid sequence comprising the sequence OPX-7C (Seq. ID No. 31), wherein each Xaa independently represents one of the 20 naturally occurring L-isomer, α-amino acids or a derivative thereof, and together with said 7 cysteine residues define said polypeptide chain,
such that the dimeric species comprising said subunit has a conformation capable of inducing endochondral bone formation in a mammal when implanted in said mammal in association with a matrix.

56. The polypeptide chain of claim 55 wherein the sequence further comprises the amino acid sequence:

| Cys 1 | Xaa | Xaa | Xaa | Xaa 5 |
|---|---|---|---|---|

(OPX-8C, Seq. ID No. 32), and wherein each Xaa independently represents one of the 20 naturally occurring L-isomer, α-amino acids or a derivative thereof, and together with said 8 cysteine residues define said polypeptide chain.

57. An isolated protein comprising a pair of oxidized subunits disulfide bonded to produce a dimeric species, one of said subunits comprising a polypeptide chain having an amino acid sequence comprising OPX (Seq. ID No. 30) such that the dimeric species comprising said subunit has a conformation capable of inducing cartilage and endochondral bone formation in a mammal when implanted in said mammal in association on with a matrix.

58. A protein expressed from recombinant DNA in a host cell, said protein comprising an amino acid sequence encoded by a nucleic acid capable of hybridizing to a nucleic acid encoding residues 306–402 of hOP2 (Seq. ID No. 28) under stringent hybridization conditions.

* * * * *

Adverse Decision in Interference

Patent No. 5,266,683, Hermann Oppermann, Engin Ozkaynak, Thangavel Kuberasampath, David C. Rueger, Roy H.L. Pang, OSTEOGENIC PROTEINS, Interference No. 105,508, final judgment adverse to the patentees rendered May 21, 2007, as to claims 21-26, 27/21, 28, 29, 39, 45-54, and 58.

*(Official Gazette July 29, 2008)*

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 1822 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: HOMO SAPIENS
        ( F ) TISSUE TYPE: HIPPOCAMPUS ( i x ) FEATURE:
        ( A ) NAME/KEY: CDS
        ( B ) LOCATION: 49..1341
        ( C ) IDENTIFICATION METHOD: experimental
        ( D ) OTHER INFORMATION: /function="OSTEOGENIC PROTEIN"
            / product="OP1"
            / evidence=EXPERIMENTAL
            / standardname="OP1"

( x i ) SEQUENCE DESCRIPTION: SEQ ID NO:1:

```
GGTGCGGGCC CGGAGCCCGG AGCCCGGGTA GCGCGTAGAG CCGGCGCG  ATG  CAC  GTG         57
                                                      Met  His  Val
                                                        1

CGC  TCA  CTG  CGA  GCT  GCG  GCG  CCG  CAC  AGC  TTC  GTG  GCG  CTC  TGG  GCA    105
Arg  Ser  Leu  Arg  Ala  Ala  Ala  Pro  His  Ser  Phe  Val  Ala  Leu  Trp  Ala
      5                        10                      15

CCC  CTG  TTC  CTG  CTG  CGC  TCC  GCC  CTG  GCC  GAC  TTC  AGC  CTG  GAC  AAC    153
Pro  Leu  Phe  Leu  Leu  Arg  Ser  Ala  Leu  Ala  Asp  Phe  Ser  Leu  Asp  Asn
 20                      25                      30                      35

GAG  GTG  CAC  TCG  AGC  TTC  ATC  CAC  CGG  CGC  CTC  CGC  AGC  CAG  GAG  CGG    201
Glu  Val  His  Ser  Ser  Phe  Ile  His  Arg  Arg  Leu  Arg  Ser  Gln  Glu  Arg
                     40                      45                      50

CGG  GAG  ATG  CAG  CGC  GAG  ATC  CTC  TCC  ATT  TTG  GGC  TTG  CCC  CAC  CGC    249
Arg  Glu  Met  Gln  Arg  Glu  Ile  Leu  Ser  Ile  Leu  Gly  Leu  Pro  His  Arg
                55                      60                      65

CCG  CGC  CCG  CAC  CTC  CAG  GGC  AAG  CAC  AAC  TCG  GCA  CCC  ATG  TTC  ATG    297
Pro  Arg  Pro  His  Leu  Gln  Gly  Lys  His  Asn  Ser  Ala  Pro  Met  Phe  Met
           70                      75                      80

CTG  GAC  CTG  TAC  AAC  GCC  ATG  GCG  GTG  GAG  GAG  GGC  GGC  GGG  CCC  GGC    345
Leu  Asp  Leu  Tyr  Asn  Ala  Met  Ala  Val  Glu  Glu  Gly  Gly  Gly  Pro  Gly
      85                      90                      95

GGC  CAG  GGC  TTC  TCC  TAC  CCC  TAC  AAG  GCC  GTC  TTC  AGT  ACC  CAG  GGC    393
Gly  Gln  Gly  Phe  Ser  Tyr  Pro  Tyr  Lys  Ala  Val  Phe  Ser  Thr  Gln  Gly
100                      105                     110                     115

CCC  CCT  CTG  GCC  AGC  CTG  CAA  GAT  AGC  CAT  TTC  CTC  ACC  GAC  GCC  GAC    441
Pro  Pro  Leu  Ala  Ser  Leu  Gln  Asp  Ser  His  Phe  Leu  Thr  Asp  Ala  Asp
                120                     125                     130

ATG  GTC  ATG  AGC  TTC  GTC  AAC  CTC  GTG  GAA  CAT  GAC  AAG  GAA  TTC  TTC    489
```

```
                Met Val Met Ser Phe Val Asn Leu Val Glu His Asp Lys Glu Phe Phe
                            135             140              145

CAC CCA CGC TAC CAC CAT CGA GAG TTC CGG TTT GAT CTT TCC AAG ATC                537
His Pro Arg Tyr His His Arg Glu Phe Arg Phe Asp Leu Ser Lys Ile
        150             155              160

CCA GAA GGG GAA GCT GTC ACG GCA GCC GAA TTC CGG ATC TAC AAG GAC                585
Pro Glu Gly Glu Ala Val Thr Ala Ala Glu Phe Arg Ile Tyr Lys Asp
        165             170              175

TAC ATC CGG GAA CGC TTC GAC AAT GAG ACG TTC CGG ATC AGC GTT TAT                633
Tyr Ile Arg Glu Arg Phe Asp Asn Glu Thr Phe Arg Ile Ser Val Tyr
180             185             190              195

CAG GTG CTC CAG GAG CAC TTG GGC AGG GAA TCG GAT CTC TTC CTG CTC                681
Gln Val Leu Gln Glu His Leu Gly Arg Glu Ser Asp Leu Phe Leu Leu
                200             205              210

GAC AGC CGT ACC CTC TGG GCC TCG GAG GAG GGC TGG CTG GTG TTT GAC                729
Asp Ser Arg Thr Leu Trp Ala Ser Glu Glu Gly Trp Leu Val Phe Asp
        215             220              225

ATC ACA GCC ACC AGC AAC CAC TGG GTG GTC AAT CCG CGG CAC AAC CTG                777
Ile Thr Ala Thr Ser Asn His Trp Val Val Asn Pro Arg His Asn Leu
        230             235              240

GGC CTG CAG CTC TCG GTG GAG ACG CTG GAT GGG CAG AGC ATC AAC CCC                825
Gly Leu Gln Leu Ser Val Glu Thr Leu Asp Gly Gln Ser Ile Asn Pro
        245             250              255

AAG TTG GCG GGC CTG ATT GGG CGG CAC GGG CCC CAG AAC AAG CAG CCC                873
Lys Leu Ala Gly Leu Ile Gly Arg His Gly Pro Gln Asn Lys Gln Pro
260             265             270              275

TTC ATG GTG GCT TTC TTC AAG GCC ACG GAG GTC CAC TTC CGC AGC ATC                921
Phe Met Val Ala Phe Phe Lys Ala Thr Glu Val His Phe Arg Ser Ile
                280             285              290

CGG TCC ACG GGG AGC AAA CAG CGC AGC CAG AAC CGC TCC AAG ACG CCC                969
Arg Ser Thr Gly Ser Lys Gln Arg Ser Gln Asn Arg Ser Lys Thr Pro
        295             300              305

AAG AAC CAG GAA GCC CTG CGG ATG GCC AAC GTG GCA GAG AAC AGC AGC                1017
Lys Asn Gln Glu Ala Leu Arg Met Ala Asn Val Ala Glu Asn Ser Ser
        310             315              320

AGC GAC CAG AGG CAG GCC TGT AAG AAG CAC GAG CTG TAT GTC AGC TTC                1065
Ser Asp Gln Arg Gln Ala Cys Lys Lys His Glu Leu Tyr Val Ser Phe
        325             330              335

CGA GAC CTG GGC TGG CAG GAC TGG ATC ATC GCG CCT GAA GGC TAC GCC                1113
Arg Asp Leu Gly Trp Gln Asp Trp Ile Ile Ala Pro Glu Gly Tyr Ala
340             345             350              355

GCC TAC TAC TGT GAG GGG GAG TGT GCC TTC CCT CTG AAC TCC TAC ATG                1161
Ala Tyr Tyr Cys Glu Gly Glu Cys Ala Phe Pro Leu Asn Ser Tyr Met
                360             365              370

AAC GCC ACC AAC CAC GCC ATC GTG CAG ACG CTG GTC CAC TTC ATC AAC                1209
Asn Ala Thr Asn His Ala Ile Val Gln Thr Leu Val His Phe Ile Asn
        375             380              385

CCG GAA ACG GTG CCC AAG CCC TGC TGT GCG CCC ACG CAG CTC AAT GCC                1257
Pro Glu Thr Val Pro Lys Pro Cys Cys Ala Pro Thr Gln Leu Asn Ala
        390             395              400

ATC TCC GTC CTC TAC TTC GAT GAC AGC TCC AAC GTC ATC CTG AAG AAA                1305
Ile Ser Val Leu Tyr Phe Asp Asp Ser Ser Asn Val Ile Leu Lys Lys
        405             410              415

TAC AGA AAC ATG GTG GTC CGG GCC TGT GGC TGC CAC TAGCTCCTCC                     1351
Tyr Arg Asn Met Val Val Arg Ala Cys Gly Cys His
420             425             430

GAGAATTCAG ACCCTTGGG  GCCAAGTTTT TCTGGATCCT CCATTGCTCG CCTTGGCCAG              1411

GAACCAGCAG ACCAACTGCC TTTTGTGAGA CCTTCCCCTC CCTATCCCCA ACTTTAAAGG              1471

TGTGAGAGTA TTAGGAAACA TGAGCAGCAT ATGGCTTTTG ATCAGTTTTT CAGTGGCAGC              1531

ATCCAATGAA CAAGATCCTA CAAGCTGTGC AGGCAAAACC TAGCAGGAAA AAAAAACAAC              1591
```

```
GCATAAAGAA AAATGGCCGG GCCAGGTCAT TGGCTGGGAA GTCTCAGCCA TGCACGGACT    1651

CGTTTCCAGA GGTAATTATG AGCGCCTACC AGCCAGGCCA CCCAGCCGTG GGAGGAAGGG    1711

GGCGTGGCAA GGGGTGGGCA CATTGGTGTC TGTGCGAAAG GAAAATTGAC CCGGAAGTTC    1771

CTGTAATAAA TGTCACAATA AAACGAATGA ATGAAAAAAA AAAAAAAAA A              1822
```

( 2 ) INFORMATION FOR SEQ ID NO:2:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met His Val Arg Ser Leu Arg Ala Ala Pro His Ser Phe Val Ala
 1           5                  10                  15

Leu Trp Ala Pro Leu Phe Leu Leu Arg Ser Ala Leu Ala Asp Phe Ser
            20              25                  30

Leu Asp Asn Glu Val His Ser Ser Phe Ile His Arg Arg Leu Arg Ser
        35              40                  45

Gln Glu Arg Arg Glu Met Gln Arg Glu Ile Leu Ser Ile Leu Gly Leu
 50                      55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
 130                 135                 140

Glu Phe Phe His Pro Arg Tyr His His Arg Glu Phe Arg Phe Asp Leu
 145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
 210                 215                 220

Val Phe Asp Ile Thr Ala Thr Ser Asn His Trp Val Val Asn Pro Arg
 225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
 290                 295                 300

Lys Thr Pro Lys Asn Gln Glu Ala Leu Arg Met Ala Asn Val Ala Glu
 305                 310                 315                 320

Asn Ser Ser Ser Asp Gln Arg Gln Ala Cys Lys Lys His Glu Leu Tyr
```

|     |     |     |     |     | 325 |     |     |     | 330 |     |     |     | 335 |     |
| --- | --- | --- | --- | --- | --- | --- | --- | --- | --- | --- | --- | --- | --- | --- |
| Val | Ser | Phe | Arg | Asp | Leu | Gly | Trp | Gln | Asp | Trp | Ile | Ile | Ala | Pro | Glu |
|     |     |     | 340 |     |     |     | 345 |     |     |     |     |     | 350 |     |     |
| Gly | Tyr | Ala | Ala | Tyr | Tyr | Cys | Glu | Gly | Glu | Cys | Ala | Phe | Pro | Leu | Asn |
|     |     | 355 |     |     |     |     | 360 |     |     |     |     | 365 |     |     |     |
| Ser | Tyr | Met | Asn | Ala | Thr | Asn | His | Ala | Ile | Val | Gln | Thr | Leu | Val | His |
|     | 370 |     |     |     |     | 375 |     |     |     |     | 380 |     |     |     |     |
| Phe | Ile | Asn | Pro | Glu | Thr | Val | Pro | Lys | Pro | Cys | Cys | Ala | Pro | Thr | Gln |
| 385 |     |     |     |     | 390 |     |     |     |     | 395 |     |     |     |     | 400 |
| Leu | Asn | Ala | Ile | Ser | Val | Leu | Tyr | Phe | Asp | Asp | Ser | Ser | Asn | Val | Ile |
|     |     |     |     | 405 |     |     |     |     | 410 |     |     |     |     | 415 |     |
| Leu | Lys | Lys | Tyr | Arg | Asn | Met | Val | Val | Arg | Ala | Cys | Gly | Cys | His |     |
|     |     |     | 420 |     |     |     |     | 425 |     |     |     |     | 430 |     |     |

( 2 ) INFORMATION FOR SEQ ID NO:3:

( i ) SEQUENCE CHARACTERISTICS:
  ( A ) LENGTH: 17410 base pairs
  ( B ) TYPE: nucleic acid
  ( C ) STRANDEDNESS: single
  ( D ) TOPOLOGY: linear ( i i ) MOLECULE TYPE: DNA (genomic)

( v i ) ORIGINAL SOURCE:
  ( A ) ORGANISM: homo sapiens ( i x ) FEATURE:
  ( A ) NAME/KEY: exon
  ( B ) LOCATION: 3192..3730
  ( D ) OTHER INFORMATION: /label=EXON-1
   / note="START CODON BEGINS AT POSITION 3313"

( i x ) FEATURE:
  ( A ) NAME/KEY: miscfeature
  ( B ) LOCATION: 10413..10414
  ( D ) OTHER INFORMATION: /label=GAP-1
   / note="APPROXIMATELY BASES ARE ESTIMATED TO
   BE MISSING BETWEEN POSITIONS 10413 AND 10414 IN
   THIS SEQUENCE."

( i x ) FEATURE:
  ( A ) NAME/KEY: exon
  ( B ) LOCATION: 10696..10891
  ( D ) OTHER INFORMATION: /label=EXON-2

( i x ) FEATURE:
  ( A ) NAME/KEY: miscfeature
  ( B ) LOCATION: 10960..10961
  ( D ) OTHER INFORMATION: /label=GAP-2
   / note="APPROXIMATELY BASES ARE ESTIMATED TO
   BE MISSING BETWEEN POSITION 10960 AND 10961 IN
   THIS SEQUENCE."

( i x ) FEATURE:
  ( A ) NAME/KEY: exon
  ( B ) LOCATION: 11059..11211
  ( D ) OTHER INFORMATION: /label=EXON-3

( i x ) FEATURE:
  ( A ) NAME/KEY: miscfeature
  ( B ) LOCATION: 11351..11352
  ( D ) OTHER INFORMATION: /label=GAP-3
   / note="APPROXIMATELY BASES ARE ESTIMATED TO
   BE MISSING BETWEEN POSITIONS 11351 AND 11352 IN
   THIS SEQUENCE."

( i x ) FEATURE:
  ( A ) NAME/KEY: exon
  ( B ) LOCATION: 11420..11617
  ( D ) OTHER INFORMATION: /label=EXON-4

( i x ) FEATURE:
  ( A ) NAME/KEY: miscfeature
  ( B ) LOCATION: 11721..11722

( D ) OTHER INFORMATION: /label=GAP-4
/ note="APPROXIMATELY BASES ARE ESTIMATED TO
BE MISSING BETWEEN POSITIONS 11721 AND 11722 IN
THIS SEQUENCE."

( i x ) FEATURE:
( A ) NAME/KEY: exon
( B ) LOCATION: 13354..13436
( D ) OTHER INFORMATION: /label=EXON-5

( i x ) FEATURE:
( A ) NAME/KEY: exon
( B ) LOCATION: 15044..15160
( D ) OTHER INFORMATION: /label=EXON-6

( i x ) FEATURE:
( A ) NAME/KEY: exon
( B ) LOCATION: 17245..17410
( D ) OTHER INFORMATION: /label=EXON-7

( x i ) SEQUENCE DESCRIPTION: SEQ ID NO:3:

| | | | | | | |
|---|---|---|---|---|---|---|
| TCAACCGGTC | TCTTTAGGTT | TTGGCTGTGC | TTATTACTAT | TCATTCAACA | GGTACTAATT | 60 |
| GAGCACCTGC | TGTGTGCCAG | GCTCAGAATA | GGCTCAGGTG | AGATGCACAA | AGAAGGGTAA | 120 |
| ACTAGAATCC | TTGCTTAGAC | ACTGACGGAT | CAGTTGTTTC | ATATGTAAAT | TGTAGCACCA | 180 |
| AGACCTGCTG | CCCCTGCCCC | CAGCCTCACC | TGCTTGTGAA | GATCCCTCCA | AAAGATTTGA | 240 |
| GAGTAGATAA | AAAGCAGAGA | CTACTACTGA | AGAACAGGGC | TGCTTTGGCT | CCTTATTATT | 300 |
| TCAGACTTTG | GAAGAAAATG | ACCTCCTTTT | TCTCTACTGG | CACTGAGTGC | ATAGCTGACC | 360 |
| TAGCAAGCCA | GGCCTGGAGG | GCGTGTGCAG | GGCTGGGGAC | CGAGCCTGGT | TTCTGTTCCC | 420 |
| TGCTCTGCAG | CTCAAGCACT | TGCTGTTCCT | CCACCTGGGA | TGCCTTTCCC | TGGAAAAGCC | 480 |
| TGTCTCTTTC | TTGTCTTTCA | GGACTCAGGT | CAGTGGCATC | TCCTCCAAAA | ACTCCCCTTC | 540 |
| CCACCCTCCA | TCACCTCACC | CTGTTTATCT | GCGCCCCGC | CCCCACTGCC | TGTCACTTAT | 600 |
| TGCAGGCTGA | AGTGACCCAG | GCTCTCCAGT | TGTACACTCT | CAGATGGACC | CTGGACGACT | 660 |
| GTGGCACTCC | TGCAATTTCC | CCAGTCTCCC | TGGGGTAGGA | TTCCTGCTTG | CCAGGATGCC | 720 |
| CACCTTTCCT | TCTCCCTCCT | GCATGTCCTC | CTCTGCCTGG | CTTCTGAATT | GTTTCCAGAG | 780 |
| AGAGTGATAG | ACAAGATCTG | CCTCTCCTTC | AGTCCCTGAA | TCTTATTTAA | GGCTCTTGCT | 840 |
| TTGCTTCCTG | GCTGGAGGCG | GCTCTTGATG | GAGTCTGCCA | TGTGGGTTCG | CTCATGGCCA | 900 |
| TGTCTTCCTG | CCCAGCATGG | TGCTTGGCCC | TGGGACTGGC | CACATAATAT | CTGGGCCAGG | 960 |
| TGCAAAATTA | GTACGGGGCA | GGGGGTACTT | TGTTCATAGG | TGATTCAGAA | CCACATATGG | 1020 |
| TGACCTCAGA | GTAGGAAACC | AAGTGTGGGG | CCCTTAAGAG | CTGGGGGGCC | CTGTACGACT | 1080 |
| GTCCAGGTTG | CAGGCCCCAC | AGCTCGCCTC | CTGATATCCT | GTGCTCCATG | CTTGTCTGTT | 1140 |
| GAAGGAAGGA | GTGAATGGAT | GAAGAGCAGG | TGGTGGGGGG | TGGTTTGAGG | GCCTTGCTGG | 1200 |
| TGGGTGGGTA | GAGGCCCCTC | CCTGGCATGG | GGCTCAAGAC | CTGTTCCATC | CCACAGCCTG | 1260 |
| GGGCCTGTGT | GTAAATGGCC | AGGACCTGCA | GGCTGGCATT | TTTCTGCTCC | TTGCCTGGCT | 1320 |
| CTGGCTCCCC | TTTCTCCACC | CATGTGGCCC | CTCAGGCTGC | CATCTAGTCC | AAAAGTCCCA | 1380 |
| AGGGAGACCC | AGAGGCCACT | TGGCAAACTA | CTTCTGCTCC | AGAAAACTGT | AGAAGACCAT | 1440 |
| AATTCTCTTC | CCCAGCTCTC | CTGCTCCAGG | AAGGACAGCC | CCAAAGTGAG | GCTTAGCAGA | 1500 |
| GCCCCTCCCA | GACAAGCGCC | CCCGCTTCCC | CAACCTCAGC | CCTTCCCAGT | TCATCCCAAA | 1560 |
| GGCCCTCTGG | GGACCCACTC | TCTCACCCAG | CCCCAGGAGG | GAAGGAGACA | GGATGAACTT | 1620 |
| TTACCCCACC | CCGCTGCCCT | CACTGCCACT | CTGGGTGCAG | TAATTCCCTT | GAGATCCCAC | 1680 |
| ACCGGCAGAG | GGACCGGTGG | GTTCTGAGTG | GTCTGGGGAC | TCCCTGTGAC | AGCGTGCATG | 1740 |
| GCTCGGTATT | GATTGAGGGA | TGAATGGATG | AGGAGAGACA | GGAGAGGAGG | CCGATGGGGA | 1800 |

```
GGTCTCAGGC ACAGACCCTT GGAGGGGAAG AGGATGTGAA GACCAGCGGC TGGCTCCCCA      1860
GGCACTGCCA CGAGGAGGGC TGATGGGAAG CCCTAGTGGT GGGGCTGGGG TGTCTGGTCT      1920
CAGGCTGAGG GGTGGCTGGA AAGATACAGG GCCCCGAAGA GGAGGAGGTG GGAAGAACCC      1980
CCCCAGCTCA CACGCAGAAC ACTTATTCAC TCAACAAATC GTGACTGCGC ACGTACAGTG      2040
GCTACCAGGC GCTGGGTTCA AGGCACTGCG GGTACCAGAG GTGCGGAGAA GATCGCTGAT      2100
CCGGGCCCCA GTGCTCTGGG TGTCTAGCGG GGGTAAGAAG GCAATAAAGA AGGCACGGAG      2160
TAACTCAAAC AGCAATTCCA GACAGCAAGA GAAACTACAG GAAAGAAAAC AAACGTGCGA      2220
GGGGCGAGGC GAGGAAACAA CCTCAGCTTG GCAGGTCTTG GAGGTCTCTG GGAGGAGAAA      2280
GCAGCGTCTG ATGGGGCGG GAGGTGGTGA GTGGGGAGAG GTCCAGGCGG AGGGAATGGC       2340
GAGCGAGAGA CAGGCTGGCA ACGGCTTCAG GGAGGCGCGG AGGGGTCAGC GTGGCTGGCT      2400
TAAAAGGATA CATGGGACTA GGGGCAAGAC CGGCTCAAGG TCACCGCTTC CAGGACCTTC      2460
TATTTCCGCG CCATTATTGC CACCTCCGCG CTCCCCAAC TTTTCCCACC GCGGTCCGCA       2520
GCCCACCCGT CCTGCTCGGG CCGCCTTCCT GGTCCGGACC GCGAGTGCCG AGAGGCAGGG     2580
CGGCTCCGAT TCCTCCAGCC GCATCCCCGC GACGTCCCGC CAGCTCTAGG CACCCCGTGG     2640
CACTCAGTAA ACATTTGTCG AGCGCTCTAG AGGGAATGAA TGAACCCACT GGGCACAGCT     2700
GGGGGAGGG CGGGGCGAGG GAGGTGGGAG GCCGCCGGCG CGGAGGGGCC CCTCGAAGCC       2760
CGTCCTCCTC CTCCTCCTCC TCCGCCCAGG CCCCAGCGCG TACCACTCTG GCGCTCCCGA     2820
GGCGGCCTCT TGTGCGATCC AGGGCGCACA AGGCTGGGAG AGCGCCCCGG GGCCCCTGCT     2880
ATCCGCGCCG GAGTTGGAAG AGGGTGGGTT GCCGCCGCCC GAGGGCAGAC GGCCAGAGGA     2940
GCGGAAGAAG GAGCGCTCGC CCGCCCGCCT GCCTCCTCGC TGCCTCCCCG GCGTTGGCTC     3000
TCTGGACTCC TAGGCTTGCT GGCTGCTCCT CCCACCCGCG CCCGCCTCCT CACTCGCCTT     3060
TTCGTTCGCC GGGGCTGCTT TCCAAGCCCT GCGTGCGCCC GGGGAGTGCG GGCGAGGGG      3120
CCGGGGCAGC ACCGAGCAGG GGGCGGGGGT CCGGGCAGAC GCGCCGGCCG GGGAGGGGCC     3180
ATGTCTGGCG CGGGCGAGCG GGGCCCGTCT GCAGCAAGTG ACCGACGGCC GGGACGGCCG     3240
CCTGCCCCCT CTGCCACCTG GGGCGGTGCG GGCCCGGAGC CCGGAGCCCG GGTAGCGCGT     3300
AGAGCCGGCG CGATGCACGT GCGCTCACTG CGAGCTGCGG CGCCGCACAG CTTCGTGGCG     3360
CTCTGGGCAC CCCTGTTCCT GCTGCGCTCC GCCCTGGCCG ACTTCAGCCT GGACAACGAG     3420
GTGCACTCGA GCTTCATCCA CCGGCGCCTC CGCAGCCAGG AGCGGCGGGA GATGCAGCGC     3480
GAGATCCTCT CCATTTTGGG CTTGCCCCAC CGCCGCGCC CGCACCTCCA GGGCAAGCAC      3540
AACTCGGCAC CCATGTTCAT GCTGGACCTG TACAACGCCA TGGCGGTGGA GGAGGGCGGC    3600
GGGCCCGGCG GCCAGGGCTT CTCCTACCCC TACAAGGCCG TCTTCAGTAC CCAGGGCCCC    3660
CCTCTGGCCA GCCTGCAAGA TAGCCATTTC CTCACCGACG CCGACATGGT CATGAGCTTC    3720
GTCAACCTCG GTGAGTAAGG GCAGGCGAGG GTACGCCGTC TCCTTTCGGG GGCACTTTGA    3780
GACTGGGAGG GAGGGAGCCG CTTCTTCTAT GCAGCCCGCC CAGCTTTCCG CTCCTGGCTG    3840
AAATCGCAGT GCCTGCCCGA GGGTCTCCCA CCCACAGCCC TATGACTCCC AAGCTGTGTG    3900
CGCCCCCAGG TCGGGCCGCT GGGTCGGTGA GCCTGTAGGG GTTACTGGGA AGGAGGGATC    3960
CTCCGAAGTC CCCTCCATGT TACGCCGCCG GCCGCATCTC TGGGGCTGGA GGCAAGGGCG    4020
TTCAAAGCGC GGGGCTCGGT CATGTGAGCT GTCCCGGGCC GGCGCCGGTC CGTGACCTGG    4080
ATGTAAAGGG CCCTTCCCGG CGAGGCTGCC TTGCCGCCCT TCCTGGGCCC CTCTCAGCCC    4140
TGCCTGGCTC TGGCATCGCG GCCGTCGCAC CCCCTTACCC TCCCTGTCAA GCCCTACCTG    4200
TCCCCTCGTG GTGCGCCCGC CTTAGGCTAC CGGCCGCTCC GAGCCTTGGG GCCCCTCTCC    4260
```

-continued

| | | | | | |
|---|---|---|---|---|---|
| GGGCGCCGAT | GCCCCATTCT | CTCTTGGCTG | GAGCTGGGGA | AGAAACGGTG | CCATTGCTAA | 4320 |
| TTTTCTTTGT | TTTCTTTCTT | TGTTTATTTT | TTTCTTTTTT | CTTTTTTTTT | CTTTTCTTTT | 4380 |
| CTTTTCTTTT | TTTTTTTTTT | TGAGACGGAG | TTTCACTCTT | GCTCGCCCAG | ACTGGAGTGC | 4440 |
| AATGGCGCGA | TCTCTGCTCA | CCGCAACCTC | TGCCTCCCGG | GTTCAAGCGA | TTCTCGTGCC | 4500 |
| TCAGCCTCCC | GAGTAGCTGG | GATTACAGGC | ATGCGCACCA | TGCCTGGCTA | ATTTTGTATT | 4560 |
| TTAGTAGAGA | CAGGGTTTCT | CCATGTTAGG | CAGGCTGGTC | TCGAACTCCC | GATCTCAGGT | 4620 |
| GATCCTCCCG | CCTCAGCCTC | CCAAAGTGGT | GCTGGGATTA | CAGGCGTGAA | GCTGTGCCCT | 4680 |
| GCCGCTAGTC | TTCTATTTTA | AGTATTTAGT | GGTAGGTCCC | GGGCCGGCAG | AATCTATTTT | 4740 |
| CAGCATTTAC | CACGTGTGGC | GCGCAAACCA | CAGGTTTTGG | CGATTGGGTT | GCGCGGGATC | 4800 |
| TCAGAGCTGA | CGACCGCGGG | GGCCTGGGGG | TCCCGGTTTC | CGACTGGAGC | CGCGACGACC | 4860 |
| CCGGCGACGG | CAGCCTGGGG | CTGCAGCCGA | GGGCCGGGGA | GCTCCCCCTC | CATATGTGCG | 4920 |
| CGCACATTCT | CCAGACTTGC | TCAAACTAAC | CCCCGGAGC | AGCGCACGGG | CTGGGACTGA | 4980 |
| TGATCAAATA | TTTGGTTTCC | GAGATAACAC | ACCCCGATAG | CGCTGTTTCC | TGAGCCGCTT | 5040 |
| TCATTCTACT | TGTGTAACTT | GCTGCGAAAA | CCCGAACCAA | GTCAAGACAG | CAAACTCACG | 5100 |
| CCCACGGGCC | TGTGTCAACA | TGGAAATAAT | GATACTGAAG | CCCCACGCTG | GGCACCTGGG | 5160 |
| GCGTGGACTG | GGGCGCGGG | GGAAGCGCAG | ATCCGCCTTC | ATGCTTCCCC | TCCTCCTGAT | 5220 |
| AAGGTCCCTG | GAGTTCCCGG | GAGCCATTGT | CTGTACTTAA | TAATAACTAA | ATCCAACTAG | 5280 |
| TGAACCAAGC | TTCAGCGAGG | CAAGGGGAGG | GAGGTTTAGA | TGCCAAAATT | ACCTTCAAAA | 5340 |
| AAGTTTAAAT | TATACTAAGC | AGCCAGTTAA | GAAGGAAGCA | GCAATATATG | ACCTGATTTA | 5400 |
| GAACCATCTC | CAAGATGTAT | GAGGTGGAAA | GAAGCAAGGT | GCAGATGAGT | GGGCTGCATG | 5460 |
| TGTGCTTGTA | TATCATCGTG | TCCTCCTGGA | GGAAGACACC | AGGAACTGGA | GAGAGATTTT | 5520 |
| ACTGGAGGGG | TATATGGCGG | GGGCATAGCT | GGGGCTTACG | GAGTGGGAGG | TGGGGTCTGA | 5580 |
| TTTTTCGTCG | TCTGCACTTC | TGTATTTGTG | ATTTTTTTAA | AACAATGTGT | ATTTATTAAC | 5640 |
| TATACCAAAA | AATAAAGGAA | AATTCCAAAT | ACATACATAT | AAATAATGAA | CCGCAGAGCT | 5700 |
| CTGTCGCCCT | CCTGAAGCCT | GGGGTTAGCC | AGGGCCCTTT | CTCTGGTGGG | GGATTTATAG | 5760 |
| CATCTTCCCT | TCTGTTGGGT | ACCCCGGACT | CCCACTGAAT | GTGCAGGTCC | CAGTGGCTGC | 5820 |
| CTTCAGAGCC | TGGCTGGAAT | CATTAAAAAG | GTATTTGTAA | TCTCTGGCTT | CTGCAGAAGG | 5880 |
| CCCTGCAAAC | CAAGAGCAAA | AAAGCCCCCA | GTGCTTATGG | GCCGGCAGTG | TGGGCTAGGC | 5940 |
| CCGGGGCTCC | CTGTCCCCAA | GAGAAAGACC | AGGTTGCTCG | GAGGGTGCCT | CTGGGAACTT | 6000 |
| TGGTGCGGGC | TATTTGCTCC | CCCCATGGCG | GCAGGAGCAA | GCTGGGACTT | GTTTGGGAAG | 6060 |
| GCCACAGCTG | GGTGGTTTTC | CTCCTCTGGC | TGTACATACA | CCTTTCAATC | CATTTCTTTC | 6120 |
| ATCTTGAAAG | GACAAAGACC | GGCTTGTCTG | AGCCTCTTAA | TCAGTCAGGC | TGGCTTTGGG | 6180 |
| CTTTGGGGAC | CCTGACTTTC | TCAGGTCTAG | CTTTCTGGGA | CATCACTCCA | AATTAGATGG | 6240 |
| CAGAGTGGCT | TTTAACAGAG | CGCACTGACC | TTGTTTTCTT | TCTCTCTCTG | TCCCTAAACT | 6300 |
| CGAGGTCATT | AGTTAGGTGA | AGACCTGGGC | TGCAGTTTGG | CGAGACACTT | CCTGTAGATG | 6360 |
| CTTCTAATGT | TGGCCTTTAA | TTTCTGCTAA | GCAGCAGCAC | ACAAATAAAT | GGCCTGTCCC | 6420 |
| TTCTATCCTG | TTGTAGCTTG | GAATTTCTCC | ATAGGAGGGA | CTTGGGGGTG | CAGTAGGGT | 6480 |
| TGGAGAGGGT | TGGGGGGAGG | TGTAGGAGAC | TTGTCTGGCC | ACTGAGTTTG | CTGAGAAAGT | 6540 |
| ACTGCTATAG | TGTTTTTCCT | TGGATTGCAA | ATCATGTTGA | TCTGAACTGC | TGATTTGAAG | 6600 |
| TGGATTGAGA | GGATGGAACA | ATAGAAGGAG | GATATGGCTC | AGGACAGTCA | AGTACTGGAA | 6660 |
| GAGGGAAAGG | TACAAAGAGG | TGTTGGCACT | GAATGACCCT | GAACAGGGCT | GCCCTGGAAA | 6720 |

| | | | | | | |
|---|---|---|---|---|---|---|
| TATCAGAGGT | GAGTGACAAA | GAGAACTCTA | GTCGAAGGTC | TGGAAGTCAA | TTATTGTCTC | 6780 |
| CAGCTTTTGT | CCCACCCTAA | GGGATGGAGC | ATGAACTTCA | TGCATGTAAC | ATCCCTCCAG | 6840 |
| GAGCGCTGAG | GTTCTGGGAA | TTCCCAGTGC | TGGCTACCAT | GCCATTCTTT | TCTCATTCAC | 6900 |
| TCAAGAGCGT | ATTGGGATAT | GCGTGCATGA | AAGCAATGTA | ATTATGGGCA | CAACCTCAAA | 6960 |
| ACCTGCTCTA | ATTTTTTTT | TTTTGGAGA | TGGAGTCTCG | CTCCATCACC | CAGGCTGGAG | 7020 |
| TGCAATGGCG | CGATCTCAGC | TCACTGCAAG | CTCAGACCTC | CAGGGTTCAC | ACCATTCTCC | 7080 |
| TGCCTCAGCC | TCCCGAGTAG | CTGGGAATAC | AGGCGCCCGC | ACCATGCGCG | GCTAATTTTT | 7140 |
| TTGTATTTTT | AGTAGAGACG | GGGTTTCACT | GTGTTAGCCA | GGATGGTCTC | GATCTCCTGA | 7200 |
| CCTCGTGATC | CACCCGCCTC | GGCCTCCCAA | AGTTCTGGGA | TTACAGGCGT | GACAGCCGTG | 7260 |
| CCCGGAATCT | GCTCTAATTT | TTTAAAGATA | TCATTTGCAA | ACTTTGGGCA | CTTGAGTCAC | 7320 |
| TCAGTAAGAT | ATTATTTACA | ACCCCACCAT | AGATTCAAAC | CTCTGTCCTA | GAATGTTGTC | 7380 |
| GAGTTAGGCA | TCTGGCTTGC | AGCAACAGCT | GGCTTTCCTG | TCTATGCTGT | CTCCTTCCAG | 7440 |
| GGAGGATGTT | TCACCCTTCA | TATTGAGGAA | ATGGGCACAG | AGAACCCATT | TCTCTTACTC | 7500 |
| ATCATGTAAC | TTCAGTGGGA | TGGTCAGATC | TATCTTTAAC | CTGGCCACTC | TTCCACAAGC | 7560 |
| TCACACTGAC | TCCAGCAAGA | TCTTAAACTA | GAAGGCAGGA | GTTCAAATCC | TAGCTGGTGC | 7620 |
| AGTGGCCAAA | TCTCGGCTCA | CAGCACCTTC | TGCCTCCTGG | GCTCAAGCGA | TCCTCTGACC | 7680 |
| TCAGTCTCCC | AAGTAGCTGG | GACCATAGGC | ATGCACCACT | ATGCCTGGCT | AATTTTTGTA | 7740 |
| TTTTTGTAAT | TTTTTGTAGA | GACAGAGTTT | CACCATGTTG | CCCAGCCCAG | TCTTGAACTC | 7800 |
| CTGGACTCAA | GCAATCTTCC | CACCTTTGCC | TACCAGAGTG | CCGGGATTAC | AGGTGTGAGC | 7860 |
| CATCATGCTA | GTTGCGCACA | GTTGGGCGAA | ACTGACAGAT | GAGAAAGCAG | AACCTCGTGA | 7920 |
| GTCCACTCAG | TAAGAGACTC | CCTACTTTCT | TTCTGAGTCT | TTGTTTCTCA | TCAATTGAAT | 7980 |
| GGCAATAAAC | AACTTGGTGG | CCCAAGAGTT | GATGACAACA | GTCCTATAAG | ATTATACATG | 8040 |
| TAAAAGAAAC | AGAGTATTCT | ACAAATATCA | GTTATTGATA | GTTCAATAGG | CAACCTGACA | 8100 |
| TTACCTTTTC | TTGGAACTTG | ATGAACAACT | CAGAAACTCA | TTAATATCAA | ACCCAATGGT | 8160 |
| GAGCACTTGG | TCTTTATTTA | TGGCTGTAAG | AGAAGAAATT | GAATTAACTC | TATGTAAATG | 8220 |
| CCAACTAAGA | ACATCGAAGT | CTGAAATCAA | CAGTTTTCCT | CGCTCATACG | ACACACCCAA | 8280 |
| ACTCAAGCAG | TGGTTCCAAG | CCCCTTTGGA | AAATACCATG | GGCTAACGAC | TTTAAAAGCT | 8340 |
| TAGAAGTGAA | TTCTACTTAC | TTATTACTTA | AAAGTGGTTC | TCAAACTTCA | AGGTGAATCA | 8400 |
| AAATCATCTG | TAGAGCTTGT | TAAAACACAG | GTTGCTGGTC | CACCCCAAGA | GTGTCTTGAG | 8460 |
| TCAGTAGGTC | TCAAGTAGGG | CTCAAGAATA | TGCATTTCTA | ATGAGCTCCA | GGTGAGTCTA | 8520 |
| AGTGTTAGTC | GTCGGTCTTG | GGACCACAAC | TTTGGGAACA | ATTGATTTAG | AAGAACTCAA | 8580 |
| AGATCAGAAA | GGGGTGGAAT | ATTTTTAAAA | TTGTGGTAAA | ATACGCATAA | ACAGAAAAGG | 8640 |
| TACAATTTTA | ACCACTTAGA | GAGAGGTGGG | ATCTAAGAAC | AGAAATTGTT | ATGCCATCAA | 8700 |
| AGGTGAGTTC | AGATAAGCAT | TATTAAATGG | TATCTATGGA | TAAACTTCAG | GGGCCCTGTG | 8760 |
| GAGCAACCCA | ATGCTGGGAT | GGGGTCCAGG | TGTGCTATGG | TTTGGATGTG | GTTTGTCCCT | 8820 |
| ACAAAAACTC | ATGTTGAAAT | TTAATTGCCA | GTGTAACATT | ATTGAGAGGT | TATGGACTTT | 8880 |
| TAAGAGGCAT | TTGGGTCATG | AGGGATCCAC | CTTCAGGGAT | TAGTGCAGTC | TCCAGGGAGT | 8940 |
| GAGTGAGTTC | CCATTCTAGT | GGGACTGGAT | TAGTTACCAT | ACAGTGGTTG | TTATAAAGTG | 9000 |
| AGGCTGCTTC | TGGTGTTTTA | TCTGTTTGCA | GGCACTTCCT | TCCCCTTCCA | CTTCTCTGCC | 9060 |
| AGGTTAGGAT | GCAGCATGAG | GCCCTCACCA | GAAGCTGACC | AGATGTGGCT | GCCTGATCTT | 9120 |
| GAACTTCCCA | GTCCCCAGAA | CCATGAGCTA | AATAAACCTT | TTTTCTCTAT | AAATTACGCA | 9180 |

```
GTCTAGAGTA TTCTATTATA GCAACACAAG ACAGACTAAG ACACAGTGGT AGAAAGAACA    9240
CTACTGACTT CTCCCATACT CTGGCCTATG GACAAGAGTG ACAGACAGAC AAGAGTGAAT    9300
ATCAGGGCCC TCAGGCACAT TCCTCTCTGC CCCTTCCTCC CTTCTTGCAG AGTCTCCAGT    9360
GACTGCCAGC TAATGCTATC ATAGACCCCA CCTTTCCCCT GACTTGATTG GACCAGAAGC    9420
AGCCTCCTGA TCCATGGCCA ACAATCAGAT TCACTTTCAA GAATTTGAAC TAAGAGACAC    9480
TAGGAAGATG GCCCTTGAGC TGTGAGTCCT ACACTTGAAA GTTCTTAGCA TCTTGGTCAG    9540
GTACCCACCA GGGCCATGTG CAAACTGAGA TAATGGGGAC ATGGAACAAG GGTAAGTGGA    9600
GAGGGCTGGC TGGAGAGAGA CGGGCAGAGG AAAGCCCTGC CAAGAGGAGC AGAGATGAGA    9660
GACCTTGGAG GGAGAGGTAA TAAAAGGAGG CAAAGATGAT TTTCCATGCT TACAACTCAC    9720
AGCTGAGGCC TAACTATCTT TATGTCCATA AGAGGCATCC TTGTGTCGAA CCTCTCCTCT    9780
TTCTTGGGTC AATGGGGGAT GGTTGCAAGG GACCATCAGT AGGAAGGCAT AGTACACTAA    9840
CCCAGTCTGG GGTGGGCTTT TAGACTAGTC TTCCTCCCAT GCTCCTCCTC CCATTGGAAC    9900
CCCGGACTTT CAAGACTGCT ACCTAGCACA CCAGTGCACC AGATGTCACT CAAAACCTCT    9960
TCAGCAATGG CCCACTCACC TTCAAAAGG CTGAAGAGCA GACTGGCTGG GTTCTTCATG    10020
GTGGAGGGGC AGTCTGGGAG GTTTTAAGGT TGAAGATGAA AACTTTCACT TTTGGCTCAA    10080
TGGTCTGAAA AAGAGAAGGA CCAGCAAGTG AACTGAAGCC TCCTGGAAAG CATCTTGATA    10140
ACAGGGGCAG AGTTTCAAGA TGAGAAGCTG TGGCACTTAC TCTGGCTTTG GAAATGACCT    10200
CTAAGTATCT CAGTTAATTA AAGGAGTCAA ACTCTAGACT CGAAGGAGAA GATCTACAAT    10260
TTTCAATAAC ATAGTCTACC CTCCCCTCCT TCCCCCACCT TCACCTCTTC TTTCATCACA    10320
GGCTTACAGG GCACCTCTTA GAGCCAGGCA CGGTGTTGGG ATCAGGAACA AGGCCACTGC    10380
TCACATCCAG AGCCTGTGCT ACTTAAGAAG CTTCCAGGAC CTCTTGGATG GCTGTGGTTA    10440
GTGCCCTACT TTTCCCAGCA GGTTGGATGC AGAATCATGC TCTTGTCGTT CAGGATGACC    10500
ATGGGACCA TGGGTCTGAG CCTGTGACCC TCCAGTCTAC AGTGTGTTGG TGAGGAAGGA    10560
GCAGTTGTCA CTGGGGTCAC TGGCAATGGG CATGCCTCCA TCTAGCTTAG GCAAGATGCT    10620
TAGACTCAGA GCCAGAGAGT GAAACCCAGA CACTAATGAG CTGTCGGTGT TGGTGTGTGT    10680
TCTCTTCCTC TTCCAGTGGA ACATGACAAG GAATTCTTCC ACCCACGCTA CCACCATCGA    10740
GAGTTCCGGT TTGATCTTTC CAAGATCCCA GAAGGGGAAG CTGTCACGGC AGCCGAATTC    10800
CGGATCTACA AGGACTACAT CCGGGAACGC TTCGACAATG AGACGTTCCG GATCAGCGTT    10860
TATCAGGTGC TCCAGGAGCA CTTGGGCAGG TGGGTGCTAT ACGGGTATCT GGGAGAGGTG    10920
CTGAGTTTCC TCTGGGGGCA GAGGAAGAAG GTGGTGAGGG TTTCCCTCCC CTCCCACCCC    10980
ATGAGCTCTG CTTCCCATCT GTTGGGGTAG TGGAGCTGTG ACCTGCTAAC GCGAAGCCCG    11040
TGTCTCTCCT CCTCTCTCGC AGGGAATCGG ATCTCTTCCT GCTCGACAGC CGTACCTCTG    11100
GGCCTCGGAG GAGGGCTGGC TGGTGTTTGA CATCACAGCC ACCAGCAACC ACTGGGTGGT    11160
CAATCCGCGG CACAACCTGG GCCTGCAGCT CTCGGTGGAG ACGCTGGATG GTGAGTCCCC    11220
CGCCACTGCC AGTCCTAATG CAGCCTGTGC TCCTGGACTT CAGGAGGGTC TCAGCAGTGC    11280
TCATGCTTGC TTCACTACAA ACAGGCTTCC CCGCCCCTCC CAACCAGTAC TCCATGTTCA    11340
GCCTTTTGAT CCTGCAGCCC TGTCCCGCTC GTGGCCCTCC TGTAACTGCT CTTCTGTGCA    11400
CTTGGCTGCT TCCTGTCCAG GGCAGACGAT CAACCCCAAG TTGGCGGGCC TGATTGGGCG    11460
GCACGGGCCC CAGAACAAGC AGCCCTTCAT GGTGGCTTTC TTCAAGGCCA CGGAGGTCCA    11520
CTTCCGCAGC ATCCGGTCCA CGGGGAGCAA ACAGCGCAGC CAGAACCGCT CCAAGACGCC    11580
CAAGAACCAG GAAGCCCTCG GATGGCCAAC GTGGCAGGGT ATCTTAGGTG GGAGGGATCA    11640
```

| | | | | | | |
|---|---|---|---|---|---|---|
| CAGACCCACC | ACAGGAACCC | AGCAGGCCCC | GGCGACCGCA | GGAGACTGAC | TAAAATCATT | 11700 |
| CAGTGCTCAC | CAAGATGCTC | TGAGCTCTCT | TCGATTTTAG | CAAACCAGGA | GTCCGAAGAT | 11760 |
| CTAAGGAGAG | CTGGGGGTTT | GACTCCGAGA | GCTCGAGCAG | TCCCCAAGAC | CTGGTCTTGA | 11820 |
| CTCACGAGTT | AGACTCCACT | CAGAGGCTGA | CTGTCTCCAG | GGTCTACACC | TCTAAGGGCG | 11880 |
| ACACTGGGCT | CAAGCAGACT | GCCGTTTTCT | ATATGGGATG | AGCCTTCACA | GGGCAGCCAG | 11940 |
| TTGGGATGGG | TTGAGGTTTG | GCTGTAGACA | TCAGAAACCC | AAGTCAAATG | CGCTTCAACC | 12000 |
| AGTAGAAAAT | TCACCAGCCC | GCAGAGCTAA | GGTTGGGTGG | ACATTAGGGT | TGGTTGATCC | 12060 |
| AGGAGCTCAA | CAGTGTCCTC | TGAGCCCCAG | CTCCTTCTGC | CCCACCCCAC | CATCTTCAGT | 12120 |
| GCTGCTTCCT | CTCAAGGCCA | CAGCTGTAGT | TGGCCAGGGG | GGCTTCATTA | TTTTTTGCTC | 12180 |
| CTGGGCAGTA | GGAGGAAGAG | AATGAATGTC | TCTCCATGGG | TCTTTCTTAG | GAATGTGGGA | 12240 |
| ACTTTTTCCA | GAAGTCTCTA | TGTCTTTTAG | TTTGTGTTGG | GTCACTTGCC | CTTCCTGAAC | 12300 |
| CACTTCCTGA | CTCCTGGACA | GGATGTGCAC | TGATGAGCTT | AGCTTTGGGG | ATCTAATAGT | 12360 |
| GACTTTACAA | AGCCTCTTTG | AGAAGGTGAC | ATTGGAACCA | AGGCTTGAGC | AGACACAACA | 12420 |
| AAGATTGCAG | GGAGGGGCAT | TGCAGGTGGA | GGAAACGGCA | CATGCAAGAG | CCCTGCGTGG | 12480 |
| GAGTGAGCTT | GGTGTTTGGT | CAATCAGTTG | TCAGAGCACA | CCGGGCCCTG | TCAGCAGGCA | 12540 |
| CAGCCTGGGC | CTGCTCTGAG | TATGACAGAG | AGCCCTGGG | AAGTTGTAGG | TGGAGGAAAG | 12600 |
| ACAGGTCATG | ACTAGGAAAA | AAGCAATCCC | TCTGTTGTGG | GGTGGAAGGA | AGGTTGCAGT | 12660 |
| GTGTGTGAGA | GAGAGACAAG | ACAGACAGAC | AGACACTTCT | CAATGTTTAC | AAGTGCTCAG | 12720 |
| GCCCTGACCC | GAATGCTTCC | AAATTTACGT | AGTTCTGGAA | AACCCCCTGT | ATCATTTTCA | 12780 |
| CTACTCAAAG | AAACCTCGGG | AGTGTTTTCT | TCTGAAAGGT | CATCAGGTTT | TGACTCTCTG | 12840 |
| CTGTCTCATT | TCTTCTTGCT | GGTGGTGGTG | ATGGTTGCTT | GTCCCAGGCC | CTGTCCCGCA | 12900 |
| TCCTCTTGCC | CCTGCAGAGG | GATGAGTGTG | TTGGGGCCTC | ACGAGTTGAG | GTTGTTCATA | 12960 |
| AGCAGATCTC | TTTGAGCAGG | GCGCCTGCAG | TGGCCTTGTG | TGAGGCTGGA | GGGGTTTCGA | 13020 |
| TTCCCTTATG | GAATCCAGGC | AGATGTAGCA | TTTAAACAAC | ACACGTGTAT | AAAAGAAACC | 13080 |
| AGTGTCCGCA | GAAGGTTCCA | GAAAGTATTA | TGGGATAAGA | CTACATGAGA | GAGGAATGGG | 13140 |
| GCATTGGCAC | CTCCCTTAGT | AGGGCCTTTG | CTGGGGGTAG | AAATGAGTTT | TAAGGCAGGT | 13200 |
| TAGACCCTCG | AACTGGCTTT | TGAATCGGGA | AATTTACCCC | CCAGCCGTTC | TGTGCTTCAT | 13260 |
| TGCTGTTCAC | ATCACTGCCT | AAGATGGAGG | AACTTTGATG | TGTGTGTGTT | TCTTTCTCCT | 13320 |
| CACTGGGCTC | TGCTTCTTCA | CTTCCTTGTC | AATGCAGAGA | ACAGCAGCAG | GCACCAGAGG | 13380 |
| CAGGCCTTGT | AAGAAGCACG | AGCTGTATGT | CAGCTTCCGA | GACCTGGGCT | GGCAGGTAAG | 13440 |
| GGCTGGCTG | GGTCTGTCTT | GGGTGTGGGC | CCTCTGGCGT | GGGCTCCCAC | AGGCAGCGGG | 13500 |
| TGCTGTGCTC | AGTCTTGTTT | CTCATCTCTG | CCAGTTAAGA | CTCCAGTATC | AAGTGGCCTC | 13560 |
| GCTAGGGAAG | GGGACTTGGG | CTAAGGATAC | AGGGAGGCCT | CATGAAATCC | GAGAGCAGAA | 13620 |
| ATGTGGTTGA | GACTTGAACT | CGAACCAGGA | ACCCAAACAC | TTTGGACTCT | GAACCCCATT | 13680 |
| CTCTGCATGC | ACCTCATTCC | CATCCCTTGG | CTGGCTGCTT | CTCAAGATGA | TGCCGGGCCG | 13740 |
| TGTGTTTGAA | TGTAGATACC | TGGGGAGCCA | TCTCCCCCTC | TGCCCTCTGA | CTTCATTTAC | 13800 |
| CCCATTCCCA | TTCCCACGGG | AGGGACGGAT | CTCCCCAGCT | TGGTTCAGGC | GCTTGTTCCT | 13860 |
| GAACCAGTCA | ACTGTTTCAG | GGGTGGGGTC | ATGTTACTGG | CACATGGCTG | CCCCCTCTGG | 13920 |
| AGCCATTTGC | ATGGAGTGAG | GCAAAAGGCA | GGGGATGAAT | CTAGGAGAGG | AGTGAGGGTC | 13980 |
| ATGTGATCCA | CCTGCCGTGA | GCTCTGGATC | GTGATTCTCA | TTCAGCAGTC | ACGAGCATCT | 14040 |
| CGAGCGTTCT | GGGCCCTGTT | CTAGGTACTG | GATTGGAGAT | GCAGCGATGA | ACACTGCAAT | 14100 |

-continued

```
GTGTCTGCCC TGTGGGGCTC AAATATCCCT GGAGAGGGTA TTGTCATGAG GTCATCAGGG    14160
CAACTGGTGG TATTCTACCC TCAGGGAGCT TGTAGTTCAG TGGGAGAGTC CAGAATCTTC    14220
CCTGGGGATT ATGCCCAGAC ACACTCAGGG CGTACGTGCA CACAGCCAGC TCTGAGCCCT    14280
CCTGTGAGCC TGCCCTCAGG ACTGATGACC ACATCTACCT GCAGCTGGGA CAGAACCCAA    14340
ACTCCAGGGG CCTCTGCTGG AAGATTCCAT GTGCTTAAGC ATCACTGAGG AGTATATTGA    14400
TTATTGGGCA ACATTTCTGT GCCACCCAGA CCCTAGAGGC AAGGATGGCA CATGGATCCC    14460
TTACTGACCA GTGCACCCGG AGCCAGCATG GGTGATGCCA TTATGAGTTA TTAGCCTCTC    14520
TGGCAGGTGG GCAAACCGAG GCATGGAGGT TTGTTTAAGG TGAACTGCCA GTGTGTGACC    14580
ACCTAGTGGG GGTAGAGCTG ATGATTGCCT CACACCGGAG GCTCCTTCCT GTGCCGCGTT    14640
CTGTCCAGAA GACACAGCCA TGGATGTCCA TTTTAGGATC AGCCAAGCCC GTGGGGCTTT    14700
CCTTCATTTT TATTTTATGT TTTTTTAGAA ATGGGGTCTT GCTCTGTCAC CCAGGCTGGG    14760
GTGCAGTGGT GTGATCATAC GTCACCGCAG CTTTGAGCCG TCTTCCCACT CAGTCTACTA    14820
AGCTTGGACT ATAGGCCAAG ACTATAGAGT GGTCCTTCTT TCCATTCTTT TGGGACCATG    14880
AGAGGCCACC CATGTTTCCT GCCCCTGCTG GGCCCTGCTG CTCAGAAGGC ATGGTCTGAG    14940
GCTTTCACCT TGGTCGTGAG CCTTCGTGGT GGTTTCTTTC AGCATGGGGT TGGGATGCTG    15000
TGCTCAGGCT TCTGCATGGT TTCCCACACT CTCTTCTCCT CCTCAGGACT GGATCATCGC    15060
GCCTGAAGGC TACGCGCGCT ACTACTGTGA GGGGGAGTGT GCCTTCCCTC TGAACTCCTA    15120
CATGAACGCC ACCAACCACG CCATCGTGCA GACGCTGGTG GGTGTCACGC ATCTTGGGG    15180
TGTGGTCACC TGGGCCGGGC AGGCTGCGGG GCCACCAGAT CCTGCTGCCT CCAAGCTGGG    15240
GCCTGAGTAG ATGTCAGCCC ATTGCCATGT CATGACTTTT GGGGCCCCT TGCGCCGTTA    15300
AAAAAAAATC AAAAATTGTA CTTTATGACT GGTTTGGTAT AAAGAGGAGT ATAATCTTCG    15360
ACCCTGGAGT TCATTTATTT CTCCTAATTT TTAAAGTAAC TAAAAGTTGT ATGGGCTCCT    15420
TTGAGGATGC TTGTAGTATT GTGGGTGCTG GTTACGGTGC CTAAGAGCAC TGGGCCCCTG    15480
CTTCATTTTC CAGTAGAGGA AACAGGTAAA CAGATGAGAA ATTTCAGTGA GGGGCACAGT    15540
GATCAGAAGC GGGCCAGCAG GATAATGGGA TGGAGAGATG AGTGGGGACC CATGGGCCAT    15600
TTCAAGTTAA ATTTCAGTCG GGTCACCAGG AAGATTCCAT GTGATAATGA GATTAACGTG    15660
CCCAGTCACG GCGACACTCA GTAGGTGTTA TTCCTGCTCT GCCAACAGCA ACCATAGTTG    15720
ATAAGAGCTG TTAGGGATTT TGTCCTTTTG CTTAGAATCC AAGGTTCAAG ACCTTGGTT    15780
ATGTAGCTCC CTGTCATGAA CATCATCTGA GCCTTTCCTG CCTACTGATC ATCCACCCTG    15840
CCTTGAATGC TTCTAGTGAC AGAGAGCTCA CTACCAGGAC TACTCCCTCC TTTCATTTAG    15900
TAATCTGCCT CCTTCTTTTC TTGTCCCTGT CCTGTGTGTT AAGTCCTGGA GAAAAATCTC    15960
ATCTATCCCT TTCATTTGAT TCTGCTCTTT GAGGGCAGGG GTTTTTGTTT CTTTGTTTGT    16020
TTTTTTAAGT GTTGGTTTTC CAAAGCCCTT GCTCCCCTCC TCAATTGAAA CTTCAAAGCC    16080
CTCATTGGGA TTGAAGGTCC TTAGGCTGGA AACAGAAGAG TCCTCCCCAA CCTGTTCCCT    16140
GGCCTGGATG TGCTGTGCTG TGCCAGTATC CCCTGGAAGG TGCCAGGCAT GTCTCCCCGG    16200
CTGCCAGGGG ACACATCTCT ATCCTTCTCC AACCCCTGCC TTCATGGCCC ATGGAACAGG    16260
AGTGCCATCG CCCTGTGTGC ACCTACTTCC ATCAGTATTT CACCAGAGAT CTGCAGGATC    16320
AAAGTGAATT CTCCAGGGAT TGTGAAATGA TGCGATTGTG GTCATGTTTA AAAGGGGGCA    16380
ACTGTCTTCT AGAGAGTCCT GATGAAATGC TTCCAGAGGA AATGAGCTGA TGGCTGGAAT    16440
TTGCTTTAAA ATCATTCAAG GTGGAGCAGG TGGGAAGGG TATGGATGTG TAAGAGTTTG    16500
AAATTGTCCA TCATAAAATG TGTAAAAAGC ATGCTGGCCT ATGTCAGCAG TCACAGCCTG    16560
```

| | | | | | |
|---|---|---|---|---|---|
| GAGGTGGTAA | CAGAGTGCCA | GTCACTGATG | CTCAAGCCTG | GCACCTACAG | TTGCTGGAAA | 16620
| CCCAGAAGTT | TCACGTTGAA | AACAACAGGA | CAGTGGAATC | TCTGGCCCTG | TCTTGAACAC | 16680
| GTGGCAGATC | TGCTAACACT | GATCTTGGTT | GGCTGCCGTC | AGCTTAGGTT | GAGTGGCGGT | 16740
| CTTCCCTTAG | TTTGCTTAGT | CCCCGCTATT | CCCTATTGTC | TTACCTCGGT | CTATTTTGCT | 16800
| TATCAGTGGA | CCTCACGAGG | CACTCATAGG | CATTTGAGTC | TATGTGTCCC | TGTCCCACAT | 16860
| CCTCTGTAAG | GTGCAGAGAA | GTCCATGAGC | AAGATGGAGC | ACTTCTAGTG | GGTCCAAGTC | 16920
| AGGGACACTA | TTCAGCAATC | TACAGTGCAC | AGGGCAGTTC | CCAACAGAG | AATTACCTGG | 16980
| TCCTGAATGT | CGGATCTGGC | CCCTTCCTTC | CCACTGTAT | AATGTGAAAA | CCTCTATGCT | 17040
| TTGTTCCCCT | TGTCTGCAAA | ACAGGGATAA | TCCCAGAACT | GAGTTGTCCA | TGTAAAGTGC | 17100
| TTAGAACAGG | GAGTGCTTGG | CTTGGGGAGT | GTCACCTGCA | GTCATTCATT | ATGCCCAGAC | 17160
| AGGATGTTTC | TTTATAGAAA | CGTGGAGGCC | AGTTAGAACG | ACTCACCGCT | TCTCACCACT | 17220
| GCCCATGTTT | TGGTGTGTGT | TTCAGGTCCA | CTTCATCAAC | CCGGAAACGG | TGCCCAAGCC | 17280
| CTGCTGTGCG | CCCACGCAGC | TCAATGCCAT | CTCCGTCCTC | TACTTCGATG | ACAGCTCCAA | 17340
| CGTCATCCTG | AAGAAATACA | GAAACATGGT | GGTCCGGGCC | TGTGGCTGCC | ACTAGCTCCT | 17400
| CCGAGAATTC | | | | | | 17410

( 2 ) INFORMATION FOR SEQ ID NO:4:

( i ) SEQUENCE CHARACTERISTICS:
        ( A ) LENGTH: 1260 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: HOMO SAPIENS ( i x ) FEATURE:
        ( A ) NAME/KEY: CDS
        ( B ) LOCATION: 9..1196
        ( D ) OTHER INFORMATION: /function="OSTEOGENIC PROTEIN"
                          / product="CBMP2A"
                          / note="CBMP2A (CDNA)"

( x i ) SEQUENCE DESCRIPTION: SEQ ID NO:4:

```
GGTCGACC ATG GTG GCC GGG ACC CGC TGT CTT CTA GCG TTG CTG CTT CCC         50
         Met Val Ala Gly Thr Arg Cys Leu Leu Ala Leu Leu Leu Pro
          1               5                  10

CAG GTC CTC CTG GGC GGC GCG GCT GGC CTC GTT CCG GAG CTG GGC CGC          98
Gln Val Leu Leu Gly Gly Ala Ala Gly Leu Val Pro Glu Leu Gly Arg
 15                  20                  25                  30

AGG AAG TTC GCG GCG GCG TCG TCG GGC CGC CCC TCA TCC CAG CCC TCT        146
Arg Lys Phe Ala Ala Ala Ser Ser Gly Arg Pro Ser Ser Gln Pro Ser
                 35                  40                  45

GAC GAG GTC CTG AGC GAG TTC GAG TTG CGG CTG CTC AGC ATG TTC GGC        194
Asp Glu Val Leu Ser Glu Phe Glu Leu Arg Leu Leu Ser Met Phe Gly
             50                  55                  60

CTG AAA CAG AGA CCC ACC CCC AGC AGG GAC GCC GTG GTG CCC CCC TAC        242
Leu Lys Gln Arg Pro Thr Pro Ser Arg Asp Ala Val Val Pro Pro Tyr
 65                  70                  75

ATG CTA GAC CTG TAT CGC AGG CAC TCG GGT CAG CCG GGC TCA CCC GCC        290
Met Leu Asp Leu Tyr Arg Arg His Ser Gly Gln Pro Gly Ser Pro Ala
 80                  85                  90
```

```
CCA GAC CAC CGG TTG GAG AGG GCA GCC AGC CGA GCC AAC ACT GTG CGC           338
Pro Asp His Arg Leu Glu Arg Ala Ala Ser Arg Ala Asn Thr Val Arg
 95             100                 105                 110

AGC TTC CAC CAT GAA GAA TCT TTG GAA GAA CTA CCA GAA ACG AGT GGG           386
Ser Phe His His Glu Glu Ser Leu Glu Glu Leu Pro Glu Thr Ser Gly
                115                 120                 125

AAA ACA ACC CGG AGA TTC TTC TTT AAT TTA AGT TCT ATC CCC ACG GAG           434
Lys Thr Thr Arg Arg Phe Phe Phe Asn Leu Ser Ser Ile Pro Thr Glu
            130                 135                 140

GAG TTT ATC ACC TCA GCA GAG CTT CAG GTT TTC CGA GAA CAG ATG CAA           482
Glu Phe Ile Thr Ser Ala Glu Leu Gln Val Phe Arg Glu Gln Met Gln
        145                 150                 155

GAT GCT TTA GGA AAC AAT AGC AGT TTC CAT CAC CGA ATT AAT ATT TAT           530
Asp Ala Leu Gly Asn Asn Ser Ser Phe His His Arg Ile Asn Ile Tyr
    160                 165                 170

GAA ATC ATA AAA CCT GCA ACA GCC AAC TCG AAA TTC CCC GTG ACC AGT           578
Glu Ile Ile Lys Pro Ala Thr Ala Asn Ser Lys Phe Pro Val Thr Ser
175                 180                 185                 190

CTT TTG GAC ACC AGG TTG GTG AAT CAG AAT GCA AGC AGG TGG GAA AGT           626
Leu Leu Asp Thr Arg Leu Val Asn Gln Asn Ala Ser Arg Trp Glu Ser
                195                 200                 205

TTT GAT GTC ACC CCC GCT GTG ATG CGG TGG ACT GCA CAG GGA CAC GCC           674
Phe Asp Val Thr Pro Ala Val Met Arg Trp Thr Ala Gln Gly His Ala
            210                 215                 220

AAC CAT GGA TTC GTG GTG GAA GTG GCC CAC TTG GAG GAG AAA CAA GGT           722
Asn His Gly Phe Val Val Glu Val Ala His Leu Glu Glu Lys Gln Gly
        225                 230                 235

GTC TCC AAG AGA CAT GTT AGG ATA AGC AGG TCT TTG CAC CAA GAT GAA           770
Val Ser Lys Arg His Val Arg Ile Ser Arg Ser Leu His Gln Asp Glu
    240                 245                 250

CAC AGC TGG TCA CAG ATA AGG CCA TTG CTA GTA ACT TTT GGC CAT GAT           818
His Ser Trp Ser Gln Ile Arg Pro Leu Leu Val Thr Phe Gly His Asp
255                 260                 265                 270

GGA AAA GGG CAT CCT CTC CAC AAA AGA GAA AAA CGT CAA GCC AAA CAC           866
Gly Lys Gly His Pro Leu His Lys Arg Glu Lys Arg Gln Ala Lys His
                275                 280                 285

AAA CAG CGG AAA CGC CTT AAG TCC AGC TGT AAG AGA CAC CCT TTG TAC           914
Lys Gln Arg Lys Arg Leu Lys Ser Ser Cys Lys Arg His Pro Leu Tyr
            290                 295                 300

GTG GAC TTC AGT GAC GTG GGG TGG AAT GAC TGG ATT GTG GCT CCC CCG           962
Val Asp Phe Ser Asp Val Gly Trp Asn Asp Trp Ile Val Ala Pro Pro
        305                 310                 315

GGG TAT CAC GCC TTT TAC TGC CAC GGA GAA TGC CCT TTT CCT CTG GCT          1010
Gly Tyr His Ala Phe Tyr Cys His Gly Glu Cys Pro Phe Pro Leu Ala
    320                 325                 330

GAT CAT CTG AAC TCC ACT AAT CAT GCC ATT GTT CAG ACG TTG GTC AAC          1058
Asp His Leu Asn Ser Thr Asn His Ala Ile Val Gln Thr Leu Val Asn
335                 340                 345                 350

TCT GTT AAC TCT AAG ATT CCT AAG GCA TGC TGT GTC CCG ACA GAA CTC          1106
Ser Val Asn Ser Lys Ile Pro Lys Ala Cys Cys Val Pro Thr Glu Leu
                355                 360                 365

AGT GCT ATC TCG ATG CTG TAC CTT GAC GAG AAT GAA AAG GTT GTA TTA          1154
Ser Ala Ile Ser Met Leu Tyr Leu Asp Glu Asn Glu Lys Val Val Leu
            370                 375                 380

AAG AAC TAT CAG GAT ATG GTT GTG GAG GGT TGT GGG TGT CGC                  1196
Lys Asn Tyr Gln Asp Met Val Val Glu Gly Cys Gly Cys Arg
        385                 390                 395

TAGTACAGCA AAATTAAATA CATAAATATA TATATATATA TATATTTTAG AAAAAAGAAA        1256

AAAA                                                                     1260
```

( 2 ) INFORMATION FOR SEQ ID NO:5:

( i ) SEQUENCE CHARACTERISTICS:
    ( A ) LENGTH: 396 amino acids
    ( B ) TYPE: amino acid
    ( D ) TOPOLOGY: linear ( i i ) MOLECULE TYPE: protein ( x i ) SEQUENCE DESCRIPTION: SEQ ID NO:5:

| Met | Val | Ala | Gly | Thr | Arg | Cys | Leu | Leu | Ala | Leu | Leu | Leu | Pro | Gln | Val |
|---|---|---|---|---|---|---|---|---|---|---|---|---|---|---|---|
| 1 | | | | 5 | | | | | 10 | | | | | 15 | |
| Leu | Leu | Gly | Gly | Ala | Ala | Gly | Leu | Val | Pro | Glu | Leu | Gly | Arg | Arg | Lys |
| | | | 20 | | | | | 25 | | | | | 30 | | |
| Phe | Ala | Ala | Ala | Ser | Ser | Gly | Arg | Pro | Ser | Ser | Gln | Pro | Ser | Asp | Glu |
| | | 35 | | | | | 40 | | | | | 45 | | | |
| Val | Leu | Ser | Glu | Phe | Glu | Leu | Arg | Leu | Leu | Ser | Met | Phe | Gly | Leu | Lys |
| | 50 | | | | | 55 | | | | | 60 | | | | |
| Gln | Arg | Pro | Thr | Pro | Ser | Arg | Asp | Ala | Val | Val | Pro | Pro | Tyr | Met | Leu |
| 65 | | | | | 70 | | | | | 75 | | | | | 80 |
| Asp | Leu | Tyr | Arg | Arg | His | Ser | Gly | Gln | Pro | Gly | Ser | Pro | Ala | Pro | Asp |
| | | | | 85 | | | | | 90 | | | | | 95 | |
| His | Arg | Leu | Glu | Arg | Ala | Ala | Ser | Arg | Ala | Asn | Thr | Val | Arg | Ser | Phe |
| | | | 100 | | | | | 105 | | | | | 110 | | |
| His | His | Glu | Glu | Ser | Leu | Glu | Glu | Leu | Pro | Glu | Thr | Ser | Gly | Lys | Thr |
| | | 115 | | | | | 120 | | | | | 125 | | | |
| Thr | Arg | Arg | Phe | Phe | Phe | Asn | Leu | Ser | Ser | Ile | Pro | Thr | Glu | Glu | Phe |
| | 130 | | | | | 135 | | | | | 140 | | | | |
| Ile | Thr | Ser | Ala | Glu | Leu | Gln | Val | Phe | Arg | Glu | Gln | Met | Gln | Asp | Ala |
| 145 | | | | | 150 | | | | | 155 | | | | | 160 |
| Leu | Gly | Asn | Asn | Ser | Ser | Phe | His | His | Arg | Ile | Asn | Ile | Tyr | Glu | Ile |
| | | | | 165 | | | | | 170 | | | | | 175 | |
| Ile | Lys | Pro | Ala | Thr | Ala | Asn | Ser | Lys | Phe | Pro | Val | Thr | Ser | Leu | Leu |
| | | | 180 | | | | | 185 | | | | | 190 | | |
| Asp | Thr | Arg | Leu | Val | Asn | Gln | Asn | Ala | Ser | Arg | Trp | Glu | Ser | Phe | Asp |
| | | 195 | | | | | 200 | | | | | 205 | | | |
| Val | Thr | Pro | Ala | Val | Met | Arg | Trp | Thr | Ala | Gln | Gly | His | Ala | Asn | His |
| | 210 | | | | | 215 | | | | | 220 | | | | |
| Gly | Phe | Val | Val | Glu | Val | Ala | His | Leu | Glu | Glu | Lys | Gln | Gly | Val | Ser |
| 225 | | | | | 230 | | | | | 235 | | | | | 240 |
| Lys | Arg | His | Val | Arg | Ile | Ser | Arg | Ser | Leu | His | Gln | Asp | Glu | His | Ser |
| | | | | 245 | | | | | 250 | | | | | 255 | |
| Trp | Ser | Gln | Ile | Arg | Pro | Leu | Leu | Val | Thr | Phe | Gly | His | Asp | Gly | Lys |
| | | | 260 | | | | | 265 | | | | | 270 | | |
| Gly | His | Pro | Leu | His | Lys | Arg | Glu | Lys | Arg | Gln | Ala | Lys | His | Lys | Gln |
| | | 275 | | | | | 280 | | | | | 285 | | | |
| Arg | Lys | Arg | Leu | Lys | Ser | Ser | Cys | Lys | Arg | His | Pro | Leu | Tyr | Val | Asp |
| | 290 | | | | | 295 | | | | | 300 | | | | |
| Phe | Ser | Asp | Val | Gly | Trp | Asn | Asp | Trp | Ile | Val | Ala | Pro | Pro | Gly | Tyr |
| 305 | | | | | 310 | | | | | 315 | | | | | 320 |
| His | Ala | Phe | Tyr | Cys | His | Gly | Glu | Cys | Pro | Phe | Pro | Leu | Ala | Asp | His |
| | | | | 325 | | | | | 330 | | | | | 335 | |
| Leu | Asn | Ser | Thr | Asn | His | Ala | Ile | Val | Gln | Thr | Leu | Val | Asn | Ser | Val |
| | | | 340 | | | | | 345 | | | | | 350 | | |
| Asn | Ser | Lys | Ile | Pro | Lys | Ala | Cys | Cys | Val | Pro | Thr | Glu | Leu | Ser | Ala |
| | | 355 | | | | | 360 | | | | | 365 | | | |
| Ile | Ser | Met | Leu | Tyr | Leu | Asp | Glu | Asn | Glu | Lys | Val | Val | Leu | Lys | Asn |
| | 370 | | | | | 375 | | | | | 380 | | | | |

```
Tyr Gln Asp Met Val Val Glu Gly Cys Gly Cys Arg
385                 390                 395
```

( 2 ) INFORMATION FOR SEQ ID NO:6:

( i ) SEQUENCE CHARACTERISTICS:
        ( A ) LENGTH: 1788 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: HOMO SAPIENS
        ( F ) TISSUE TYPE: HIPPOCAMPUS ( i x ) FEATURE:
        ( A ) NAME/KEY: CDS
        ( B ) LOCATION: 403..1626
        ( C ) IDENTIFICATION METHOD: experimental
        ( D ) OTHER INFORMATION: /function="OSTEOGENIC PROTEIN"
            / product="CBMP2B"
            / evidence=EXPERIMENTAL
            / note="CBMP2B (CDNA)"

( x i ) SEQUENCE DESCRIPTION: SEQ ID NO:6:

```
GAATTCGGGG CAGAGGAGGA GGGAGGGAGG GAAGGAGCGC GGAGCCCGGC CCGGAAGCTA      60

GGTGAGTGTG GCATCCGAGC TGAGGGACGC GAGCCTGAGA CGCCGCTGCT GCTCCGGCTG     120

AGTATCTAGC TTGTCTCCCC GATGGGATTC CCGTCCAAGC TATCTCGAGC CTGCAGCGCC     180

ACAGTCCCCG GCCCTCGCCC AGGTTCACTG CAACCGTTCA GAGGTCCCCA GGAGCTGCTG     240

CTGGCGAGCC CGCTACTGCA GGGACCTATG GAGCCATTCC GTAGTGCCAT CCCGAGCAAC     300

GCACTGCTGC AGCTTCCCTG AGCCTTTCCA GCAAGTTTGT TCAAGATTGG CTGTCAAGAA     360

TCATGGACTG TTATTATATG CCTTGTTTTC TGTCAAGACA CC ATG ATT CCT GGT       414
                                                  Met Ile Pro Gly
                                                   1

AAC CGA ATG CTG ATG GTC GTT TTA TTA TGC CAA GTC CTG CTA GGA GGC       462
Asn Arg Met Leu Met Val Val Leu Leu Cys Gln Val Leu Leu Gly Gly
 5              10                  15                  20

GCG AGC CAT GCT AGT TTG ATA CCT GAG ACG GGG AAG AAA AAA GTC GCC       510
Ala Ser His Ala Ser Leu Ile Pro Glu Thr Gly Lys Lys Lys Val Ala
                 25                  30                  35

GAG ATT CAG GGC CAC GCG GGA GGA CGC CGC TCA GGG CAG AGC CAT GAG       558
Glu Ile Gln Gly His Ala Gly Gly Arg Arg Ser Gly Gln Ser His Glu
             40                  45                  50

CTC CTG CGG GAC TTC GAG GCG ACA CTT CTG CAG ATG TTT GGG CTG CGC       606
Leu Leu Arg Asp Phe Glu Ala Thr Leu Leu Gln Met Phe Gly Leu Arg
         55                  60                  65

CGC CGC CCG CAG CCT AGC AAG AGT GCC GTC ATT CCG GAC TAC ATG CGG       654
Arg Arg Pro Gln Pro Ser Lys Ser Ala Val Ile Pro Asp Tyr Met Arg
     70                  75                  80

GAT CTT TAC CGG CTT CAG TCT GGG GAG GAG GAG GAA GAG CAG ATC CAC       702
Asp Leu Tyr Arg Leu Gln Ser Gly Glu Glu Glu Glu Glu Gln Ile His
 85                  90                  95                 100

AGC ACT GGT CTT GAG TAT CCT GAG CGC CCG GCC AGC CGG GCC AAC ACC       750
Ser Thr Gly Leu Glu Tyr Pro Glu Arg Pro Ala Ser Arg Ala Asn Thr
                105                 110                 115

GTG AGG AGC TTC CAC CAC GAA GAA CAT CTG GAG AAC ATC CCA GGG ACC       798
Val Arg Ser Phe His His Glu Glu His Leu Glu Asn Ile Pro Gly Thr
            120                 125                 130
```

```
AGT GAA AAC TCT GCT TTT CGT TTC CTC TTT AAC CTC AGC AGC ATC CCT       846
Ser Glu Asn Ser Ala Phe Arg Phe Leu Phe Asn Leu Ser Ser Ile Pro
        135                 140                 145

GAG AAC GAG GTG ATC TCC TCT GCA GAG CTT CGG CTC TTC CGG GAG CAG       894
Glu Asn Glu Val Ile Ser Ser Ala Glu Leu Arg Leu Phe Arg Glu Gln
        150                 155                 160

GTG GAC CAG GGC CCT GAT TGG GAA AGG GGC TTC CAC CGT ATA AAC ATT       942
Val Asp Gln Gly Pro Asp Trp Glu Arg Gly Phe His Arg Ile Asn Ile
165                 170                 175                 180

TAT GAG GTT ATG AAG CCC CCA GCA GAA GTG GTG CCT GGG CAC CTC ATC       990
Tyr Glu Val Met Lys Pro Pro Ala Glu Val Val Pro Gly His Leu Ile
        185                 190                 195

ACA CGA CTA CTG GAC ACG AGA CTG GTC CAC CAC AAT GTG ACA CGG TGG      1038
Thr Arg Leu Leu Asp Thr Arg Leu Val His His Asn Val Thr Arg Trp
        200                 205                 210

GAA ACT TTT GAT GTG AGC CCT GCG GTC CTT CGC TGG ACC CGG GAG AAG      1086
Glu Thr Phe Asp Val Ser Pro Ala Val Leu Arg Trp Thr Arg Glu Lys
        215                 220                 225

CAG CCA AAC TAT GGG CTA GCC ATT GAG GTG ACT CAC CTC CAT CAG ACT      1134
Gln Pro Asn Tyr Gly Leu Ala Ile Glu Val Thr His Leu His Gln Thr
        230                 235                 240

CGG ACC CAC CAG GGC CAG CAT GTC AGG ATT AGC CGA TCG TTA CCT CAA      1182
Arg Thr His Gln Gly Gln His Val Arg Ile Ser Arg Ser Leu Pro Gln
245                 250                 255                 260

GGG AGT GGG AAT TGG GCC CAG CTC CGG CCC CTC CTG GTC ACC TTT GGC      1230
Gly Ser Gly Asn Trp Ala Gln Leu Arg Pro Leu Leu Val Thr Phe Gly
                265                 270                 275

CAT GAT GGC CGG GGC CAT GCC TTG ACC CGA CGC CGG AGG GCC AAG CGT      1278
His Asp Gly Arg Gly His Ala Leu Thr Arg Arg Arg Ala Lys Arg
        280                 285                 290

AGC CCT AAG CAT CAC TCA CAG CGG GCC AGG AAG AAG AAT AAG AAC TGC      1326
Ser Pro Lys His His Ser Gln Arg Ala Arg Lys Lys Asn Lys Asn Cys
        295                 300                 305

CGG CGC CAC TCG CTC TAT GTG GAC TTC AGC GAT GTG GGC TGG AAT GAC      1374
Arg Arg His Ser Leu Tyr Val Asp Phe Ser Asp Val Gly Trp Asn Asp
310                 315                 320

TGG ATT GTG GCC CCA CCA GGC TAC CAG GCC TTC TAC TGC CAT GGG GAC      1422
Trp Ile Val Ala Pro Pro Gly Tyr Gln Ala Phe Tyr Cys His Gly Asp
325                 330                 335                 340

TGC CCC TTT CCA CTG GCT GAC CAC CTC AAC TCA ACC AAC CAT GCC ATT      1470
Cys Pro Phe Pro Leu Ala Asp His Leu Asn Ser Thr Asn His Ala Ile
                345                 350                 355

GTG CAG ACC CTG GTC AAT TCT GTC AAT TCC AGT ATC CCC AAA GCC TGT      1518
Val Gln Thr Leu Val Asn Ser Val Asn Ser Ser Ile Pro Lys Ala Cys
        360                 365                 370

TGT GTG CCC ACT GAA CTG AGT GCC ATC TCC ATG CTG TAC CTG GAT GAG      1566
Cys Val Pro Thr Glu Leu Ser Ala Ile Ser Met Leu Tyr Leu Asp Glu
        375                 380                 385

TAT GAT AAG GTG GTA CTG AAA AAT TAT CAG GAG ATG GTA GTA GAG GGA      1614
Tyr Asp Lys Val Val Leu Lys Asn Tyr Gln Glu Met Val Val Glu Gly
390                 395                 400

TGT GGG TGC CGC TGAGATCAGG CAGTCCTTGA GGATAGACAG ATATACACAC          1666
Cys Gly Cys Arg
405

ACACACACAC ACACCACATA CACCACACAC ACACGTTCCC ATCCACTCAC CCACACACTA    1726

CACAGACTGC TTCCTTATAG CTGGACTTTT ATTTAAAAAA AAAAAAAAAA AAACCCGAAT    1786

TC                                                                  1788
```

( 2 ) INFORMATION FOR SEQ ID NO:7:

( i ) SEQUENCE CHARACTERISTICS:

( A ) LENGTH: 408 amino acids
( B ) TYPE: amino acid
( D ) TOPOLOGY: linear ( i i ) MOLECULE TYPE: protein ( x i ) SEQUENCE DESCRIPTION: SEQ ID NO:7:

```
Met Ile Pro Gly Asn Arg Met Leu Met Val Val Leu Leu Cys Gln Val
 1               5                  10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
                100                 105                 110

Arg Ala Asn Thr Val Arg Ser Phe His His Glu Glu His Leu Glu Asn
            115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
    195                 200                 205

Val Thr Arg Trp Glu Thr Phe Asp Val Ser Pro Ala Val Leu Arg Trp
210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
    275                 280                 285

Arg Ala Lys Arg Ser Pro Lys His His Ser Gln Arg Ala Arg Lys Lys
290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
    355                 360                 365

Pro Lys Ala Cys Cys Val Pro Thr Glu Leu Ser Ala Ile Ser Met Leu
370                 375                 380

Tyr Leu Asp Glu Tyr Asp Lys Val Val Leu Lys Asn Tyr Gln Glu Met
385                 390                 395                 400
```

Val Val Glu Gly Cys Gly Cys Arg
          405

( 2 ) INFORMATION FOR SEQ ID NO:8:

( i ) SEQUENCE CHARACTERISTICS:
        ( A ) LENGTH: 516 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( i x ) FEATURE:
        ( A ) NAME/KEY: CDS
        ( B ) LOCATION: 1..507
        ( D ) OTHER INFORMATION: /function="OSTEOGENIC PROTEIN"
            / product="OP1A"
            / note="OP1A FUSION"

( x i ) SEQUENCE DESCRIPTION: SEQ ID NO:8:

```
ATG AAA GCA ATT TTC GTA CTG AAA GGT TCA CTG GAC AGA GAT CTG GAC       48
Met Lys Ala Ile Phe Val Leu Lys Gly Ser Leu Asp Arg Asp Leu Asp
 1               5                  10                  15

TCT CGT CTG GAT CTG GAC GTT CGT ACC GAC CAC AAA GAC CTG TCT GAT       96
Ser Arg Leu Asp Leu Asp Val Arg Thr Asp His Lys Asp Leu Ser Asp
                20                  25                  30

CAC CTG GTT CTG GTC GAC CTG GCT CGT AAC GAC CTG GCT CGT ATC GTT      144
His Leu Val Leu Val Asp Leu Ala Arg Asn Asp Leu Ala Arg Ile Val
         35                  40                  45

ACT CCC GGG TCT CGT TAC GTT GCG GAT CTG GAA TTC GAT CCT CAC CAG      192
Thr Pro Gly Ser Arg Tyr Val Ala Asp Leu Glu Phe Asp Pro His Gln
     50                  55                  60

AGG CAG GCC TGT AAG AAG CAC GAG CTG TAT GTC AGC TTC CGA GAC CTG      240
Arg Gln Ala Cys Lys Lys His Glu Leu Tyr Val Ser Phe Arg Asp Leu
 65                  70                  75                  80

GGC TGG CAG GAC TGG ATC ATC GCG CCT GAA GGC TAC GCG GCC TAC TAC      288
Gly Trp Gln Asp Trp Ile Ile Ala Pro Glu Gly Tyr Ala Ala Tyr Tyr
                 85                  90                  95

TGT GAG GGG GAG TGT GCC TTC CCT CTG AAC TCC TAC ATG AAC GCC ACC      336
Cys Glu Gly Glu Cys Ala Phe Pro Leu Asn Ser Tyr Met Asn Ala Thr
                100                 105                 110

AAC CAC GCC ATC GTG CAG ACG CTG GTC CAC TTC ATC AAC CCG GAA ACG      384
Asn His Ala Ile Val Gln Thr Leu Val His Phe Ile Asn Pro Glu Thr
         115                 120                 125

GTG CCC AAG CCC TGC TGT GCG CCC ACG CAG CTC AAT GCC ATC TCC GTC      432
Val Pro Lys Pro Cys Cys Ala Pro Thr Gln Leu Asn Ala Ile Ser Val
     130                 135                 140

CTC TAC TTC GAT GAC AGC TCC AAC GTC ATC CTG AAG AAA TAC AGA AAC      480
Leu Tyr Phe Asp Asp Ser Ser Asn Val Ile Leu Lys Lys Tyr Arg Asn
145                 150                 155                 160

ATG GTG GTC CGG GCC TGT GGC TGC CAC TAACTGCAG                         516
Met Val Val Arg Ala Cys Gly Cys His
                165
```

( 2 ) INFORMATION FOR SEQ ID NO:9:

( i ) SEQUENCE CHARACTERISTICS:
        ( A ) LENGTH: 169 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Met | Lys | Ala | Ile | Phe | Val | Leu | Lys | Gly | Ser | Leu | Asp | Arg | Asp | Leu | Asp |
|---|---|---|---|---|---|---|---|---|---|---|---|---|---|---|---|
| 1 | | | | 5 | | | | | 10 | | | | | 15 | |

| Ser | Arg | Leu | Asp | Leu | Asp | Val | Arg | Thr | Asp | His | Lys | Asp | Leu | Ser | Asp |
|---|---|---|---|---|---|---|---|---|---|---|---|---|---|---|---|
| | | | 20 | | | | | 25 | | | | | 30 | | |

| His | Leu | Val | Leu | Val | Asp | Leu | Ala | Arg | Asn | Asp | Leu | Ala | Arg | Ile | Val |
|---|---|---|---|---|---|---|---|---|---|---|---|---|---|---|---|
| | | 35 | | | | | 40 | | | | | 45 | | | |

| Thr | Pro | Gly | Ser | Arg | Tyr | Val | Ala | Asp | Leu | Glu | Phe | Asp | Pro | His | Gln |
|---|---|---|---|---|---|---|---|---|---|---|---|---|---|---|---|
| | 50 | | | | | 55 | | | | | 60 | | | | |

| Arg | Gln | Ala | Cys | Lys | Lys | His | Glu | Leu | Tyr | Val | Ser | Phe | Arg | Asp | Leu |
|---|---|---|---|---|---|---|---|---|---|---|---|---|---|---|---|
| 65 | | | | | 70 | | | | | 75 | | | | | 80 |

| Gly | Trp | Gln | Asp | Trp | Ile | Ile | Ala | Pro | Glu | Gly | Tyr | Ala | Ala | Tyr | Tyr |
|---|---|---|---|---|---|---|---|---|---|---|---|---|---|---|---|
| | | | | 85 | | | | | 90 | | | | | 95 | |

| Cys | Glu | Gly | Glu | Cys | Ala | Phe | Pro | Leu | Asn | Ser | Tyr | Met | Asn | Ala | Thr |
|---|---|---|---|---|---|---|---|---|---|---|---|---|---|---|---|
| | | | 100 | | | | | 105 | | | | | 110 | | |

| Asn | His | Ala | Ile | Val | Gln | Thr | Leu | Val | His | Phe | Ile | Asn | Pro | Glu | Thr |
|---|---|---|---|---|---|---|---|---|---|---|---|---|---|---|---|
| | | 115 | | | | | 120 | | | | | 125 | | | |

| Val | Pro | Lys | Pro | Cys | Cys | Ala | Pro | Thr | Gln | Leu | Asn | Ala | Ile | Ser | Val |
|---|---|---|---|---|---|---|---|---|---|---|---|---|---|---|---|
| | 130 | | | | | 135 | | | | | 140 | | | | |

| Leu | Tyr | Phe | Asp | Asp | Ser | Ser | Asn | Val | Ile | Leu | Lys | Lys | Tyr | Arg | Asn |
|---|---|---|---|---|---|---|---|---|---|---|---|---|---|---|---|
| 145 | | | | | 150 | | | | | 155 | | | | | 160 |

| Met | Val | Val | Arg | Ala | Cys | Gly | Cys | His |
|---|---|---|---|---|---|---|---|---|
| | | | | 165 | | | | |

( 2 ) INFORMATION FOR SEQ ID NO:10:

( i ) SEQUENCE CHARACTERISTICS:
        ( A ) LENGTH: 1004 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( i x ) FEATURE:
        ( A ) NAME/KEY: CDS
        ( B ) LOCATION: 1..951
        ( D ) OTHER INFORMATION: /function="OSTEOGENIC PROTEIN"
            / product="OP1B"
            / note="OP1B - FUSION"

( x i ) SEQUENCE DESCRIPTION: SEQ ID NO:10:

| ATG | AAA | GCA | ATT | TTC | GTA | CTG | AAA | GGT | TCA | CTG | GAC | AGA | GAT | CTG | GAC | 48 |
|---|---|---|---|---|---|---|---|---|---|---|---|---|---|---|---|---|
| Met | Lys | Ala | Ile | Phe | Val | Leu | Lys | Gly | Ser | Leu | Asp | Arg | Asp | Leu | Asp | |
| 1 | | | | 5 | | | | | 10 | | | | | 15 | | |

| TCT | CGT | CTG | GAT | CTG | GAC | GTT | CGT | ACC | GAC | CAC | AAA | GAC | CTG | TCT | GAT | 96 |
|---|---|---|---|---|---|---|---|---|---|---|---|---|---|---|---|---|
| Ser | Arg | Leu | Asp | Leu | Asp | Val | Arg | Thr | Asp | His | Lys | Asp | Leu | Ser | Asp | |
| | | | 20 | | | | | 25 | | | | | 30 | | | |

| CAC | CTG | GTT | CTG | GTC | GAC | CTG | GCT | CGT | AAC | GAC | CTG | GCT | CGT | ATC | GTT | 144 |
|---|---|---|---|---|---|---|---|---|---|---|---|---|---|---|---|---|
| His | Leu | Val | Leu | Val | Asp | Leu | Ala | Arg | Asn | Asp | Leu | Ala | Arg | Ile | Val | |
| | | 35 | | | | | 40 | | | | | 45 | | | | |

| ACT | CCC | GGG | TCT | CGT | TAC | GTT | GCG | GAT | CTG | GAA | TTC | CGG | ATC | TAC | AAG | 192 |
|---|---|---|---|---|---|---|---|---|---|---|---|---|---|---|---|---|
| Thr | Pro | Gly | Ser | Arg | Tyr | Val | Ala | Asp | Leu | Glu | Phe | Arg | Ile | Tyr | Lys | |
| | 50 | | | | | 55 | | | | | 60 | | | | | |

| GAC | TAC | ATC | CGG | GAA | CGC | TTC | GAC | AAT | GAG | ACG | TTC | CGG | ATC | AGC | GTT | 240 |
|---|---|---|---|---|---|---|---|---|---|---|---|---|---|---|---|---|
| Asp | Tyr | Ile | Arg | Glu | Arg | Phe | Asp | Asn | Glu | Thr | Phe | Arg | Ile | Ser | Val | |
| 65 | | | | | 70 | | | | | 75 | | | | | 80 | |

| TAT | CAG | GTG | CTC | CAG | GAG | CAC | TTG | GGC | AGG | GAA | TCG | GAT | CTC | TTC | CTG | 288 |
|---|---|---|---|---|---|---|---|---|---|---|---|---|---|---|---|---|
| Tyr | Gln | Val | Leu | Gln | Glu | His | Leu | Gly | Arg | Glu | Ser | Asp | Leu | Phe | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| CTC | GAC | AGC | CGT | ACC | CTC | TGG | GCC | TCG | GAG | GAG | GGC | TGG | CTG | GTG | TTT | 336 |
| Leu | Asp | Ser | Arg | Thr | Leu | Trp | Ala | Ser | Glu | Glu | Gly | Trp | Leu | Val | Phe | |
| | | 100 | | | | 105 | | | | | | 110 | | | | |
| GAC | ATC | ACA | GCC | ACC | AGC | AAC | CAC | TGG | GTG | GTC | AAT | CCG | CGG | CAC | AAC | 384 |
| Asp | Ile | Thr | Ala | Thr | Ser | Asn | His | Trp | Val | Val | Asn | Pro | Arg | His | Asn | |
| | | 115 | | | | 120 | | | | | 125 | | | | | |
| CTG | GGC | CTG | CAG | CTC | TCG | GTG | GAG | ACG | CTG | GAT | GGG | CAG | AGC | ATC | AAC | 432 |
| Leu | Gly | Leu | Gln | Leu | Ser | Val | Glu | Thr | Leu | Asp | Gly | Gln | Ser | Ile | Asn | |
| | | 130 | | | | 135 | | | | | 140 | | | | | |
| CCC | AAG | TTG | GCG | GGC | CTG | ATT | GGG | CGG | CAC | GGG | CCC | CAG | AAC | AAG | CAG | 480 |
| Pro | Lys | Leu | Ala | Gly | Leu | Ile | Gly | Arg | His | Gly | Pro | Gln | Asn | Lys | Gln | |
| 145 | | | | | 150 | | | | 155 | | | | | | 160 | |
| CCC | TTC | ATG | GTG | GCT | TTC | TTC | AAG | GCC | ACG | GAG | GTC | CAC | TTC | CGC | AGC | 528 |
| Pro | Phe | Met | Val | Ala | Phe | Phe | Lys | Ala | Thr | Glu | Val | His | Phe | Arg | Ser | |
| | | | | 165 | | | | | 170 | | | | | 175 | | |
| ATC | CGG | TCC | ACG | GGG | AGC | AAA | CAG | CGC | AGC | CAG | AAC | CGC | TCC | AAG | ACG | 576 |
| Ile | Arg | Ser | Thr | Gly | Ser | Lys | Gln | Arg | Ser | Gln | Asn | Arg | Ser | Lys | Thr | |
| | | | 180 | | | | | 185 | | | | | 190 | | | |
| CCC | AAG | AAC | CAG | GAA | GCC | CTG | CGG | ATG | GCC | AAC | GTG | GCA | GAG | AAC | AGC | 624 |
| Pro | Lys | Asn | Gln | Glu | Ala | Leu | Arg | Met | Ala | Asn | Val | Ala | Glu | Asn | Ser | |
| | | 195 | | | | | 200 | | | | | 205 | | | | |
| AGC | AGC | GAC | CAG | AGG | CAG | GCC | TGT | AAG | AAG | CAC | GAG | CTG | TAT | GTC | AGC | 672 |
| Ser | Ser | Asp | Gln | Arg | Gln | Ala | Cys | Lys | Lys | His | Glu | Leu | Tyr | Val | Ser | |
| | 210 | | | | | 215 | | | | | 220 | | | | | |
| TTC | CGA | GAC | CTG | GGC | TGG | CAG | GAC | TGG | ATC | ATC | GCG | CCT | GAA | GGC | TAC | 720 |
| Phe | Arg | Asp | Leu | Gly | Trp | Gln | Asp | Trp | Ile | Ile | Ala | Pro | Glu | Gly | Tyr | |
| 225 | | | | | 230 | | | | | 235 | | | | | 240 | |
| GCC | GCC | TAC | TAC | TGT | GAG | GGG | GAG | TGT | GCC | TTC | CCT | CTG | AAC | TCC | TAC | 768 |
| Ala | Ala | Tyr | Tyr | Cys | Glu | Gly | Glu | Cys | Ala | Phe | Pro | Leu | Asn | Ser | Tyr | |
| | | | | 245 | | | | | 250 | | | | | 255 | | |
| ATG | AAC | GCC | ACC | AAC | CAC | GCC | ATC | GTG | CAG | ACG | CTG | GTC | CAC | TTC | ATC | 816 |
| Met | Asn | Ala | Thr | Asn | His | Ala | Ile | Val | Gln | Thr | Leu | Val | His | Phe | Ile | |
| | | | 260 | | | | | 265 | | | | | 270 | | | |
| AAC | CCG | GAA | ACG | GTG | CCC | AAG | CCC | TGC | TGT | GCG | CCC | ACG | CAG | CTC | AAT | 864 |
| Asn | Pro | Glu | Thr | Val | Pro | Lys | Pro | Cys | Cys | Ala | Pro | Thr | Gln | Leu | Asn | |
| | | 275 | | | | | 280 | | | | | 285 | | | | |
| GCC | ATC | TCC | GTC | CTC | TAC | TTC | GAT | GAC | AGC | TCC | AAC | GTC | ATC | CTG | AAG | 912 |
| Ala | Ile | Ser | Val | Leu | Tyr | Phe | Asp | Asp | Ser | Ser | Asn | Val | Ile | Leu | Lys | |
| | | 290 | | | | | 295 | | | | | 300 | | | | |
| AAA | TAC | AGA | AAC | ATG | GTG | GTC | CGG | GCC | TGT | GGC | TGC | CAC | TAGCTCCTTC | | | 961 |
| Lys | Tyr | Arg | Asn | Met | Val | Val | Arg | Ala | Cys | Gly | Cys | His | | | | |
| 305 | | | | | 310 | | | | | 315 | | | | | | |

CGAGAATTCC AGACCTTTGG GGCCCAAAGG TTTTTCTGGA TCC    1004

( 2 ) INFORMATION FOR SEQ ID NO:11:

( i ) SEQUENCE CHARACTERISTICS:
        ( A ) LENGTH: 317 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

| | | | | | | | | | | | | | | |
|---|---|---|---|---|---|---|---|---|---|---|---|---|---|---|
| Met | Lys | Ala | Ile | Phe | Val | Leu | Lys | Gly | Ser | Leu | Asp | Arg | Asp | Leu | Asp |
| 1 | | | | 5 | | | | | 10 | | | | | 15 | |
| Ser | Arg | Leu | Asp | Leu | Asp | Val | Arg | Thr | Asp | His | Lys | Asp | Leu | Ser | Asp |
| | | | 20 | | | | | 25 | | | | | 30 | | |
| His | Leu | Val | Leu | Val | Asp | Leu | Ala | Arg | Asn | Asp | Leu | Ala | Arg | Ile | Val |
| | | 35 | | | | | 40 | | | | | 45 | | | |
| Thr | Pro | Gly | Ser | Arg | Tyr | Val | Ala | Asp | Leu | Glu | Phe | Arg | Ile | Tyr | Lys |
| | 50 | | | | | 55 | | | | | 60 | | | | |

| | | | | | | | | | | | | | | | |
|---|---|---|---|---|---|---|---|---|---|---|---|---|---|---|---|
|Asp|Tyr|Ile|Arg|Glu|Arg|Phe|Asp|Asn|Glu|Thr|Phe|Arg|Ile|Ser|Val|
|65| | | | |70| | | |75| | | | | |80|
|Tyr|Gln|Val|Leu|Gln|Glu|His|Leu|Gly|Arg|Glu|Ser|Asp|Leu|Phe|Leu|
| | | | |85| | | |90| | | | |95| | |
|Leu|Asp|Ser|Arg|Thr|Leu|Trp|Ala|Ser|Glu|Glu|Gly|Trp|Leu|Val|Phe|
| | | |100| | | |105| | | | |110| | | |
|Asp|Ile|Thr|Ala|Thr|Ser|Asn|His|Trp|Val|Val|Asn|Pro|Arg|His|Asn|
| | |115| | | | |120| | | | |125| | | |
|Leu|Gly|Leu|Gln|Leu|Ser|Val|Glu|Thr|Leu|Asp|Gly|Gln|Ser|Ile|Asn|
| |130| | | | |135| | | | |140| | | | |
|Pro|Lys|Leu|Ala|Gly|Leu|Ile|Gly|Arg|His|Gly|Pro|Gln|Asn|Lys|Gln|
|145| | | | |150| | | |155| | | | | |160|
|Pro|Phe|Met|Val|Ala|Phe|Phe|Lys|Ala|Thr|Glu|Val|His|Phe|Arg|Ser|
| | | | |165| | | |170| | | | |175| | |
|Ile|Arg|Ser|Thr|Gly|Ser|Lys|Gln|Arg|Ser|Gln|Asn|Arg|Ser|Lys|Thr|
| | | |180| | | |185| | | | |190| | | |
|Pro|Lys|Asn|Gln|Glu|Ala|Leu|Arg|Met|Ala|Asn|Val|Ala|Glu|Asn|Ser|
| | |195| | | | |200| | | | |205| | | |
|Ser|Ser|Asp|Gln|Arg|Gln|Ala|Cys|Lys|Lys|His|Glu|Leu|Tyr|Val|Ser|
| |210| | | | |215| | | | |220| | | | |
|Phe|Arg|Asp|Leu|Gly|Trp|Gln|Asp|Trp|Ile|Ile|Ala|Pro|Glu|Gly|Tyr|
|225| | | | |230| | | |235| | | | | |240|
|Ala|Ala|Tyr|Tyr|Cys|Glu|Gly|Glu|Cys|Ala|Phe|Pro|Leu|Asn|Ser|Tyr|
| | | | |245| | | |250| | | | |255| | |
|Met|Asn|Ala|Thr|Asn|His|Ala|Ile|Val|Gln|Thr|Leu|Val|His|Phe|Ile|
| | | |260| | | |265| | | | |270| | | |
|Asn|Pro|Glu|Thr|Val|Pro|Lys|Pro|Cys|Cys|Ala|Pro|Thr|Gln|Leu|Asn|
| | |275| | | | |280| | | | |285| | | |
|Ala|Ile|Ser|Val|Leu|Tyr|Phe|Asp|Asp|Ser|Ser|Asn|Val|Ile|Leu|Lys|
| |290| | | | |295| | | | |300| | | | |
|Lys|Tyr|Arg|Asn|Met|Val|Val|Arg|Ala|Cys|Gly|Cys|His| | | |
|305| | | | |310| | | |315| | | | | | |

(2) INFORMATION FOR SEQ ID NO:12:

(i) SEQUENCE CHARACTERISTICS:
        (A) LENGTH: 1505 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (ix) FEATURE:
        (A) NAME/KEY: CDS
        (B) LOCATION: 1..1452
        (D) OTHER INFORMATION: /function="OSTEOGENIC PROTEIN"
            / product="OP1C"
            / note="OP1C - FUSION"

(xi) SEQUENCE DESCRIPTION: SEQ ID NO:12:

| | | | | | | | | | | | | | | | |
|---|---|---|---|---|---|---|---|---|---|---|---|---|---|---|---|
|ATG|AAA|GCA|ATT|TTC|GTA|CTG|AAA|GGT|TCA|CTG|GAC|AGA|GAT|CTG|GAC|48|
|Met|Lys|Ala|Ile|Phe|Val|Leu|Lys|Gly|Ser|Leu|Asp|Arg|Asp|Leu|Asp|
|1| | | |5| | | |10| | | | |15| | |
|TCT|CGT|CTG|GAT|CTG|GAC|GTT|CGT|ACC|GAC|CAC|AAA|GAC|CTG|TCT|GAT|96|
|Ser|Arg|Leu|Asp|Leu|Asp|Val|Arg|Thr|Asp|His|Lys|Asp|Leu|Ser|Asp|
| | | |20| | | |25| | | | |30| | | |
|CAC|CTG|GTT|CTG|GTC|GAC|CTG|GCT|CGT|AAC|GAG|AAT|TCC|CGG|GTA|GCG|144|

```
            His Leu Val Leu Val Asp Leu Ala Arg Asn Glu Asn Ser Arg Val Ala
                    35              40              45

CGT AGA GCC GGC GCG ATG CAC GTG CGC TCA CTG CGA GCT GCG GCG CCG            192
Arg Arg Ala Gly Ala Met His Val Arg Ser Leu Arg Ala Ala Ala Pro
        50              55              60

CAC AGC TTC GTG GCG CTC TGG GCA CCC CTG TTC CTG CTG CGC TCC GCC            240
His Ser Phe Val Ala Leu Trp Ala Pro Leu Phe Leu Leu Arg Ser Ala
65              70              75              80

CTG GCC GAC TTC AGC CTG GAC AAC GAG GTG CAC TCG AGC TTC ATC CAC            288
Leu Ala Asp Phe Ser Leu Asp Asn Glu Val His Ser Ser Phe Ile His
                85              90              95

CGG CGC CTC CGC AGC CAG GAG CGG CGG GAG ATG CAG CGC GAG ATC CTC            336
Arg Arg Leu Arg Ser Gln Glu Arg Arg Glu Met Gln Arg Glu Ile Leu
            100             105             110

TCC ATT TTG GGC TTG CCC CAC CGC CCG CGC CCG CAC CTC CAG GGC AAG            384
Ser Ile Leu Gly Leu Pro His Arg Pro Arg Pro His Leu Gln Gly Lys
        115             120             125

CAC AAC TCG GCA CCC ATG TTC ATG CTG GAC CTG TAC AAC GCC CAT GGC            432
His Asn Ser Ala Pro Met Phe Met Leu Asp Leu Tyr Asn Ala His Gly
130             135             140

GGT GGA GGA GGG CGG CGG CCC GGC GGC CAG GGC TTC TCC TAC CCC TAC            480
Gly Gly Gly Gly Arg Arg Pro Gly Gly Gln Gly Phe Ser Tyr Pro Tyr
145             150             155             160

AAG GCC GTC TTC AGT ACC CAG GGC CCC CCT CTG GCC AGC CTG CAA GAT            528
Lys Ala Val Phe Ser Thr Gln Gly Pro Pro Leu Ala Ser Leu Gln Asp
                165             170             175

AGC CAT TTC CTC ACC GAC GCC GAC ATG GTC ATG AGC TTC GTC AAC CTC            576
Ser His Phe Leu Thr Asp Ala Asp Met Val Met Ser Phe Val Asn Leu
            180             185             190

GTG GAA CAT GAC AAG GAA TTC TTC CAC CCA CGC TAC CAC CAT CGA GAG            624
Val Glu His Asp Lys Glu Phe Phe His Pro Arg Tyr His His Arg Glu
        195             200             205

TTC CGG TTT GAT CTT TCC AAG ATC CCA GAA GGG GAA GCT GTC ACG GCA            672
Phe Arg Phe Asp Leu Ser Lys Ile Pro Glu Gly Glu Ala Val Thr Ala
210             215             220

GCC GAA TTC CGG ATC TAC AAG GAC TAC ATC CGG GAA CGC TTC GAC AAT            720
Ala Glu Phe Arg Ile Tyr Lys Asp Tyr Ile Arg Glu Arg Phe Asp Asn
225             230             235             240

GAG ACG TTC CGG ATC AGC GTT TAT CAG GTG CTC CAG GAG CAC TTG GGC            768
Glu Thr Phe Arg Ile Ser Val Tyr Gln Val Leu Gln Glu His Leu Gly
                245             250             255

AGG GAA TCG GAT CTC TTC CTG CTC GAC AGC CGT ACC CTC TGG GCC TCG            816
Arg Glu Ser Asp Leu Phe Leu Leu Asp Ser Arg Thr Leu Trp Ala Ser
            260             265             270

GAG GAG GGC TGG CTG GTG TTT GAC ATC ACA GCC ACC AGC AAC CAC TGG            864
Glu Glu Gly Trp Leu Val Phe Asp Ile Thr Ala Thr Ser Asn His Trp
        275             280             285

GTG GTC AAT CCG CGG CAC AAC CTG GGC CTG CAG CTC TCG GTG GAG ACG            912
Val Val Asn Pro Arg His Asn Leu Gly Leu Gln Leu Ser Val Glu Thr
290             295             300

CTG GAT GGG CAG AGC ATC AAC CCC AAG TTG GCG GGC CTG ATT GGG CGG            960
Leu Asp Gly Gln Ser Ile Asn Pro Lys Leu Ala Gly Leu Ile Gly Arg
305             310             315             320

CAC GGG CCC CAG AAC AAG CAG CCC TTC ATG GTG GCT TTC TTC AAG GCC           1008
His Gly Pro Gln Asn Lys Gln Pro Phe Met Val Ala Phe Phe Lys Ala
                325             330             335

ACG GAG GTC CAC TTC CGC AGC ATC CGG TCC ACG GGG AGC AAA CAG CGC           1056
Thr Glu Val His Phe Arg Ser Ile Arg Ser Thr Gly Ser Lys Gln Arg
            340             345             350

AGC CAG AAC CGC TCC AAG ACG CCC AAG AAC CAG GAA GCC CTG CGG ATG           1104
Ser Gln Asn Arg Ser Lys Thr Pro Lys Asn Gln Glu Ala Leu Arg Met
        355             360             365
```

| | | | | | | | | | | | | | | | | |
|---|---|---|---|---|---|---|---|---|---|---|---|---|---|---|---|---|
| GCC | AAC | GTG | GCA | GAG | AAC | AGC | AGC | AGC | GAC | CAG | AGG | CAG | GCC | TGT | AAG | 1152 |
| Ala | Asn | Val | Ala | Glu | Asn | Ser | Ser | Ser | Asp | Gln | Arg | Gln | Ala | Cys | Lys | |
| | 370 | | | | | 375 | | | | | | 380 | | | | |
| AAG | CAC | GAG | CTG | TAT | GTC | AGC | TTC | CGA | GAC | CTG | GGC | TGG | CAG | GAC | TGG | 1200 |
| Lys | His | Glu | Leu | Tyr | Val | Ser | Phe | Arg | Asp | Leu | Gly | Trp | Gln | Asp | Trp | |
| 385 | | | | | 390 | | | | | 395 | | | | | 400 | |
| ATC | ATC | GCG | CCT | GAA | GGC | TAC | GCC | GCC | TAC | TAC | TGT | GAG | GGG | GAG | TGT | 1248 |
| Ile | Ile | Ala | Pro | Glu | Gly | Tyr | Ala | Ala | Tyr | Tyr | Cys | Glu | Gly | Glu | Cys | |
| | | | | 405 | | | | | 410 | | | | | 415 | | |
| GCC | TTC | CCT | CTG | AAC | TCC | TAC | ATG | AAC | GCC | ACC | AAC | CAC | GCC | ATC | GTG | 1296 |
| Ala | Phe | Pro | Leu | Asn | Ser | Tyr | Met | Asn | Ala | Thr | Asn | His | Ala | Ile | Val | |
| | | | 420 | | | | | 425 | | | | | 430 | | | |
| CAG | ACG | CTG | GTC | CAC | TTC | ATC | AAC | CCG | GAA | ACG | GTG | CCC | AAG | CCC | TGC | 1344 |
| Gln | Thr | Leu | Val | His | Phe | Ile | Asn | Pro | Glu | Thr | Val | Pro | Lys | Pro | Cys | |
| | | 435 | | | | | | 440 | | | | | 445 | | | |
| TGT | GCG | CCC | ACG | CAG | CTC | AAT | GCC | ATC | TCC | GTC | CTC | TAC | TTC | GAT | GAC | 1392 |
| Cys | Ala | Pro | Thr | Gln | Leu | Asn | Ala | Ile | Ser | Val | Leu | Tyr | Phe | Asp | Asp | |
| 450 | | | | | | 455 | | | | | 460 | | | | | |
| AGC | TCC | AAC | GTC | ATC | CTG | AAG | AAA | TAC | AGA | AAC | ATG | GTG | GTC | CGG | GCC | 1440 |
| Ser | Ser | Asn | Val | Ile | Leu | Lys | Lys | Tyr | Arg | Asn | Met | Val | Val | Arg | Ala | |
| 465 | | | | 470 | | | | | 475 | | | | | | 480 | |
| TGT | GGC | TGC | CAC | TAGCTCCTTC | | CGAGAATTCC | | AGACCTTTGG | | GGCCCAAAGG | | | | | | 1492 |
| Cys | Gly | Cys | His | | | | | | | | | | | | | |
| TTTTTCTGGA TCC | | | | | | | | | | | | | | | | 1505 |

(2) INFORMATION FOR SEQ ID NO:13:

(i) SEQUENCE CHARACTERISTICS:
        (A) LENGTH: 484 amino acids
        (B) TYPE: amino acid
        (D) TOPOLOGY: linear (ii) MOLECULE TYPE: protein (xi) SEQUENCE DESCRIPTION: SEQ ID NO:13:

```
Met Lys Ala Ile Phe Val Leu Lys Gly Ser Leu Asp Arg Asp Leu Asp
 1               5                  10                  15

Ser Arg Leu Asp Leu Asp Val Arg Thr Asp His Lys Asp Leu Ser Asp
                20                  25                  30

His Leu Val Leu Val Asp Leu Ala Arg Asn Glu Asn Ser Arg Val Ala
            35                  40                  45

Arg Arg Ala Gly Ala Met His Val Arg Ser Leu Arg Ala Ala Ala Pro
        50                  55                  60

His Ser Phe Val Ala Leu Trp Ala Pro Leu Phe Leu Leu Arg Ser Ala
 65                  70                  75                  80

Leu Ala Asp Phe Ser Leu Asp Asn Glu Val His Ser Ser Phe Ile His
                85                  90                  95

Arg Arg Leu Arg Ser Gln Glu Arg Arg Glu Met Gln Arg Glu Ile Leu
               100                 105                 110

Ser Ile Leu Gly Leu Pro His Arg Pro Arg Pro His Leu Gln Gly Lys
           115                 120                 125

His Asn Ser Ala Pro Met Phe Met Leu Asp Leu Tyr Asn Ala His Gly
       130                 135                 140

Gly Gly Gly Gly Arg Arg Pro Gly Gly Gln Gly Phe Ser Tyr Pro Tyr
145                 150                 155                 160

Lys Ala Val Phe Ser Thr Gln Gly Pro Pro Leu Ala Ser Leu Gln Asp
               165                 170                 175

Ser His Phe Leu Thr Asp Ala Asp Met Val Met Ser Phe Val Asn Leu
           180                 185                 190

Val Glu His Asp Lys Glu Phe Phe His Pro Arg Tyr His His Arg Glu
```

-continued

```
              195                         200                         205
Phe  Arg  Phe  Asp  Leu  Ser  Lys  Ile  Pro  Glu  Gly  Glu  Ala  Val  Thr  Ala
     210                      215                     220

Ala  Glu  Phe  Arg  Ile  Tyr  Lys  Asp  Tyr  Ile  Arg  Glu  Arg  Phe  Asp  Asn
225                      230                     235                          240

Glu  Thr  Phe  Arg  Ile  Ser  Val  Tyr  Gln  Val  Leu  Gln  Glu  His  Leu  Gly
                    245                     250                     255

Arg  Glu  Ser  Asp  Leu  Phe  Leu  Leu  Asp  Ser  Arg  Thr  Leu  Trp  Ala  Ser
               260                     265                     270

Glu  Glu  Gly  Trp  Leu  Val  Phe  Asp  Ile  Thr  Ala  Thr  Ser  Asn  His  Trp
          275                     280                     285

Val  Val  Asn  Pro  Arg  His  Asn  Leu  Gly  Leu  Gln  Leu  Ser  Val  Glu  Thr
     290                     295                     300

Leu  Asp  Gly  Gln  Ser  Ile  Asn  Pro  Lys  Leu  Ala  Gly  Leu  Ile  Gly  Arg
305                      310                     315                          320

His  Gly  Pro  Gln  Asn  Lys  Gln  Pro  Phe  Met  Val  Ala  Phe  Phe  Lys  Ala
                    325                     330                     335

Thr  Glu  Val  His  Phe  Arg  Ser  Ile  Arg  Ser  Thr  Gly  Ser  Lys  Gln  Arg
               340                     345                     350

Ser  Gln  Asn  Arg  Ser  Lys  Thr  Pro  Lys  Asn  Gln  Glu  Ala  Leu  Arg  Met
          355                     360                     365.

Ala  Asn  Val  Ala  Glu  Asn  Ser  Ser  Ser  Asp  Gln  Arg  Gln  Ala  Cys  Lys
     370                     375                     380

Lys  His  Glu  Leu  Tyr  Val  Ser  Phe  Arg  Asp  Leu  Gly  Trp  Gln  Asp  Trp
385                      390                     395                          400

Ile  Ile  Ala  Pro  Glu  Gly  Tyr  Ala  Ala  Tyr  Tyr  Cys  Glu  Gly  Glu  Cys
                    405                     410                     415

Ala  Phe  Pro  Leu  Asn  Ser  Tyr  Met  Asn  Ala  Thr  Asn  His  Ala  Ile  Val
               420                     425                     430

Gln  Thr  Leu  Val  His  Phe  Ile  Asn  Pro  Glu  Thr  Val  Pro  Lys  Pro  Cys
          435                     440                     445

Cys  Ala  Pro  Thr  Gln  Leu  Asn  Ala  Ile  Ser  Val  Leu  Tyr  Phe  Asp  Asp
     450                     455                     460

Ser  Ser  Asn  Val  Ile  Leu  Lys  Lys  Tyr  Arg  Asn  Met  Val  Val  Arg  Ala
465                      470                     475                          480

Cys  Gly  Cys  His
```

( 2 ) INFORMATION FOR SEQ ID NO:14:

( i ) SEQUENCE CHARACTERISTICS:
        ( A ) LENGTH: 1277 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( i x ) FEATURE:
        ( A ) NAME/KEY: CDS
        ( B ) LOCATION: 1..1224
        ( D ) OTHER INFORMATION: /function="OSTEOGENIC PROTEIN"
            / product="OP1D"
            / note="OP1D - FUSION"

( x i ) SEQUENCE DESCRIPTION: SEQ ID NO:14:

```
ATG  AAA  GCA  ATT  TTC  GTA  CTG  AAA  GGT  TCA  CTG  GAC  AGA  GAT  CCG  TCG      48
Met  Lys  Ala  Ile  Phe  Val  Leu  Lys  Gly  Ser  Leu  Asp  Arg  Asp  Pro  Ser
1                        5                        10                       15
```

-continued

| | | | | | | | | | | | | | | | | |
|---|---|---|---|---|---|---|---|---|---|---|---|---|---|---|---|---|
| AGC | TTC | ATC | CAC | CGG | CGC | CTC | CGC | AGC | CAG | GAG | CGG | CGG | GAG | ATG | CAG | 96 |
| Ser | Phe | Ile | His | Arg | Arg | Leu | Arg | Ser | Gln | Glu | Arg | Arg | Glu | Met | Gln | |
| | | | 20 | | | | | 25 | | | | | 30 | | | |
| CGC | GAG | ATC | CTC | TCC | ATT | TTG | GGC | TTG | CCC | CAC | CGC | CCG | CGC | CCG | CAC | 144 |
| Arg | Glu | Ile | Leu | Ser | Ile | Leu | Gly | Leu | Pro | His | Arg | Pro | Arg | Pro | His | |
| | | | 35 | | | | | 40 | | | | | 45 | | | |
| CTC | CAG | GGC | AAG | CAC | AAC | TCG | GCA | CCC | ATG | TTC | ATG | CTG | GAC | CTG | TAC | 192 |
| Leu | Gln | Gly | Lys | His | Asn | Ser | Ala | Pro | Met | Phe | Met | Leu | Asp | Leu | Tyr | |
| | 50 | | | | | 55 | | | | | 60 | | | | | |
| AAC | GCC | CAT | GGC | GGT | GGA | GGA | GGG | CGG | CGG | CCC | GGC | GGC | CAG | GGC | TTC | 240 |
| Asn | Ala | His | Gly | Gly | Gly | Gly | Gly | Arg | Arg | Pro | Gly | Gly | Gln | Gly | Phe | |
| 65 | | | | | 70 | | | | | 75 | | | | | 80 | |
| TCC | TAC | CCC | TAC | AAG | GCC | GTC | TTC | AGT | ACC | CAG | GGC | CCC | CCT | CTG | GCC | 288 |
| Ser | Tyr | Pro | Tyr | Lys | Ala | Val | Phe | Ser | Thr | Gln | Gly | Pro | Pro | Leu | Ala | |
| | | | | 85 | | | | | 90 | | | | | 95 | | |
| AGC | CTG | CAA | GAT | AGC | CAT | TTC | CTC | ACC | GAC | GCC | GAC | ATG | GTC | ATG | AGC | 336 |
| Ser | Leu | Gln | Asp | Ser | His | Phe | Leu | Thr | Asp | Ala | Asp | Met | Val | Met | Ser | |
| | | | | 100 | | | | | 105 | | | | | 110 | | |
| TTC | GTC | AAC | CTC | GTG | GAA | CAT | GAC | AAG | GAA | TTC | TTC | CAC | CCA | CGC | TAC | 384 |
| Phe | Val | Asn | Leu | Val | Glu | His | Asp | Lys | Glu | Phe | Phe | His | Pro | Arg | Tyr | |
| | | | 115 | | | | | 120 | | | | | 125 | | | |
| CAC | CAT | CGA | GAG | TTC | CGG | TTT | GAT | CTT | TCC | AAG | ATC | CCA | GAA | GGG | GAA | 432 |
| His | His | Arg | Glu | Phe | Arg | Phe | Asp | Leu | Ser | Lys | Ile | Pro | Glu | Gly | Glu | |
| | 130 | | | | | 135 | | | | | 140 | | | | | |
| GCT | GTC | ACG | GCA | GCC | GAA | TTC | CGG | ATC | TAC | AAG | GAC | TAC | ATC | CGG | GAA | 480 |
| Ala | Val | Thr | Ala | Ala | Glu | Phe | Arg | Ile | Tyr | Lys | Asp | Tyr | Ile | Arg | Glu | |
| 145 | | | | | 150 | | | | | 155 | | | | | 160 | |
| CGC | TTC | GAC | AAT | GAG | ACG | TTC | CGG | ATC | AGC | GTT | TAT | CAG | GTG | CTC | CAG | 528 |
| Arg | Phe | Asp | Asn | Glu | Thr | Phe | Arg | Ile | Ser | Val | Tyr | Gln | Val | Leu | Gln | |
| | | | | 165 | | | | | 170 | | | | | 175 | | |
| GAG | CAC | TTG | GGC | AGG | GAA | TCG | GAT | CTC | TTC | CTG | CTC | GAC | AGC | CGT | ACC | 576 |
| Glu | His | Leu | Gly | Arg | Glu | Ser | Asp | Leu | Phe | Leu | Leu | Asp | Ser | Arg | Thr | |
| | | | 180 | | | | | 185 | | | | | 190 | | | |
| CTC | TGG | GCC | TCG | GAG | GAG | GGC | TGG | CTG | GTG | TTT | GAC | ATC | ACA | GCC | ACC | 624 |
| Leu | Trp | Ala | Ser | Glu | Glu | Gly | Trp | Leu | Val | Phe | Asp | Ile | Thr | Ala | Thr | |
| | | 195 | | | | | 200 | | | | | 205 | | | | |
| AGC | AAC | CAC | TGG | GTG | GTC | AAT | CCG | CGG | CAC | AAC | CTG | GGC | CTG | CAG | CTC | 672 |
| Ser | Asn | His | Trp | Val | Val | Asn | Pro | Arg | His | Asn | Leu | Gly | Leu | Gln | Leu | |
| | 210 | | | | | 215 | | | | | 220 | | | | | |
| TCG | GTG | GAG | ACG | CTG | GAT | GGG | CAG | AGC | ATC | AAC | CCC | AAG | TTG | GCG | GGC | 720 |
| Ser | Val | Glu | Thr | Leu | Asp | Gly | Gln | Ser | Ile | Asn | Pro | Lys | Leu | Ala | Gly | |
| 225 | | | | | 230 | | | | | 235 | | | | | 240 | |
| CTG | ATT | GGG | CGG | CAC | GGG | CCC | CAG | AAC | AAG | CAG | CCC | TTC | ATG | GTG | GCT | 768 |
| Leu | Ile | Gly | Arg | His | Gly | Pro | Gln | Asn | Lys | Gln | Pro | Phe | Met | Val | Ala | |
| | | | | 245 | | | | | 250 | | | | | 255 | | |
| TTC | TTC | AAG | GCC | ACG | GAG | GTC | CAC | TTC | CGC | AGC | ATC | CGG | TCC | ACG | GGG | 816 |
| Phe | Phe | Lys | Ala | Thr | Glu | Val | His | Phe | Arg | Ser | Ile | Arg | Ser | Thr | Gly | |
| | | | 260 | | | | | 265 | | | | | 270 | | | |
| AGC | AAA | CAG | CGC | AGC | CAG | AAC | CGC | TCC | AAG | ACG | CCC | AAG | AAC | CAG | GAA | 864 |
| Ser | Lys | Gln | Arg | Ser | Gln | Asn | Arg | Ser | Lys | Thr | Pro | Lys | Asn | Gln | Glu | |
| | 275 | | | | | 280 | | | | | 285 | | | | | |
| GCC | CTG | CGG | ATG | GCC | AAC | GTG | GCA | GAG | AAC | AGC | AGC | AGC | GAC | CAG | AGG | 912 |
| Ala | Leu | Arg | Met | Ala | Asn | Val | Ala | Glu | Asn | Ser | Ser | Ser | Asp | Gln | Arg | |
| 290 | | | | | 295 | | | | | 300 | | | | | | |
| CAG | GCC | TGT | AAG | AAG | CAC | GAG | CTG | TAT | GTC | AGC | TTC | CGA | GAC | CTG | GGC | 960 |
| Gln | Ala | Cys | Lys | Lys | His | Glu | Leu | Tyr | Val | Ser | Phe | Arg | Asp | Leu | Gly | |
| 305 | | | | | 310 | | | | | 315 | | | | | 320 | |
| TGG | CAG | GAC | TGG | ATC | ATC | GCG | CCT | GAA | GGC | TAC | GCC | GCC | TAC | TAC | TGT | 1008 |
| Trp | Gln | Asp | Trp | Ile | Ile | Ala | Pro | Glu | Gly | Tyr | Ala | Ala | Tyr | Tyr | Cys | |
| | | | | 325 | | | | | 330 | | | | | 335 | | |
| GAG | GGG | GAG | TGT | GCC | TTC | CCT | CTG | AAC | TCC | TAC | ATG | AAC | GCC | ACC | AAC | 1056 |

|     |     |     |     |     |     |     |     |     |     |     |     |     |     |     |      |
| --- | --- | --- | --- | --- | --- | --- | --- | --- | --- | --- | --- | --- | --- | --- | ---- |
| Glu | Gly | Glu | Cys | Ala | Phe | Pro | Leu | Asn | Ser | Tyr | Met | Asn | Ala | Thr | Asn  |
|     |     |     | 340 |     |     |     |     | 345 |     |     |     |     | 350 |     |      |
| CAC | GCC | ATC | GTG | CAG | ACG | CTG | GTC | CAC | TTC | ATC | AAC | CCG | GAA | ACG | GTG  | 1104 |
| His | Ala | Ile | Val | Gln | Thr | Leu | Val | His | Phe | Ile | Asn | Pro | Glu | Thr | Val  |
|     |     | 355 |     |     |     |     | 360 |     |     |     |     | 365 |     |     |      |
| CCC | AAG | CCC | TGC | TGT | GCG | CCC | ACG | CAG | CTC | AAT | GCC | ATC | TCC | GTC | CTC  | 1152 |
| Pro | Lys | Pro | Cys | Cys | Ala | Pro | Thr | Gln | Leu | Asn | Ala | Ile | Ser | Val | Leu  |
|     | 370 |     |     |     |     | 375 |     |     |     |     | 380 |     |     |     |      |
| TAC | TTC | GAT | GAC | AGC | TCC | AAC | GTC | ATC | CTG | AAG | AAA | TAC | AGA | AAC | ATG  | 1200 |
| Tyr | Phe | Asp | Asp | Ser | Ser | Asn | Val | Ile | Leu | Lys | Lys | Tyr | Arg | Asn | Met  |
| 385 |     |     |     |     | 390 |     |     |     |     | 395 |     |     |     |     | 400  |
| GTG | GTC | CGG | GCC | TGT | GGC | TGC | CAC | TAGCTCCTTC | CGAGAATTCC | AGACCTTTGG |  |  |  |  |  | 1254 |
| Val | Val | Arg | Ala | Cys | Gly | Cys | His |     |     |     |     |     |     |     |      |
|     |     |     |     | 405 |     |     |     |     |     |     |     |     |     |     |      |

GGCCCAAAGG TTTTTCTGGA TCC    1277

( 2 ) INFORMATION FOR SEQ ID NO:15:

( i ) SEQUENCE CHARACTERISTICS:
        ( A ) LENGTH: 408 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Lys | Ala | Ile | Phe | Val | Leu | Lys | Gly | Ser | Leu | Asp | Arg | Asp | Pro | Ser |
| 1   |     |     |     | 5   |     |     |     |     | 10  |     |     |     |     | 15  |     |
| Ser | Phe | Ile | His | Arg | Arg | Leu | Arg | Ser | Gln | Glu | Arg | Arg | Glu | Met | Gln |
|     |     |     | 20  |     |     |     |     | 25  |     |     |     |     | 30  |     |     |
| Arg | Glu | Ile | Leu | Ser | Ile | Leu | Gly | Leu | Pro | His | Arg | Pro | Arg | Pro | His |
|     |     | 35  |     |     |     |     | 40  |     |     |     |     | 45  |     |     |     |
| Leu | Gln | Gly | Lys | His | Asn | Ser | Ala | Pro | Met | Phe | Met | Leu | Asp | Leu | Tyr |
|     | 50  |     |     |     |     | 55  |     |     |     |     | 60  |     |     |     |     |
| Asn | Ala | His | Gly | Gly | Gly | Gly | Arg | Arg | Pro | Gly | Gly | Gln | Gly | Phe |     |
| 65  |     |     |     |     | 70  |     |     |     |     | 75  |     |     |     |     | 80  |
| Ser | Tyr | Pro | Tyr | Lys | Ala | Val | Phe | Ser | Thr | Gln | Gly | Pro | Pro | Leu | Ala |
|     |     |     |     | 85  |     |     |     |     | 90  |     |     |     |     | 95  |     |
| Ser | Leu | Gln | Asp | Ser | His | Phe | Leu | Thr | Asp | Ala | Asp | Met | Val | Met | Ser |
|     |     |     | 100 |     |     |     |     | 105 |     |     |     |     | 110 |     |     |
| Phe | Val | Asn | Leu | Val | Glu | His | Asp | Lys | Glu | Phe | Phe | His | Pro | Arg | Tyr |
|     |     |     | 115 |     |     |     |     | 120 |     |     |     |     | 125 |     |     |
| His | His | Arg | Glu | Phe | Arg | Phe | Asp | Leu | Ser | Lys | Ile | Pro | Glu | Gly | Glu |
|     | 130 |     |     |     |     | 135 |     |     |     |     | 140 |     |     |     |     |
| Ala | Val | Thr | Ala | Ala | Glu | Phe | Arg | Ile | Tyr | Lys | Asp | Tyr | Ile | Arg | Glu |
| 145 |     |     |     |     | 150 |     |     |     |     | 155 |     |     |     |     | 160 |
| Arg | Phe | Asp | Asn | Glu | Thr | Phe | Arg | Ile | Ser | Val | Tyr | Gln | Val | Leu | Gln |
|     |     |     |     | 165 |     |     |     |     | 170 |     |     |     |     | 175 |     |
| Glu | His | Leu | Gly | Arg | Glu | Ser | Asp | Leu | Phe | Leu | Leu | Asp | Ser | Arg | Thr |
|     |     |     | 180 |     |     |     |     | 185 |     |     |     |     | 190 |     |     |
| Leu | Trp | Ala | Ser | Glu | Glu | Gly | Trp | Leu | Val | Phe | Asp | Ile | Thr | Ala | Thr |
|     |     | 195 |     |     |     |     | 200 |     |     |     |     | 205 |     |     |     |
| Ser | Asn | His | Trp | Val | Val | Asn | Pro | Arg | His | Asn | Leu | Gly | Leu | Gln | Leu |
|     | 210 |     |     |     |     | 215 |     |     |     |     | 220 |     |     |     |     |
| Ser | Val | Glu | Thr | Leu | Asp | Gly | Gln | Ser | Ile | Asn | Pro | Lys | Leu | Ala | Gly |
| 225 |     |     |     |     | 230 |     |     |     |     | 235 |     |     |     |     | 240 |
| Leu | Ile | Gly | Arg | His | Gly | Pro | Gln | Asn | Lys | Gln | Pro | Phe | Met | Val | Ala |
|     |     |     |     | 245 |     |     |     |     | 250 |     |     |     |     | 255 |     |
| Phe | Phe | Lys | Ala | Thr | Glu | Val | His | Phe | Arg | Ser | Ile | Arg | Ser | Thr | Gly |

|                                         |                    |     |
|-----------------------------------------|--------------------|-----|
|                          260            | 265                | 270 |

Ser Lys Gln Arg Ser Gln Asn Arg Ser Lys Thr Pro Lys Asn Gln Glu
      275                   280             285

Ala Leu Arg Met Ala Asn Val Ala Glu Asn Ser Ser Ser Asp Gln Arg
    290                295               300

Gln Ala Cys Lys Lys His Glu Leu Tyr Val Ser Phe Arg Asp Leu Gly
305                 310              315             320

Trp Gln Asp Trp Ile Ile Ala Pro Glu Gly Tyr Ala Ala Tyr Tyr Cys
               325              330             335

Glu Gly Glu Cys Ala Phe Pro Leu Asn Ser Tyr Met Asn Ala Thr Asn
        340             345              350

His Ala Ile Val Gln Thr Leu Val His Phe Ile Asn Pro Glu Thr Val
      355              360             365

Pro Lys Pro Cys Cys Ala Pro Thr Gln Leu Asn Ala Ile Ser Val Leu
    370               375             380

Tyr Phe Asp Asp Ser Ser Asn Val Ile Leu Lys Lys Tyr Arg Asn Met
385                 390              395           400

Val Val Arg Ala Cys Gly Cys His
          405

( 2 ) INFORMATION FOR SEQ ID NO:16:

( i ) SEQUENCE CHARACTERISTICS:
        ( A ) LENGTH: 525 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i x ) FEATURE:
        ( A ) NAME/KEY: CDS
        ( B ) LOCATION: 1..516
        ( D ) OTHER INFORMATION: /function="OSTEOGENIC PROTEIN"
            / product="CBMP2B-1"
            / note="CBMP2B-1 - FUSION"

( x i ) SEQUENCE DESCRIPTION: SEQ ID NO:16:

ATG AAA GCA ATT TTC GTA CTG AAA GGT TCA CTG GAC AGA GAT CTG GAC    48
Met Lys Ala Ile Phe Val Leu Lys Gly Ser Leu Asp Arg Asp Leu Asp
1                5                   10               15

TCT CGT CTG GAT CTG GAC GTT CGT ACC GAC CAC AAA GAC CTG TCT GAT    96
Ser Arg Leu Asp Leu Asp Val Arg Thr Asp His Lys Asp Leu Ser Asp
          20                   25               30

CAC CTG GTT CTG GTC GAC CTG GCT CGT AAC GAC CTG GCT CGT ATC GTT    144
His Leu Val Leu Val Asp Leu Ala Arg Asn Asp Leu Ala Arg Ile Val
          35                   40               45

ACT CCC GGG TCT CGT TAC GTT GCG GAT CCT AAG CAT CAC TCA CAG CGG    192
Thr Pro Gly Ser Arg Tyr Val Ala Asp Pro Lys His His Ser Gln Arg
    50                 55              60

GCC AGG AAG AAG AAT AAG AAC TGC CGG CGC CAC TCG CTC TAT GTG GAC    240
Ala Arg Lys Lys Asn Lys Asn Cys Arg Arg His Ser Leu Tyr Val Asp
65               70               75              80

TTC AGC GAT GTG GGC TGG AAT GAC TGG ATT GTG GCC CCA CCA GGC TAC    288
Phe Ser Asp Val Gly Trp Asn Asp Trp Ile Val Ala Pro Pro Gly Tyr
              85               90               95

CAG GCC TTC TAC TGC CAT GGC GAA TGC CCT TTC CCG CTA GCG GAT CAC    336
Gln Ala Phe Tyr Cys His Gly Glu Cys Pro Phe Pro Leu Ala Asp His
         100                105             110

TTC AAC AGC ACC AAC CAC GCC GTG GTG CAG ACC CTG GTG AAC TCT GTC    384
Phe Asn Ser Thr Asn His Ala Val Val Gln Thr Leu Val Asn Ser Val
        115                120             125

| | | | | | | | | | | | | | | | |
|---|---|---|---|---|---|---|---|---|---|---|---|---|---|---|---|
| AAC | TCC | AAG | ATC | CCT | AAG | GCT | TGC | TGC | GTG | CCC | ACC | GAG | CTG | TCC | GCC |
| Asn | Ser | Lys | Ile | Pro | Lys | Ala | Cys | Cys | Val | Pro | Thr | Glu | Leu | Ser | Ala |
| | | 130 | | | | 135 | | | | | 140 | | | | |

432

| | | | | | | | | | | | | | | | |
|---|---|---|---|---|---|---|---|---|---|---|---|---|---|---|---|
| ATC | AGC | ATG | CTG | TAC | CTG | GAC | GAG | AAT | GAG | AAG | GTG | GTG | CTG | AAG | AAC |
| Ile | Ser | Met | Leu | Tyr | Leu | Asp | Glu | Asn | Glu | Lys | Val | Val | Leu | Lys | Asn |
| 145 | | | | | 150 | | | | | 155 | | | | | 160 |

480

| | | | | | | | | | | |
|---|---|---|---|---|---|---|---|---|---|---|
| TAC | CAG | GAG | ATG | GTA | GTA | GAG | GGC | TGC | GGC | TGC | CGC | TAACTGCAG |
| Tyr | Gln | Glu | Met | Val | Val | Glu | Gly | Cys | Gly | Cys | Arg | |
| | | | | 165 | | | | 170 | | | | |

525

( 2 ) INFORMATION FOR SEQ ID NO:17:

( i ) SEQUENCE CHARACTERISTICS:
        ( A ) LENGTH: 172 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| | | | | | | | | | | | | | | |
|---|---|---|---|---|---|---|---|---|---|---|---|---|---|---|
| Met | Lys | Ala | Ile | Phe | Val | Leu | Lys | Gly | Ser | Leu | Asp | Arg | Asp | Leu | Asp |
| 1 | | | | 5 | | | | | 10 | | | | | 15 | |

| | | | | | | | | | | | | | | |
|---|---|---|---|---|---|---|---|---|---|---|---|---|---|---|
| Ser | Arg | Leu | Asp | Leu | Asp | Val | Arg | Thr | Asp | His | Lys | Asp | Leu | Ser | Asp |
| | | | 20 | | | | | 25 | | | | | 30 | | |

| | | | | | | | | | | | | | | |
|---|---|---|---|---|---|---|---|---|---|---|---|---|---|---|
| His | Leu | Val | Leu | Val | Asp | Leu | Ala | Arg | Asn | Asp | Leu | Ala | Arg | Ile | Val |
| | | 35 | | | | | 40 | | | | | 45 | | | |

| | | | | | | | | | | | | | | |
|---|---|---|---|---|---|---|---|---|---|---|---|---|---|---|
| Thr | Pro | Gly | Ser | Arg | Tyr | Val | Ala | Asp | Pro | Lys | His | His | Ser | Gln | Arg |
| | 50 | | | | | 55 | | | | | 60 | | | | |

| | | | | | | | | | | | | | | |
|---|---|---|---|---|---|---|---|---|---|---|---|---|---|---|
| Ala | Arg | Lys | Lys | Asn | Lys | Asn | Cys | Arg | Arg | His | Ser | Leu | Tyr | Val | Asp |
| 65 | | | | | 70 | | | | | 75 | | | | | 80 |

| | | | | | | | | | | | | | | |
|---|---|---|---|---|---|---|---|---|---|---|---|---|---|---|
| Phe | Ser | Asp | Val | Gly | Trp | Asn | Asp | Trp | Ile | Val | Ala | Pro | Pro | Gly | Tyr |
| | | | | 85 | | | | | 90 | | | | | 95 | |

| | | | | | | | | | | | | | | |
|---|---|---|---|---|---|---|---|---|---|---|---|---|---|---|
| Gln | Ala | Phe | Tyr | Cys | His | Gly | Glu | Cys | Pro | Phe | Pro | Leu | Ala | Asp | His |
| | | | 100 | | | | | 105 | | | | | 110 | | |

| | | | | | | | | | | | | | | |
|---|---|---|---|---|---|---|---|---|---|---|---|---|---|---|
| Phe | Asn | Ser | Thr | Asn | His | Ala | Val | Val | Gln | Thr | Leu | Val | Asn | Ser | Val |
| | | 115 | | | | | 120 | | | | | 125 | | | |

| | | | | | | | | | | | | | | |
|---|---|---|---|---|---|---|---|---|---|---|---|---|---|---|
| Asn | Ser | Lys | Ile | Pro | Lys | Ala | Cys | Cys | Val | Pro | Thr | Glu | Leu | Ser | Ala |
| | 130 | | | | | 135 | | | | | 140 | | | | |

| | | | | | | | | | | | | | | |
|---|---|---|---|---|---|---|---|---|---|---|---|---|---|---|
| Ile | Ser | Met | Leu | Tyr | Leu | Asp | Glu | Asn | Glu | Lys | Val | Val | Leu | Lys | Asn |
| 145 | | | | | 150 | | | | | 155 | | | | | 160 |

| | | | | | | | | |
|---|---|---|---|---|---|---|---|---|
| Tyr | Gln | Glu | Met | Val | Val | Glu | Gly | Cys | Gly | Cys | Arg |
| | | | | 165 | | | | 170 | | | |

( 2 ) INFORMATION FOR SEQ ID NO:18:

( i ) SEQUENCE CHARACTERISTICS:
        ( A ) LENGTH: 1586 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( i x ) FEATURE:
        ( A ) NAME/KEY: CDS
        ( B ) LOCATION: 1..1257
        ( D ) OTHER INFORMATION: /function="OSTEOGENIC PROTEIN"
            / product="CBMP2B-2"
            / note="CBMP2B-2 - FUSION"

( x i ) SEQUENCE DESCRIPTION: SEQ ID NO:18:

| | | | | | | | | | | | | | | | | |
|---|---|---|---|---|---|---|---|---|---|---|---|---|---|---|---|---|
| ATG | AAA | GCA | ATT | TTC | GTA | CTG | AAA | GGT | TCA | CTG | GAC | AGA | GAT | CTG | GAC | 48 |
| Met | Lys | Ala | Ile | Phe | Val | Leu | Lys | Gly | Ser | Leu | Asp | Arg | Asp | Leu | Asp | |
| 1 | | | | 5 | | | | | 10 | | | | | 15 | | |
| TCT | CGT | CTG | GAT | CTG | GAC | GTT | CGT | ACC | GAC | CAC | AAA | GAC | CTG | TCT | GAT | 96 |
| Ser | Arg | Leu | Asp | Leu | Asp | Val | Arg | Thr | Asp | His | Lys | Asp | Leu | Ser | Asp | |
| | | | 20 | | | | | 25 | | | | | 30 | | | |
| CAC | CTG | GTT | CTG | GTC | GAC | CTG | GCT | CGT | AAC | GAC | CTG | GCT | CGT | ATC | GTT | 144 |
| His | Leu | Val | Leu | Val | Asp | Leu | Ala | Arg | Asn | Asp | Leu | Ala | Arg | Ile | Val | |
| | | 35 | | | | | 40 | | | | | 45 | | | | |
| ACT | CCC | GGG | TCT | CGT | TAC | GTT | GCG | GAT | CTG | GAA | TTC | CCG | GGA | GAG | CTC | 192 |
| Thr | Pro | Gly | Ser | Arg | Tyr | Val | Ala | Asp | Leu | Glu | Phe | Pro | Gly | Glu | Leu | |
| | 50 | | | | | 55 | | | | | 60 | | | | | |
| CTG | CGG | GAC | TTC | GAG | GCG | ACA | CTT | CTG | CAG | ATG | TTT | GGG | CTG | CGC | CGC | 240 |
| Leu | Arg | Asp | Phe | Glu | Ala | Thr | Leu | Leu | Gln | Met | Phe | Gly | Leu | Arg | Arg | |
| 65 | | | | | 70 | | | | | 75 | | | | | 80 | |
| CGC | CCG | CAG | CCT | AGC | AAG | AGT | GCC | GTC | ATT | CCG | GAC | TAC | ATG | CGG | GAT | 288 |
| Arg | Pro | Gln | Pro | Ser | Lys | Ser | Ala | Val | Ile | Pro | Asp | Tyr | Met | Arg | Asp | |
| | | | | 85 | | | | | 90 | | | | | 95 | | |
| CTT | TAC | CGG | CTT | CAG | TCT | GGG | GAG | GAG | GAG | GAA | GAG | CAG | ATC | CAC | AGC | 336 |
| Leu | Tyr | Arg | Leu | Gln | Ser | Gly | Glu | Glu | Glu | Glu | Glu | Gln | Ile | His | Ser | |
| | | | 100 | | | | | 105 | | | | | 110 | | | |
| ACT | GGT | CTT | GAG | TAT | CCT | GAG | CGC | CCG | GCC | AGC | CGG | GCC | AAC | ACC | GTG | 384 |
| Thr | Gly | Leu | Glu | Tyr | Pro | Glu | Arg | Pro | Ala | Ser | Arg | Ala | Asn | Thr | Val | |
| | | 115 | | | | | 120 | | | | | 125 | | | | |
| AGG | AGC | TTC | CAC | CAC | GAA | GAA | CAT | CTG | GAG | AAC | ATC | CCA | GGG | ACC | AGT | 432 |
| Arg | Ser | Phe | His | His | Glu | Glu | His | Leu | Glu | Asn | Ile | Pro | Gly | Thr | Ser | |
| | 130 | | | | | 135 | | | | | 140 | | | | | |
| GAA | AAC | TCT | GCT | TTT | CGT | TTC | CTC | TTT | AAC | CTC | AGC | AGC | ATC | CCT | GAG | 480 |
| Glu | Asn | Ser | Ala | Phe | Arg | Phe | Leu | Phe | Asn | Leu | Ser | Ser | Ile | Pro | Glu | |
| 145 | | | | | 150 | | | | | 155 | | | | | 160 | |
| AAC | GAG | GCG | ATC | TCC | TCT | GCA | GAG | CTT | CGG | CTC | TTC | CGG | GAG | CAG | GTG | 528 |
| Asn | Glu | Ala | Ile | Ser | Ser | Ala | Glu | Leu | Arg | Leu | Phe | Arg | Glu | Gln | Val | |
| | | | | 165 | | | | | 170 | | | | | 175 | | |
| GAC | CAG | GGC | CCT | GAT | TGG | GAA | AGG | GGC | TTC | CAC | CGT | ATA | AAC | ATT | TAT | 576 |
| Asp | Gln | Gly | Pro | Asp | Trp | Glu | Arg | Gly | Phe | His | Arg | Ile | Asn | Ile | Tyr | |
| | | | 180 | | | | | 185 | | | | | 190 | | | |
| GAG | GTT | ATG | AAG | CCC | CCA | GCA | GAA | GTG | GTG | CCT | GGG | CAC | CTC | ATC | ACA | 624 |
| Glu | Val | Met | Lys | Pro | Pro | Ala | Glu | Val | Val | Pro | Gly | His | Leu | Ile | Thr | |
| | | 195 | | | | | 200 | | | | | 205 | | | | |
| CGA | CTA | CTG | GAC | ACG | AGA | CTG | GTC | CAC | CAC | AAT | GTG | ACA | CGG | TGG | GAA | 672 |
| Arg | Leu | Leu | Asp | Thr | Arg | Leu | Val | His | His | Asn | Val | Thr | Arg | Trp | Glu | |
| | 210 | | | | | 215 | | | | | 220 | | | | | |
| ACT | TTT | GAT | GTG | AGC | CCT | GCG | GTC | CTT | CGC | TGG | ACC | CGG | GAG | AAG | CAG | 720 |
| Thr | Phe | Asp | Val | Ser | Pro | Ala | Val | Leu | Arg | Trp | Thr | Arg | Glu | Lys | Gln | |
| 225 | | | | | 230 | | | | | 235 | | | | | 240 | |
| CCA | AAC | TAT | GGG | CTA | GCC | ATT | GAG | GTG | ACT | CAC | CTC | CAT | CAG | ACT | CGG | 768 |
| Pro | Asn | Tyr | Gly | Leu | Ala | Ile | Glu | Val | Thr | His | Leu | His | Gln | Thr | Arg | |
| | | | | 245 | | | | | 250 | | | | | 255 | | |
| ACC | CAC | CAG | GGC | CAG | CAT | GTC | AGG | ATT | AGC | CGA | TCG | TTA | CCT | CAA | GGG | 816 |
| Thr | His | Gln | Gly | Gln | His | Val | Arg | Ile | Ser | Arg | Ser | Leu | Pro | Gln | Gly | |
| | | | 260 | | | | | 265 | | | | | 270 | | | |
| AGT | GGG | AAT | TGG | GCC | CAG | CTC | CGG | CCC | CTC | CTG | GTC | ACC | TTT | GGC | CAT | 864 |
| Ser | Gly | Asn | Trp | Ala | Gln | Leu | Arg | Pro | Leu | Leu | Val | Thr | Phe | Gly | His | |
| | | 275 | | | | | 280 | | | | | 285 | | | | |
| GAT | GGC | CGG | GGC | CAT | GCC | TTG | ACC | CGA | CGC | CGG | AGG | GCC | AAG | CGT | AGC | 912 |
| Asp | Gly | Arg | Gly | His | Ala | Leu | Thr | Arg | Arg | Arg | Arg | Ala | Lys | Arg | Ser | |
| | 290 | | | | | 295 | | | | | 300 | | | | | |
| CCT | AAG | CAT | CAC | TCA | CAG | CGG | GCC | AGG | AAG | AAG | AAT | AAG | AAC | TGC | CGG | 960 |
| Pro | Lys | His | His | Ser | Gln | Arg | Ala | Arg | Lys | Lys | Asn | Lys | Asn | Cys | Arg | |
| 305 | | | | | 310 | | | | | 315 | | | | | 320 | |
| CGC | CAC | TCG | CTC | TAT | GTG | GAC | TTC | AGC | GAT | GTG | GGC | TGG | AAT | GAC | TGG | 1008 |
| Arg | His | Ser | Leu | Tyr | Val | Asp | Phe | Ser | Asp | Val | Gly | Trp | Asn | Asp | Trp | |

|   |   |   |   |   |   |   |   |   |   |   |   |   |   |   |   |      |
|---|---|---|---|---|---|---|---|---|---|---|---|---|---|---|---|------|
|   |   |   |   | 325 |   |   |   |   | 330 |   |   |   |   | 335 |   |      |
| ATT | GTG | GCC | CCA | CCA | GGC | TAC | CAG | GCC | TTC | TAC | TGC | CAT | GGG | GAC | TGC | 1056 |
| Ile | Val | Ala | Pro | Pro | Gly | Tyr | Gln | Ala | Phe | Tyr | Cys | His | Gly | Asp | Cys |      |
|   |   |   | 340 |   |   |   | 345 |   |   |   |   |   | 350 |   |   |      |
| CCC | TTT | CCA | CTG | GCT | GAC | CAC | CTC | AAC | TCA | ACC | AAC | CAT | GCC | ATT | GTG | 1104 |
| Pro | Phe | Pro | Leu | Ala | Asp | His | Leu | Asn | Ser | Thr | Asn | His | Ala | Ile | Val |      |
|   |   | 355 |   |   |   |   | 360 |   |   |   |   | 365 |   |   |   |      |
| CAG | ACC | CTG | GTC | AAT | TCT | GTC | AAT | TCC | AGT | ATC | CCC | AAA | GCC | TGT | TGT | 1152 |
| Gln | Thr | Leu | Val | Asn | Ser | Val | Asn | Ser | Ser | Ile | Pro | Lys | Ala | Cys | Cys |      |
|   | 370 |   |   |   |   | 375 |   |   |   |   | 380 |   |   |   |   |      |
| GTG | CCC | ACT | GAA | CTG | AGT | GCC | ATC | TCC | ATG | CTG | TAC | CTG | GAT | GAG | TAT | 1200 |
| Val | Pro | Thr | Glu | Leu | Ser | Ala | Ile | Ser | Met | Leu | Tyr | Leu | Asp | Glu | Tyr |      |
| 385 |   |   |   |   | 390 |   |   |   |   | 395 |   |   |   |   | 400 |      |
| GAT | AAG | GTG | GTA | CTG | AAA | AAT | TAT | CAG | GAG | ATG | GTA | GTA | GAG | GGA | TGT | 1248 |
| Asp | Lys | Val | Val | Leu | Lys | Asn | Tyr | Gln | Glu | Met | Val | Val | Glu | Gly | Cys |      |
|   |   |   |   | 405 |   |   |   |   | 410 |   |   |   |   | 415 |   |      |
| GGG | TGC | CGC | TGAGATCAGG | CAGTCCTTGA | GGATAGACAG | ATATACACAC |   |   |   |   |   |   |   |   |   | 1297 |
| Gly | Cys | Arg |   |   |   |   |   |   |   |   |   |   |   |   |   |      |

```
ACACACACAC   ACACCACATA   CACCACACAC   ACACGTTCCC   ATCCACTCAC   CCACACACTA   1357

CACAGACTGC   TTCCTTATAG   ATGGACTTTT   ATTTAAAAAA   AAAAAAAAAA   AAATGGAAAA   1417

AATCCCTAAA   CATTCACCTT   GACCTTATTT   ATGACTTTAC   GTGCAAATGT   TTTGACCATA   1477

TTGATCATAT   ATTTTGACAA   AATATATTTA   TAACTACGTA   TTAAAAGAAA   AAAATAAAAT   1537

GAGTCATTAT   TTTAAAAAAA   AAAAAAAAAC   TCTAGAGTCG   ACGGAATTC                 1586
```

( 2 ) INFORMATION FOR SEQ ID NO:19:

( i ) SEQUENCE CHARACTERISTICS:
    ( A ) LENGTH: 419 amino acids
    ( B ) TYPE: amino acid
    ( D ) TOPOLOGY: linear ( i i ) MOLECULE TYPE: protein ( x i ) SEQUENCE DESCRIPTION: SEQ ID NO:19:

| Met | Lys | Ala | Ile | Phe | Val | Leu | Lys | Gly | Ser | Leu | Asp | Arg | Asp | Leu | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Arg | Leu | Asp | Leu | Asp | Val | Arg | Thr | Asp | His | Lys | Asp | Leu | Ser | Asp |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| His | Leu | Val | Leu | Val | Asp | Leu | Ala | Arg | Asn | Asp | Leu | Ala | Arg | Ile | Val |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Thr | Pro | Gly | Ser | Arg | Tyr | Val | Ala | Asp | Leu | Glu | Phe | Pro | Gly | Glu | Leu |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Leu | Arg | Asp | Phe | Glu | Ala | Thr | Leu | Leu | Gln | Met | Phe | Gly | Leu | Arg | Arg |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Arg | Pro | Gln | Pro | Ser | Lys | Ser | Ala | Val | Ile | Pro | Asp | Tyr | Met | Arg | Asp |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Leu | Tyr | Arg | Leu | Gln | Ser | Gly | Glu | Glu | Glu | Glu | Gln | Ile | His | Ser |
|-----|-----|-----|-----|-----|-----|-----|-----|-----|-----|-----|-----|-----|-----|-----|
|     |     |     | 100 |     |     |     |     | 105 |     |     |     |     | 110 |     |

| Thr | Gly | Leu | Glu | Tyr | Pro | Glu | Arg | Pro | Ala | Ser | Arg | Ala | Asn | Thr | Val |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Arg | Ser | Phe | His | His | Glu | Glu | His | Leu | Glu | Asn | Ile | Pro | Gly | Thr | Ser |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Glu | Asn | Ser | Ala | Phe | Arg | Phe | Leu | Phe | Asn | Leu | Ser | Ser | Ile | Pro | Glu |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Asn | Glu | Ala | Ile | Ser | Ser | Ala | Glu | Leu | Arg | Leu | Phe | Arg | Glu | Gln | Val |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Asp | Gln | Gly | Pro | Asp | Trp | Glu | Arg | Gly | Phe | His | Arg | Ile | Asn | Ile | Tyr |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

-continued

| | | | | | | | | | | | | | |
|---|---|---|---|---|---|---|---|---|---|---|---|---|---|
| Glu | Val | Met<br>195 | Lys | Pro | Pro | Ala<br>200 | Glu | Val | Val | Pro | Gly<br>205 | His | Leu | Ile | Thr |
| Arg | Leu<br>210 | Leu | Asp | Thr | Arg<br>215 | Leu | Val | His | His | Asn<br>220 | Val | Thr | Arg | Trp | Glu |
| Thr<br>225 | Phe | Asp | Val | Ser | Pro<br>230 | Ala | Val | Leu | Arg | Trp<br>235 | Thr | Arg | Glu | Lys | Gln<br>240 |
| Pro | Asn | Tyr | Gly | Leu<br>245 | Ala | Ile | Glu | Val | Thr<br>250 | His | Leu | His | Gln | Thr<br>255 | Arg |
| Thr | His | Gln | Gly<br>260 | Gln | His | Val | Arg | Ile<br>265 | Ser | Arg | Ser | Leu | Pro<br>270 | Gln | Gly |
| Ser | Gly | Asn<br>275 | Trp | Ala | Gln | Leu | Arg<br>280 | Pro | Leu | Leu | Val | Thr<br>285 | Phe | Gly | His |
| Asp | Gly<br>290 | Arg | Gly | His | Ala | Leu<br>295 | Thr | Arg | Arg | Arg | Arg<br>300 | Ala | Lys | Arg | Ser |
| Pro<br>305 | Lys | His | His | Ser | Gln<br>310 | Arg | Ala | Arg | Lys | Lys<br>315 | Asn | Lys | Asn | Cys | Arg<br>320 |
| Arg | His | Ser | Leu | Tyr<br>325 | Val | Asp | Phe | Ser | Asp<br>330 | Val | Gly | Trp | Asn | Asp<br>335 | Trp |
| Ile | Val | Ala | Pro<br>340 | Pro | Gly | Tyr | Gln | Ala<br>345 | Phe | Tyr | Cys | His | Gly<br>350 | Asp | Cys |
| Pro | Phe | Pro<br>355 | Leu | Ala | Asp | His | Leu<br>360 | Asn | Ser | Thr | Asn | His<br>365 | Ala | Ile | Val |
| Gln | Thr<br>370 | Leu | Val | Asn | Ser | Val<br>375 | Asn | Ser | Ser | Ile | Pro<br>380 | Lys | Ala | Cys | Cys |
| Val<br>385 | Pro | Thr | Glu | Leu | Ser<br>390 | Ala | Ile | Ser | Met | Leu<br>395 | Tyr | Leu | Asp | Glu | Tyr<br>400 |
| Asp | Lys | Val | Val | Leu<br>405 | Lys | Asn | Tyr | Gln | Glu<br>410 | Met | Val | Val | Glu | Gly<br>415 | Cys |
| Gly | Cys | Arg | | | | | | | | | | | | | |

( 2 ) INFORMATION FOR SEQ ID NO:20:

( i ) SEQUENCE CHARACTERISTICS:
        ( A ) LENGTH: 574 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: HOMO SAPIENS ( i x ) FEATURE:
        ( A ) NAME/KEY: CDS
        ( B ) LOCATION: 1..327
        ( D ) OTHER INFORMATION: /product="MATURE hCBMP3 (PARTIAL)"
        / note="THIS PARTIAL SEQUENCE OF THE MATURE HUMAN
        CBMP3 PROTEIN INCLUDE THE FIRST THREE CYSTEINES OF
        THE CONSERVED 7 CYSTEINE SKELETON."

( i x ) FEATURE:
        ( A ) NAME/KEY: intron
        ( B ) LOCATION: 328..574

( x i ) SEQUENCE DESCRIPTION: SEQ ID NO:20:

| CGA | GCT | TCT | AAA | ATA | GAA | TAC | CAG | TAT | AAA | AAG | GAT | GAG | GTG | TGG | GAG | 48 |
|---|---|---|---|---|---|---|---|---|---|---|---|---|---|---|---|---|
| Arg<br>1 | Ala | Ser | Lys | Ile<br>5 | Glu | Tyr | Gln | Tyr | Lys<br>10 | Lys | Asp | Glu | Val | Trp<br>15 | Glu | |
| GAG | AGA | AAG | CCT | TAC | AAG | ACC | CTT | CAG | GGC | TCA | GGC | CCT | GAA | AAG | AGT | 96 |
| Glu | Arg | Lys | Pro<br>20 | Tyr | Lys | Thr | Leu | Gln<br>25 | Gly | Ser | Gly | Pro | Glu<br>30 | Lys | Ser | |
| AAG | AAT | AAA | AAG | AAA | CAG | AGA | AAG | GGG | CCT | CAT | CGG | AAG | AGC | CAG | ACG | 144 |
| Lys | Asn | Lys | Lys | Lys<br>35 | Gln | Arg | Lys | Gly<br>40 | Pro | His | Arg | Lys | Ser<br>45 | Gln | Thr | |

|  |  |  |  |  |  |  |  |  |  |  |  |  |  |  |  |
|---|---|---|---|---|---|---|---|---|---|---|---|---|---|---|---|
|  | 35 |  |  |  | 40 |  |  |  |  | 45 |  |  |  |  |  |
| CTC | CAA | TTT | GAT | GAG | CAG | ACC | CTG | AAA | AAG | GCA | AGG | AGA | AAG | CAG | TGG | 192 |
| Leu | Gln | Phe | Asp | Glu | Gln | Thr | Leu | Lys | Lys | Ala | Arg | Arg | Lys | Gln | Trp |  |
|  | 50 |  |  |  | 55 |  |  |  |  | 60 |  |  |  |  |  |  |
| ATT | GAA | CCT | CGG | AAT | TGC | GCC | AGG | AGA | TAC | CTC | AAG | GTA | GAC | TTT | GCA | 240 |
| Ile | Glu | Pro | Arg | Asn | Cys | Ala | Arg | Arg | Tyr | Leu | Lys | Val | Asp | Phe | Ala |  |
| 65 |  |  |  |  | 70 |  |  |  |  | 75 |  |  |  |  | 80 |  |
| GAT | ATT | GGC | TGG | AGT | GAA | TGG | ATT | ATC | TCC | CCC | AAG | TCC | TTT | GAT | GCC | 288 |
| Asp | Ile | Gly | Trp | Ser | Glu | Trp | Ile | Ile | Ser | Pro | Lys | Ser | Phe | Asp | Ala |  |
|  |  |  |  | 85 |  |  |  |  | 90 |  |  |  |  | 95 |  |  |
| TAT | TAT | TGC | TCT | GGA | GCA | TGC | CAG | TTC | CCC | ATG | CCA | AAG | GTAGCCATTG |  |  | 337 |
| Tyr | Tyr | Cys | Ser | Gly | Ala | Cys | Gln | Phe | Pro | Met | Pro | Lys |  |  |  |  |
|  |  |  | 100 |  |  |  |  | 105 |  |  |  |  |  |  |  |  |

```
TTCTCTGTCC   TGTACTTACT   TCCTATTTCC   ATTAGTAGAA   AGACACATTG   ACTAAGTTAG    397

TGTGCATATA   GGGGGTTTGT   GTAAGTGTTT   GTGTTTCCAT   TTGCAAAATC   CATTGGGACC    457

CTTATTTACT   ACATTCTAAA   CCATAATAGG   TAATATGGTT   ATTCTTGGTT   TCTCTTTAAT    517

GGTTGTTAAA   GTCATATGAA   GTCAGTATTG   GTATAAAGAA   GGATATGAGA   AAAAAAA      574
```

( 2 ) INFORMATION FOR SEQ ID NO:21:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

| Arg | Ala | Ser | Lys | Ile | Glu | Tyr | Gln | Tyr | Lys | Lys | Asp | Glu | Val | Trp | Glu |
|---|---|---|---|---|---|---|---|---|---|---|---|---|---|---|---|
| 1 |  |  |  | 5 |  |  |  |  | 10 |  |  |  |  | 15 |  |
| Glu | Arg | Lys | Pro | Tyr | Lys | Thr | Leu | Gln | Gly | Ser | Gly | Pro | Glu | Lys | Ser |
|  |  |  | 20 |  |  |  |  | 25 |  |  |  | 30 |  |  |  |
| Lys | Asn | Lys | Lys | Lys | Gln | Arg | Lys | Gly | Pro | His | Arg | Lys | Ser | Gln | Thr |
|  |  | 35 |  |  |  |  | 40 |  |  |  |  | 45 |  |  |  |
| Leu | Gln | Phe | Asp | Glu | Gln | Thr | Leu | Lys | Lys | Ala | Arg | Arg | Lys | Gln | Trp |
|  | 50 |  |  |  |  | 55 |  |  |  |  | 60 |  |  |  |  |
| Ile | Glu | Pro | Arg | Asn | Cys | Ala | Arg | Arg | Tyr | Leu | Lys | Val | Asp | Phe | Ala |
| 65 |  |  |  |  | 70 |  |  |  |  | 75 |  |  |  |  | 80 |
| Asp | Ile | Gly | Trp | Ser | Glu | Trp | Ile | Ile | Ser | Pro | Lys | Ser | Phe | Asp | Ala |
|  |  |  |  | 85 |  |  |  |  | 90 |  |  |  |  | 95 |  |
| Tyr | Tyr | Cys | Ser | Gly | Ala | Cys | Gln | Phe | Pro | Met | Pro | Lys |  |  |  |
|  |  |  | 100 |  |  |  |  | 105 |  |  |  |  |  |  |  |

( 2 ) INFORMATION FOR SEQ ID NO:22:

( i ) SEQUENCE CHARACTERISTICS:
        ( A ) LENGTH: 779 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: MURINE ( i x ) FEATURE:
        ( A ) NAME/KEY: CDS
        ( B ) LOCATION: 1..549
        ( D ) OTHER INFORMATION: /product="MATURE mBMP3"

( x i ) SEQUENCE DESCRIPTION: SEQ ID NO:22:

| TCT | ACG | GGG | GTC | CTT | CTG | CCC | TTG | CAG | AAC | AAT | GAG | CTA | CCT | GGG | GCA | 48 |
|---|---|---|---|---|---|---|---|---|---|---|---|---|---|---|---|---|
| Ser | Thr | Gly | Val | Leu | Leu | Pro | Leu | Gln | Asn | Asn | Glu | Leu | Pro | Gly | Ala |  |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| 1 | | | | 5 | | | | | | 10 | | | | | 15 | |
| GAG | TAT | CAG | TAC | AAG | GAG | GAG | GGA | GCG | TGG | GAG | GAG | AGA | AAG | CCT | TAT | 96 |
| Glu | Tyr | Gln | Tyr | Lys | Glu | Glu | Gly | Ala | Trp | Glu | Glu | Arg | Lys | Pro | Tyr | |
| | | | 20 | | | | | 25 | | | | | 30 | | | |
| AAG | AGC | CTT | CAG | ACT | CAG | CCC | CCT | GAG | AAG | AGT | AGG | AAC | AAA | AAG | AAA | 144 |
| Lys | Ser | Leu | Gln | Thr | Gln | Pro | Pro | Glu | Lys | Ser | Arg | Asn | Lys | Lys | Lys | |
| | | 35 | | | | | 40 | | | | | 45 | | | | |
| CAG | AGG | AAA | GGG | TCC | CAT | CAG | AAG | GGA | CAG | ACG | CTG | CAA | TTT | GAT | GAG | 192 |
| Gln | Arg | Lys | Gly | Ser | His | Gln | Lys | Gly | Gln | Thr | Leu | Gln | Phe | Asp | Glu | |
| | 50 | | | | | 55 | | | | | 60 | | | | | |
| CAG | ACC | CTG | AAG | AAG | GCA | AGG | CGA | AAG | CAG | TGG | GTC | GAA | CCT | CGG | AAC | 240 |
| Gln | Thr | Leu | Lys | Lys | Ala | Arg | Arg | Lys | Gln | Trp | Val | Glu | Pro | Arg | Asn | |
| 65 | | | | | 70 | | | | | 75 | | | | | 80 | |
| TGT | GCC | AGG | AGG | TAC | CTT | AAA | GTG | GAC | TTT | GCT | GAT | ATC | GGC | TGG | AGC | 288 |
| Cys | Ala | Arg | Arg | Tyr | Leu | Lys | Val | Asp | Phe | Ala | Asp | Ile | Gly | Trp | Ser | |
| | | | | 85 | | | | | 90 | | | | | 95 | | |
| GAA | TGG | ATT | ATC | TCT | CCC | AAG | TCA | TTT | GAT | GCT | TTC | TAC | TGC | TCT | GGA | 336 |
| Glu | Trp | Ile | Ile | Ser | Pro | Lys | Ser | Phe | Asp | Ala | Phe | Tyr | Cys | Ser | Gly | |
| | | | 100 | | | | | 105 | | | | | 110 | | | |
| GCC | TGC | CAG | TTC | CCC | ATG | CCA | AAG | TCT | TTG | AAA | CCA | TCA | AAT | CAC | GCC | 384 |
| Ala | Cys | Gln | Phe | Pro | Met | Pro | Lys | Ser | Leu | Lys | Pro | Ser | Asn | His | Ala | |
| | | 115 | | | | | 120 | | | | | 125 | | | | |
| ACC | ATC | CAG | AGC | ATA | GTG | CGA | GCG | GTG | GGG | GTC | GTC | TCC | GGG | ATT | CCC | 432 |
| Thr | Ile | Gln | Ser | Ile | Val | Arg | Ala | Val | Gly | Val | Val | Ser | Gly | Ile | Pro | |
| | 130 | | | | | 135 | | | | | 140 | | | | | |
| GAG | CCT | TGC | TGT | GTG | CCG | GAA | AAG | ATG | TCC | TCA | CTC | AGC | ATC | TTG | TTC | 480 |
| Glu | Pro | Cys | Cys | Val | Pro | Glu | Lys | Met | Ser | Ser | Leu | Ser | Ile | Leu | Phe | |
| 145 | | | | | 150 | | | | | 155 | | | | | 160 | |
| TTT | GAT | GAA | AAC | AAG | AAT | GTA | GTG | CTC | AAA | GTC | TAC | CCT | AAC | ATG | ACA | 528 |
| Phe | Asp | Glu | Asn | Lys | Asn | Val | Val | Leu | Lys | Val | Tyr | Pro | Asn | Met | Thr | |
| | | | | 165 | | | | | 170 | | | | | 175 | | |
| GTC | GAC | TCC | TGT | GCT | TGT | AGA | | | | | | | | | | 579 |
| Val | Asp | Ser | Cys | Ala | Cys | Arg | | | | | | | | | | |
| | | | 180 | | | | | | | | | | | | | |

TAACCTCTTC AAGAACTCAC AGATGCTCCA

TCCAATCACG AGTTGGGTTT TATGGGCTTT TTTTTTTTTT TTTTGTCCC AAAAGATGTT 639

TGATAGCAGG AAGAAAATGA ACAAATAGAT TGAAGGTTTC CACCAAACAA AACCGGACTG 699

TATTTTCCTT CGAATGTAAC TAAAAGTGAG ATTTAGTAA ATGTGGATCT CTAAAAAAAA 759

AAAAAAAAAA AAAAAAAAA 779

(2) INFORMATION FOR SEQ ID NO:23:

(i) SEQUENCE CHARACTERISTICS:
        (A) LENGTH: 183 amino acids
        (B) TYPE: amino acid
        (D) TOPOLOGY: linear (ii) MOLECULE TYPE: protein (xi) SEQUENCE DESCRIPTION: SEQ ID NO:23:

|     |     |     |     |     |     |     |     |     |     |     |     |     |     |     |     |
| --- | --- | --- | --- | --- | --- | --- | --- | --- | --- | --- | --- | --- | --- | --- | --- |
| Ser | Thr | Gly | Val | Leu | Leu | Pro | Leu | Gln | Asn | Asn | Glu | Leu | Pro | Gly | Ala |
| 1 | | | | 5 | | | | | 10 | | | | | 15 | |
| Glu | Tyr | Gln | Tyr | Lys | Glu | Glu | Gly | Ala | Trp | Glu | Glu | Arg | Lys | Pro | Tyr |
| | | | 20 | | | | | 25 | | | | | 30 | | |
| Lys | Ser | Leu | Gln | Thr | Gln | Pro | Pro | Glu | Lys | Ser | Arg | Asn | Lys | Lys | Lys |
| | | 35 | | | | | 40 | | | | | 45 | | | |
| Gln | Arg | Lys | Gly | Ser | His | Gln | Lys | Gly | Gln | Thr | Leu | Gln | Phe | Asp | Glu |
| | 50 | | | | | 55 | | | | | 60 | | | | |
| Gln | Thr | Leu | Lys | Lys | Ala | Arg | Arg | Lys | Gln | Trp | Val | Glu | Pro | Arg | Asn |
| 65 | | | | | 70 | | | | | 75 | | | | | 80 |
| Cys | Ala | Arg | Arg | Tyr | Leu | Lys | Val | Asp | Phe | Ala | Asp | Ile | Gly | Trp | Ser |

|  | 85 |  |  |  |  | 90 |  |  |  |  | 95 |  |  |
|---|---|---|---|---|---|---|---|---|---|---|---|---|---|

Glu Trp Ile Ile Ser Pro Lys Ser Phe Asp Ala Phe Tyr Cys Ser Gly
                100                 105             110

Ala Cys Gln Phe Pro Met Pro Lys Ser Leu Lys Pro Ser Asn His Ala
        115                 120                 125

Thr Ile Gln Ser Ile Val Arg Ala Val Gly Val Val Ser Gly Ile Pro
    130             135                 140

Glu Pro Cys Cys Val Pro Glu Lys Met Ser Ser Leu Ser Ile Leu Phe
145             150                 155                 160

Phe Asp Glu Asn Lys Asn Val Val Leu Lys Val Tyr Pro Asn Met Thr
                165                 170                 175

Val Asp Ser Cys Ala Cys Arg
            180

(2) INFORMATION FOR SEQ ID NO:24:

(i) SEQUENCE CHARACTERISTICS:
　　　　　　(A) LENGTH: 1873 base pairs
　　　　　　(B) TYPE: nucleic acid
　　　　　　(C) STRANDEDNESS: single
　　　　　　(D) TOPOLOGY: linear (ii) MOLECULE TYPE: cDNA (iii) HYPOTHETICAL: NO (iv) ANTI-SENSE: NO (vi) ORIGINAL SOURCE:
　　　　　　(A) ORGANISM: MURIDAE
　　　　　　(F) TISSUE TYPE: EMBRYO (ix) FEATURE:
　　　　　　(A) NAME/KEY: CDS
　　　　　　(B) LOCATION: 104..1393
　　　　　　(D) OTHER INFORMATION: /function="OSTEOGENIC PROTEIN"
　　　　　　　　/ product="MOP1"
　　　　　　　　/ note="MOP1 (CDNA)"

(xi) SEQUENCE DESCRIPTION: SEQ ID NO:24:

```
CTGCAGCAAG TGACCTCGGG TCGTGGACCG CTGCCCTGCC CCCTCCGCTG CCACCTGGGG        60

CGGCGCGGGC CCGGTGCCCC GGATCGCGCG TAGAGCCGGC GCG ATG CAC GTG CGC        115
                                              Met His Val Arg
                                                1
```

TCG CTG CGC GCT GCG GCG CCA CAC AGC TTC GTG GCG CTC TGG GCG CCT        163
Ser Leu Arg Ala Ala Ala Pro His Ser Phe Val Ala Leu Trp Ala Pro
    5               10                  15                  20

CTG TTC TTG CTG CGC TCC GCC CTG GCC GAT TTC AGC CTG GAC AAC GAG        211
Leu Phe Leu Leu Arg Ser Ala Leu Ala Asp Phe Ser Leu Asp Asn Glu
            25                  30                  35

GTG CAC TCC AGC TTC ATC CAC CGG CGC CTC CGC AGC CAG GAG CGG CGG        259
Val His Ser Ser Phe Ile His Arg Arg Leu Arg Ser Gln Glu Arg Arg
        40                  45                  50

GAG ATG CAG CGG GAG ATC CTG TCC ATC TTA GGG TTG CCC CAT CGC CCG        307
Glu Met Gln Arg Glu Ile Leu Ser Ile Leu Gly Leu Pro His Arg Pro
    55                  60                  65

CGC CCG CAC CTC CAG GGA AAG CAT AAT TCG GCG CCC ATG TTC ATG TTG        355
Arg Pro His Leu Gln Gly Lys His Asn Ser Ala Pro Met Phe Met Leu
70                  75                  80

GAC CTG TAC AAC GCC ATG GCG GTG GAG GAG AGC GGG CCG GAC GGA CAG        403
Asp Leu Tyr Asn Ala Met Ala Val Glu Glu Ser Gly Pro Asp Gly Gln
85                  90                  95                  100

GGC TTC TCC TAC CCC TAC AAG GCC GTC TTC AGT ACC CAG GGC CCC CCT        451
Gly Phe Ser Tyr Pro Tyr Lys Ala Val Phe Ser Thr Gln Gly Pro Pro
            105                 110                 115

```
TTA GCC AGC CTG CAG GAC AGC CAT TTC CTC ACT GAC GCC GAC ATG GTC       499
Leu Ala Ser Leu Gln Asp Ser His Phe Leu Thr Asp Ala Asp Met Val
            120                 125                 130

ATG AGC TTC GTC AAC CTA GTG GAA CAT GAC AAA GAA TTC TTC CAC CCT       547
Met Ser Phe Val Asn Leu Val Glu His Asp Lys Glu Phe Phe His Pro
        135                 140                 145

CGA TAC CAC CAT CGG GAG TTC CGG TTT GAT CTT TCC AAG ATC CCC GAG       595
Arg Tyr His His Arg Glu Phe Arg Phe Asp Leu Ser Lys Ile Pro Glu
    150                 155                 160

GGC GAA GCG GTG ACC GCA GCC GAA TTC AGG ATC TAT AAG GAC TAC ATC       643
Gly Glu Ala Val Thr Ala Ala Glu Phe Arg Ile Tyr Lys Asp Tyr Ile
165                 170                 175                 180

CGG GAG CGA TTT GAC AAC GAG ACC TTC CAG ATC ACA GTC TAT CAG TGG       691
Arg Glu Arg Phe Asp Asn Glu Thr Phe Gln Ile Thr Val Tyr Gln Trp
                185                 190                 195

CTC CAG GAG CAC TCA GGC AGG GAG TCG GAC CTC TTC TTG CTG GAC AGC       739
Leu Gln Glu His Ser Gly Arg Glu Ser Asp Leu Phe Leu Leu Asp Ser
            200                 205                 210

CGC ACC ATC TGG GCT TCT GAG GAG GGC TGG TTG GTG TTT GAT ATC ACA       787
Arg Thr Ile Trp Ala Ser Glu Glu Gly Trp Leu Val Phe Asp Ile Thr
        215                 220                 225

GCC ACC AGC AAC CAC TGG GTG GTC AAC CCT CGG CAC AAC CTG GGC TTA       835
Ala Thr Ser Asn His Trp Val Val Asn Pro Arg His Asn Leu Gly Leu
    230                 235                 240

CAG CTC TCT GTG GAG ACC CTG GAT GGG CAG AGC ATC AAC CCC AAG TTG       883
Gln Leu Ser Val Glu Thr Leu Asp Gly Gln Ser Ile Asn Pro Lys Leu
245                 250                 255                 260

GCA GGC CTG ATT GGA CGG CAT GGA CCC CAG AAC AAG CAA CCC TTC ATG       931
Ala Gly Leu Ile Gly Arg His Gly Pro Gln Asn Lys Gln Pro Phe Met
                265                 270                 275

GTG GCC TTC TTC AAG GCC ACG GAA GTC CAT CTC CGT AGT ATC CGG TCC       979
Val Ala Phe Phe Lys Ala Thr Glu Val His Leu Arg Ser Ile Arg Ser
            280                 285                 290

ACG GGG GGC AAG CAG CGC AGC CAG AAT CGC TCC AAG ACG CCA AAG AAC      1027
Thr Gly Gly Lys Gln Arg Ser Gln Asn Arg Ser Lys Thr Pro Lys Asn
        295                 300                 305

CAA GAG GCC CTG AGG ATG GCC AGT GTG GCA GAA AAC AGC AGC AGT GAC      1075
Gln Glu Ala Leu Arg Met Ala Ser Val Ala Glu Asn Ser Ser Ser Asp
    310                 315                 320

CAG AGG CAG GCC TGC AAG AAA CAT GAG CTG TAC GTC AGC TTC CGA GAC      1123
Gln Arg Gln Ala Cys Lys Lys His Glu Leu Tyr Val Ser Phe Arg Asp
325                 330                 335                 340

CTT GGC TGG CAG GAC TGG ATC ATT GCA CCT GAA GGC TAT GCT GCC TAC      1171
Leu Gly Trp Gln Asp Trp Ile Ile Ala Pro Glu Gly Tyr Ala Ala Tyr
                345                 350                 355

TAC TGT GAG GGA GAG TGC GCC TTC CCT CTG AAC TCC TAC ATG AAC GCC      1219
Tyr Cys Glu Gly Glu Cys Ala Phe Pro Leu Asn Ser Tyr Met Asn Ala
            360                 365                 370

ACC AAC CAC GCC ATC GTC CAG ACA CTG GTT CAC TTC ATC AAC CCA GAC      1267
Thr Asn His Ala Ile Val Gln Thr Leu Val His Phe Ile Asn Pro Asp
        375                 380                 385

ACA GTA CCC AAG CCC TGC TGT GCG CCC ACC CAG CTC AAC GCC ATC TCT      1315
Thr Val Pro Lys Pro Cys Cys Ala Pro Thr Gln Leu Asn Ala Ile Ser
    390                 395                 400

GTC CTC TAC TTC GAC GAC AGC TCT AAT GTC GAC CTG AAG AAG TAC AGA      1363
Val Leu Tyr Phe Asp Asp Ser Ser Asn Val Asp Leu Lys Lys Tyr Arg
405                 410                 415                 420

AAC ATG GTG GTC CGG GCC TGT GGC TGC CAC TAGCTCTTCC TGAGACCCTG        1413
Asn Met Val Val Arg Ala Cys Gly Cys His
                425                 430

ACCTTTGCGG GGCCACACCT TTCCAAATCT TCGATGTCTC ACCATCTAAG TCTCTCACTG    1473
```

| | | | | | | |
|---|---|---|---|---|---|---|
| CCCACCTTGG | CGAGGAGAAC | AGACCAACCT | CTCCTGAGCC | TTCCCTCACC | TCCCAACCGG | 1533 |
| AAGCATGTAA | GGGTTCCAGA | AACCTGAGCG | TGCAGCAGCT | GATGAGCGCC | CTTTCCTTCT | 1593 |
| GGCACGTGAC | GGACAAGATC | CTACCAGCTA | CCACAGCAAA | CGCCTAAGAG | CAGGAAAAAT | 1653 |
| GTCTGCCAGG | AAAGTGTCCA | GTGTCCACAT | GGCCCCTGGC | GCTCTGAGTC | TTTGAGGAGT | 1713 |
| AATCGCAAGC | CTCGTTCAGC | TGCAGCAGAA | GGAAGGGCTT | AGCCAGGGTG | GGCGCTGGCG | 1773 |
| TCTGTGTTGA | AGGGAAACCA | AGCAGAAGCC | ACTGTAATGA | TATGTCACAA | TAAAACCCAT | 1833 |
| GAATGAAAAA | AAAAAAAAAA | AAAAAAAAAA | AAAAGAATTC | | | 1873 |

(2) INFORMATION FOR SEQ ID NO:25:

(i) SEQUENCE CHARACTERISTICS:
        (A) LENGTH: 430 amino acids
        (B) TYPE: amino acid
        (D) TOPOLOGY: linear (ii) MOLECULE TYPE: protein (xi) SEQUENCE DESCRIPTION: SEQ ID NO:25:

| Met | His | Val | Arg | Ser | Leu | Arg | Ala | Ala | Ala | Pro | His | Ser | Phe | Val | Ala |
|---|---|---|---|---|---|---|---|---|---|---|---|---|---|---|---|
| 1 | | | | 5 | | | | | 10 | | | | | 15 | |
| Leu | Trp | Ala | Pro | Leu | Phe | Leu | Leu | Arg | Ser | Ala | Leu | Ala | Asp | Phe | Ser |
| | | | 20 | | | | | 25 | | | | | 30 | | |
| Leu | Asp | Asn | Glu | Val | His | Ser | Ser | Phe | Ile | His | Arg | Arg | Leu | Arg | Ser |
| | | 35 | | | | | 40 | | | | | 45 | | | |
| Gln | Glu | Arg | Arg | Glu | Met | Gln | Arg | Glu | Ile | Leu | Ser | Ile | Leu | Gly | Leu |
| | 50 | | | | | 55 | | | | | 60 | | | | |
| Pro | His | Arg | Pro | Arg | Pro | His | Leu | Gln | Gly | Lys | His | Asn | Ser | Ala | Pro |
| 65 | | | | | 70 | | | | 75 | | | | | 80 | |
| Met | Phe | Met | Leu | Asp | Leu | Tyr | Asn | Ala | Met | Ala | Val | Glu | Glu | Ser | Gly |
| | | | | 85 | | | | | 90 | | | | | 95 | |
| Pro | Asp | Gly | Gln | Gly | Phe | Ser | Tyr | Pro | Tyr | Lys | Ala | Val | Phe | Ser | Thr |
| | | | | 100 | | | | 105 | | | | | 110 | | |
| Gln | Gly | Pro | Pro | Leu | Ala | Ser | Leu | Gln | Asp | Ser | His | Phe | Leu | Thr | Asp |
| | | | 115 | | | | | 120 | | | | | 125 | | |
| Ala | Asp | Met | Val | Met | Ser | Phe | Val | Asn | Leu | Val | Glu | His | Asp | Lys | Glu |
| | 130 | | | | | 135 | | | | | 140 | | | | |
| Phe | Phe | His | Pro | Arg | Tyr | His | His | Arg | Glu | Phe | Arg | Phe | Asp | Leu | Ser |
| 145 | | | | | 150 | | | | | 155 | | | | | 160 |
| Lys | Ile | Pro | Glu | Gly | Glu | Ala | Val | Thr | Ala | Ala | Glu | Phe | Arg | Ile | Tyr |
| | | | | 165 | | | | | 170 | | | | | 175 | |
| Lys | Asp | Tyr | Ile | Arg | Glu | Arg | Phe | Asp | Asn | Glu | Thr | Phe | Gln | Ile | Thr |
| | | | 180 | | | | | 185 | | | | | 190 | | |
| Val | Tyr | Gln | Trp | Leu | Gln | Glu | His | Ser | Gly | Arg | Glu | Ser | Asp | Leu | Phe |
| | | 195 | | | | | 200 | | | | | 205 | | | |
| Leu | Leu | Asp | Ser | Arg | Thr | Ile | Trp | Ala | Ser | Glu | Glu | Gly | Trp | Leu | Val |
| | 210 | | | | | 215 | | | | | 220 | | | | |
| Phe | Asp | Ile | Thr | Ala | Thr | Ser | Asn | His | Trp | Val | Val | Asn | Pro | Arg | His |
| 225 | | | | | 230 | | | | | 235 | | | | | 240 |
| Asn | Leu | Gly | Leu | Gln | Leu | Ser | Val | Glu | Thr | Leu | Asp | Gly | Gln | Ser | Ile |
| | | | | 245 | | | | | 250 | | | | | 255 | |
| Asn | Pro | Lys | Leu | Ala | Gly | Leu | Ile | Gly | Arg | His | Gly | Pro | Gln | Asn | Lys |
| | | | 260 | | | | | 265 | | | | | 270 | | |
| Gln | Pro | Phe | Met | Val | Ala | Phe | Phe | Lys | Ala | Thr | Glu | Val | His | Leu | Arg |
| | | 275 | | | | | 280 | | | | | 285 | | | |
| Ser | Ile | Arg | Ser | Thr | Gly | Gly | Lys | Gln | Arg | Ser | Gln | Asn | Arg | Ser | Lys |

|  | 290 |  |  |  | 295 |  |  |  | 300 |  |  |
|---|---|---|---|---|---|---|---|---|---|---|---|

Thr Pro Lys Asn Gln Glu Ala Leu Arg Met Ala Ser Val Ala Glu Asn
305                     310                 315                     320

Ser Ser Ser Asp Gln Arg Gln Ala Cys Lys Lys His Glu Leu Tyr Val
                325                 330                     335

Ser Phe Arg Asp Leu Gly Trp Gln Asp Trp Ile Ile Ala Pro Glu Gly
            340                 345                 350

Tyr Ala Ala Tyr Tyr Cys Glu Gly Glu Cys Ala Phe Pro Leu Asn Ser
        355                 360                 365

Tyr Met Asn Ala Thr Asn His Ala Ile Val Gln Thr Leu Val His Phe
370                 375                 380

Ile Asn Pro Asp Thr Val Pro Lys Pro Cys Cys Ala Pro Thr Gln Leu
385             390                 395                     400

Asn Ala Ile Ser Val Leu Tyr Phe Asp Asp Ser Ser Asn Val Asp Leu
            405                 410                 415

Lys Lys Tyr Arg Asn Met Val Val Arg Ala Cys Gly Cys His
        420                 425             430

( 2 ) INFORMATION FOR SEQ ID NO:26:

( i ) SEQUENCE CHARACTERISTICS:
( A ) LENGTH: 1929 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: MURIDAE
( F ) TISSUE TYPE: EMBRYO ( i x ) FEATURE:
( A ) NAME/KEY: CDS
( B ) LOCATION: 103..1293
( D ) OTHER INFORMATION: /function="osteogenic protein"
/ product="mop2"
/ note="mop2 cdna"

( x i ) SEQUENCE DESCRIPTION: SEQ ID NO:26:

GAATTCCGCT GCCAGGCACA GGTGCGCCGT CTGGTCCTCC CCGTCTGGCG TCAGCCGAGC        60

CCGACCAGCT ACCAGTGGAT GCGCGCCGGC TGAAAGTCCG AG ATG GCT ATG CGT        114
                                                  Met Ala Met Arg
                                                   1

CCC GGG CCA CTC TGG CTA TTG GGC CTT GCT CTG TGC GCG CTG GGA GGC        162
Pro Gly Pro Leu Trp Leu Leu Gly Leu Ala Leu Cys Ala Leu Gly Gly
 5              10                  15                      20

GGC CAC GGT CCC GGT CCC CCG CAC ACC TGT CCC CAG CGT CGC CTG GGA        210
Gly His Gly Pro Gly Pro Pro His Thr Cys Pro Gln Arg Arg Leu Gly
                25                  30                  35

GCG CGC GAC CGG GAC ATG CAG CGT GAA ATC CTG CCG GTG CTC GGG CTA        258
Ala Arg Asp Arg Asp Met Gln Arg Glu Ile Leu Pro Val Leu Gly Leu
            40                  45                  50

CCG GGA CGC CCC GAC CCC GTG CAC AAC CCG CCG CTG CCC GGC ACG CAG        306
Pro Gly Arg Pro Asp Pro Val His Asn Pro Pro Leu Pro Gly Thr Gln
        55                  60                  65

CGT GCG CCC CTC TTC ATG TTG GAC CTA TAC CAC GCC ATG ACC GAT GAC        354
Arg Ala Pro Leu Phe Met Leu Asp Leu Tyr His Ala Met Thr Asp Asp
    70                  75                  80

GAC GAC GGC GGG CCA CCA CAG GCT CAC TTA GGC CGT GCC GAC CTG GTC        402

| | | | | | | | | | | | | | | | | |
|---|---|---|---|---|---|---|---|---|---|---|---|---|---|---|---|---|
| | Asp<br>85 | Asp | Gly | Gly | Pro<br>90 | Pro | Gln | Ala | His | Leu<br>95 | Gly | Arg | Ala | Asp | Leu<br>100 | Val |
| ATG<br>Met | AGC<br>Ser | TTC<br>Phe | GTC<br>Val | AAC<br>Asn | ATG<br>Met<br>105 | GTG<br>Val | GAA<br>Glu | CGC<br>Arg | GAC<br>Asp | CGT<br>Arg<br>110 | ACC<br>Thr | CTG<br>Leu | GGC<br>Gly | TAC<br>Tyr | CAG<br>Gln<br>115 | 450 |
| GAG<br>Glu | CCA<br>Pro | CAC<br>His | TGG<br>Trp<br>120 | AAG<br>Lys | GAA<br>Glu | TTC<br>Phe | CAC<br>His | TTT<br>Phe<br>125 | GAC<br>Asp | CTA<br>Leu | ACC<br>Thr | CAG<br>Gln | ATC<br>Ile<br>130 | CCT<br>Pro | GCT<br>Ala | 498 |
| GGG<br>Gly | GAG<br>Glu | GCT<br>Ala<br>135 | GTC<br>Val | ACA<br>Thr | GCT<br>Ala | GCT<br>Ala | GAG<br>Glu<br>140 | TTC<br>Phe | CGG<br>Arg | ATC<br>Ile | TAC<br>Tyr | AAA<br>Lys<br>145 | GAA<br>Glu | CCC<br>Pro | AGC<br>Ser | 546 |
| ACC<br>Thr | CAC<br>His<br>150 | CCG<br>Pro | CTC<br>Leu | AAC<br>Asn | ACA<br>Thr | ACC<br>Thr<br>155 | CTC<br>Leu | CAC<br>His | ATC<br>Ile | AGC<br>Ser | ATG<br>Met<br>160 | TTC<br>Phe | GAA<br>Glu | GTG<br>Val | GTC<br>Val | 594 |
| CAA<br>Gln<br>165 | GAG<br>Glu | CAC<br>His | TCC<br>Ser | AAC<br>Asn | AGG<br>Arg<br>170 | GAG<br>Glu | TCT<br>Ser | GAC<br>Asp | TTG<br>Leu | TTC<br>Phe<br>175 | TTT<br>Phe | TTG<br>Leu | GAT<br>Asp | CTT<br>Leu | CAG<br>Gln<br>180 | 642 |
| ACG<br>Thr | CTC<br>Leu | CGA<br>Arg | TCT<br>Ser | GGG<br>Gly<br>185 | GAC<br>Asp | GAG<br>Glu | GGC<br>Gly | TGG<br>Trp | CTG<br>Leu<br>190 | GTG<br>Val | CTG<br>Leu | GAC<br>Asp | ATC<br>Ile | ACA<br>Thr<br>195 | GCA<br>Ala | 690 |
| GCC<br>Ala | AGT<br>Ser | GAC<br>Asp | CGA<br>Arg<br>200 | TGG<br>Trp | CTG<br>Leu | CTG<br>Leu | AAC<br>Asn | CAT<br>His<br>205 | CAC<br>His | AAG<br>Lys | GAC<br>Asp | CTG<br>Leu | GGA<br>Gly<br>210 | CTC<br>Leu | CGC<br>Arg | 738 |
| CTC<br>Leu | TAT<br>Tyr | GTG<br>Val<br>215 | GAA<br>Glu | ACC<br>Thr | GCG<br>Ala | GAT<br>Asp | GGG<br>Gly<br>220 | CAC<br>His | AGC<br>Ser | ATG<br>Met | GAT<br>Asp | CCT<br>Pro<br>225 | GGC<br>Gly | CTG<br>Leu | GCT<br>Ala | 786 |
| GGT<br>Gly | CTG<br>Leu | CTT<br>Leu<br>230 | GGA<br>Gly | CGA<br>Arg | CAA<br>Gln | GCA<br>Ala | CCA<br>Pro<br>235 | CGC<br>Arg | TCC<br>Ser | AGA<br>Arg | CAG<br>Gln | CCT<br>Pro<br>240 | TTC<br>Phe | ATG<br>Met | GTA<br>Val | 834 |
| ACC<br>Thr<br>245 | TTC<br>Phe | TTC<br>Phe | AGG<br>Arg | GCC<br>Ala | AGC<br>Ser<br>250 | CAG<br>Gln | AGT<br>Ser | CCT<br>Pro | GTG<br>Val | CGG<br>Arg<br>255 | GCC<br>Ala | CCT<br>Pro | CGG<br>Arg | GCA<br>Ala | GCG<br>Ala<br>260 | 882 |
| AGA<br>Arg | CCA<br>Pro | CTG<br>Leu | AAG<br>Lys | AGG<br>Arg<br>265 | AGG<br>Arg | CAG<br>Gln | CCA<br>Pro | AAG<br>Lys | AAA<br>Lys<br>270 | ACG<br>Thr | AAC<br>Asn | GAG<br>Glu | CTT<br>Leu | CCG<br>Pro<br>275 | CAC<br>His | 930 |
| CCC<br>Pro | AAC<br>Asn | AAA<br>Lys | CTC<br>Leu<br>280 | CCA<br>Pro | GGG<br>Gly | ATC<br>Ile | TTT<br>Phe | GAT<br>Asp<br>285 | GAT<br>Asp | GGC<br>Gly | CAC<br>His | GGT<br>Gly | TCC<br>Ser<br>290 | CGC<br>Arg | GGC<br>Gly | 978 |
| AGA<br>Arg | GAG<br>Glu | GTT<br>Val<br>295 | TGC<br>Cys | CGC<br>Arg | AGG<br>Arg | CAT<br>His | GAG<br>Glu<br>300 | CTC<br>Leu | TAC<br>Tyr | GTC<br>Val | AGA<br>Arg | TTC<br>Phe<br>305 | CGT<br>Arg | GAC<br>Asp | CTT<br>Leu | 1026 |
| GGC<br>Gly | TGG<br>Trp<br>310 | CTG<br>Leu | GAC<br>Asp | TGG<br>Trp | GTC<br>Val | ATC<br>Ile<br>315 | GCC<br>Ala | CCC<br>Pro | CAG<br>Gln | GGC<br>Gly | TAC<br>Tyr<br>320 | TCT<br>Ser | GCC<br>Ala | TAT<br>Tyr | TAC<br>Tyr | 1074 |
| TGT<br>Cys<br>325 | GAG<br>Glu | GGG<br>Gly | GAG<br>Glu | TGT<br>Cys | GCT<br>Ala<br>330 | TTC<br>Phe | CCA<br>Pro | CTG<br>Leu | GAC<br>Asp | TCC<br>Ser<br>335 | TGT<br>Cys | ATG<br>Met | AAC<br>Asn | GCC<br>Ala | ACC<br>Thr<br>340 | 1122 |
| AAC<br>Asn | CAT<br>His | GCC<br>Ala | ATC<br>Ile | TTG<br>Leu<br>345 | CAG<br>Gln | TCT<br>Ser | CTG<br>Leu | GTG<br>Val | CAC<br>His<br>350 | CTG<br>Leu | ATG<br>Met | AAG<br>Lys | CCA<br>Pro | GAT<br>Asp<br>355 | GTT<br>Val | 1170 |
| GTC<br>Val | CCC<br>Pro | AAG<br>Lys | GCA<br>Ala<br>360 | TGC<br>Cys | TGT<br>Cys | GCA<br>Ala | CCC<br>Pro | ACC<br>Thr<br>365 | AAA<br>Lys | CTG<br>Leu | AGT<br>Ser | GCC<br>Ala | ACC<br>Thr<br>370 | TCT<br>Ser | GTG<br>Val | 1218 |
| CTG<br>Leu | TAC<br>Tyr | TAT<br>Tyr<br>375 | GAC<br>Asp | AGC<br>Ser | AGC<br>Ser | AAC<br>Asn | AAT<br>Asn<br>380 | GTC<br>Val | ATC<br>Ile | CTG<br>Leu | CGT<br>Arg | AAA<br>Lys<br>385 | CAC<br>His | CGT<br>Arg | AAC<br>Asn | 1266 |
| ATG<br>Met | GTG<br>Val | GTC<br>Val<br>390 | AAG<br>Lys | GCC<br>Ala | TGT<br>Cys | GGC<br>Gly<br>395 | TGC<br>Cys | CAC<br>His | TGAGGCCCCG | CCCAGCATCC | | | | | | 1313 |

TGCTTCTACT ACCTTACCAT CTGGCCGGGC CCCTCTCCAG AGGCAGAAAC CCTTCTATGT       1373

TATCATAGCT CAGACAGGGG CAATGGGAGG CCCTTCACTT CCCCTGGCCA CTTCCTGCTA       1433

-continued

```
AAATTCTGGT CTTTCCCAGT TCCTCTGTCC TTCATGGGGT TTCGGGGCTA TCACCCCGCC    1493
CTCTCCATCC TCCTACCCCA AGCATAGACT GAATGCACAC AGCATCCCAG AGCTATGCTA    1553
ACTGAGAGGT CTGGGGTCAG CACTGAAGGC CCACATGAGG AAGACTGATC CTTGGCCATC    1613
CTCAGCCCAC AATGGCAAAT TCTGGATGGT CTAAGAAGCC CTGGAATTCT AAACTAGATG    1673
ATCTGGGCTC TCTGCACCAT TCATTGTGGC AGTTGGGACA TTTTTAGGTA TAACAGACAC    1733
ATACACTTAG ATCAATGCAT CGCTGTACTC CTTGAAATCA GAGCTAGCTT GTTAGAAAAA    1793
GAATCAGAGC CAGGTATAGC GGTGCATGTC ATTAATCCCA GCGCTAAAGA GACAGAGACA    1853
GGAGAATCTC TGTGAGTTCA AGGCCACATA GAAAGAGCCT GTCTCGGGAG CAGGAAAAAA    1913
AAAAAAAACG GAATTC                                                   1929
```

( 2 ) INFORMATION FOR SEQ ID NO:27:

( i ) SEQUENCE CHARACTERISTICS:
        ( A ) LENGTH: 397 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

```
Met Ala Met Arg Pro Gly Pro Leu Trp Leu Gly Leu Ala Leu Cys
 1               5                  10                  15

Ala Leu Gly Gly Gly His Gly Pro Gly Pro Pro His Thr Cys Pro Gln
            20                  25                  30

Arg Arg Leu Gly Ala Arg Asp Arg Asp Met Gln Arg Glu Ile Leu Pro
            35                  40                  45

Val Leu Gly Leu Pro Gly Arg Pro Asp Pro Val His Asn Pro Pro Leu
        50                  55                  60

Pro Gly Thr Gln Arg Ala Pro Leu Phe Met Leu Asp Leu Tyr His Ala
65                  70                  75                  80

Met Thr Asp Asp Asp Asp Gly Gly Pro Pro Gln Ala His Leu Gly Arg
                    85                  90                  95

Ala Asp Leu Val Met Ser Phe Val Asn Met Val Glu Arg Asp Arg Thr
                100                 105                 110

Leu Gly Tyr Gln Glu Pro His Trp Lys Glu Phe His Phe Asp Leu Thr
            115                 120                 125

Gln Ile Pro Ala Gly Glu Ala Val Thr Ala Ala Glu Phe Arg Ile Tyr
        130                 135                 140

Lys Glu Pro Ser Thr His Pro Leu Asn Thr Thr Leu His Ile Ser Met
145                 150                 155                 160

Phe Glu Val Val Gln Glu His Ser Asn Arg Glu Ser Asp Leu Phe Phe
                    165                 170                 175

Leu Asp Leu Gln Thr Leu Arg Ser Gly Asp Glu Gly Trp Leu Val Leu
                180                 185                 190

Asp Ile Thr Ala Ala Ser Asp Arg Trp Leu Leu Asn His His Lys Asp
            195                 200                 205

Leu Gly Leu Arg Leu Tyr Val Glu Thr Ala Asp Gly His Ser Met Asp
        210                 215                 220

Pro Gly Leu Ala Gly Leu Leu Gly Arg Gln Ala Pro Arg Ser Arg Gln
225                 230                 235                 240

Pro Phe Met Val Thr Phe Phe Arg Ala Ser Gln Ser Pro Val Arg Ala
                    245                 250                 255

Pro Arg Ala Ala Arg Pro Leu Lys Arg Arg Gln Pro Lys Lys Thr Asn
                260                 265                 270
```

```
Glu  Leu  Pro  His  Pro  Asn  Lys  Leu  Pro  Gly  Ile  Phe  Asp  Asp  Gly  His
          275                      280                     285

Gly  Ser  Arg  Gly  Arg  Glu  Val  Cys  Arg  Arg  His  Glu  Leu  Tyr  Val  Arg
          290                      295                     300

Phe  Arg  Asp  Leu  Gly  Trp  Leu  Asp  Trp  Val  Ile  Ala  Pro  Gln  Gly  Tyr
305                      310                     315                     320

Ser  Ala  Tyr  Tyr  Cys  Glu  Gly  Glu  Cys  Ala  Phe  Pro  Leu  Asp  Ser  Cys
                    325                     330                     335

Met  Asn  Ala  Thr  Asn  His  Ala  Ile  Leu  Gln  Ser  Leu  Val  His  Leu  Met
               340                     345                     350

Lys  Pro  Asp  Val  Val  Pro  Lys  Ala  Cys  Cys  Ala  Pro  Thr  Lys  Leu  Ser
          355                     360                     365

Ala  Thr  Ser  Val  Leu  Tyr  Tyr  Asp  Ser  Ser  Asn  Asn  Val  Ile  Leu  Arg
     370                     375                     380

Lys  His  Arg  Asn  Met  Val  Val  Lys  Ala  Cys  Gly  Cys  His
385                      390                     395
```

(2) INFORMATION FOR SEQ ID NO:28:

(i) SEQUENCE CHARACTERISTICS:
        (A) LENGTH: 1723 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens
        (F) TISSUE TYPE: HIPPOCAMPUS (ix) FEATURE:
        (A) NAME/KEY: CDS
        (B) LOCATION: 490..1696
        (D) OTHER INFORMATION: /function="OSTEOGENIC PROTEIN"
                      / product="hOP2-PP"
                      / note="hOP2 (cDNA)"

(xi) SEQUENCE DESCRIPTION: SEQ ID NO:28:

```
GGCGCCGGCA  GAGCAGGAGT  GGCTGGAGGA  GCTGTGGTTG  GAGCAGGAGG  TGGCACGGCA      60

GGGCTGGAGG  GCTCCCTATG  AGTGGCGGAG  ACGGCCCAGG  AGGCGCTGGA  GCAACAGCTC     120

CCACACCGCA  CCAAGCGGTG  GCTGCAGGAG  CTCGCCCATC  GCCCCTGCGC  TGCTCGGACC     180

GCGGCCACAG  CCGGACTGGC  GGGTACGGCG  GCGACAGAGG  CATTGGCCGA  GAGTCCCAGT     240

CCGCAGAGTA  GCCCCGGCCT  CGAGGCGGTG  GCGTCCCGGT  CCTCTCCGTC  CAGGAGCCAG     300

GACAGGTGTC  GCGCGGCGGG  GCTCCAGGGA  CCGCGCCTGA  GGCCGGCTGC  CCGCCCGTCC     360

CGCCCCGCCC  CGCCGCCCGC  CGCCCGCCGA  GCCCAGCCTC  CTTGCCGTCG  GGGCGTCCCC     420

AGGCCCTGGG  TCGGCCGCGG  AGCCGATGCG  CGCCCGCTGA  GCGCCCAGC   TGAGCGCCCC     480

CGGCCTGCC ATG ACC GCG CTC CCC GGC CCG CTC TGG CTC CTG GGC CTG              528
          Met Thr Ala Leu Pro Gly Pro Leu Trp Leu Leu Gly Leu
           1               5                   10

GCG CTA TGC GCG CTG GGC GGG GGC GGC CCC GGC CTG CGA CCC CCG CCC            576
Ala Leu Cys Ala Leu Gly Gly Gly Gly Pro Gly Leu Arg Pro Pro Pro
         15              20                  25

GGC TGT CCC CAG CGA CGT CTG GGC GCG CGC GAG CGC CGG GAC GTG CAG            624
Gly Cys Pro Gln Arg Arg Leu Gly Ala Arg Glu Arg Arg Asp Val Gln
 30              35                  40                      45

CGC GAG ATC CTG GCG GTG CTC GGG CTG CCT GGG CGG CCC CGG CCC CGC            672
Arg Glu Ile Leu Ala Val Leu Gly Leu Pro Gly Arg Pro Arg Pro Arg
                 50                  55                      60

GCG CCA CCC GCC GCC TCC CGG CTG CCC GCG TCC GCG CCG CTC TTC ATG            720
```

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| Ala   | Pro   | Pro   | Ala   | Ala   | Ser   | Arg   | Leu   | Pro   | Ala   | Ser   | Ala   | Pro   | Leu   | Phe   | Met   |      |
|       |       |       |       | 65    |       |       |       | 70    |       |       |       | 75    |       |       |       |      |
| CTG   | GAC   | CTG   | TAC   | CAC   | GCC   | ATG   | GCC   | GGC   | GAC   | GAC   | GAC   | GAG   | GAC   | GGC   | GCG   | 768  |
| Leu   | Asp   | Leu   | Tyr   | His   | Ala   | Met   | Ala   | Gly   | Asp   | Asp   | Asp   | Glu   | Asp   | Gly   | Ala   |      |
|       |       |       | 80    |       |       |       | 85    |       |       |       |       | 90    |       |       |       |      |
| CCC   | GCG   | GAG   | CGG   | CGC   | CTG   | GGC   | CGC   | GCC   | GAC   | CTG   | GTC   | ATG   | AGC   | TTC   | GTT   | 816  |
| Pro   | Ala   | Glu   | Arg   | Arg   | Leu   | Gly   | Arg   | Ala   | Asp   | Leu   | Val   | Met   | Ser   | Phe   | Val   |      |
|       | 95    |       |       |       |       | 100   |       |       |       |       | 105   |       |       |       |       |      |
| AAC   | ATG   | GTG   | GAG   | CGA   | GAC   | CGT   | GCC   | CTG   | GGC   | CAC   | CAG   | GAG   | CCC   | CAT   | TGG   | 864  |
| Asn   | Met   | Val   | Glu   | Arg   | Asp   | Arg   | Ala   | Leu   | Gly   | His   | Gln   | Glu   | Pro   | His   | Trp   |      |
| 110   |       |       |       |       | 115   |       |       |       |       | 120   |       |       |       |       | 125   |      |
| AAG   | GAG   | TTC   | CGC   | TTT   | GAC   | CTG   | ACC   | CAG   | ATC   | CCG   | GCT   | GGG   | GAG   | GCG   | GTC   | 912  |
| Lys   | Glu   | Phe   | Arg   | Phe   | Asp   | Leu   | Thr   | Gln   | Ile   | Pro   | Ala   | Gly   | Glu   | Ala   | Val   |      |
|       |       |       |       | 130   |       |       |       |       | 135   |       |       |       |       | 140   |       |      |
| ACA   | GCT   | GCG   | GAG   | TTC   | CGG   | ATT   | TAC   | AAG   | GTG   | CCC   | AGC   | ATC   | CAC   | CTG   | CTC   | 960  |
| Thr   | Ala   | Ala   | Glu   | Phe   | Arg   | Ile   | Tyr   | Lys   | Val   | Pro   | Ser   | Ile   | His   | Leu   | Leu   |      |
|       |       |       | 145   |       |       |       |       | 150   |       |       |       |       | 155   |       |       |      |
| AAC   | AGG   | ACC   | CTC   | CAC   | GTC   | AGC   | ATG   | TTC   | CAG   | GTG   | GTC   | CAG   | GAG   | CAG   | TCC   | 1008 |
| Asn   | Arg   | Thr   | Leu   | His   | Val   | Ser   | Met   | Phe   | Gln   | Val   | Val   | Gln   | Glu   | Gln   | Ser   |      |
|       |       | 160   |       |       |       |       | 165   |       |       |       |       | 170   |       |       |       |      |
| AAC   | AGG   | GAG   | TCT   | GAC   | TTG   | TTC   | TTT   | TTG   | GAT   | CTT   | CAG   | ACG   | CTC   | CGA   | GCT   | 1056 |
| Asn   | Arg   | Glu   | Ser   | Asp   | Leu   | Phe   | Phe   | Leu   | Asp   | Leu   | Gln   | Thr   | Leu   | Arg   | Ala   |      |
|       |       | 175   |       |       |       |       | 180   |       |       |       |       | 185   |       |       |       |      |
| GGA   | GAC   | GAG   | GGC   | TGG   | CTG   | GTG   | CTG   | GAT   | GTC   | ACA   | GCA   | GCC   | AGT   | GAC   | TGC   | 1104 |
| Gly   | Asp   | Glu   | Gly   | Trp   | Leu   | Val   | Leu   | Asp   | Val   | Thr   | Ala   | Ala   | Ser   | Asp   | Cys   |      |
| 190   |       |       |       |       | 195   |       |       |       |       | 200   |       |       |       |       | 205   |      |
| TGG   | TTG   | CTG   | AAG   | CGT   | CAC   | AAG   | GAC   | CTG   | GGA   | CTC   | CGC   | CTC   | TAT   | GTG   | GAG   | 1152 |
| Trp   | Leu   | Leu   | Lys   | Arg   | His   | Lys   | Asp   | Leu   | Gly   | Leu   | Arg   | Leu   | Tyr   | Val   | Glu   |      |
|       |       |       |       | 210   |       |       |       |       | 215   |       |       |       |       | 220   |       |      |
| ACT   | GAG   | GAC   | GGG   | CAC   | AGC   | GTG   | GAT   | CCT   | GGC   | CTG   | GCC   | GGC   | CTG   | CTG   | GGT   | 1200 |
| Thr   | Glu   | Asp   | Gly   | His   | Ser   | Val   | Asp   | Pro   | Gly   | Leu   | Ala   | Gly   | Leu   | Leu   | Gly   |      |
|       |       |       | 225   |       |       |       |       | 230   |       |       |       |       | 235   |       |       |      |
| CAA   | CGG   | GCC   | CCA   | CGC   | TCC   | CAA   | CAG   | CCT   | TTC   | GTG   | GTC   | ACT   | TTC   | TTC   | AGG   | 1248 |
| Gln   | Arg   | Ala   | Pro   | Arg   | Ser   | Gln   | Gln   | Pro   | Phe   | Val   | Val   | Thr   | Phe   | Phe   | Arg   |      |
|       |       | 240   |       |       |       |       | 245   | .     |       |       |       | 250   |       |       |       |      |
| GCC   | AGT   | CCG   | AGT   | CCC   | ATC   | CGC   | ACC   | CCT   | CGG   | GCA   | GTG   | AGG   | CCA   | CTG   | AGG   | 1296 |
| Ala   | Ser   | Pro   | Ser   | Pro   | Ile   | Arg   | Thr   | Pro   | Arg   | Ala   | Val   | Arg   | Pro   | Leu   | Arg   |      |
|       | 255   |       |       |       |       | 260   |       |       |       |       | 265   |       |       |       |       |      |
| AGG   | AGG   | CAG   | CCG   | AAG   | AAA   | AGC   | AAC   | GAG   | CTG   | CCG   | CAG   | GCC   | AAC   | CGA   | CTC   | 1344 |
| Arg   | Arg   | Gln   | Pro   | Lys   | Lys   | Ser   | Asn   | Glu   | Leu   | Pro   | Gln   | Ala   | Asn   | Arg   | Leu   |      |
| 270   |       |       |       |       | 275   |       |       |       |       | 280   |       |       |       |       | 285   |      |
| CCA   | GGG   | ATC   | TTT   | GAT   | GAC   | GTC   | CAC   | GGC   | TCC   | CAC   | GGC   | CGG   | CAG   | GTC   | TGC   | 1392 |
| Pro   | Gly   | Ile   | Phe   | Asp   | Asp   | Val   | His   | Gly   | Ser   | His   | Gly   | Arg   | Gln   | Val   | Cys   |      |
|       |       |       |       | 290   |       |       |       |       | 295   |       |       |       |       | 300   |       |      |
| CGT   | CGG   | CAC   | GAG   | CTC   | TAC   | GTC   | AGC   | TTC   | CAG   | GAC   | CTC   | GGC   | TGG   | CTG   | GAC   | 1440 |
| Arg   | Arg   | His   | Glu   | Leu   | Tyr   | Val   | Ser   | Phe   | Gln   | Asp   | Leu   | Gly   | Trp   | Leu   | Asp   |      |
|       |       |       |       | 305   |       |       |       |       | 310   |       |       |       |       | 315   |       |      |
| TGG   | GTC   | ATC   | GCT   | CCC   | CAA   | GGC   | TAC   | TCG   | GCC   | TAT   | TAC   | TGT   | GAG   | GGG   | GAG   | 1488 |
| Trp   | Val   | Ile   | Ala   | Pro   | Gln   | Gly   | Tyr   | Ser   | Ala   | Tyr   | Tyr   | Cys   | Glu   | Gly   | Glu   |      |
|       |       |       | 320   |       |       |       |       | 325   |       |       |       |       | 330   |       |       |      |
| TGC   | TCC   | TTC   | CCA   | CTG   | GAC   | TCC   | TGC   | ATG   | AAT   | GCC   | ACC   | AAC   | CAC   | GCC   | ATC   | 1536 |
| Cys   | Ser   | Phe   | Pro   | Leu   | Asp   | Ser   | Cys   | Met   | Asn   | Ala   | Thr   | Asn   | His   | Ala   | Ile   |      |
|       | 335   |       |       |       |       | 340   |       |       |       |       | 345   |       |       |       |       |      |
| CTG   | CAG   | TCC   | CTG   | GTG   | CAC   | CTG   | ATG   | AAG   | CCA   | AAC   | GCA   | GTC   | CCC   | AAG   | GCG   | 1584 |
| Leu   | Gln   | Ser   | Leu   | Val   | His   | Leu   | Met   | Lys   | Pro   | Asn   | Ala   | Val   | Pro   | Lys   | Ala   |      |
| 350   |       |       |       |       | 355   |       |       |       |       | 360   |       |       |       |       | 365   |      |
| TGC   | TGT   | GCA   | CCC   | ACC   | AAG   | CTG   | AGC   | GCC   | ACC   | TCT   | GTG   | CTC   | TAC   | TAT   | GAC   | 1632 |
| Cys   | Cys   | Ala   | Pro   | Thr   | Lys   | Leu   | Ser   | Ala   | Thr   | Ser   | Val   | Leu   | Tyr   | Tyr   | Asp   |      |
|       |       |       |       | 370   |       |       |       |       | 375   |       |       |       |       | 380   |       |      |
| AGC   | AGC   | AAC   | AAC   | GTC   | ATC   | CTG   | CGC   | AAA   | GCC   | CGC   | AAC   | ATG   | GTG   | GTC   | AAG   | 1680 |
| Ser   | Ser   | Asn   | Asn   | Val   | Ile   | Leu   | Arg   | Lys   | Ala   | Arg   | Asn   | Met   | Val   | Val   | Lys   |      |
|       |       |       |       | 385   |       |       |       |       | 390   |       |       |       |       | 395   |       |      |

```
GCC TGC GGC TGC CAC T GAGTCAGCCC GCCCAGCCCT ACTGCAG                                          1723
Ala Cys Gly Cys His
        400
```

( 2 ) INFORMATION FOR SEQ ID NO:29:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Met Thr Ala Leu Pro Gly Pro Leu Trp Leu Leu Gly Leu Ala Leu Cys
 1               5                  10                  15
Ala Leu Gly Gly Gly Gly Pro Gly Leu Arg Pro Pro Pro Gly Cys Pro
                20                  25                  30
Gln Arg Arg Leu Gly Ala Arg Glu Arg Arg Asp Val Gln Arg Glu Ile
            35                  40                  45
Leu Ala Val Leu Gly Leu Pro Gly Arg Pro Arg Pro Arg Ala Pro Pro
50                  55                  60
Ala Ala Ser Arg Leu Pro Ala Ser Ala Pro Leu Phe Met Leu Asp Leu
65                  70                  75                  80
Tyr His Ala Met Ala Gly Asp Asp Asp Glu Asp Gly Ala Pro Ala Glu
                85                  90                  95
Arg Arg Leu Gly Arg Ala Asp Leu Val Met Ser Phe Val Asn Met Val
            100                 105                 110
Glu Arg Asp Arg Ala Leu Gly His Gln Glu Pro His Trp Lys Glu Phe
        115                 120                 125
Arg Phe Asp Leu Thr Gln Ile Pro Ala Gly Glu Ala Val Thr Ala Ala
130                 135                 140
Glu Phe Arg Ile Tyr Lys Val Pro Ser Ile His Leu Leu Asn Arg Thr
145                 150                 155                 160
Leu His Val Ser Met Phe Gln Val Val Gln Glu Gln Ser Asn Arg Glu
                165                 170                 175
Ser Asp Leu Phe Phe Leu Asp Leu Gln Thr Leu Arg Ala Gly Asp Glu
            180                 185                 190
Gly Trp Leu Val Leu Asp Val Thr Ala Ala Ser Asp Cys Trp Leu Leu
        195                 200                 205
Lys Arg His Lys Asp Leu Gly Leu Arg Leu Tyr Val Glu Thr Glu Asp
210                 215                 220
Gly His Ser Val Asp Pro Gly Leu Ala Gly Leu Leu Gly Gln Arg Ala
225                 230                 235                 240
Pro Arg Ser Gln Gln Pro Phe Val Val Thr Phe Phe Arg Ala Ser Pro
                245                 250                 255
Ser Pro Ile Arg Thr Pro Arg Ala Val Arg Pro Leu Arg Arg Arg Gln
            260                 265                 270
Pro Lys Lys Ser Asn Glu Leu Pro Gln Ala Asn Arg Leu Pro Gly Ile
        275                 280                 285
Phe Asp Asp Val His Gly Ser His Gly Arg Gln Val Cys Arg Arg His
290                 295                 300
Glu Leu Tyr Val Ser Phe Gln Asp Leu Gly Trp Leu Asp Trp Val Ile
305                 310                 315                 320
Ala Pro Gln Gly Tyr Ser Ala Tyr Tyr Cys Glu Gly Glu Cys Ser Phe
                325                 330                 335
Pro Leu Asp Ser Cys Met Asn Ala Thr Asn His Ala Ile Leu Gln Ser
            340                 345                 350
```

Leu Val His Leu Met Lys Pro Asn Ala Val Pro Lys Ala Cys Cys Ala
    355                 360                 365

Pro Thr Lys Leu Ser Ala Thr Ser Val Leu Tyr Tyr Asp Ser Ser Asn
    370                 375                 380

Asn Val Ile Leu Arg Lys Ala Arg Asn Met Val Val Lys Ala Cys Gly
385                 390                 395                 400

Cys His ( 2 ) INFORMATION FOR SEQ ID NO:30:

( i ) SEQUENCE CHARACTERISTICS:
        ( A ) LENGTH: 102 amino acids
        ( B ) TYPE: amino acid
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=OPX
            / note="WHEREIN EACH XAA IS INDEPENDENTLY SELECTED
            FROM A GROUP OF ONE OR MORE SPECIFIED AMINO ACIDS
            AS DEFINED IN THE SPECIFICATION (SECTION II.B.2.)"

( x i ) SEQUENCE DESCRIPTION: SEQ ID NO:30:

Cys Xaa Xaa His Glu Leu Tyr Val Xaa Phe Xaa Asp Leu Gly Trp Xaa
1               5                   10                  15

Asp Trp Xaa Ile Ala Pro Xaa Gly Tyr Xaa Ala Tyr Tyr Cys Glu Gly
            20              25                  30

Glu Cys Xaa Phe Pro Leu Xaa Ser Xaa Met Asn Ala Thr Asn His Ala
        35              40              45

Ile Xaa Gln Xaa Leu Val His Xaa Xaa Xaa Pro Xaa Xaa Val Pro Lys
    50              55              60

Xaa Cys Cys Ala Pro Thr Xaa Leu Xaa Ala Xaa Ser Val Leu Tyr Xaa
65              70              75              80

Asp Xaa Ser Xaa Asn Val Xaa Leu Xaa Lys Xaa Arg Asn Met Val Val
        85              90              95

Xaa Ala Cys Gly Cys His
            100

( 2 ) INFORMATION FOR SEQ ID NO:31:

( i ) SEQUENCE CHARACTERISTICS:
        ( A ) LENGTH: 97 amino acids
        ( B ) TYPE: amino acid
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label=OPX-7C
            / note="WHEREIN EACH XAA INDEPENDENTLY INDICATES
            ONE OF THE 20 NATURALLY-OCCURRING L-ISOMER,
            A-AMINO ACIDS, OR A DERIVATIVE THEREOF."

( x i ) SEQUENCE DESCRIPTION: SEQ ID NO:31:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Cys Xaa Xaa Xaa Cys Xaa Xaa Xaa
            20              25                  30

Xaa Xaa Xaa Cys Xaa Xaa Xaa Xaa Xaa Xaa Xaa Xaa Xaa Xaa Xaa Xaa
        35              40              45

| Xaa | Xaa | Xaa | Xaa | Xaa | Xaa | Xaa | Xaa | Xaa | Xaa | Xaa | Xaa | Cys | Cys | Xaa | Xaa |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Xaa | Xaa | Xaa | Xaa | Xaa | Xaa | Xaa | Xaa | Xaa | Xaa | Xaa | Xaa | Xaa | Xaa | Xaa | Xaa |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Xaa | Xaa | Xaa | Xaa | Xaa | Xaa | Xaa | Xaa | Xaa | Xaa | Xaa | Xaa | Cys | Xaa | Cys |
|-----|-----|-----|-----|-----|-----|-----|-----|-----|-----|-----|-----|-----|-----|-----|
|     |     |     |     | 85  |     |     |     |     | 90  |     |     |     |     | 95  |

Xaa (2) INFORMATION FOR SEQ ID NO:32:

(i) SEQUENCE CHARACTERISTICS:
        (A) LENGTH: 102 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label=OPX-8C
            / note="WHEREIN EACH XAA INDEPENDENTLY INDICATES
            ONE OF THE 20 NATURALLY-OCCURRING L-ISOMER A-AMINO
            AICDS, OR A DERIVATIVE THEREOF."

(xi) SEQUENCE DESCRIPTION

```
GACGAGAATT CCACCGTGGT GCTGAAGAAC TACCAGGAGA TGACCGTGGT GGGCTGCGGC    300

TGCCGCTAAC TGCA                                                      314
```